(12) United States Patent
Kanouni et al.

(10) Patent No.: US 10,526,327 B2
(45) Date of Patent: Jan. 7, 2020

(54) HISTONE DEMETHYLASE INHIBITORS

(71) Applicant: CELGENE QUANTICEL RESEARCH, INC., San Diego, CA (US)

(72) Inventors: Toufike Kanouni, Rancho Santa Fe, CA (US); Jeffrey Alan Stafford, San Diego, CA (US); James Marvin Veal, Apex, NC (US); Michael Brennan Wallace, San Diego, CA (US)

(73) Assignee: Celgene Quanticel Research, Inc., San Diego, CA (US)

( * ) Notice: Subject to any disclaimer, the term of this patent is extended or adjusted under 35 U.S.C. 154(b) by 0 days.

(21) Appl. No.: 15/971,912

(22) Filed: May 4, 2018

(65) Prior Publication Data

US 2018/0319793 A1    Nov. 8, 2018

Related U.S. Application Data

(62) Division of application No. 14/774,335, filed as application No. PCT/US2014/024998 on Mar. 12, 2014, now Pat. No. 9,994,562.

(60) Provisional application No. 61/791,406, filed on Mar. 15, 2013.

(51) Int. Cl.
*A61K 31/535* (2006.01)
*C07D 471/04* (2006.01)

(52) U.S. Cl.
CPC ................. *C07D 471/04* (2013.01)

(58) Field of Classification Search
USPC .................................................... 514/234.2
See application file for complete search history.

(56) References Cited

U.S. PATENT DOCUMENTS

| 9,643,965 B2 | 5/2017 | Boloor |
| 2007/0190634 A1 | 8/2007 | Bebbington et al. |
| 2007/0254901 A1 | 11/2007 | Bilodeau et al. |

FOREIGN PATENT DOCUMENTS

| WO | 2012/052390 A1 | 4/2012 |
| WO | 2014/151106 A1 | 9/2014 |

OTHER PUBLICATIONS

Berge et al., Pharmaceutical Salts. Journal of Pharmaceutical Sciences 66(1):1-19 (Jan. 1977).
Bundgard et al., Design of Prodrugs pp. 7-9, 21-24 (1985).
Extended European Search Report dated Jul. 4, 2016 in related European Patent Application No. 14768099.5, filed Mar. 12, 2014.
Hamada, S. et al., "Design, Synthesis, Enzyme-inhibitory Activity, and Effect on Human Cancer Cells of a Novel Series of Jumonji Domain-Containing Protein 2 Histonic Demethylase Inhibitors," Journal of Medicinal Chemistry, American Chemical Socieity, U.S., 53(15):5629-5632 (Aug. 12, 2010).
Higuchi et al., Pro-drugs as Novel Delivery Systems. A.C.S. Symposium Series, 1975, vol. 14.
International Preliminary Report on Patentability dated Sep. 24, 2015 issued in International Application No. PCT/US2014/024998, filed Mar. 12, 2014.
International Search Report and Written Opinion dated Jul. 10, 2014 issued in International Application No. PCT/US2014/024998, filed Mar. 12, 2014.
International Search Report and Written Opinion dated Dec. 14, 2015 issued in International Application No. PCT/US2015/050432, filed Sep. 16, 2015.
King, O.N.F. et al, "Quantitative High-Throughput Screening Indentifies 8-Hydroxyquinolines as Cell-Active Histone Demethylase Inhibitors," PLOS ONE, 5(11):e15535, pp. 1-12 (Nov. 23, 2010).
Labbe, R.M. et al., "Histone lysine demethylase (KDM) subfamily 4: structures, functions and therapeutic potential," Am. J. Transl. Res., Jan. 1, 2014, 6(1):1-15, Retrieved from the Internet: URL: http://www.ajtr.orgifiles/AJTR1311006.
Lachner et al, An epigenetic road map for histone lysine methylation. Journal of Cell Science 116:2117-2124 (Jun. 1, 2003).
Lin et al., Loss of the retinoblastoma binding protein 2 (RBP2) histone demethylase suppresses tumorigenesis in mice lacking RB1 or Men1. PNAS108(33):13379-13386 (2011).
Margueron et al. The key to development: interpreting the histone code? Current Opinion in Genetics & Development 15:163-176 (2005).
Stahl et al, "Handbook of Pharmaceutical Salts." Verlag Helvetica Chimica Acta, Zurich (2002).

*Primary Examiner* — Marcos L Sznaidman
(74) *Attorney, Agent, or Firm* — Wiley Rein LLP

(57) ABSTRACT

The present invention relates generally to compositions and methods for treating cancer and neoplastic disease. Provided herein are substituted pyrido[3,4-d]pyrimidin-4-one derivative compounds and pharmaceutical compositions comprising said compounds. The subject compounds and compositions are useful for inhibition of histone demethylase. Furthermore, the subject compounds and compositions are useful for the treatment of cancer, such as prostate cancer, breast cancer, bladder cancer, lung cancer and/or melanoma and the like.

11 Claims, No Drawings

HISTONE DEMETHYLASE INHIBITORS

CROSS REFERENCE

This application is a divisional of U.S. patent application Ser. No. 14/774,335, filed Sep. 10, 2015, which is a 371 of International Patent Application No. PCT/US2014/024998, filed Mar. 12, 2014, which claims the benefit of U.S. Provisional Application 61/791,406, filed Mar. 15, 2013, the contents of which are hereby incorporated by reference in their entireties.

BACKGROUND

A need exists in the art for an effective treatment of cancer and neoplastic disease.

BRIEF SUMMARY OF THE INVENTION

Provided herein are substituted pyrido[3,4-d]pyrimidin-4-one derivative compounds and pharmaceutical compositions comprising said compounds. The subject compounds and compositions are useful for inhibition histone demethylase. Furthermore, the subject compounds and compositions are useful for the treatment of cancer, such as prostate cancer, breast cancer, bladder cancer, lung cancer and/or melanoma and the like. The substituted pyrido[3,4-d]pyrimidin-4-one derivative compounds described herein are based upon a substituted pyrido[3,4-d]pyrimidin-4-one ring system bearing a hydroxy group at the 4-position, and an oxygen-based substituent at the 2-position. The 8-position substituent, in various embodiments, is selected from a wide variety of groups, such as, but not limited to, hydrogen, alkyl, aryl, carbocyclyl, and the like.

One embodiment provides a compound of Formula (I), or pharmaceutically acceptable salt thereof,

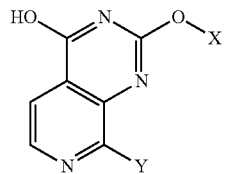

Formula (I)

wherein,
X is alkyl, or -L-R$^1$;
L is a bond, or C1-C6 alkylene;
R$^1$ is carbocyclyl, aryl, heterocyclyl, or heteroaryl;
Y is hydrogen or

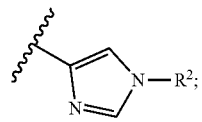

and
R$^2$ is alkyl, heterocyclyl, heterocyclylalkyl, or carbocyclylalkyl.

One embodiment provides a pharmaceutical composition comprising a compound of Formula (I), or pharmaceutically acceptable salt thereof, and at least one pharmaceutically acceptable excipient.

One embodiment provides a method for inhibiting a histone demethylase enzyme comprising contacting a histone demethylase enzyme with a compound of Formula (I).

One embodiment provides a method for treating cancer in subject comprising administering to the subject in need thereof a composition comprising a compound of Formula (I), or a pharmaceutically acceptable salt thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =  radical.
"Thioxo" refers to the =S radical.
"Imino" refers to the =N—H radical.
"Oximo" refers to the =N—OH radical.
"Hydrazine" refers to the =N—NH$_2$ radical.
"Alkyl" refers to a straight or branched hydrocarbon chain radical consisting solely of carbon and hydrogen atoms, containing no unsaturation, having from one to fifteen carbon atoms (e.g., C$_1$-C$_{15}$ alkyl). In certain embodiments, an alkyl comprises one to thirteen carbon atoms (e.g., C$_1$-C$_{13}$ alkyl). In certain embodiments, an alkyl comprises one to eight carbon atoms (e.g., C$_1$-C$_8$ alkyl). In other embodiments, an alkyl comprises one to five carbon atoms (e.g., C$_1$-C$_5$ alkyl). In other embodiments, an alkyl comprises one to four carbon atoms (e.g., C$_1$-C$_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)$S(O)$_t R^a$ (where t is 1 or 2), —S(O)$_t OR^a$ (where t is 1 or 2), —S(O)$_t R^a$ (where t is 1 or 2) and —S(O)$_t N(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)$S(O)$_t R^a$ (where t is 1 or 2), —S(O)$_t OR^a$ (where t is 1 or 2), —S(O)$_t R^a$ (where t is 1 or 2) and —S(O)$_t N(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)$S(O)$_t R^a$ (where t is 1 or 2), —S(O)$_t OR^a$ (where t is 1 or 2), —S(O)$_t R^a$ (where t is 1 or 2) and —S(O)$_t N(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)$OR^a$, —C(O)$N(R^a)_2$, —$N(R^a)$C(O)$OR^a$, —OC(O)—$N(R^a)_2$, —$N(R^a)$C(O)$R^a$, —$N(R^a)$S(O)$_t R^a$ (where t is 1 or 2), —S(O)$_t OR^a$ (where t is 1 or 2), —S(O)$_t R^a$ (where t is 1 or 2) and —S(O)$_t N(R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$ S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Aralkyl" refers to a radical of the formula —R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —R$^d$-aryl where R$^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —R$^e$-aryl, where R$^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula —O—R$^c$-aryl where R$^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)$_t$R$^a$ (where t is 1 or 2), —R$^b$—S(O)$_t$OR$^a$ (where t is 1 or 2), —R$^b$—S(O)$_t$R$^a$ (where t is 1 or 2) and —R$^b$—S(O)$_t$N(R$^a$)$_2$ (where t is 1 or 2), where each R$^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each R$^b$ is independently a direct bond or a straight or branched alkylene or alkenylene chain, and R$^c$ is a straight or branched alkylene or alkenylene chain, and where each of the above substituents is unsubstituted unless otherwise indicated.

"Carbocyclylalkyl" refers to a radical of the formula —R$^c$-carbocyclyl where R$^c$ is an alkylene chain as defined above. The alkylene chain and the carbocyclyl radical is optionally substituted as defined above.

"Carbocyclylalkoxy" refers to a radical bonded through an oxygen atom of the formula —O—R$^c$-carbocyclyl where R$^c$ is an alkylene chain as defined above. The alkylene chain and the carbocyclyl radical is optionally substituted as defined above.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which may include fused or bridged ring systems. The heteroatoms in the heterocyclyl radical may be optionally oxidized. One or more nitrogen atoms, if present, are optionally quaternized. The heterocyclyl radical is partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—

$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$O$R^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—O$R^a$, —$R^b$—OC(O)—$R^a$, —$R^b$—OC(O)—O$R^a$, —$R^b$—OC(O)—N($R^a$)$_2$, —$R^b$—N($R^a$)$_2$, —$R^b$—C(O)$R^a$, —$R^b$—C(O)O$R^a$, —$R^b$—C(O)N($R^a$)$_2$, —$R^b$—O—$R^c$—C(O)N($R^a$)$_2$, —$R^b$—N($R^a$)C(O)O$R^a$, —$R^b$—N($R^a$)C(O)$R^a$, —$R^b$—N($R^a$)S(O)$_t$$R^a$ (where t is 1 or 2), —$R^b$—S(O)$_t$O$R^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein may contain one or more asymmetric centers and may thus give rise to enantiomers, diastereomers, and other stereoisomeric forms that may be defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

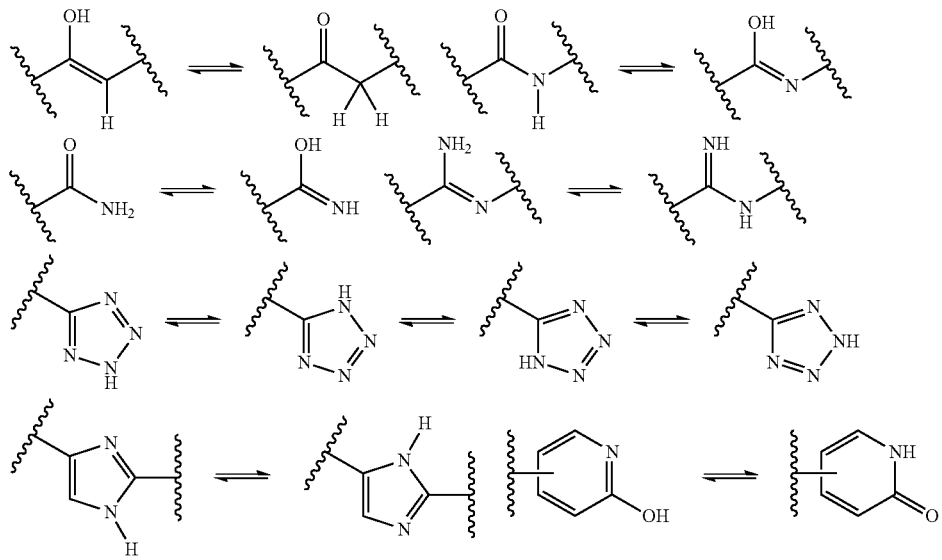

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the substituted pyrido[3,4-d]pyrimidin-4-one derivative compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997), which is hereby incorporated by reference in its entirety). Acid addition salts of basic compounds may be prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts may be formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Substituted Pyrido[3,4-d]pyrimidin-4-one Derivative Compounds

Substituted pyrido[3,4-d]pyrimidin-4-one derivative compounds are described herein that inhibit a histone demethylase enzyme. These compounds, and compositions comprising these compounds, are useful for the treatment of cancer and neoplastic disease. The compounds described herein are useful for treating prostate cancer, breast cancer, bladder cancer, lung cancer and/or melanoma and the like.

One embodiment provides a compound of Formula (I), or pharmaceutically acceptable salt thereof,

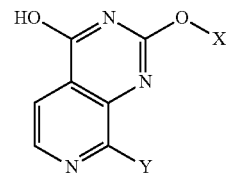

Formula (I)

wherein,

X is alkyl, or -L-R$^1$;

L is a bond, or C1-C6 alkylene;

R$^1$ is carbocyclyl, aryl, heterocyclyl, or heteroaryl;

Y is hydrogen or

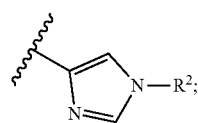

and

R$^2$ is alkyl, heterocyclyl, heterocyclylalkyl, or carbocyclylalkyl.

Another embodiment provides the compound of Formula (I), wherein Y is hydrogen. Another embodiment provides the compound of Formula (I), wherein Y is

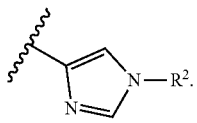

Another embodiment provides the compound of Formula (I), wherein X is alkyl. Another embodiment provides the compound of Formula (I), wherein X is alkyl and Y is hydrogen. Another embodiment provides the compound of Formula (I), wherein X is alkyl and Y is

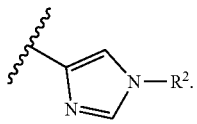

Another embodiment provides the compound of Formula (I), wherein the alkyl is a C1-C6 alkyl. Another embodiment provides the compound of Formula (I), wherein the alkyl is substituted with at least one fluoro substituent. Another embodiment provides the compound of Formula (I), wherein the alkyl is substituted with at least one group selected from hydroxy, alkoxy, aryloxy, amino, alkylamino, arylamino, or diakylamino. Another embodiment provides the compound of Formula (I), wherein the alkyl is substituted with at least one group selected from —NHCOR$^3$, —NHCO$_2$R$^3$, —NHCONHR$^3$, —N(R$^4$)COR$^3$, —N(R$^4$)CO$_2$R$^3$, —N(R$^4$)CONHR$^3$, —N(R$^4$)CON(R$^4$)R$^3$, —NHSO$_2$R$^3$, or —NR$^4$SO$_2$R$^3$, wherein each R$^3$ is independently selected from alkyl, aryl, heteroaryl, carbocyclyl, or heterocyclyl, and each R$^4$ is an alkyl. Another embodiment provides the compound of Formula (I), wherein the alkyl is substituted with at least one group selected from —CONH$_2$, —CONHR$^3$, —CON(R$^3$)$_2$, —COR$^3$, —SO$_2$NH$_2$, —SO$_2$NHR$^3$, —SO$_2$N(R$^3$)$_2$, or —SO$_2$R$^3$, wherein each R$^3$ is independently selected from alkyl, aryl, heteroaryl, carbocyclyl, or heterocyclyl.

Another embodiment provides the compound of Formula (I), wherein X is -L-R$^1$. Another embodiment provides the compound of Formula (I), wherein X is -L-R$^1$ and Y is hydrogen. Another embodiment provides the compound of Formula (I), wherein X is -L-R$^1$ and Y is

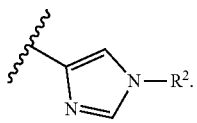

Another embodiment provides the compound of Formula (I), wherein L is a bond.

Another embodiment provides the compound of Formula (I), wherein L is a bond and R$^1$ is carbocyclyl. The compound of claim 8 or 9, wherein L is a bond. Another embodiment provides the compound of Formula (I), wherein R$^1$ is heterocyclyl. Another embodiment provides the compound of Formula (I), wherein L is a bond. Another embodiment provides the compound of Formula (I), wherein R$^1$ is aryl. Another embodiment provides the compound of Formula (I), wherein the aryl is a phenyl group. Another embodiment provides the compound of Formula (I), wherein the phenyl is substituted with at least one halogen substituent. Another embodiment provides the compound of Formula (I), wherein the phenyl is substituted with at least one alkyl substituent. Another embodiment provides the compound of Formula (I), wherein the phenyl is substituted with at least one group selected from hydroxy, alkoxy, aryloxy, amino, alkylamino, arylamino, or diakylamino. Another embodiment provides the compound of Formula (I), wherein the phenyl is substituted with at least one group selected from —NHCOR$^3$, —NHCO$_2$R$^3$, —NHCONHR$^3$, —N(R$^4$)COR$^3$, —N(R$^4$)CO$_2$R$^3$, —N(R$^4$)CONHR$^3$, —N(R$^4$)CON(R$^4$)R$^3$, —NHSO$_2$R$^3$, or —NR$^4$SO$_2$R$^3$, wherein each R$^3$ is independently selected from alkyl, aryl, heteroaryl, carbocyclyl, or heterocyclyl, and each R$^4$ is an alkyl. Another embodiment provides the compound of Formula (I), wherein the phenyl is substituted with at least one group selected from —CONH$_2$, —CONHR$^3$, —CON(R$^3$)$_2$, —COR$^3$, —SO$_2$NH$_2$, —SO$_2$NHR$^3$, —SO$_2$N(R$^3$)$_2$, or —SO$_2$R$^3$, wherein each R$^3$ is independently selected from alkyl, aryl, heteroaryl, carbocyclyl, or heterocyclyl. Another embodiment provides the compound of Formula (I), wherein the phenyl is substituted with a group selected from aryl, heteroaryl, carbocyclyl, or heterocyclyl.

Another embodiment provides the compound of Formula (I), wherein L is a bond and R$^1$ is heteroaryl. Another embodiment provides the compound of Formula (I), wherein the heteroaryl is a group selected from benzimidazolyl, benzofuranyl, furanyl, isothiazolyl, imidazolyl, indazolyl, indolyl, isoxazolyl, oxazolyl, pyrrolyl, pyrazolyl, pyridinyl, prrazinyl, pyrimidinyl, pyridazinyl, thiazolyl or thiophenyl. Another embodiment provides the compound of Formula (I), wherein the heteroaryl group is substituted with at least one halogen substituent. Another embodiment provides the compound of Formula (I), wherein the heteroaryl group is substituted with at least one alkyl substituent. Another embodiment provides the compound of Formula (I), wherein the heteroaryl group is substituted with at least one group selected from hydroxy, alkoxy, aryloxy, amino, alkylamino, arylamino, or diakylamino. Another embodiment provides the compound of Formula (I), wherein the heteroaryl group is substituted with at least one group selected from —NHCOR$^3$, —NHCO$_2$R$^3$, —NHCONHR$^3$, —N(R$^4$)COR$^3$, —N(R$^4$)CO$_2$R$^3$, —N(R$^4$)CONHR$^3$, —N(R$^4$)CON(R$^4$)R$^3$, —NHSO$_2$R$^3$, or —NR$^4$SO$_2$R$^3$, wherein each R$^3$ is independently selected from alkyl, aryl, heteroaryl, carbocyclyl, or heterocyclyl, and each R$^4$ is an alkyl. Another embodiment provides the compound of Formula (I), wherein the heteroaryl group is substituted with at least one group selected from —CONH$_2$, —CONHR$^3$, —CON(R$^3$)$_2$, —COR$^3$, —SO$_2$NH$_2$, —SO$_2$NHR$^3$, —SO$_2$N(R$^3$)$_2$, or —SO$_2$R$^3$, wherein each R$^3$ is independently selected from alkyl, aryl, heteroaryl, carbocyclyl, or heterocyclyl. Another embodiment provides the compound of Formula (I), wherein the heteroaryl group is substituted with a group selected from aryl, heteroaryl, carbocyclyl, or heterocyclyl. Another embodiment provides the compound of Formula (I), wherein the heteroaryl is a pyrazolyl having the structure

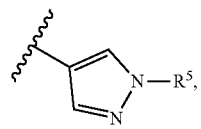

wherein R$^5$ is a group selected from alkyl, carbocyclyl, heterocyclyl, carbocyclylalkyl, heterocyclylalkyl, aralkyl, or heteroarylalkyl. Another embodiment provides the compound of Formula (I), wherein the $R^5$ group is a C1-C6 alkyl, optionally substituted with at least one group selected from hydroxy, C1-C4 alkoxy, amino, C1-C4 alkylamino, C1-C4 diakylamino, piperdinyl, pyrrolidnyl, or morpholinyl. Another embodiment provides the compound of Formula (I), wherein the $R^5$ group is a heterocyclyl selected from 4-tetrahydropyranyl, 1-morpholinyl, or 4-piperdinyl having the structure

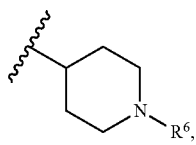

wherein $R^6$ is a —$COR^7$, —$CO_2R^7$, —$CONHR^7$, or —$SO_2R^7$, wherein each $R^7$ is independently selected from alkyl, aryl, heteroaryl, carbocyclyl, or heterocyclyl.

Another embodiment provides the compound of Formula (I), wherein X is -L-$R^1$. Another embodiment provides the compound of Formula (I), wherein L is a C1-C6 alkylene. Another embodiment provides the compound of Formula (I), wherein L is a C1-C4 alkylene. Another embodiment provides the compound of Formula (I), wherein $R^1$ is 3- to 7-membered carbocyclyl. Another embodiment provides the compound of Formula (I), wherein $R^1$ is phenyl. Another embodiment provides the compound of Formula (I), wherein $R^1$ is a 5- or 6-membered heteroaryl. Another embodiment provides the compound of Formula (I), wherein $R^1$ is a 4- to 6-membered oxygen containing heterocyclyl.

Another embodiment provides the compound of Formula (I), wherein $R^2$ is alkyl. Another embodiment provides the compound of Formula (I), wherein the alkyl is methyl. Another embodiment provides the compound of Formula (I), wherein the alkyl is C2-C4 alkyl. Another embodiment provides the compound of Formula (I), wherein the alkyl is substituted with at least one fluoro substituent. Another embodiment provides the compound of Formula (I), wherein the alkyl is substituted with at least one group selected from hydroxy, alkoxy, amino, alkylamino, or diakylamino.

Another embodiment provides the compound of Formula (I), wherein $R^2$ is heterocyclyl. Another embodiment provides the compound of Formula (I), wherein $R^2$ is heterocyclalkyl.

Another embodiment provides the compound of Formula (I), wherein the heterocyclyl is a 4- to 6-membered oxygen or nitrogen containing heterocyclyl. Another embodiment provides the compound of Formula (I), wherein the heterocyclylalkyl consists of a 4- to 6-membered oxygen or nitrogen containing heterocyclyl, and a C1-C3 alkylene.

Another embodiment provides the compound of Formula (I), wherein $R^2$ is carbocyclylalkyl. Another embodiment provides the compound of Formula (I), wherein the carbocyclylalkyl consists of a 3- to 7-membered carbocyclyl, and a C1-C3 alkylene.

One embodiment provides a compound of Formula (Ia), or pharmaceutically acceptable salt thereof,

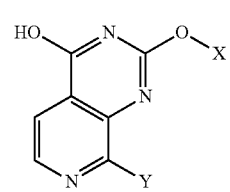

Formula (Ia)

wherein,
X is -L-$R^1$;
L is a bond, or C1-C6 alkylene;
$R^1$ is heteroaryl substituted with a methylene group bearing at least one aryl group and at least one cycloalkyl group;
Y is hydrogen or

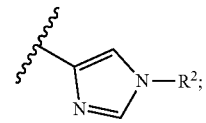

and
$R^2$ is alkyl, heterocyclyl, heterocyclylalkyl, or carbocyclylalkyl.

One embodiment provides a compound of Formula (II), or pharmaceutically acceptable salt thereof,

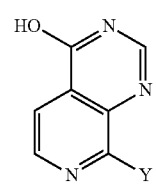

Formula (II)

wherein,
Y is

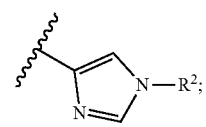

and
$R^2$ is alkyl, heterocyclyl, heterocyclylalkyl, or carbocyclylalkyl.

Another embodiment provides the compound of Formula (II), wherein $R^2$ is methyl. Another embodiment provides the compound of Formula (II), wherein $R^2$ is C1-C4 alkyl. Another embodiment provides the compound of Formula (II), wherein the alkyl is substituted with at least one fluoro substituent. Another embodiment provides the compound of Formula (II), wherein the alkyl is substituted with at least one group selected from hydroxy, alkoxy, aryloxy, amino, alkylamino, arylamino, or diakylamino. Another embodiment provides the compound of Formula (II), wherein the alkyl is substituted with at least one group selected from —$NHCOR^3$, —$NHCO_2R^3$, —$NHCONHR^3$, —$N(R^4)COR^3$, —$N(R^4)CO_2R^3$, —$N(R^4)CONHR^3$, —$N(R^4)CON(R^4)R^3$, —NHSO$_2$R$^3$, or —NR$^4$SO$_2$R$^3$, wherein each R$^3$ is independently selected from alkyl, aryl, heteroaryl, carbocyclyl, or heterocyclyl, and each R$^4$ is an alkyl. Another embodiment provides the compound of Formula (II), wherein the alkyl is substituted with at least one group selected from —CONH$_2$, —CONHR$^3$, —CON(R$^3$)$_2$, —COR$^3$, —SO$_2$NH$_2$, —SO$_2$NHR$^3$, —SO$_2$N(R$^3$)$_2$, or —SO$_2$R$^3$, wherein each R$^3$ is independently selected from alkyl, aryl, heteroaryl, carbocyclyl, or heterocyclyl. Another embodiment provides the compound of Formula (II), wherein R$^2$ is heterocyclylalkyl. Another embodiment provides the compound of Formula (II), wherein R$^2$ is heterocyclylalkyl, and the alkylene portion of the heterocyclylalkyl is a C1-C4 alkylene. Another embodiment provides the compound of Formula (II), wherein R$^2$ is heterocyclylalkyl and the heterocyclyl portion of the heterocyclylalkyl is a 4- to 7-membered heterocyclyl containing at least one nitrogen atom, or at least one oxygen atom. Another embodiment provides the compound of Formula (II), wherein R$^2$ is carbocyclylalkyl. Another embodiment provides the compound of Formula (II), wherein R$^2$ is carbocyclylalkyl, and the alkylene portion of the carbocyclylalkyl is a C1-C4 alkylene. Another embodiment provides the compound of Formula (II), wherein R$^2$ is carbocyclylalkyl, and the carbocyclyl portion of the carbocyclylalkyl is a 4- to 7-membered carbocyclyl.

In some embodiments, the compound disclosed herein has a structure provided in Table 1.

TABLE 1

| Chemical Synthesis Example | Structure | Name |
|---|---|---|
| 1 | 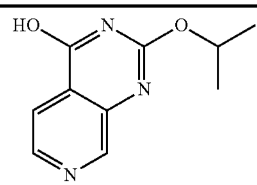 | 2-propan-2-yloxy-3H-pyrido[3,4-d]pyrimidin-4-one |
| 2 | 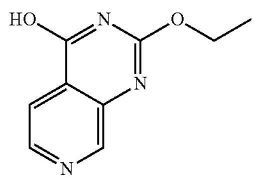 | 2-ethoxypyrido[3,4-d]pyrimidin-4-ol |
| 3 | 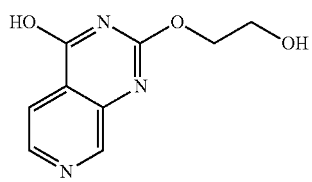 | 2-(2-hydroxyethoxy)pyrido[3,4-d]pyrimidin-4-ol |
| 4 | 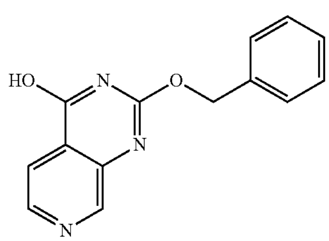 [SMILES: Oc1nc(OCc2ccccc2)nc2cnccc12] | 2-phenylmethoxypyrido[3,4-d]pyrimidin-4-ol |
| 5 | 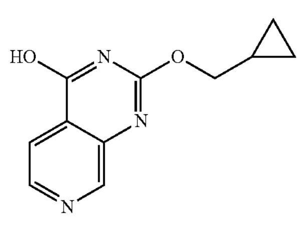 [SMILES: Oc1nc(OCC2CC2)nc2cnccc12] | 2-(cyclopropylmethoxy)-3H-pyrido[3,4-d]pyrimidin-4-one |
| 6 | 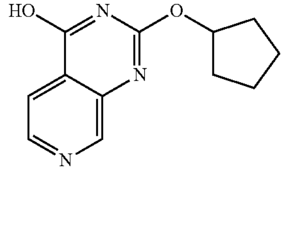 [SMILES: Oc1nc(OC2CCCC2)nc2cnccc12] | 2-cyclopentyloxy-3H-pyrido[3,4-d]pyrimidin-4-one |

TABLE 1-continued
| Chemical Synthesis Example | Structure | Name |
|---|---|---|
| 7 | 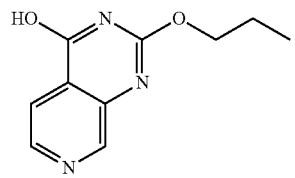 | 2-propoxy-3H-pyrido[3,4-d]pyrimidin-4-one |
| 8 | 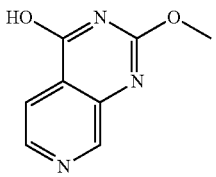 | 2-methoxypyrido[3,4-d]pyrimidin-4-ol |
| 9 | 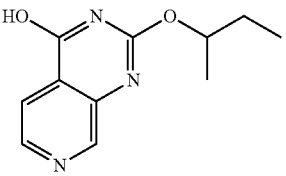 [SMILES: CCC(C)Oc1nc(O)c2ccncc2n1] | 2-butan-2-yloxy-3H-pyrido[3,4-d]pyrimidin-4-one |
| 10 | 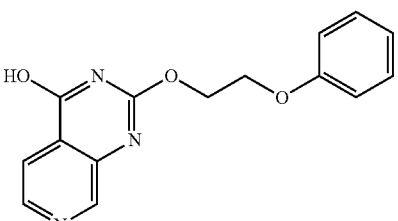 | 2-(2-phenoxyethoxy)-3H-pyrido[3,4-d]pyrimidin-4-one |
| 11 | 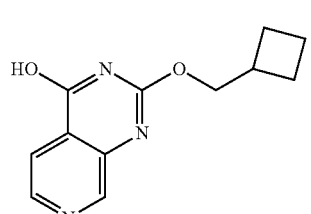 | 2-(cyclobutylmethoxy)-3H-pyrido[3,4-d]pyrimidin-4-one |
| 12 | 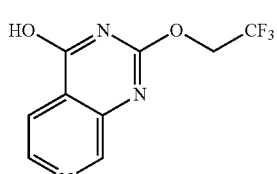 | 2-(2,2,2-trifluoroethoxy)pyrido[3,4-d]pyrimidin-4-ol |
| 13 | 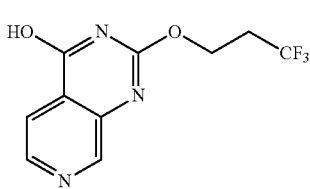 [SMILES: Oc1nc(OCCC(F)(F)F)nc2cnccc12] | 2-(3,3,3-trifluoropropoxy)pyrido[3,4-d]pyrimidin-4-ol |

TABLE 1-continued

| Chemical Synthesis Example | Structure | Name |
|---|---|---|
| 14 | 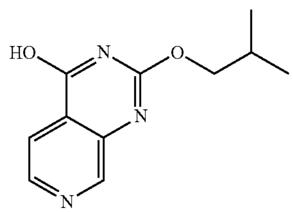 [SMILES: CC(C)COc1nc(O)c2ccncc2n1] | 2-(2-methylpropoxy)pyrido[3,4-d]pyrimidin-4-ol |
| 15 | 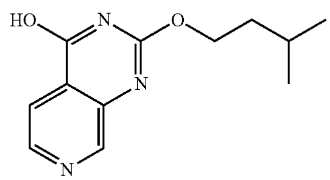 [SMILES: CC(C)CCOc1nc(O)c2ccncc2n1] | 2-(3-methylbutoxy)pyrido[3,4-d]pyrimidin-4-ol |
| 16 | 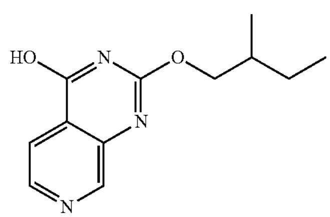 [SMILES: CCC(C)COc1nc(O)c2ccncc2n1] | 2-(2-methylbutoxy)pyrido[3,4-d]pyrimidin-4-ol |
| 17 | 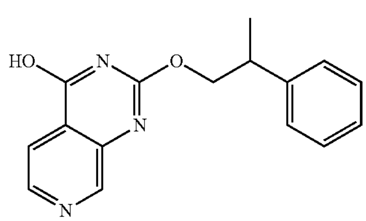 [SMILES: CC(COc1nc(O)c2ccncc2n1)c1ccccc1] | 2-(2-phenylpropoxy)pyrido[3,4-d]pyrimidin-4-ol |
| 18 | 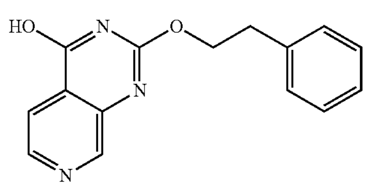 [SMILES: Oc1nc(OCCc2ccccc2)nc2cnccc12] | 2-(2-phenylethoxy)pyrido[3,4-d]pyrimidin-4-ol |
| 19 | 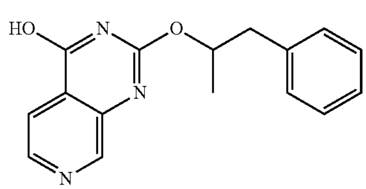 [SMILES: CC(Cc1ccccc1)Oc1nc(O)c2ccncc2n1] | 2-(1-phenylpropan-2-yloxy)pyrido[3,4-d]pyrimidin-4-ol |
| 20 | 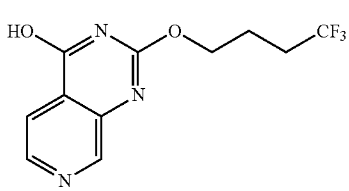 [SMILES: Oc1nc(OCCCC(F)(F)F)nc2cnccc12] | 2-(4,4,4-trifluorobutoxy)pyrido[3,4-d]pyrimidin-4-ol |

TABLE 1-continued

| Chemical Synthesis Example | Structure | Name |
|---|---|---|
| 21 | 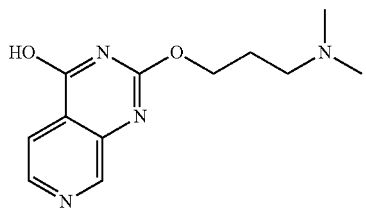 [SMILES: CN(C)CCCOc1nc(O)c2ccncc2n1] | 2-[3-(dimethylamino)propoxy]pyrido[3,4-d]pyrimidin-4-ol |
| 22 | 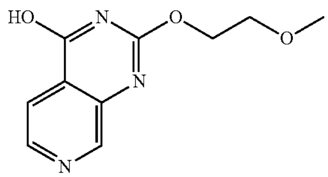 [SMILES: COCCOc1nc(O)c2ccncc2n1] | 2-(2-methoxyethoxy)pyrido[3,4-d]pyrimidin-4-ol |
| 23 | 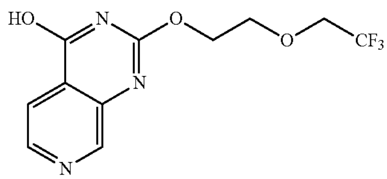 [SMILES: Oc1nc(OCCOCC(F)(F)F)nc2cnccc12] | 2-[2-(2,2,2-trifluoroethoxy)ethoxy]pyrido[3,4-d]pyrimidin-4-ol |
| 24 | 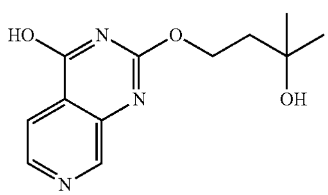 [SMILES: CC(C)(O)CCOc1nc(O)c2ccncc2n1] | 2-(3-hydroxy-3-methylbutoxy)pyrido[3,4-d]pyrimidin-4-ol |
| 25 | 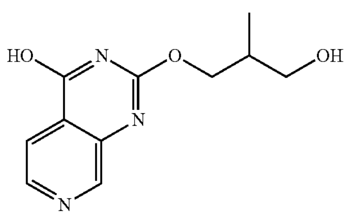 [SMILES: CC(CO)COc1nc(O)c2ccncc2n1] | 2-(3-hydroxy-2-methylpropoxy)pyrido[3,4-d]pyrimidin-4-ol |
| 26 | 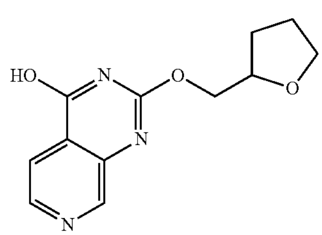 [SMILES: Oc1nc(OCC2CCCO2)nc2cnccc12] | 2-(oxolan-2-ylmethoxy)pyrido[3,4-d]pyrimidin-4-ol |
| 27 | 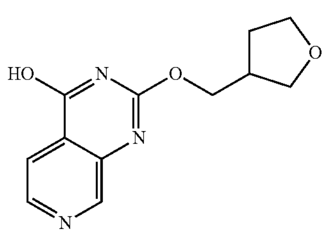 [SMILES: Oc1nc(OCC2CCOC2)nc2cnccc12] | 2-(oxolan-3-ylmethoxy)pyrido[3,4-d]pyrimidin-4-ol |

TABLE 1-continued

| Chemical Synthesis Example | Structure | Name |
|---|---|---|
| 28 | 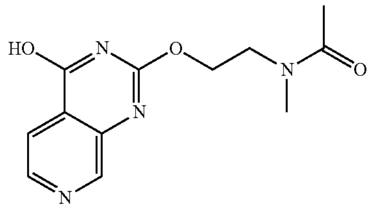 [SMILES: CC(=O)N(C)CCOc1nc(O)c2ccncc2n1] | N-[2-(4-hydroxypyrido[3,4-d]pyrimidin-2-yl)oxyethyl]-N-methylacetamide |
| 29 | 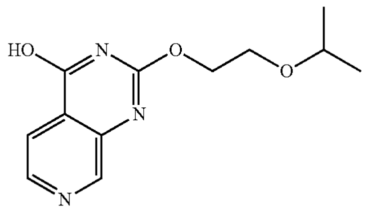 [SMILES: CC(C)OCCOc1nc(O)c2ccncc2n1] | 2-(2-propan-2-yloxyethoxy)pyrido[3,4-d]pyrimidin-4-ol |
| 30 | 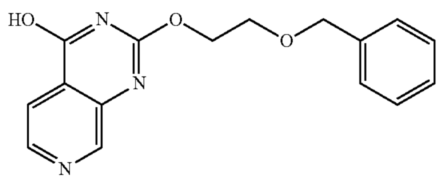 [SMILES: Oc1nc(OCCOCc2ccccc2)nc2cnccc12] | 2-(2-phenylmethoxyethoxy)pyrido[3,4-d]pyrimidin-4-ol |
| 31 | 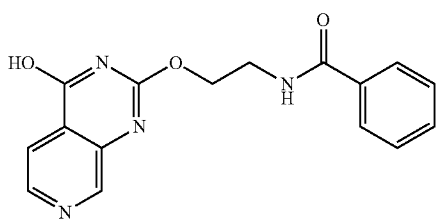 [SMILES: O=C(NCCOc1nc(O)c2ccncc2n1)c1ccccc1] | N-[2-(4-hydroxypyrido[3,4-d]pyrimidin-2-yl)oxyethyl]benzamide |
| 32 | 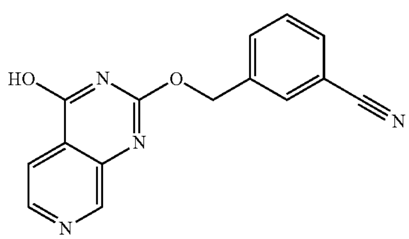 [SMILES: N#Cc1cccc(COc2nc(O)c3ccncc3n2)c1] | 3-[(4-hydroxypyrido[3,4-d]pyrimidin-2-yl)oxymethyl]benzonitrile |
| 33 | 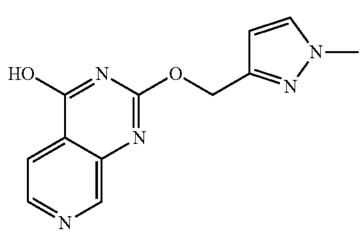 [SMILES: Cn1ccc(COc2nc(O)c3ccncc3n2)n1] | 2-[(1-methylpyrazol-3-yl)methoxy]pyrido[3,4-d]pyrimidin-4-ol |
| 34 | 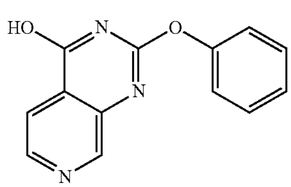 [SMILES: Oc1nc(Oc2ccccc2)nc2cnccc12] | 2-phenoxypyrido[3,4-d]pyrimidin-4-ol |

TABLE 1-continued

| Chemical Synthesis Example | Structure | Name |
|---|---|---|
| 35 | 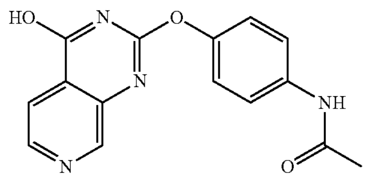 [SMILES: CC(=O)Nc1ccc(Oc2nc(O)c3ccncc3n2)cc1] | N-[4-(4-hydroxypyrido[3,4-d]pyrimidin-2-yl)oxyphenyl]acetamide |
| 36 | 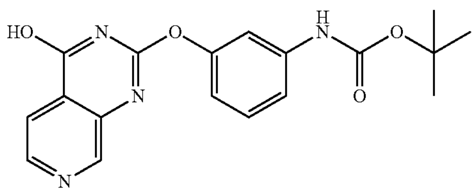 [SMILES: CC(C)(C)OC(=O)Nc1cccc(Oc2nc(O)c3ccncc3n2)c1] | tert-butyl N-[3-(4-hydroxypyrido[3,4-d]pyrimidin-2-yl)oxyphenyl]carbamate |
| 37 | 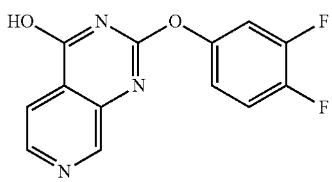 [SMILES: Oc1nc(Oc2ccc(F)c(F)c2)nc2cnccc12] | 2-(3,4-difluorophenoxy)pyrido[3,4-d]pyrimidin-4-ol |
| 38 | 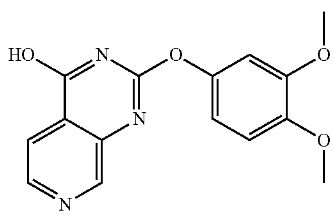 [SMILES: COc1ccc(Oc2nc(O)c3ccncc3n2)cc1OC] | 2-(3,4-dimethoxyphenoxy)pyrido[3,4-d]pyrimidin-4-ol |
| 39 | 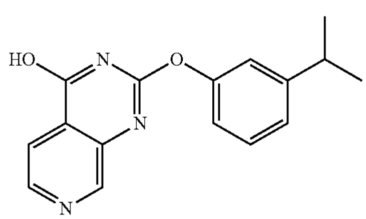 [SMILES: CC(C)c1cccc(Oc2nc(O)c3ccncc3n2)c1] | 2-(3-propan-2-ylphenoxy)pyrido[3,4-d]pyrimidin-4-ol |
| 40 | 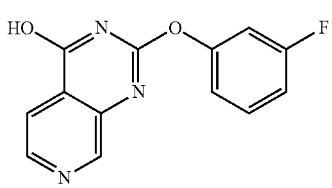 [SMILES: Oc1nc(Oc2cccc(F)c2)nc2cnccc12] | 2-(3-fluorophenoxy)pyrido[3,4-d]pyrimidin-4-ol |
| 41 | 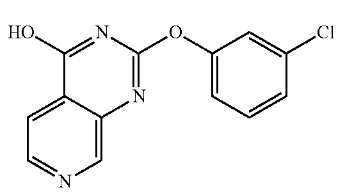 [SMILES: Oc1nc(Oc2cccc(Cl)c2)nc2cnccc12] | 2-(3-chlorophenoxy)pyrido[3,4-d]pyrimidin-4-ol |

TABLE 1-continued

| Chemical Synthesis Example | Structure | Name |
|---|---|---|
| 42 | 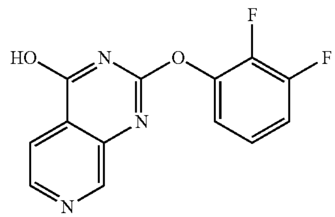 [SMILES: Oc1nc(Oc2cccc(F)c2F)nc2cnccc12] | 2-(2,3-difluorophenoxy)pyrido[3,4-d]pyrimidin-4-ol |
| 43 | 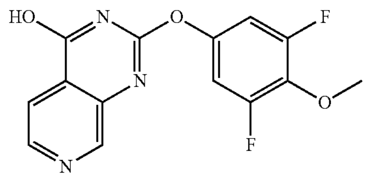 [SMILES: COc1c(F)cc(Oc2nc(O)c3ccncc3n2)cc1F] | 2-(3,5-difluoro-4-methoxyphenoxy)pyrido[3,4-d]pyrimidin-4-ol |
| 44 | 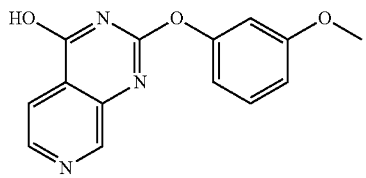 [SMILES: COc1cccc(Oc2nc(O)c3ccncc3n2)c1] | 2-(3-methoxyphenoxy)pyrido[3,4-d]pyrimidin-4-ol |
| 45 | 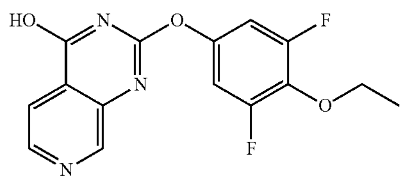 [SMILES: CCOc1c(F)cc(Oc2nc(O)c3ccncc3n2)cc1F] | 2-(4-ethoxy-3,5-difluorophenoxy)pyrido[3,4-d]pyrimidin-4-ol |
| 46 | 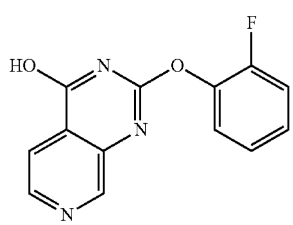 [SMILES: Oc1nc(Oc2ccccc2F)nc2cnccc12] | 2-(2-fluorophenoxy)pyrido[3,4-d]pyrimidin-4-ol |
| 47 | 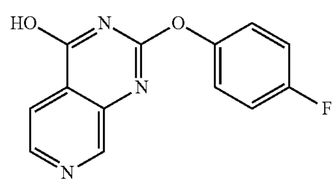 [SMILES: Oc1nc(Oc2ccc(F)cc2)nc2cnccc12] | 2-(4-fluorophenoxy)pyrido[3,4-d]pyrimidin-4-ol |
| 48 | 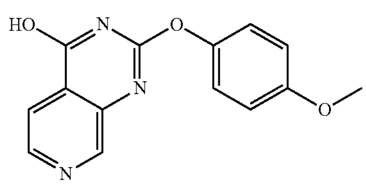 [SMILES: COc1ccc(Oc2nc(O)c3ccncc3n2)cc1] | 2-(4-methoxyphenoxy)pyrido[3,4-d]pyrimidin-4-ol |
| 49 | 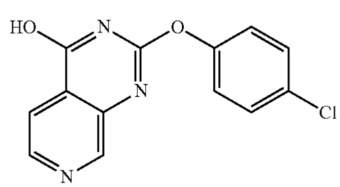 [SMILES: Oc1nc(Oc2ccc(Cl)cc2)nc2cnccc12] | 2-(4-chlorophenoxy)pyrido[3,4-d]pyrimidin-4-ol |

TABLE 1-continued

| Chemical Synthesis Example | Structure | Name |
|---|---|---|
| 50 | 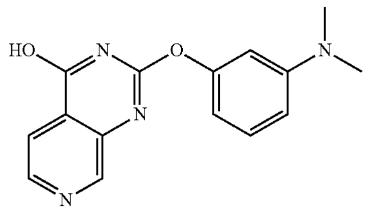 [SMILES: CN(C)c1cccc(Oc2nc(O)c3ccncc3n2)c1] | 2-[3-(dimethylamino)phenoxy]pyrido[3,4-d]pyrimidin-4-ol |
| 51 | 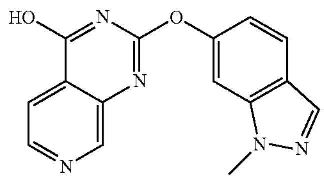 [SMILES: Cn1ncc2ccc(Oc3nc(O)c4ccncc4n3)cc21] | 2-(1-methylindazol-5-yl)oxypyrido[3,4-d]pyrimidin-4-ol |
| 52 | 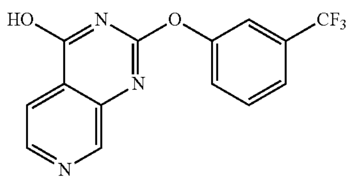 [SMILES: Oc1nc(Oc2cccc(C(F)(F)F)c2)nc2cnccc12] | 2-[3-(trifluoromethyl)phenoxy]pyrido[3,4-d]pyrimidin-4-ol |
| 53 | 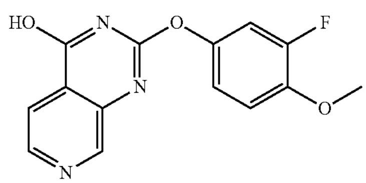 [SMILES: COc1ccc(Oc2nc(O)c3ccncc3n2)cc1F] | 2-(3-fluoro-4-methoxyphenoxy)pyrido[3,4-d]pyrimidin-4-ol |
| 54 | 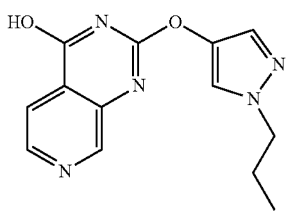 [SMILES: CCCn1cc(Oc2nc(O)c3ccncc3n2)cn1] | 2-(1-propylpyrazol-4-yl)oxypyrido[3,4-d]pyrimidin-4-ol |
| 55 | 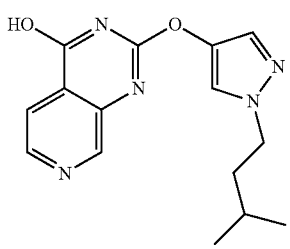 [SMILES: CC(C)CCn1cc(Oc2nc(O)c3ccncc3n2)cn1] | 2-{[1-(3-methylbutyl)pyrazol-4-yl]oxy}pyrido[3,4-d]pyrimidin-4-ol |
| 56 | 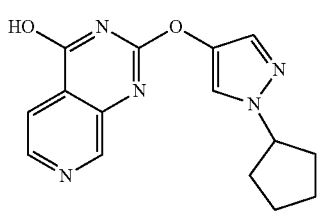 [SMILES: Oc1nc(Oc2cnn(C3CCCC3)c2)nc2cnccc12] | 2-[(1-cyclopentylpyrazol-4-yl)oxy]pyrido[3,4-d]pyrimidin-4-ol |

TABLE 1-continued

| Chemical Synthesis Example | Structure | Name |
|---|---|---|
| 57 | 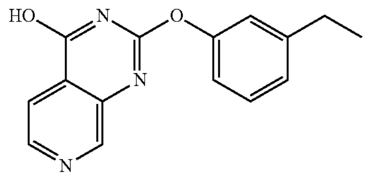 [SMILES: CCc1cccc(Oc2nc(O)c3ccncc3n2)c1] | 2-(3-ethylphenoxy)pyrido[3,4-d]pyrimidin-4-ol |
| 58 | 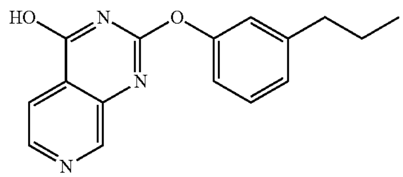 [SMILES: CCCc1cccc(Oc2nc(O)c3ccncc3n2)c1] | 2-(3-propylphenoxy)pyrido[3,4-d]pyrimidin-4-ol |
| 59 | 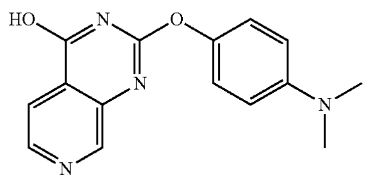 [SMILES: CN(C)c1ccc(Oc2nc(O)c3ccncc3n2)cc1] | 2-[4-(dimethylamino)phenoxy]pyrido[3,4-d]pyrimidin-4-ol |
| 60 | 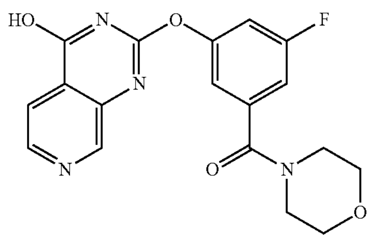 [SMILES: O=C(c1cc(F)cc(Oc2nc(O)c3ccncc3n2)c1)N1CCOCC1] | 3-fluoro-5-(4-hydroxypyrido[3,4-d]pyrimidin-2-yl)oxyphenyl]-morpholin-4-ylmethanone |
| 61 | 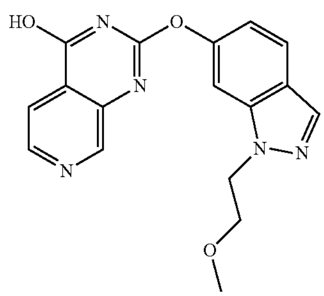 [SMILES: COCCn1ncc2ccc(Oc3nc(O)c4ccncc4n3)cc21] | 2-{[1-(2-methoxyethyl)-1H-indazol-6-yl]oxy}pyrido[3,4-d]pyrimidin-4-ol |
| 62 | 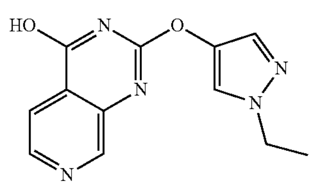 [SMILES: CCn1cc(Oc2nc(O)c3ccncc3n2)cn1] | 2-[(1-ethyl-1H-pyrazol-4-yl)oxy]pyrido[3,4-d]pyrimidin-4-ol |
| 63 | 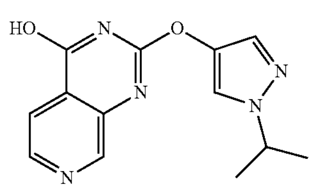 [SMILES: CC(C)n1cc(Oc2nc(O)c3ccncc3n2)cn1] | 2-{[1-(propan-2-yl)-1H-pyrazol-4-yl]oxy}pyrido[3,4-d]pyrimidin-4-ol |

TABLE 1-continued

| Chemical Synthesis Example | Structure | Name |
|---|---|---|
| 64 | 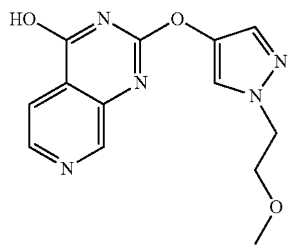 [SMILES: COCCn1cc(Oc2nc(O)c3ccncc3n2)cn1] | 2-{[1-(2-methoxyethyl)-1H-pyrazol-4-yl]oxy}pyrido[3,4-d]pyrimidin-4-ol |
| 65 | 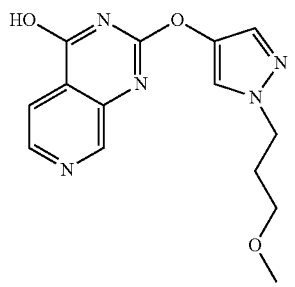 [SMILES: COCCCn1cc(Oc2nc(O)c3ccncc3n2)cn1] | 2-{[1-(3-methoxypropyl)-1H-pyrazol-4-yl]oxy}pyrido[3,4-d]pyrimidin-4-ol |
| 66 | 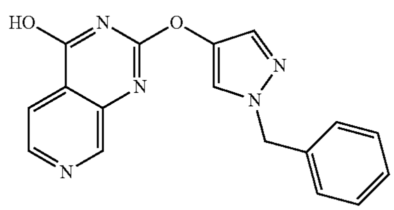 [SMILES: Oc1nc(Oc2cnn(Cc3ccccc3)c2)nc2cnccc12] | 2-[(1-benzyl-1H-pyrazol-4-yl)oxy]pyrido[3,4-d]pyrimidin-4-ol |
| 67 | 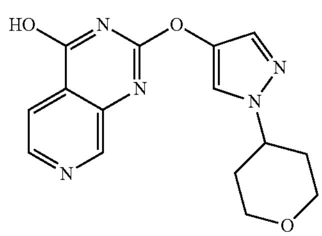 [SMILES: Oc1nc(Oc2cnn(C3CCOCC3)c2)nc2cnccc12] | 2-{[1-(tetrahydro-2H-pyran-4-yl)-1H-pyrazol-4-yl]oxy}pyrido[3,4-d]pyrimidin-4-ol |
| 68 | 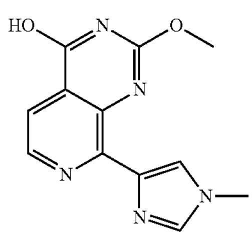 [SMILES: COc1nc(O)c2ccnc(-c3cn(C)cn3)c2n1] | 2-methoxy-8-(1-methyl-1H-imidazol-4-yl)pyrido[3,4-d]pyrimidin-4-ol |
| 69 | 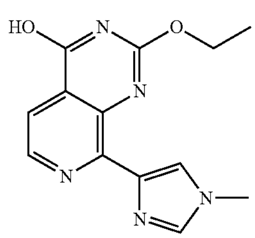 [SMILES: CCOc1nc(O)c2ccnc(-c3cn(C)cn3)c2n1] | 2-ethoxy-8-(1-methyl-1H-imidazol-4-yl)pyrido[3,4-d]pyrimidin-4-ol |

TABLE 1-continued

| Chemical Synthesis Example | Structure | Name |
|---|---|---|
| 70 | 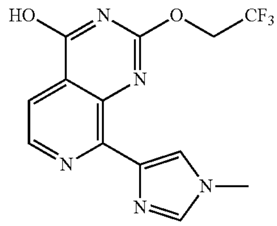 [SMILES: Cn1cnc(-c2nccc3c(O)nc(OCC(F)(F)F)nc23)c1] | 8-(1-methyl-1H-imidazol-4-yl)-2-(2,2,2-trifluoroethoxy)pyrido[3,4-d]pyrimidin-4-ol |
| 71 | 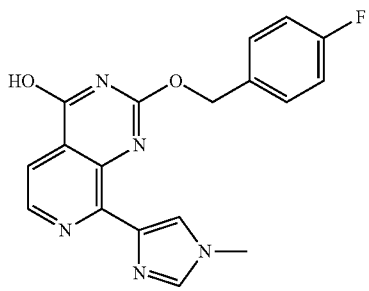 [SMILES: Cn1cnc(-c2nccc3c(O)nc(OCc4ccc(F)cc4)nc23)c1] | 2-[(4-fluorobenzyl)oxy]-8-(1-methyl-1H-imidazol-4-yl)pyrido[3,4-d]pyrimidin-4-ol |
| 72 | 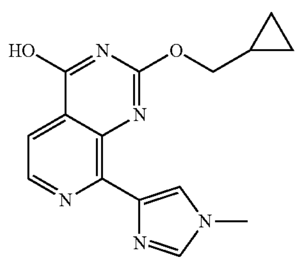 [SMILES: Cn1cnc(-c2nccc3c(O)nc(OCC4CC4)nc23)c1] | 2-(cyclopropylmethoxy)-8-(1-methylimidazol-4-yl)pyrido[3,4-d]pyrimidin-4-ol |
| 73 | 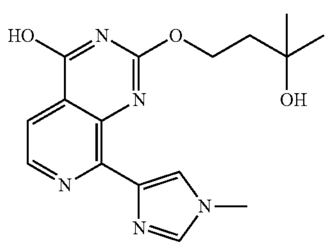 [SMILES: Cn1cnc(-c2nccc3c(O)nc(OCCC(C)(C)O)nc23)c1] | 2-(3-hydroxy-3-methylbutoxy)-8-(1-methylimidazol-4-yl)pyrido[3,4-d]pyrimidin-4-ol |
| 74 | 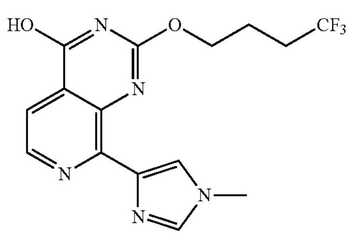 [SMILES: Cn1cnc(-c2nccc3c(O)nc(OCCCC(F)(F)F)nc23)c1] | 8-(1-methylimidazol-4-yl)-2-(4,4,4-trifluorobutoxy)pyrido[3,4-d]pyrimidin-4-ol |
| 75 | 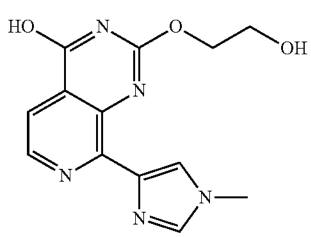 [SMILES: Cn1cnc(-c2nccc3c(O)nc(OCCO)nc23)c1] | 2-(2-hydroxyethoxy)-8-(1-methylimidazol-4-yl)pyrido[3,4-d]pyrimidin-4-ol |

TABLE 1-continued

| Chemical Synthesis Example | Structure | Name |
|---|---|---|
| 76 | 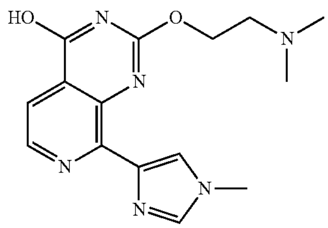 [SMILES: CN(C)CCOc1nc(O)c2ccnc(-c3cn(C)cn3)c2n1] | 2-[2-(dimethylamino)ethoxy]-8-(1-methylimidazol-4-yl)pyrido[3,4-d]pyrimidin-4-ol |
| 77 | 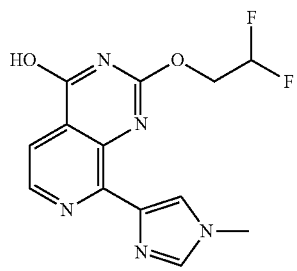 [SMILES: Cn1cnc(-c2nccc3c(O)nc(OCC(F)F)nc23)c1] | 2-(2,2-difluoroethoxy)-8-(1-methylimidazol-4-yl)pyrido[3,4-d]pyrimidin-4-ol |
| 78 | 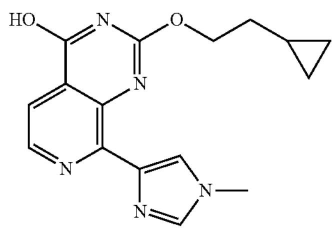 [SMILES: Cn1cnc(-c2nccc3c(O)nc(OCCC4CC4)nc23)c1] | 2-(2-cyclopropylethoxy)-8-(1-methylimidazol-4-yl)pyrido[3,4-d]pyrimidin-4-ol |
| 79 | 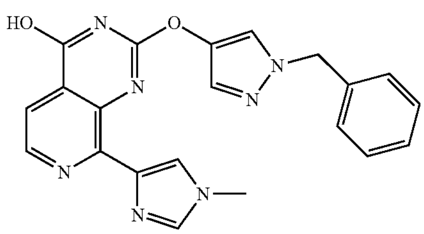 [SMILES: Cn1cnc(-c2nccc3c(O)nc(Oc4cnn(Cc5ccccc5)c4)nc23)c1] | 2-(1-benzylpyrazol-4-yl)oxy-8-(1-methylimidazol-4-yl)pyrido[3,4-d]pyrimidin-4-ol |
| 80 | 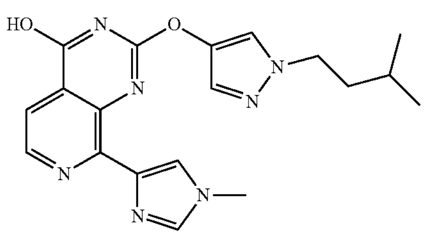 [SMILES: CC(C)CCn1cc(Oc2nc(O)c3ccnc(-c4cn(C)cn4)c3n2)cn1] | 2-[1-(3-methylbutyl)pyrazol-4-yl]oxy-8-(1-methylimidazol-4-yl)pyrido[3,4-d]pyrimidin-4-ol |
| 81 | 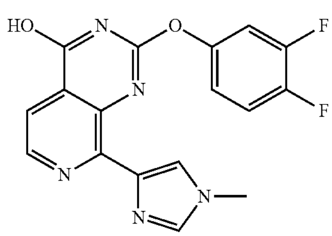 [SMILES: Cn1cnc(-c2nccc3c(O)nc(Oc4ccc(F)c(F)c4)nc23)c1] | 2-(3,4-difluorophenoxy)-8-(1-methylimidazol-4-yl)pyrido[3,4-d]pyrimidin-4-ol |

TABLE 1-continued

| Chemical Synthesis Example | Structure | Name |
|---|---|---|
| 82 | 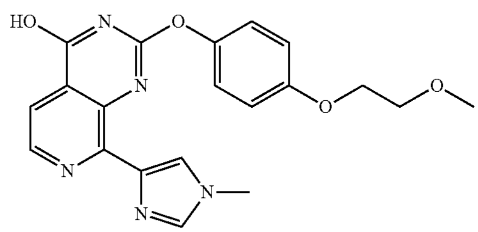 [SMILES: COCCOc1ccc(Oc2nc(O)c3ccnc(-c4cn(C)cn4)c3n2)cc1] | 2-[4-(2-methoxyethoxy)phenoxy]-8-(1-methylimidazol-4-yl)pyrido[3,4-d]pyrimidin-4-ol |
| 83 | 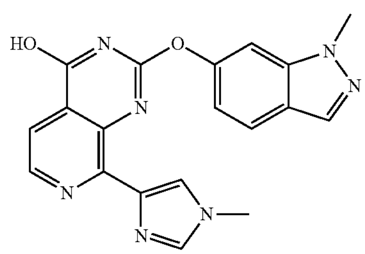 [SMILES: Cn1cnc(-c2nccc3c(O)nc(Oc4ccc5cnn(C)c5c4)nc23)c1] | 8-(1-methylimidazol-4-yl)-2-(1-methylindazol-6-yl)oxypyrido[3,4-d]pyrimidin-4-ol |
| 84 | 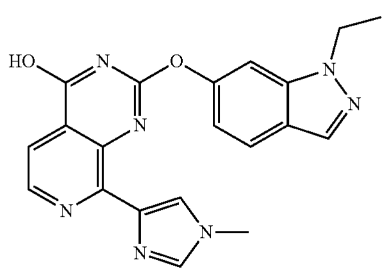 [SMILES: CCn1ncc2ccc(Oc3nc(O)c4ccnc(-c5cn(C)cn5)c4n3)cc21] | 2-(1-ethylindazol-6-yl)oxy-8-(1-methylimidazol-4-yl)pyrido[3,4-d]pyrimidin-4-ol |
| 85 | 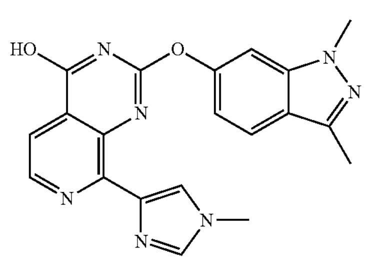 [SMILES: Cc1nn(C)c2cc(Oc3nc(O)c4ccnc(-c5cn(C)cn5)c4n3)ccc12] | 2-(1,3-dimethylindazol-6-yl)oxy-8-(1-methylimidazol-4-yl)pyrido[3,4-d]pyrimidin-4-ol |
| 86 | 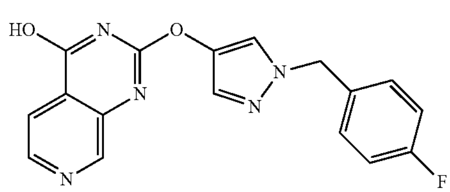 [SMILES: Oc1nc(Oc2cnn(Cc3ccc(F)cc3)c2)nc2cnccc12] | 2-[1-[(4-fluorophenyl)methyl]pyrazol-4-yl]oxypyrido[3,4-d]pyrimidin-4-ol |
| 87 | 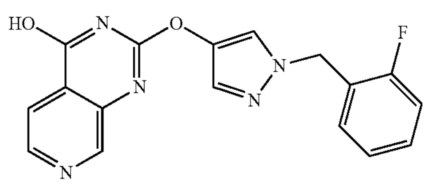 [SMILES: Oc1nc(Oc2cnn(Cc3ccccc3F)c2)nc2cnccc12] | 2-[1-[(2-fluorophenyl)methyl]pyrazol-4-yl]oxypyrido[3,4-d]pyrimidin-4-ol |

TABLE 1-continued

| Chemical Synthesis Example | Structure | Name |
|---|---|---|
| 88 | 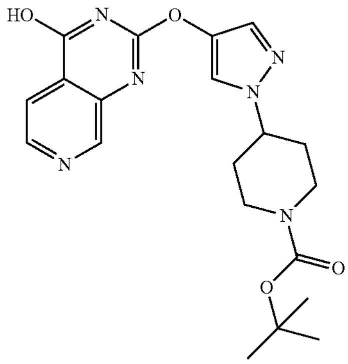 [SMILES: CC(C)(C)OC(=O)N1CCC(n2cc(Oc3nc(O)c4ccncc4n3)cn2)CC1] | tert-butyl 4-[4-(4-hydroxypyrido[3,4-d]pyrimidin-2-yl)oxypyrazol-1-yl]piperidine-1-carboxylate |
| 89 | 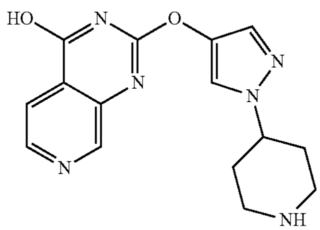 [SMILES: Oc1nc(Oc2cnn(C3CCNCC3)c2)nc2cnccc12] | 2-(1-piperidin-4-ylpyrazol-4-yl)oxypyrido[3,4-d]pyrimidin-4-ol |
| 90 | 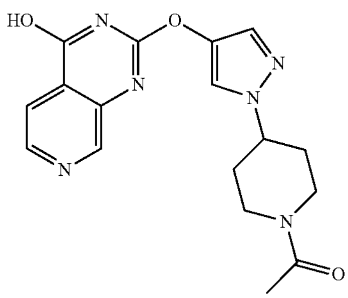 [SMILES: CC(=O)N1CCC(n2cc(Oc3nc(O)c4ccncc4n3)cn2)CC1] | 1-[4-[4-(4-hydroxypyrido[3,4-d]pyrimidin-2-yl)oxypyrazol-1-yl]piperidin-1-yl]ethanone |
| 91 | 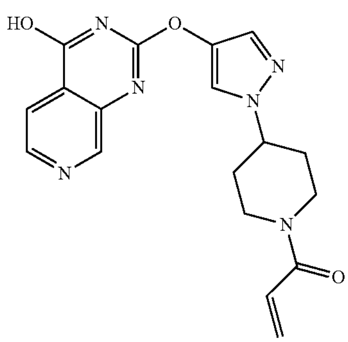 [SMILES: C=CC(=O)N1CCC(n2cc(Oc3nc(O)c4ccncc4n3)cn2)CC1] | 1-[4-[4-(4-hydroxypyrido[3,4-d]pyrimidin-2-yl)oxypyrazol-1-yl]piperidin-1-yl]prop-2-en-1-one |
| 92 | 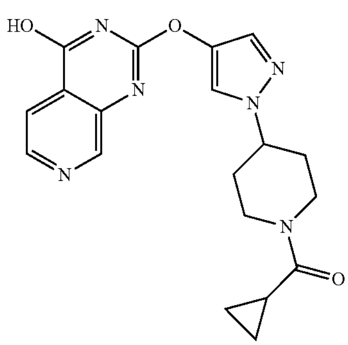 [SMILES: O=C(C1CC1)N1CCC(n2cc(Oc3nc(O)c4ccncc4n3)cn2)CC1] | cyclopropyl-[4-[4-(4-hydroxypyrido[3,4-d]pyrimidin-2-yl)oxypyrazol-1-yl]piperidin-1-yl]methanone |

TABLE 1-continued

| Chemical Synthesis Example | Structure | Name |
|---|---|---|
| 93 | 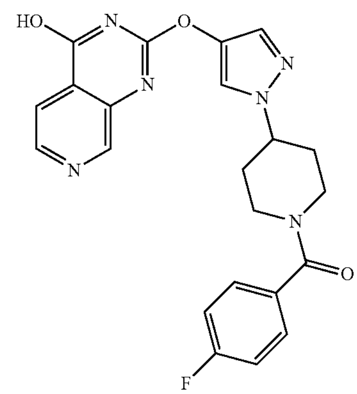 [SMILES: O=C(c1ccc(F)cc1)N1CCC(n2cc(Oc3nc(O)c4ccncc4n3)cn2)CC1] | (4-fluorophenyl)-[4-[4-(4-hydroxypyrido[3,4-d]pyrimidin-2-yl)oxypyrazol-1-yl]piperidin-1-yl]methanone |
| 94 | 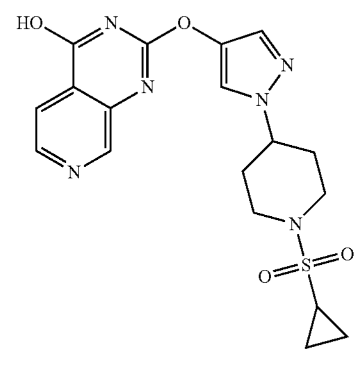 [SMILES: O=S(=O)(C1CC1)N1CCC(n2cc(Oc3nc(O)c4ccncc4n3)cn2)CC1] | 2-[1-(1-cyclopropylsulfonylpiperidin-4-yl)pyrazol-4-yl]oxypyrido[3,4-d]pyrimidin-4-ol |
| 95 | 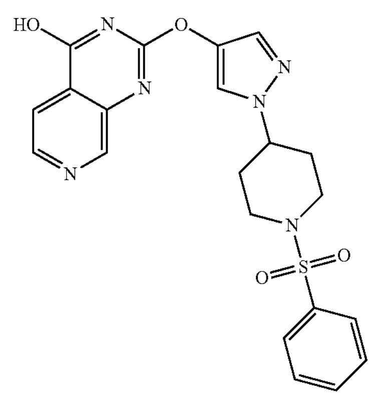 [SMILES: O=S(=O)(c1ccccc1)N1CCC(n2cc(Oc3nc(O)c4ccncc4n3)cn2)CC1] | 2-[1-[1-(benzenesulfonyl)piperidin-4-yl]pyrazol-4-yl]oxypyrido[3,4-d]pyrimidin-4-ol |
| 96 | 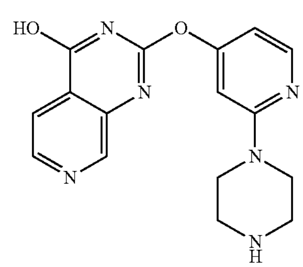 [SMILES: Oc1nc(Oc2ccnc(N3CCNCC3)c2)nc2cnccc12] | 2-(2-piperazin-1-ylpyridin-4-yl)oxypyrido[3,4-d]pyrimidin-4-ol |

TABLE 1-continued

| Chemical Synthesis Example | Structure | Name |
|---|---|---|
| 97 | 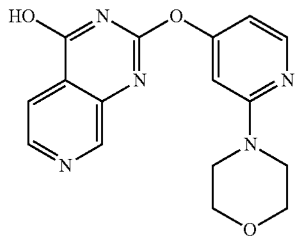 [SMILES: Oc1nc(Oc2ccnc(N3CCOCC3)c2)nc2cnccc12] | 2-(2-morpholin-4-ylpyridin-4-yl)oxypyrido[3,4-d]pyrimidin-4-ol |
| 98 | 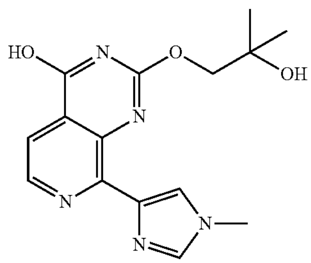 [SMILES: Cn1cnc(-c2nccc3c(O)nc(OCC(C)(C)O)nc23)c1] | 2-(2-hydroxy-2-methylpropoxy)-8-(1-methylimidazol-4-yl)pyrido[3,4-d]pyrimidin-4-ol |
| 99 | 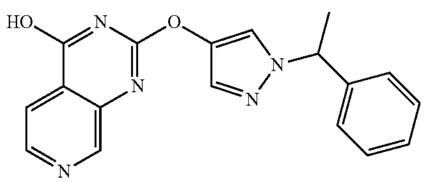 [SMILES: CC(c1ccccc1)n1cc(Oc2nc(O)c3ccncc3n2)cn1] | 1-(1-phenylethyl)-4-(4,4,5,5-tetramethyl-1,3,2-dioxaborolan-2-yl)pyrazole |
| 100 | 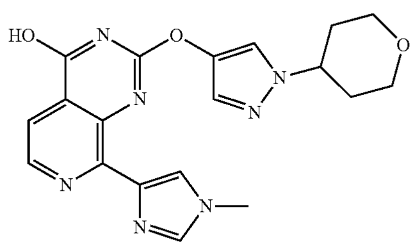 [SMILES: Cn1cnc(-c2nccc3c(O)nc(Oc4cnn(C5CCOCC5)c4)nc23)c1] | 8-(1-methylimidazol-4-yl)-2-[1-(oxan-4-yl)pyrazol-4-yl]oxypyrido[3,4-d]pyrimidin-4-ol |
| 101 | 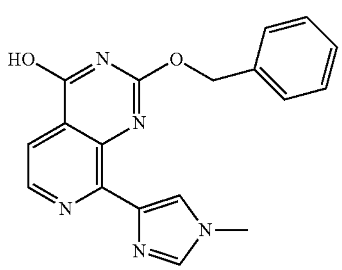 [SMILES: Cn1cnc(-c2nccc3c(O)nc(OCc4ccccc4)nc23)c1] | 8-(1-methylimidazol-4-yl)-2-phenylmethoxypyrido[3,4-d]pyrimidin-4-ol |
| 102 | 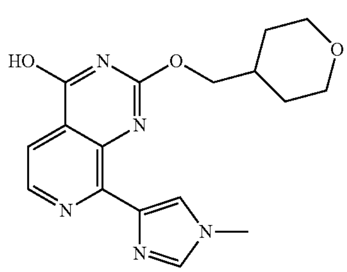 [SMILES: Cn1cnc(-c2nccc3c(O)nc(OCC4CCOCC4)nc23)c1] | 8-(1-methyl-1H-imidazol-4-yl)-2-(oxan-4-ylmethoxy)pyrido[3,4-d]pyrimidin-4-ol |

TABLE 1-continued

| Chemical Synthesis Example | Structure | Name |
|---|---|---|
| 103 | 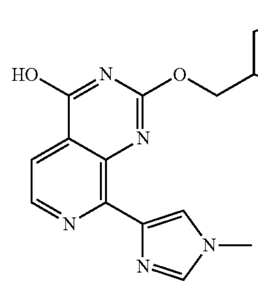 | 8-(1-methyl-1H-imidazol-4-yl)-2-(oxolan-3-ylmethoxy)pyrido[3,4-d]pyrimidin-4-ol |
| 104 | 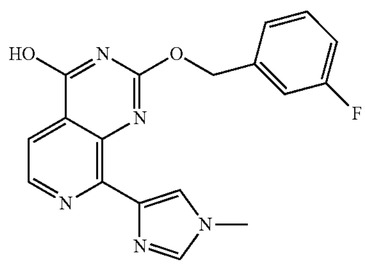 [SMILES: Cn1cnc(-c2nccc3c(O)nc(OCc4cccc(F)c4)nc23)c1] | 2-[(3-fluorophenyl)methoxy]-8-(1-methyl-1H-imidazol-4-yl)pyrido[3,4-d]pyrimidin-4-ol |
| 105 | 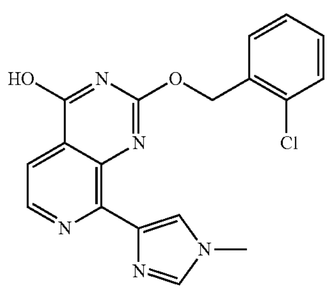 [SMILES: Cn1cnc(-c2nccc3c(O)nc(OCc4ccccc4Cl)nc23)c1] | 2-[(2-chlorophenyl)methoxy]-8-(1-methyl-1H-imidazol-4-yl)pyrido[3,4-d]pyrimidin-4-ol |
| 106 | 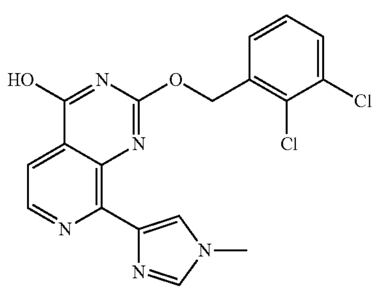 [SMILES: Cn1cnc(-c2nccc3c(O)nc(OCc4cccc(Cl)c4Cl)nc23)c1] | 2-[(2,3-dichlorophenyl)methoxy]-8-(1-methyl-1H-imidazol-4-yl)pyrido[3,4-d]pyrimidin-4-ol |
| 107 | 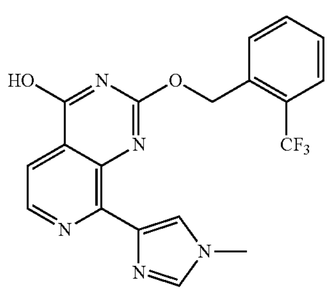 [SMILES: Cn1cnc(-c2nccc3c(O)nc(OCc4ccccc4C(F)(F)F)nc23)c1] | 8-(1-methyl-1H-imidazol-4-yl)-2-{[2-(trifluoromethyl)phenyl]methoxy}pyrido[3,4-d]pyrimidin-4-ol |

TABLE 1-continued

| Chemical Synthesis Example | Structure | Name |
|---|---|---|
| 108 | 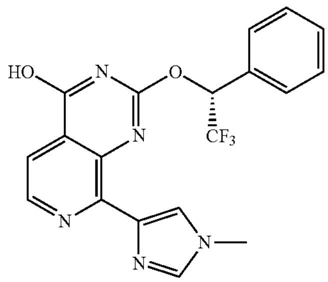 [SMILES: Cn1cnc(-c2nccc3c(O)nc(O[C@H](c4ccccc4)C(F)(F)F)nc23)c1] | 8-(1-methyl-1H-imidazol-4-yl)-2-[(1R)-2,2,2-trifluoro-1-phenylethoxy]pyrido[3,4-d]pyrimidin-4-ol |
| 109 | 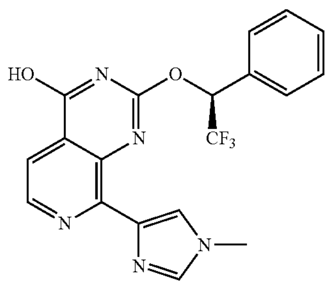 [SMILES: Cn1cnc(-c2nccc3c(O)nc(O[C@@H](c4ccccc4)C(F)(F)F)nc23)c1] | 8-(1-methyl-1H-imidazol-4-yl)-2-[(1S)-2,2,2-trifluoro-1-phenylethoxy]pyrido[3,4-d]pyrimidin-4-ol |
| 110 | 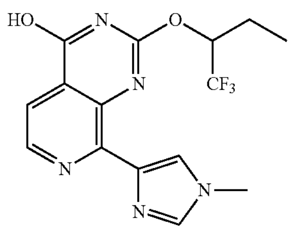 [SMILES: CCC(Oc1nc(O)c2ccnc(-c3cn(C)cn3)c2n1)C(F)(F)F] | 8-(1-methyl-1H-imidazol-4-yl)-2-[(1,1,1-trifluorobutan-2-yl)oxy]pyrido[3,4-d]pyrimidin-4-ol |
| 111 | 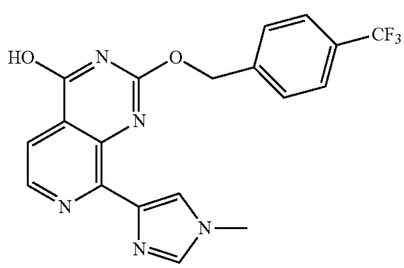 [SMILES: Cn1cnc(-c2nccc3c(O)nc(OCc4ccc(C(F)(F)F)cc4)nc23)c1] | 8-(1-methyl-1H-imidazol-4-yl)-2-{[4-(trifluoromethyl)phenyl]methoxy}pyrido[3,4-d]pyrimidin-4-ol |
| 112 | 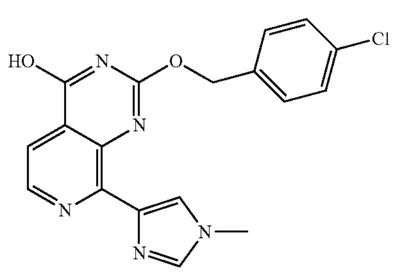 [SMILES: Cn1cnc(-c2nccc3c(O)nc(OCc4ccc(Cl)cc4)nc23)c1] | 2-[(4-chlorophenyl)methoxy]-8-(1-methyl-1H-imidazol-4-yl)pyrido[3,4-d]pyrimidin-4-ol |
| 113 | 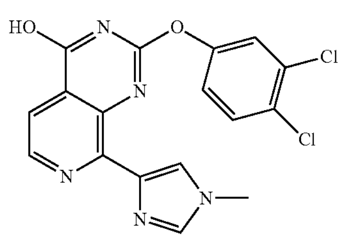 [SMILES: Cn1cnc(-c2nccc3c(O)nc(Oc4ccc(Cl)c(Cl)c4)nc23)c1] | 2-(3,4-dichlorophenoxy)-8-(1-methyl-1H-imidazol-4-yl)pyrido[3,4-d]pyrimidin-4-ol |

TABLE 1-continued

| Chemical Synthesis Example | Structure | Name |
|---|---|---|
| 114 | 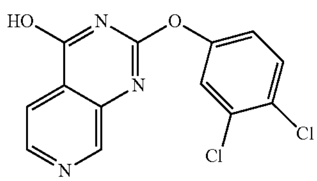 [SMILES: Oc1nc(Oc2ccc(Cl)c(Cl)c2)nc2cnccc12] | 2-(3,4-dichlorophenoxy)pyrido[3,4-d]pyrimidin-4-ol |
| 115 | 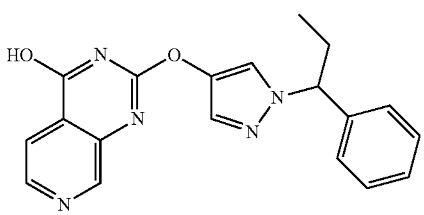 [SMILES: CCC(c1ccccc1)n1cc(Oc2nc(O)c3ccncc3n2)cn1] | 2-{[1-(1-phenylpropyl)-1H-pyrazol-4-yl]oxy}pyrido[3,4-d]pyrimidin-4-ol |
| 116 | 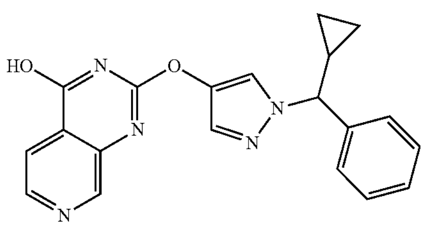 [SMILES: Oc1nc(Oc2cnn(C(c3ccccc3)C3CC3)c2)nc2cnccc12] | 2-({1-[cyclopropyl(phenyl)methyl]-1H-pyrazol-4-yl}oxy)pyrido[3,4-d]pyrimidin-4-ol |
| 117 | 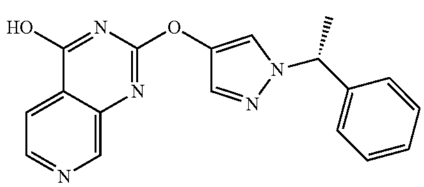 [SMILES: C[C@H](c1ccccc1)n1cc(Oc2nc(O)c3ccncc3n2)cn1] | 2-({1-[(1R)-1-phenylethyl]-1H-pyrazol-4-yl}oxy)pyrido[3,4-d]pyrimidin-4-ol |
| 118 | 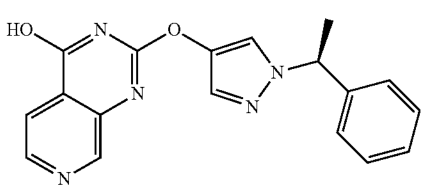 [SMILES: C[C@@H](c1ccccc1)n1cc(Oc2nc(O)c3ccncc3n2)cn1] | 2-({1-[(1S)-1-phenylethyl]-1H-pyrazol-4-yl}oxypyrido) [3,4-d]pyrimidin-4-ol |
| 119 | 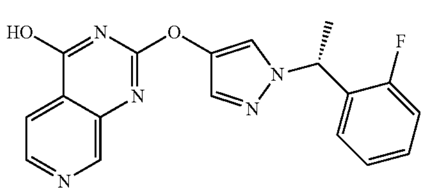 [SMILES: C[C@H](c1ccccc1F)n1cc(Oc2nc(O)c3ccncc3n2)cn1] | 2-({1-[(1R)-1-(2-fluorophenyl)ethyl]-1H-pyrazol-4-yl}oxy)pyrido[3,4-d]pyrimidin-4-ol |
| 120 | 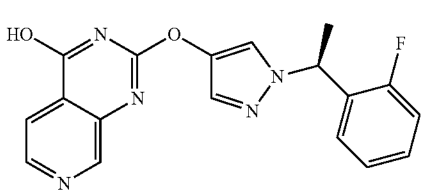 [SMILES: C[C@@H](c1ccccc1F)n1cc(Oc2nc(O)c3ccncc3n2)cn1] | 2-({1-[(1s)-1-(2-fluorophenyl)ethyl]-1H-pyrazol-4-yl}oxy)pyrido[3,4-d]pyrimidin-4-ol |

TABLE 1-continued

| Chemical Synthesis Example | Structure | Name |
|---|---|---|
| 121 | 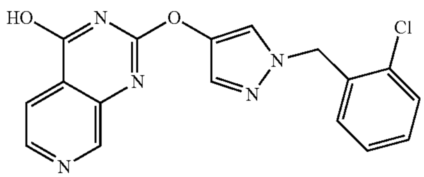 | 2-({1-[(2-chlorophenyl)methyl]-1H-pyrazol-4-yl}oxy)pyrido[3,4-d]pyrimidin-4-ol |
| 122 | 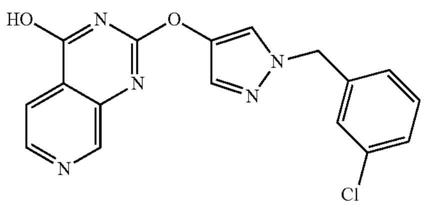 [SMILES: Oc1nc(Oc2cnn(Cc3cccc(Cl)c3)c2)nc2cnccc12] | 2-({1-[(3-chlorophenyl)methyl]-1H-pyrazol-4-yl}oxy)pyrido[3,4-d]pyrimidin-4-ol |
| 123 | 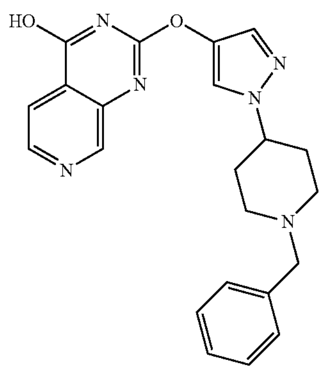 [SMILES: Oc1nc(Oc2cnn(C3CCN(Cc4ccccc4)CC3)c2)nc2cnccc12] | 2-{[1-(1-benzylpiperidin-4-yl)-1H-pyrazol-4-yl]oxy}pyrido[3,4-d]pyrimidin-4-ol |
| 124 | 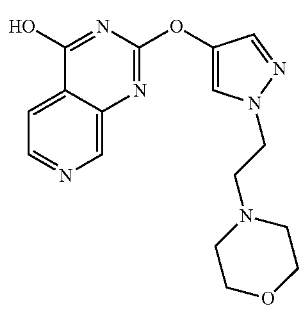 [SMILES: Oc1nc(Oc2cnn(CCN3CCOCC3)c2)nc2cnccc12] | 2-({1-[2-(morpholin-4-yl)ethyl]-1H-pyrazol-4-yl}oxy)pyrido[3,4-d]pyrimidin-4-ol |
| 125 | 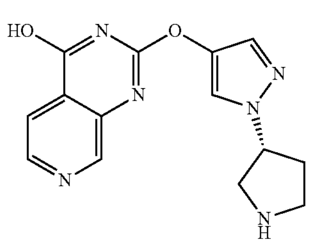 [SMILES: Oc1nc(Oc2cnn([C@@H]3CCNC3)c2)nc2cnccc12] | 2-({1-[(3R)-pyrrolidin-3-yl]-1H-pyrazol-4-yl}oxy)pyrido[3,4-d]pyrimidin-4-ol |

TABLE 1-continued

| Chemical Synthesis Example | Structure | Name |
|---|---|---|
| 126 | 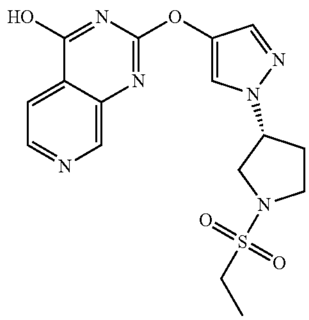 [SMILES: CCS(=O)(=O)N1CC[C@@H](n2cc(Oc3nc(O)c4ccncc4n3)cn2)C1] | 2-({1-[(3R)-1-(ethanesulfonyl)pyrrolidin-3-yl]-1H-pyrazol-4-yl}oxy)pyrido[3,4-d]pyrimidin-4-ol |
| 127 | 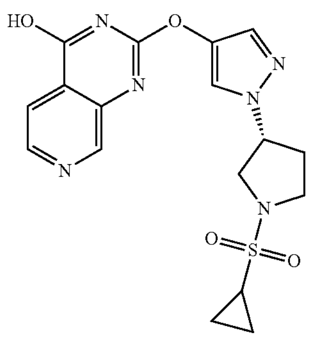 [SMILES: O=S(=O)(C1CC1)N1CC[C@@H](n2cc(Oc3nc(O)c4ccncc4n3)cn2)C1] | 2-({1-[(3R)-1-(cyclopropanesulfonyl)pyrrolidin-3-yl]-1H-pyrazol-4-yl}oxy)pyrido[3,4-d]pyrimidin-4-ol |
| 128 | 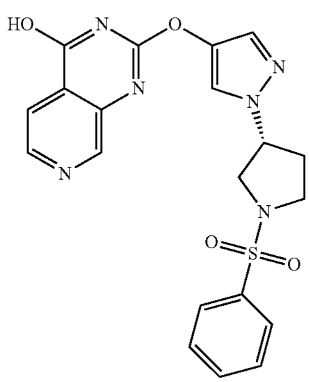 [SMILES: O=S(=O)(c1ccccc1)N1CC[C@@H](n2cc(Oc3nc(O)c4ccncc4n3)cn2)C1] | 2-({1-[(3R)-1-(benzenesulfonyl)pyrrolidin-3-yl]-1H-pyrazol-4-yl}oxy)pyrido[3,4-d]pyrimidin-4-ol |
| 129 | 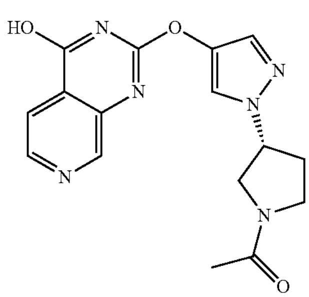 [SMILES: CC(=O)N1CC[C@@H](n2cc(Oc3nc(O)c4ccncc4n3)cn2)C1] | 1-[(3R)-3-[4-({4-hydroxypyrido[3,4-d]pyrimidin-2-yl}oxy)-1H-pyrazol-1-yl]pyrrolidin-1-yl]ethan-1-one |

TABLE 1-continued
| Chemical Synthesis Example | Structure | Name |
|---|---|---|
| 130 | 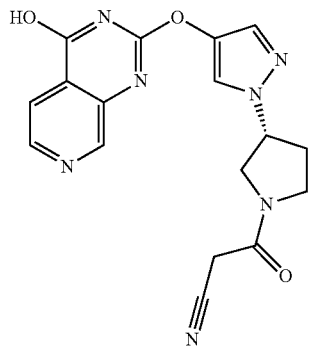 [SMILES: N#CCC(=O)N1CC[C@@H](n2cc(Oc3nc(O)c4ccncc4n3)cn2)C1] | 3-[(3R)-3-[4-({4-hydroxypyrido[3,4-d]pyrimidin-2-yl}oxy)-1H-pyrazol-1-yl]pyrrolidin-1-yl]-3-oxopropanenitrile |
| 131 | 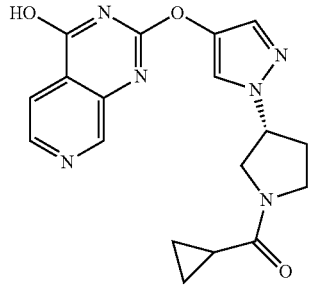 [SMILES: O=C(C1CC1)N1CC[C@@H](n2cc(Oc3nc(O)c4ccncc4n3)cn2)C1] | 2-({1-[(3R)-1-cyclopropanecarbonylpyrrolidin-3-yl]-1H-pyrazol-4-yl}oxy)pyrido[3,4-d]pyrimidin-4-ol |
| 132 | 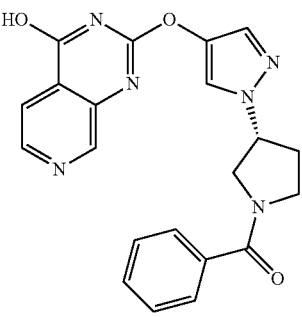 [SMILES: O=C(c1ccccc1)N1CC[C@@H](n2cc(Oc3nc(O)c4ccncc4n3)cn2)C1] | 2-({1-[(3R)-1-benzoylpyrrolidin-3-yl]-1H-pyrazol-4-yl}oxy)pyrido[3,4-d]pyrimidin-4-ol |
| 133 | 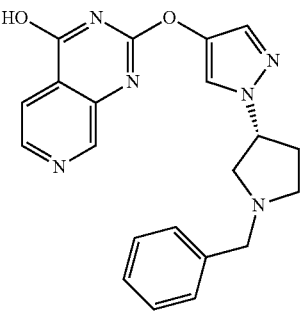 [SMILES: Oc1nc(Oc2cnn([C@@H]3CCN(Cc4ccccc4)C3)c2)nc2cnccc12] | 2-({1-[(3R)-1-benzylpyrrolidin-3-yl]-1H-pyrazol-4-yl}oxy)pyrido[3,4-d]pyrimidin-4-ol |

TABLE 1-continued

| Chemical Synthesis Example | Structure | Name |
|---|---|---|
| 134 | 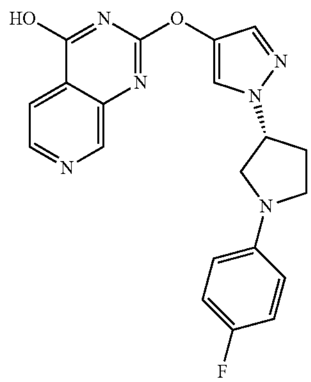 [SMILES: Oc1nc(Oc2cnn([C@@H]3CCN(c4ccc(F)cc4)C3)c2)nc2cnccc12] | 2-({1-[(3R)-1-(4-fluorophenyl)pyrrolidin-3-yl]-1H-pyrazol-4-yl}oxy)pyrido[3,4-d]pyrimidin-4-ol |
| 135 | 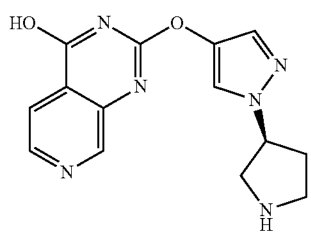 [SMILES: Oc1nc(Oc2cnn([C@H]3CCNC3)c2)nc2cnccc12] | 2-({1-[(3S)-pyrrolidin-3-yl]-1H-pyrazol-4-yl}oxy)pyrido[3,4-d]pyrimidin-4-ol |
| 136 | 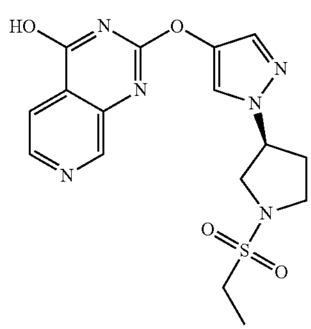 [SMILES: CCS(=O)(=O)N1CC[C@H](n2cc(Oc3nc(O)c4ccncc4n3)cn2)C1] | 2-({1-[(3S)-1-(ethanesulfonyl)pyrrolidin-3-yl]-1H-pyrazol-4-yl}oxy)pyrido[3,4-d]pyrimidin-4-ol |
| 137 | 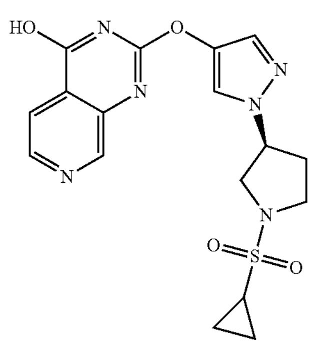 [SMILES: O=S(=O)(C1CC1)N1CC[C@H](n2cc(Oc3nc(O)c4ccncc4n3)cn2)C1] | 2-({1-[(3S)-1-(cyclopropanesulfonyl)pyrrolidin-3-yl]-1H-pyrazol-4-yl}oxy)pyrido[3,4-d]pyrimidin-4-ol |

TABLE 1-continued

| Chemical Synthesis Example | Structure | Name |
|---|---|---|
| 138 | 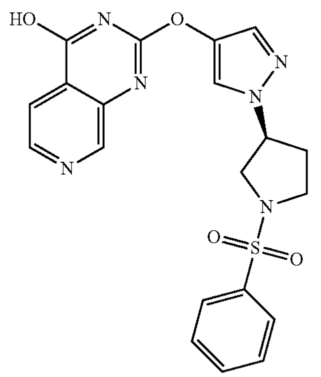 [SMILES: O=S(=O)(c1ccccc1)N1CC[C@H](n2cc(Oc3nc(O)c4ccncc4n3)cn2)C1] | 2-({1-[(3S)-1-(benzenesulfonyl)pyrrolidin-3-yl]-1H-pyrazol-4-yl}oxy)pyrido[3,4-d]pyrimidin-4-ol |
| 139 | 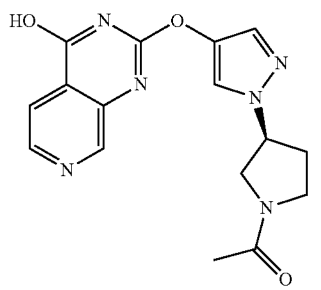 [SMILES: CC(=O)N1CC[C@H](n2cc(Oc3nc(O)c4ccncc4n3)cn2)C1] | 1-[(3S)-3-[4-({4-hydroxypyrido[3,4-d]pyrimidin-2-yl}oxy)-1H-pyrazol-1-yl]pyrrolidin-1-yl]ethan-1-one |
| 140 | 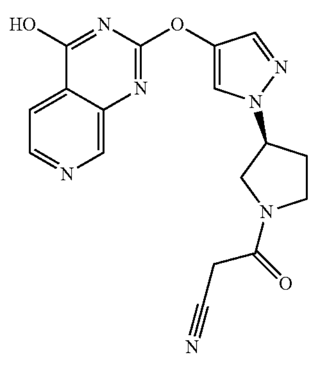 [SMILES: N#CCC(=O)N1CC[C@H](n2cc(Oc3nc(O)c4ccncc4n3)cn2)C1] | 3-[(3S)-3-[4-({4-hydroxypyrido[3,4-d]pyrimidin-2-yl}oxy)-1H-pyrazol-1-yl]pyrrolidin-1-yl]-3-oxopropanenitrile |
| 141 | 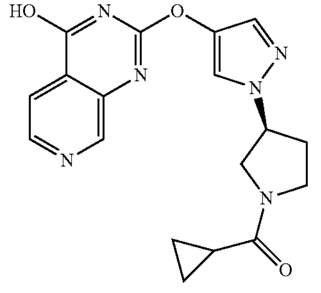 [SMILES: O=C(C1CC1)N1CC[C@H](n2cc(Oc3nc(O)c4ccncc4n3)cn2)C1] | 2-({1-[(3S)-1-cyclopropanecarbonylpyrrolidin-3-yl]-1H-pyrazol-4-yl}oxy)pyrido[3,4-d]pyrimidin-4-ol |

TABLE 1-continued

| Chemical Synthesis Example | Structure | Name |
|---|---|---|
| 142 | 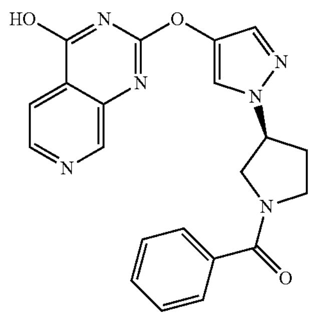 [SMILES: O=C(c1ccccc1)N1CC[C@H](n2cc(Oc3nc(O)c4ccncc4n3)cn2)C1] | 2-({1-[(3S)-1-benzoylpyrrolidin-3-yl]-1H-pyrazol-4-yl}oxy)pyrido[3,4-d]pyrimidin-4-ol |
| 143 | 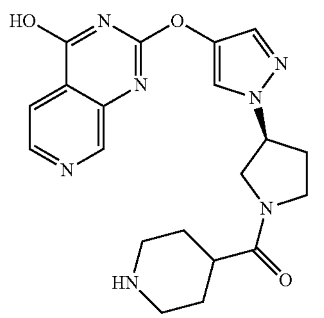 [SMILES: O=C(C1CCNCC1)N1CC[C@H](n2cc(Oc3nc(O)c4ccncc4n3)cn2)C1] | 2-({1-[(3S)-1-(piperidine-4-carbonyl)pyrrolidin-3-yl]-1H-pyrazol-4-yl}oxy)pyrido[3,4-d]pyrimidin-4-ol |
| 144 | 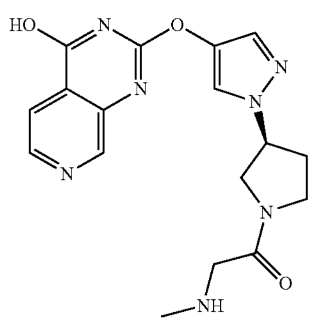 [SMILES: CNCC(=O)N1CC[C@H](n2cc(Oc3nc(O)c4ccncc4n3)cn2)C1] | 1-[(3S)-3-[4-({4-hydroxypyrido[3,4-d]pyrimidin-2-yl}oxy)-1H-pyrazol-1-yl]pyrrolidin-1-yl]-2-(methylamino)ethan-1-one |
| 145 | 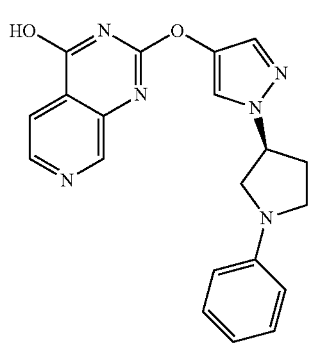 [SMILES: Oc1nc(Oc2cnn([C@H]3CCN(c4ccccc4)C3)c2)nc2cnccc12] | 2-({1-[(3S)-1-phenylpyrrolidin-3-yl]-1H-pyrazol-4-yl}oxy)pyrido[3,4-d]pyrimidin-4-ol |

TABLE 1-continued
| Chemical Synthesis Example | Structure | Name |
|---|---|---|
| 146 | 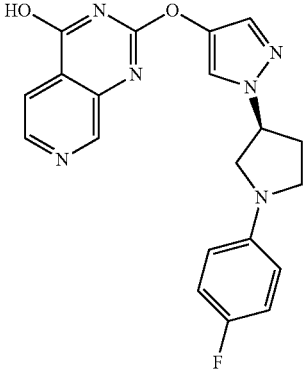 [SMILES: Oc1nc(Oc2cnn([C@H]3CCN(c4ccc(F)cc4)C3)c2)nc2cnccc12] | 2-({1-[(3S)-1-(4-fluorophenyl)pyrrolidin-3-yl]-1H-pyrazol-4-yl}oxy)pyrido[3,4-d]pyrimidin-4-ol |
| 147 | 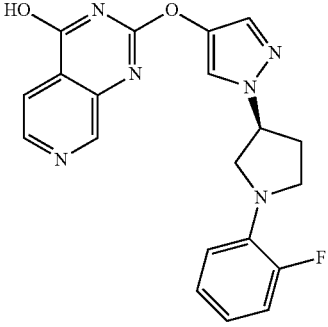 [SMILES: Oc1nc(Oc2cnn([C@H]3CCN(c4ccccc4F)C3)c2)nc2cnccc12] | 2-({1-[(3S)-1-(2-fluorophenyl)pyrrolidin-3-yl]-1H-pyrazol-4-yl}oxy)pyrido[3,4-d]pyrimidin-4-ol |
| 148 | 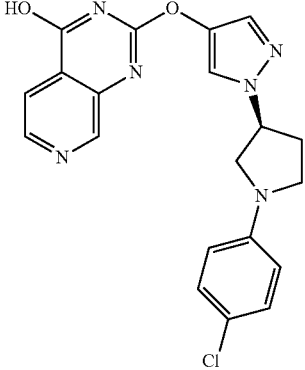 [SMILES: Oc1nc(Oc2cnn([C@H]3CCN(c4ccc(Cl)cc4)C3)c2)nc2cnccc12] | 2-({1-[(3S)-1-(4-chlorophenyl)pyrrolidin-3-yl]-1H-pyrazol-4-yl}oxy)pyrido[3,4-d]pyrimidin-4-ol |
| 149 | 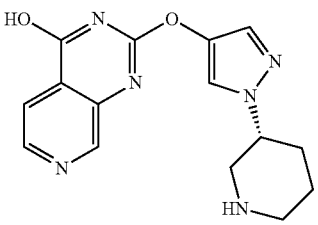 [SMILES: Oc1nc(Oc2cnn([C@@H]3CCCNC3)c2)nc2cnccc12] | 2-({1-[(3R)-piperidin-3-yl]-1H-pyrazol-4-yl}oxy)pyrido[3,4-d]pyrimidin-4-ol |

TABLE 1-continued

| Chemical Synthesis Example | Structure | Name |
|---|---|---|
| 150 | 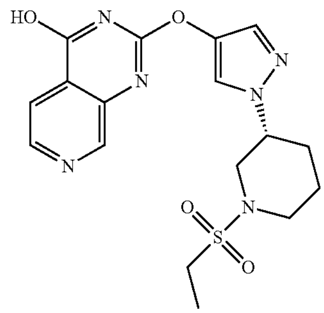 [SMILES: CCS(=O)(=O)N1CCC[C@@H](n2cc(Oc3nc(O)c4ccncc4n3)cn2)C1] | 2-({1-[(3R)-1-(ethanesulfonyl)piperidin-3-yl]-1H-pyrazol-4-yl}oxy)pyrido[3,4-d]pyrimidin-4-ol |
| 151 | 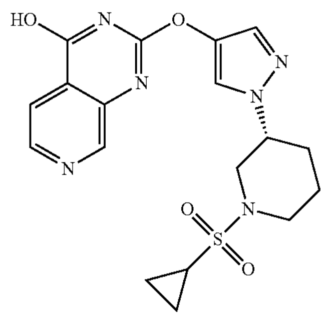 [SMILES: O=S(=O)(C1CC1)N1CCC[C@@H](n2cc(Oc3nc(O)c4ccncc4n3)cn2)C1] | 2-({1-[(3S)-1-(cyclopropanesulfonyl)piperidin-3-yl]-1H-pyrazol-4-yl}oxy)pyrido[3,4-d]pyrimidin-4-ol |
| 152 | 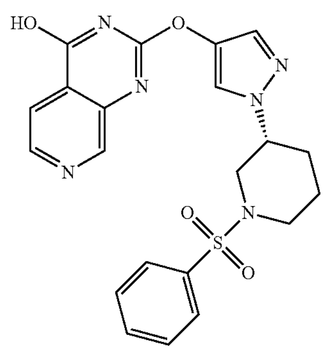 [SMILES: O=S(=O)(c1ccccc1)N1CCC[C@@H](n2cc(Oc3nc(O)c4ccncc4n3)cn2)C1] | 2-({1-[(3R)-1-(benzenesulfonyl)piperidin-3-yl]-1H-pyrazol-4-yl}oxy)pyrido[3,4-d]pyrimidin-4-ol |
| 153 | 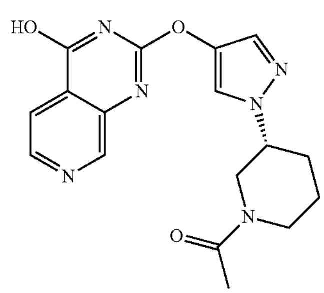 [SMILES: CC(=O)N1CCC[C@@H](n2cc(Oc3nc(O)c4ccncc4n3)cn2)C1] | 1-[(3R)-3-[4-({4-hydroxypyrido[3,4-d]pyrimidin-2-yl}oxy)-1H-pyrazol-1-yl]piperidin-1-yl]ethan-1-one |

TABLE 1-continued
| Chemical Synthesis Example | Structure | Name |
|---|---|---|
| 154 | 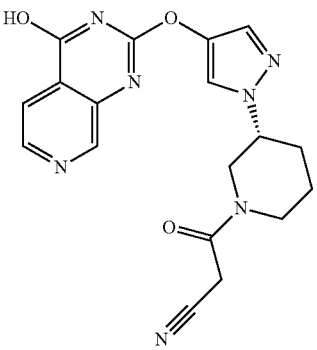 [SMILES: N#CCC(=O)N1CCC[C@@H](n2cc(Oc3nc(O)c4ccncc4n3)cn2)C1] | 3-[(3R)-3-[4-({4-hydroxypyrido[3,4-d]pyrimidin-2-yl}oxy)-1H-pyrazol-1-yl]piperidin-1-yl]-3-oxopropanenitrile |
| 155 | 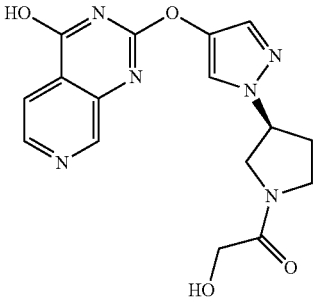 [SMILES: O=C(CO)N1CC[C@H](n2cc(Oc3nc(O)c4ccncc4n3)cn2)C1] | 2-hydroxy-1-[(3S)-3-[4-({4-hydroxypyrido[3,4-d]pyrimidin-2-yl}oxy)-1H-pyrazol-1-yl]pyrrolidin-1-yl]ethan-1-one |
| 156 | 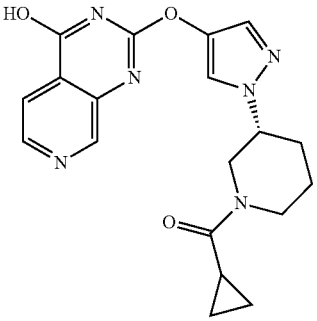 [SMILES: O=C(C1CC1)N1CCC[C@@H](n2cc(Oc3nc(O)c4ccncc4n3)cn2)C1] | 2-({1-[(3R)-1-cyclopropanecarbonylpiperidin-3-yl]-1H-pyrazol-4-yl}oxy)pyrido[3,4-d]pyrimidin-4-ol |
| 157 | 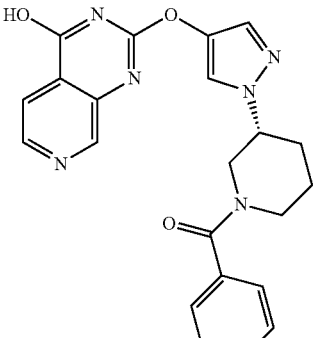 | 2-({1-[(3R)-1-benzoylpiperidin-3-yl]-1H-pyrazol-4-yl}oxy)pyrido[3,4-d]pyrimidin-4-ol |

TABLE 1-continued

| Chemical Synthesis Example | Structure | Name |
|---|---|---|
| 158 | 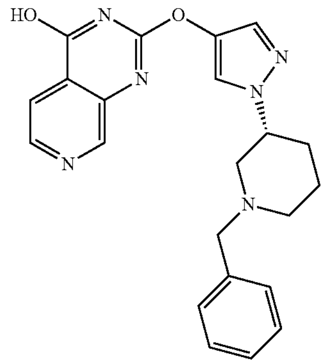 [SMILES: Oc1nc(Oc2cnn([C@@H]3CCCN(Cc4ccccc4)C3)c2)nc2cnccc12] | 2-({1-[(3R)-1-benzylpiperidin-3-yl]-1H-pyrazol-4-yl}oxy)pyrido[3,4-d]pyrimidin-4-ol |
| 159 | 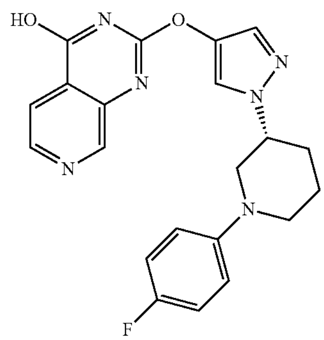 [SMILES: Oc1nc(Oc2cnn([C@@H]3CCCN(c4ccc(F)cc4)C3)c2)nc2cnccc12] | 2-({1-[(3R)-1-(4-fluorophenyl)piperidin-3-yl]-1H-pyrazol-4-yl}oxy)pyrido[3,4-d]pyrimidin-4-ol |
| 160 | 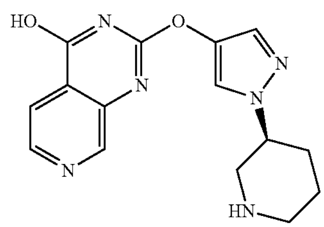 [SMILES: Oc1nc(Oc2cnn([C@H]3CCCNC3)c2)nc2cnccc12] | 2-({1-[(3S)-piperidin-3-yl]-1H-pyrazol-4-yl}oxy)pyrido[3,4-d]pyrimidin-4-ol |
| 161 | 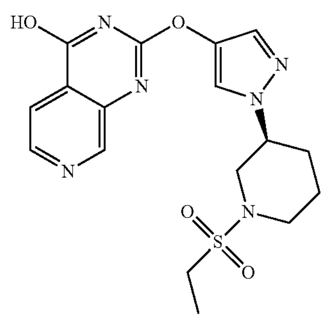 [SMILES: CCS(=O)(=O)N1CCC[C@H](n2cc(Oc3nc(O)c4ccncc4n3)cn2)C1] | 2-({1-[(3S)-1-(ethanesulfonyl)piperidin-3-yl]-1H-pyrazol-4-yl}oxy)pyrido[3,4-d]pyrimidin-4-ol |
| 162 | 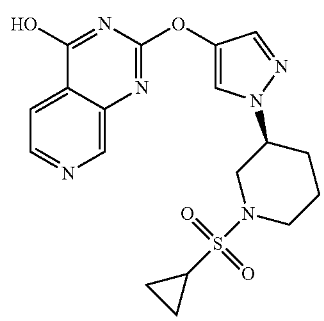 [SMILES: O=S(=O)(C1CC1)N1CCC[C@H](n2cc(Oc3nc(O)c4ccncc4n3)cn2)C1] | 2-({1-[(3S)-1-(cyclopropanesulfonyl)piperidin-3-yl]-1H-pyrazol-4-yl}oxy)pyrido[3,4-d]pyrimidin-4-ol |

TABLE 1-continued

| Chemical Synthesis Example | Structure | Name |
|---|---|---|
| 163 | 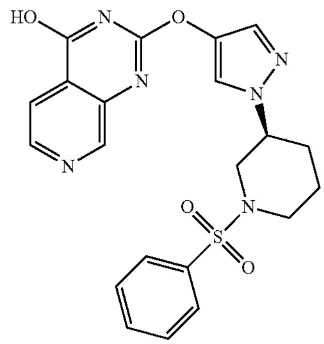 [SMILES: O=S(=O)(c1ccccc1)N1CCC[C@H](n2cc(Oc3nc(O)c4ccncc4n3)cn2)C1] | 2-({1-[(3S)-1-(benzenesulfonyl)piperidin-3-yl]-1H-pyrazol-4-yl}oxy)pyrido[3,4-d]pyrimidin-4-ol |
| 164 | 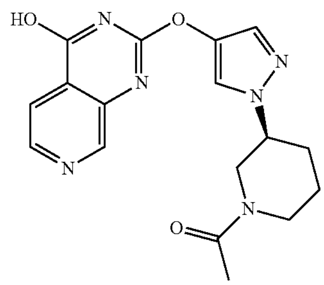 [SMILES: CC(=O)N1CCC[C@H](n2cc(Oc3nc(O)c4ccncc4n3)cn2)C1] | 1-[(3S)-3-[4-({4-hydroxypyrido[3,4-d]pyrimidin-2-yl}oxy)-1H-pyrazol-1-yl]piperidin-1-yl]ethan-1-one |
| 165 | 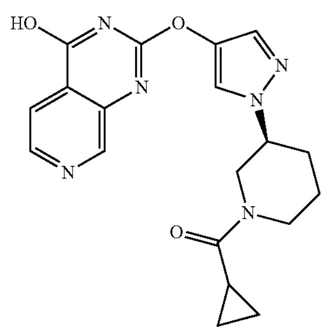 [SMILES: O=C(C1CC1)N1CCC[C@H](n2cc(Oc3nc(O)c4ccncc4n3)cn2)C1] | 2-({1-[(3S)-1-cyclopropanecarbonylpiperidin-3-yl]-1H-pyrazol-4-yl}oxy)pyrido[3,4-d]pyrimidin-4-ol |
| 166 | 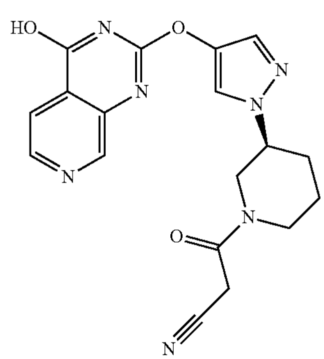 [SMILES: N#CCC(=O)N1CCC[C@H](n2cc(Oc3nc(O)c4ccncc4n3)cn2)C1] | 3-[(3S)-3-[4-({4-hydroxypyrido[3,4-d]pyrimidin-2-yl}oxy)-1H-pyrazol-1-yl]piperidin-1-yl]-3-oxopropanenitrile |

TABLE 1-continued

| Chemical Synthesis Example | Structure | Name |
|---|---|---|
| 167 | 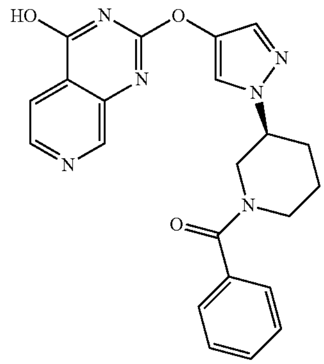 [SMILES: O=C(c1ccccc1)N1CCC[C@H](n2cc(Oc3nc(O)c4ccncc4n3)cn2)C1] | 2-({1-[(3S)-1-benzoylpiperidin-3-yl]-1H-pyrazol-4-yl}oxy)pyrido[3,4-d]pyrimidin-4-ol |
| 168 | 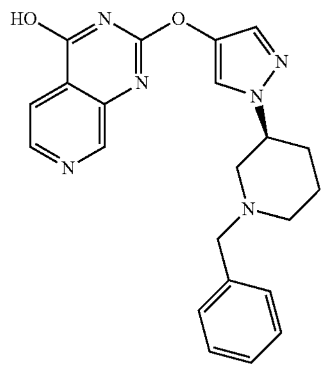 [SMILES: Oc1nc(Oc2cnn([C@H]3CCCN(Cc4ccccc4)C3)c2)nc2cnccc12] | 2-({1-[(3S)-1-benzylpiperidin-3-yl]-1H-pyrazol-4-yl}oxy)pyrido[3,4-d]pyrimidin-4-ol |
| 169 | 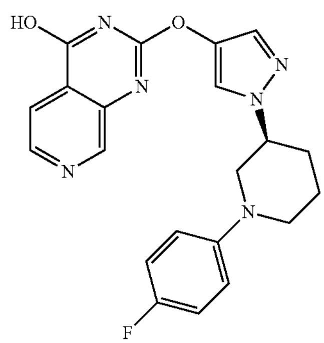 [SMILES: Oc1nc(Oc2cnn([C@H]3CCCN(c4ccc(F)cc4)C3)c2)nc2cnccc12] | 2-({1-[(3R)-1-(4-fluorophenyl)piperidin-3-yl]-1H-pyrazol-4-yl}oxy)pyrido[3,4-d]pyrimidin-4-ol |
| 170 | 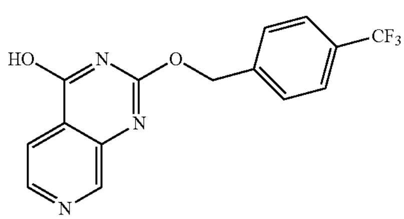 [SMILES: Oc1nc(OCc2ccc(C(F)(F)F)cc2)nc2cnccc12] | 2-{[4-(trifluoromethyl)phenyl]methoxy}pyrido[3,4-d]pyrimidin-4-ol |
| 171 | 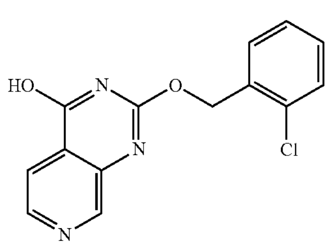 [SMILES: Oc1nc(OCc2ccccc2Cl)nc2cnccc12] | 2-[(2-chlorophenyl)methoxy]pyrido[3,4-d]pyrimidin-4-ol |

TABLE 1-continued

| Chemical Synthesis Example | Structure | Name |
|---|---|---|
| 172 | 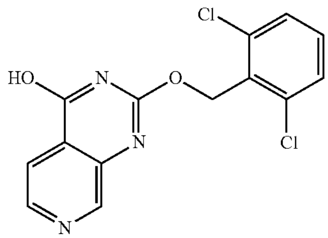 | 2-[(2,6-dichlorophenyl)methoxy]pyrido[3,4-d]pyrimidin-4-ol |
| 173 | 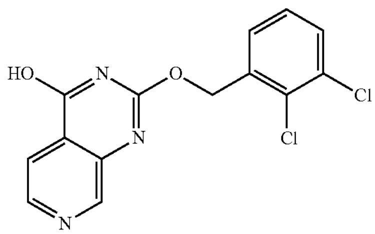 [SMILES: Oc1nc(OCc2cccc(Cl)c2Cl)nc2cnccc12] | 2-[(2,3-dichlorophenyl)methoxy]pyrido[3,4-d]pyrimidin-4-ol |
| 174 | 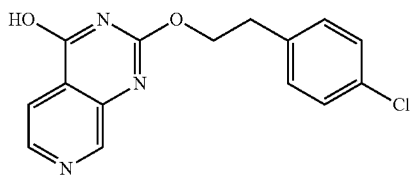 [SMILES: Oc1nc(OCCc2ccc(Cl)cc2)nc2cnccc12] | 2-[2-(4-chlorophenyl)ethoxy]pyrido[3,4-d]pyrimidin-4-ol |
| 175 | 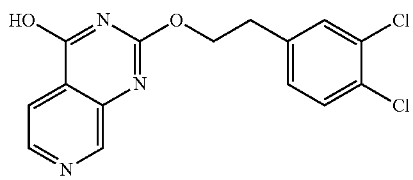 [SMILES: Oc1nc(OCCc2ccc(Cl)c(Cl)c2)nc2cnccc12] | 2-[2-(3,4-dichlorophenyl)ethoxy]pyrido[3,4-d]pyrimidin-4-ol |
| 176 | 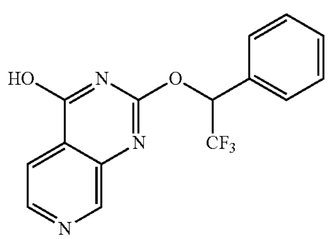 [SMILES: Oc1nc(OC(c2ccccc2)C(F)(F)F)nc2cnccc12] | 2-(2,2,2-trifluoro-1-phenylethoxy)pyrido[3,4-d]pyrimidin-4-ol |
| 177 | 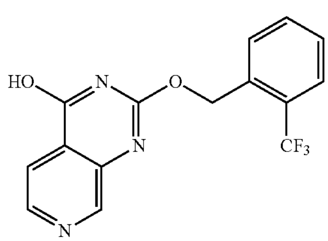 [SMILES: Oc1nc(OCc2ccccc2C(F)(F)F)nc2cnccc12] | 2-{[2-(trifluoromethyl)phenyl]methoxy}pyrido[3,4-d]pyrimidin-4-ol |
| 178 | 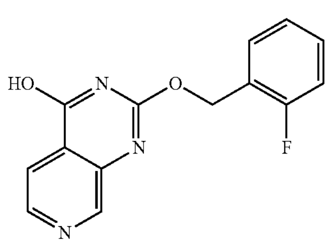 [SMILES: Oc1nc(OCc2ccccc2F)nc2cnccc12] | 2-[(2-fluorophenyl)methoxy]pyrido[3,4-d]pyrimidin-4-ol |

TABLE 1-continued

| Chemical Synthesis Example | Structure | Name |
|---|---|---|
| 179 | 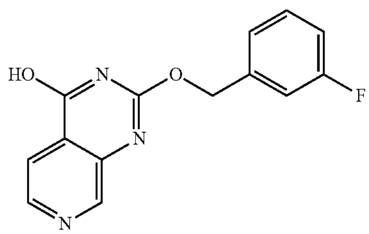 [SMILES: Oc1nc(OCc2cccc(F)c2)nc2cnccc12] | 2-[(3-fluorophenyl)methoxy]pyrido[3,4-d]pyrimidin-4-ol |
| 180 | 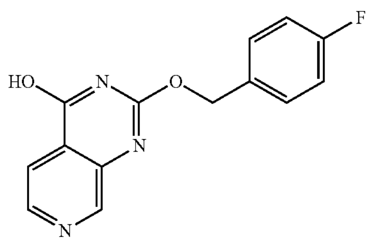 [SMILES: Oc1nc(OCc2ccc(F)cc2)nc2cnccc12] | 2-[(4-fluorophenyl)methoxy]pyrido[3,4-d]pyrimidin-4-ol |
| 181 | 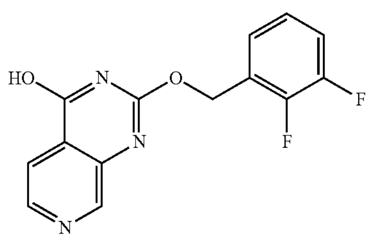 [SMILES: Oc1nc(OCc2cccc(F)c2F)nc2cnccc12] | 2-[(2,3-difluorophenyl)methoxy]pyrido[3,4-d]pyrimidin-4-ol |
| 182 | 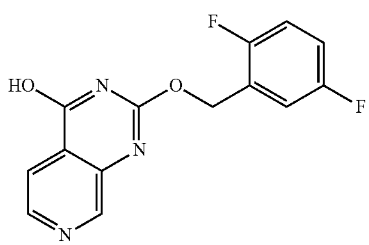 [SMILES: Oc1nc(OCc2cc(F)ccc2F)nc2cnccc12] | 2-[(2,5-difluorophenyl)methoxy]pyrido[3,4-d]pyrimidin-4-ol |
| 183 | 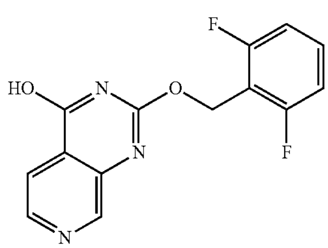 [SMILES: Oc1nc(OCc2c(F)cccc2F)nc2cnccc12] | 2-[(2,6-difluorophenyl)methoxy]pyrido[3,4-d]pyrimidin-4-ol |
| 184 | 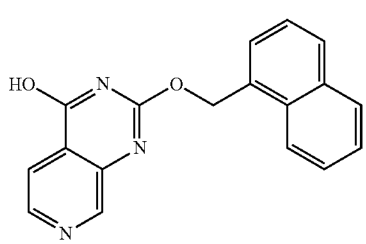 [SMILES: Oc1nc(OCc2cccc3ccccc23)nc2cnccc12] | 2-(naphthalen-1-ylmethoxy)pyrido[3,4-d]pyrimidin-4-ol |

TABLE 1-continued
| Chemical Synthesis Example | Structure | Name |
|---|---|---|
| 185 | 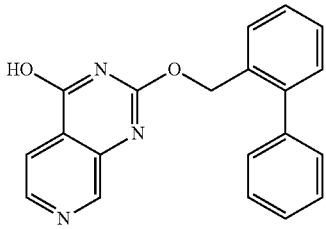 [SMILES: Oc1nc(OCc2ccccc2-c2ccccc2)nc2cnccc12] | 2-[(2-phenylphenyl)methoxy]pyrido[3,4-d]pyrimidin-4-ol |
| 186 | 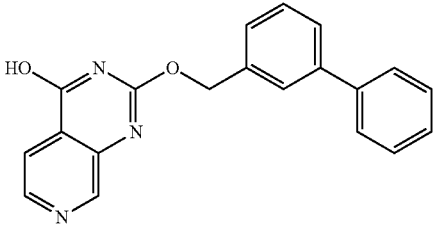 [SMILES: Oc1nc(OCc2cccc(-c3ccccc3)c2)nc2cnccc12] | 2-[(3-phenylphenyl)methoxy]pyrido[3,4-d]pyrimidin-4-ol |
| 187 | 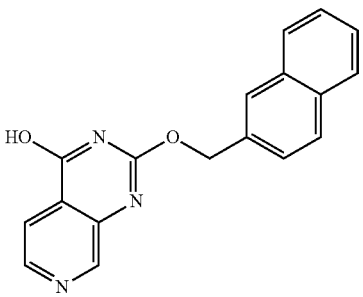 [SMILES: Oc1nc(OCc2ccc3ccccc3c2)nc2cnccc12] | 2-(naphthalen-2-ylmethoxy)pyrido[3,4-d]pyrimidin-4-ol |
| 188 | 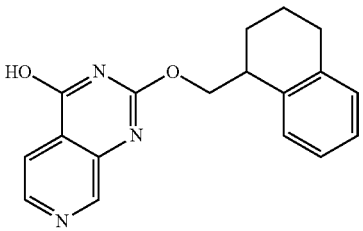 [SMILES: Oc1nc(OCC2CCCc3ccccc32)nc2cnccc12] | 2-(1,2,3,4-tetrahydronaphthalen-1-ylmethoxy)pyrido[3,4-d]pyrimidin-4-ol |
| 189 | 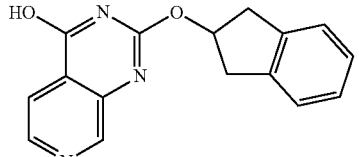 | 2-(2,3-dihydro-1H-inden-2-yloxy)pyrido[3,4-d]pyrimidin-4-ol |
| 190 | 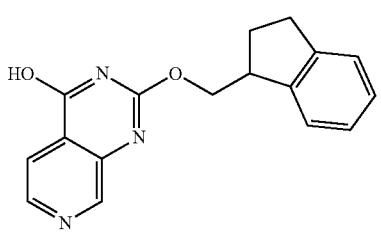 [SMILES: Oc1nc(OCC2CCc3ccccc32)nc2cnccc12] | 2-(2,3-dihydro-1H-inden-1-ylmethoxy)pyrido[3,4-d]pyrimidin-4-ol |

TABLE 1-continued

| Chemical Synthesis Example | Structure | Name |
|---|---|---|
| 191 | 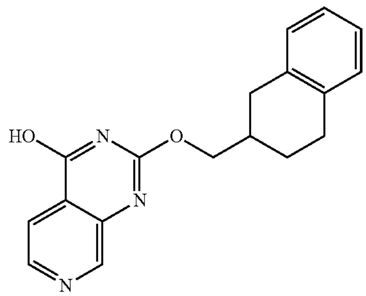 [SMILES: Oc1nc(OCC2CCc3ccccc3C2)nc2cnccc12] | 2-(1,2,3,4-tetrahydronaphthalen-2-ylmethoxy)pyrido[3,4-d]pyrimidin-4-ol |
| 192 | 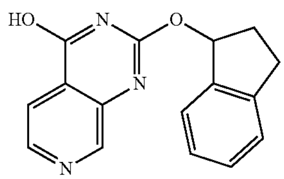 [SMILES: Oc1nc(OC2CCc3ccccc32)nc2cnccc12] | 2-(2,3-dihydro-1H-inden-1-yloxy)pyrido[3,4-d]pyrimidin-4-ol |
| 193 | 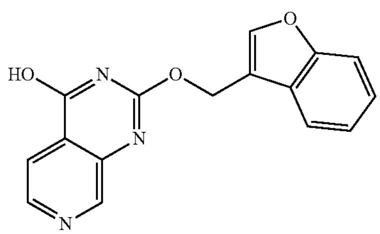 [SMILES: Oc1nc(OCc2coc3ccccc23)nc2cnccc12] | 2-(1-benzofuran-3-ylmethoxy)pyrido[3,4-d]pyrimidin-4-ol |
| 194 | 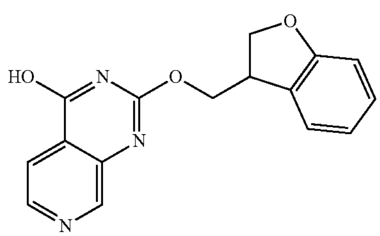 [SMILES: Oc1nc(OCC2COc3ccccc32)nc2cnccc12] | 2-(2,3-dihydro-1-benzofuran-3-ylmethoxy)pyrido[3,4-d]pyrimidin-4-ol |
| 195 | 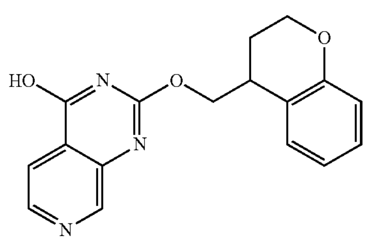 | 2-(3,4-dihydro-2H-1-benzopyran-4-ylmethoxy)pyrido[3,4-d]pyrimidin-4-ol |
| 196 | 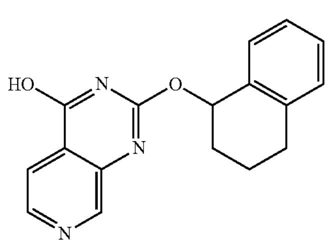 [SMILES: Oc1nc(OC2CCCc3ccccc32)nc2cnccc12] | 2-(1,2,3,4-tetrahydronaphthalen-1-yloxy)pyrido[3,4-d]pyrimidin-4-ol |

TABLE 1-continued

| Chemical Synthesis Example | Structure | Name |
|---|---|---|
| 197 | 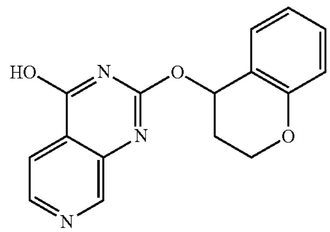 [SMILES: Oc1nc(OC2CCOc3ccccc32)nc2cnccc12] | 2-(3,4-dihydro-2H-1-benzopyran-4-yloxy)pyrido[3,4-d]pyrimidin-4-ol |
| 198 | 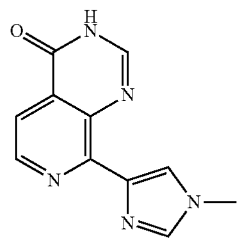 [SMILES: Cn1cnc(-c2nccc3c(=O)[nH]cnc23)c1] | 8-(1-methylimidazol-4-yl)-3H-pyrido[3,4-d]pyrimidin-4-one |

In some embodiments, the compound disclosed herein has a structure provided in Table 2.

TABLE 2

8-[1-(2-hydroxyethyl)imidazol-4-yl]-2-(2,2,2-trifluoroethoxy)pyrido[3,4-d]pyrimidin-4-ol 8-[1-[2-(dimethylamino)ethyl]imidazol-4-yl]-2-(2,2,2-trifluoroethoxy)pyrido[3,4-d]pyrimidin-4-ol 8-[1-(3-hydroxypropyl)imidazol-4-yl]-2-(2,2,2-trifluoroethoxy)pyrido[3,4-d]pyrimidin-4-ol 8-[1-[3-(dimethylamino)propyl]imidazol-4-yl]-2-(2,2,2-trifluoroethoxy)pyrido[3,4-d]pyrimidin-4-ol 8-(1-pyrrolidin-3-ylimidazol-4-yl)-2-(2,2,2-trifluoroethoxy)pyrido[3,4-d]pyrimidin-4-ol 8-(1-piperidin-3-ylimidazol-4-yl)-2-(2,2,2-trifluoroethoxy)pyrido[3,4-d]pyrimidin-4-ol TABLE 2-continued

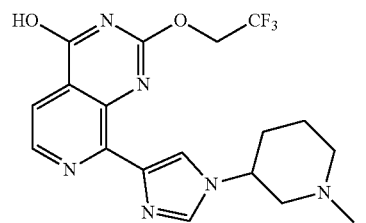 [SMILES: CN1CCCC(n2cnc(-c3nccc4c(O)nc(OCC(F)(F)F)nc34)c2)C1]

8-[1-(1-methylpiperidin-3-yl)imidazol-4-yl]-
2-(2,2,2-trifluoroethoxy)pyrido[3,4-
d]pyrimidin-4-ol

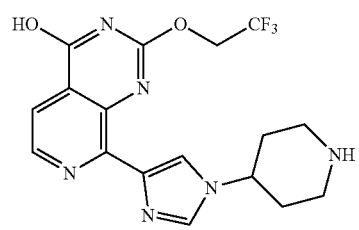 [SMILES: Oc1nc(OCC(F)(F)F)nc2c(-c3cn(C4CCNCC4)cn3)nccc12]

8-(1-piperidin-4-ylimidazol-4-yl)-2-(2,2,2-
trifluoroethoxy)pyrido[3,4-d]pyrimidin-4-ol

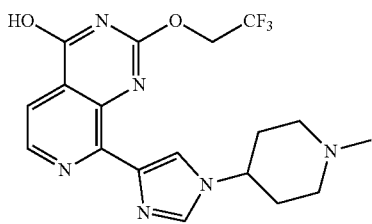 [SMILES: CN1CCC(n2cnc(-c3nccc4c(O)nc(OCC(F)(F)F)nc34)c2)CC1]

8-[1-(1-methylpiperidin-4-yl)imidazol-4-yl]-
2-(2,2,2-trifluoroethoxy)pyrido[3,4-
d]pyrimidin-4-ol

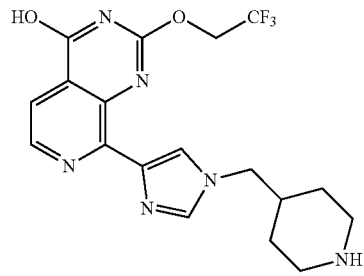 [SMILES: Oc1nc(OCC(F)(F)F)nc2c(-c3cn(CC4CCNCC4)cn3)nccc12]

8-[1-(piperidin-4-ylmethyl)imidazol-4-yl]-2-
(2,2,2-trifluoroethoxy)pyrido[3,4-
d]pyrimidin-4-ol

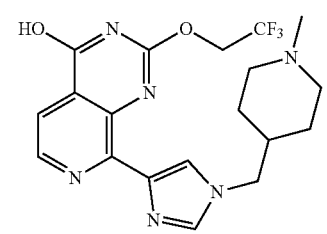 [SMILES: CN1CCC(Cn2cnc(-c3nccc4c(O)nc(OCC(F)(F)F)nc34)c2)CC1]

8-[1-[(1-methylpiperidin-4-
yl)methyl]imidazol-4-yl]-2-(2,2,2-
trifluoroethoxy)pyrido[3,4-d]pyrimidin-4-ol TABLE 2-continued

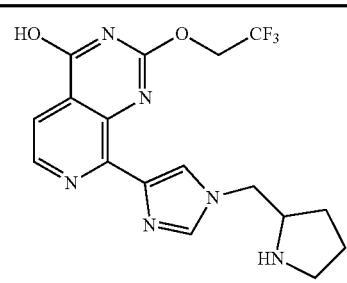

8-[1-(pyrrolidin-2-ylmethyl)imidazol-4-yl]-
2-(2,2,2-trifluoroethoxy)pyrido[3,4-
d]pyrimidin-4-ol

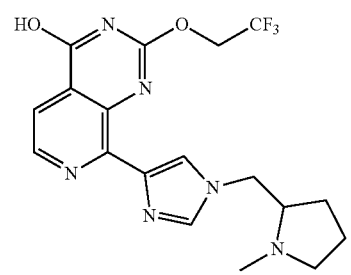 [SMILES: CN1CCCC1Cn1cnc(-c2nccc3c(O)nc(OCC(F)(F)F)nc23)c1]

8-[1-[(1-methylpyrrolidin-2-
yl)methyl]imidazol-4-yl]-2-(2,2,2-
trifluoroethoxy)pyrido[3,4-d]pyrimidin-4-ol

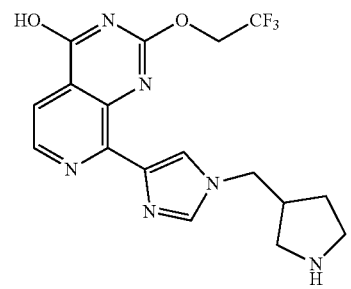 [SMILES: Oc1nc(OCC(F)(F)F)nc2c(-c3cn(CC4CCNC4)cn3)nccc12]

8-[1-(pyrrolidin-3-ylmethyl)imidazol-4-yl]-
2-(2,2,2-trifluoroethoxy)pyrido[3,4-
d]pyrimidin-4-ol

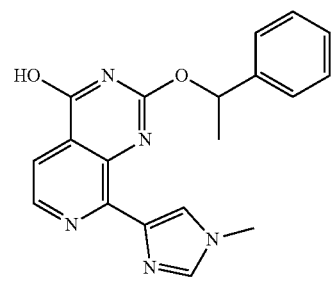 [SMILES: CC(Oc1nc(O)c2ccnc(-c3cn(C)cn3)c2n1)c1ccccc1]

8-(1-methylimidazol-4-yl)-2-(1-
phenylethoxy)pyrido[3,4-d]pyrimidin-4-ol

TABLE 2-continued

8-[1-(cyclopropylmethyl)imidazol-4-yl]-2-(2,2,2-trifluoroethoxy)pyrido[3,4-d]pyrimidin-4-ol 8-(1-(2-((4-cyclopropylbenzyl)(methyl)amino)ethyl)-1H-imidazol-4-yl)pyrido[3,4-d]pyrimidin-4-ol 8-[1-[1-(dimethylamino)propan-2-yl]imidazol-4-yl]-2-(2,2,2-trifluoroethoxy)pyrido[3,4-d]pyrimidin-4-ol 8-(1-methylimidazol-4-yl)-2-(3,3,3-trifluoropropoxy)pyrido[3,4-d]pyrimidin-4-ol 2-[1-(4-fluorophenyl)ethoxy]-8-(1-methylimidazol-4-yl)pyrido[3,4-d]pyrimidin-4-ol TABLE 2-continued 4-[[4-hydroxy-8-(1-methylimidazol-4-yl)pyrido[3,4-d]pyrimidin-2-yl]oxymethyl]benzonitrile 4-[1-[4-hydroxy-8-(1-methylimidazol-4-yl)pyrido[3,4-d]pyrimidin-2-yl]oxyethyl]benzonitrile 8-[1-(difluoromethyl)imidazol-4-yl]-2-[1-(oxan-4-yl)pyrazol-4-yl]oxypyrido[3,4-d]pyrimidin-4-ol 2-[1-(difluoromethyl)pyrazol-4-yl]oxy-8-(1-methylimidazol-4-yl)pyrido[3,4-d]pyrimidin-4-ol TABLE 2-continued

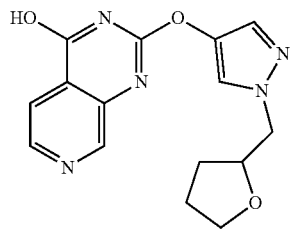 [SMILES: Oc1nc(Oc2cnn(CC3CCCO3)c2)nc2cnccc12]

2-[1-(oxolan-2-ylmethyl)pyrazol-4-yl]oxypyrido[3,4-d]pyrimidin-4-ol

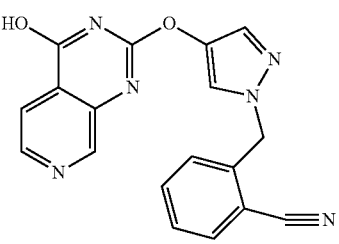 [SMILES: N#Cc1ccccc1Cn1cc(Oc2nc(O)c3ccncc3n2)cn1]

2-[[4-(4-hydroxypyrido[3,4-d]pyrimidin-2-yl)oxypyrazol-1-yl]methyl]benzonitrile

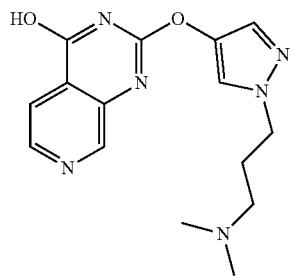 [SMILES: CN(C)CCCn1cc(Oc2nc(O)c3ccncc3n2)cn1]

2-[1-[3-(dimethylamino)propyl]pyrazol-4-yl]oxypyrido[3,4-d]pyrimidin-4-ol

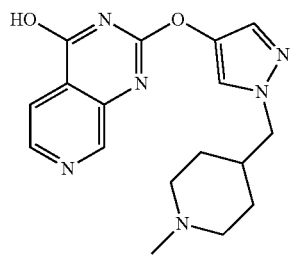 [SMILES: CN1CCC(Cn2cc(Oc3nc(O)c4ccncc4n3)cn2)CC1]

2-[1-[(1-methylpiperidin-4-yl)methyl]pyrazol-4-yl]oxypyrido[3,4-d]pyrimidin-4-ol

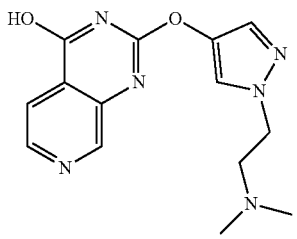 [SMILES: CN(C)CCn1cc(Oc2nc(O)c3ccncc3n2)cn1]

2-[1-[2-(dimethylamino)ethyl]pyrazol-4-yl]oxypyrido[3,4-d]pyrimidin-4-ol

TABLE 2-continued

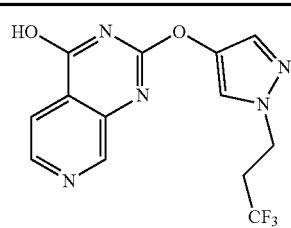

2-[1-(3,3,3-trifluoropropyl)pyrazol-4-yl]oxypyrido[3,4-d]pyrimidin-4-ol

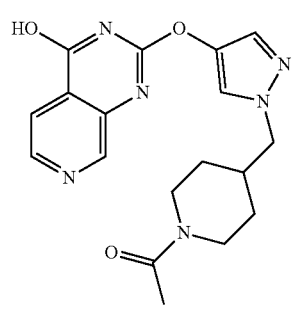 [SMILES: CC(=O)N1CCC(Cn2cc(Oc3nc(O)c4ccncc4n3)cn2)CC1]

1-[4-[[4-(4-hydroxypyrido[3,4-d]pyrimidin-2-yl)oxypyrazol-1-yl]methyl]piperidin-1-yl]ethanone

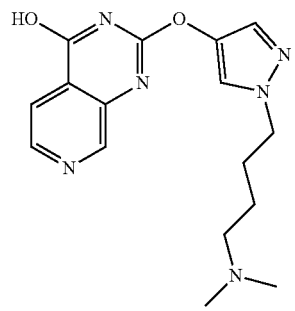 [SMILES: CN(C)CCCCn1cc(Oc2nc(O)c3ccncc3n2)cn1]

2-[1-[4-(dimethylamino)butyl]pyrazol-4-yl]oxypyrido[3,4-d]pyrimidin-4-ol

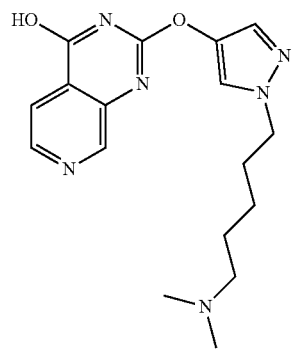 [SMILES: CN(C)CCOCCn1cc(Oc2nc(O)c3ccncc3n2)cn1]

2-[1-[5-(dimethylamino)pentyl]pyrazol-4-yl]oxypyrido[3,4-d]pyrimidin-4-ol

TABLE 2-continued

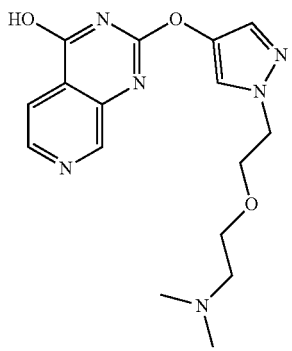

2-[1-[2-[2-(dimethylamino)ethoxy]ethyl]pyrazol-4-yl]oxypyrido[3,4-d]pyrimidin-4-ol

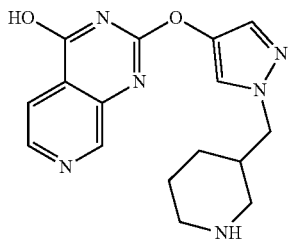 [SMILES: Oc1nc(Oc2cnn(CC3CCCNC3)c2)nc2cnccc12]

2-[1-(piperidin-3-ylmethyl)pyrazol-4-yl]oxypyrido[3,4-d]pyrimidin-4-ol

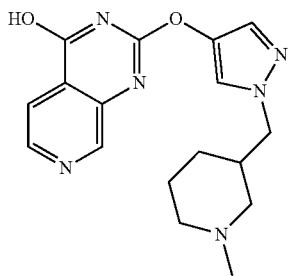 [SMILES: CN1CCCC(Cn2cc(Oc3nc(O)c4ccncc4n3)cn2)C1]

2-[1-[(1-methylpiperidin-3-yl)methyl]pyrazol-4-yl]oxypyrido[3,4-d]pyrimidin-4-ol

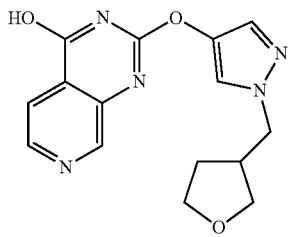 [SMILES: Oc1nc(Oc2cnn(CC3CCOC3)c2)nc2cnccc12]

2-[1-(oxolan-3-ylmethyl)pyrazol-4-yl]oxypyrido[3,4-d]pyrimidin-4-ol

TABLE 2-continued

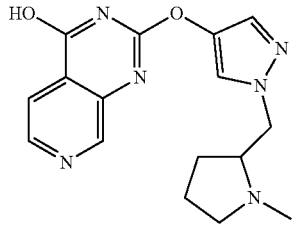 [SMILES: CN1CCCC1Cn1cc(Oc2nc(O)c3ccncc3n2)cn1]

2-[1-(oxolan-3-ylmethyl)pyrazol-4-yl]oxypyrido[3,4-d]pyrimidin-4-ol

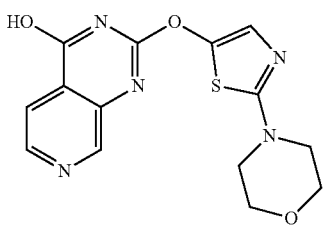 [SMILES: Oc1nc(Oc2cnc(N3CCOCC3)s2)nc2cnccc12]

2-[(2-morpholin-4-yl-1,3-thiazol-5-yl)oxy]pyrido[3,4-d]pyrimidin-4-ol

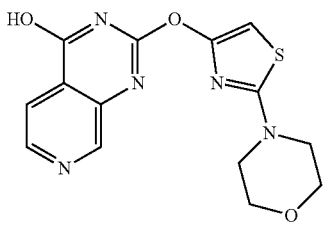 [SMILES: Oc1nc(Oc2csc(N3CCOCC3)n2)nc2cnccc12]

2-[(2-morpholin-4-yl-1,3-thiazol-4-yl)oxy]pyrido[3,4-d]pyrimidin-4-ol

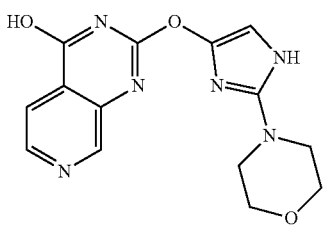 [SMILES: Oc1nc(Oc2c[nH]c(N3CCOCC3)n2)nc2cnccc12]

2-[(2-morpholin-4-yl-1H-imidazol-4-yl)oxy]pyrido[3,4-d]pyrimidin-4-ol

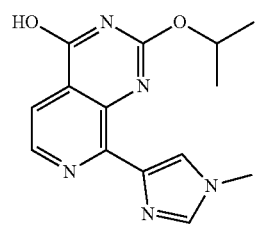

8-(1-methylimidazol-4-yl)-2-propan-2-yloxypyrido[3,4-d]pyrimidin-4-ol

TABLE 2-continued

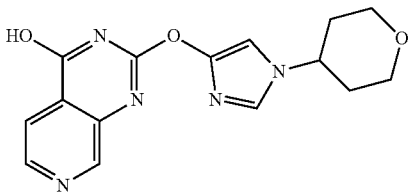 [SMILES: Oc1nc(Oc2cn(C3CCOCC3)cn2)nc2cnccc12]

2-[1-(oxan-4-yl)imidazol-4-yl]oxypyrido[3,4-d]pyrimidin-4-ol

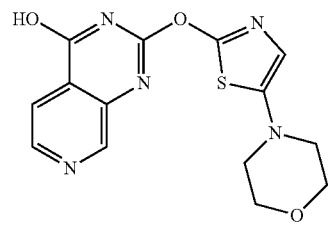 [SMILES: Oc1nc(Oc2ncc(N3CCOCC3)s2)nc2cnccc12]

2-[(5-morpholin-4-yl-1,3-thiazol-2-yl)oxy]pyrido[3,4-d]pyrimidin-4-ol

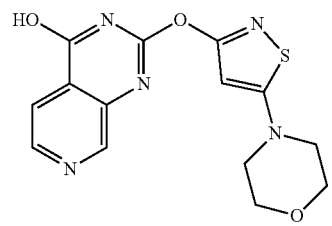

2-[(5-morpholin-4-yl-1,2-thiazol-3-yl)oxy]pyrido[3,4-d]pyrimidin-4-ol

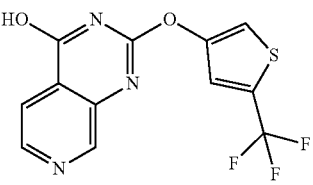 [SMILES: Oc1nc(Oc2csc(C(F)(F)F)c2)nc2cnccc12]

2-[5-(trifluoromethyl)thiophen-3-yl]oxypyrido[3,4-d]pyrimidin-4-ol

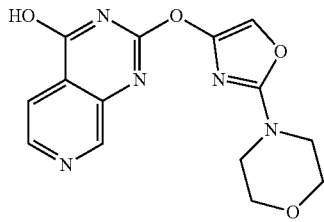 [SMILES: Oc1nc(Oc2coc(N3CCOCC3)n2)nc2cnccc12]

2-[(2-morpholin-4-yl-1,3-oxazol-4-yl)oxy]pyrido[3,4-d]pyrimidin-4-ol

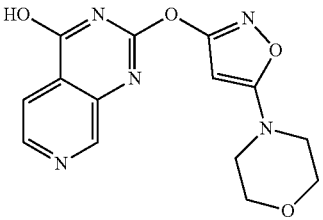 [SMILES: Oc1nc(Oc2cc(N3CCOCC3)on2)nc2cnccc12]

2-[(5-morpholin-4-yl-1,2-oxazol-3-yl)oxy]pyrido[3,4-d]pyrimidin-4-ol

TABLE 2-continued

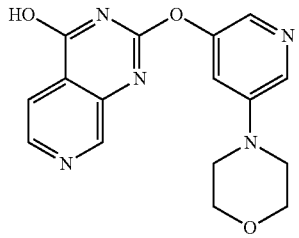 [SMILES: Oc1nc(Oc2cncc(N3CCOCC3)c2)nc2cnccc12]

2-(5-morpholin-4-ylpyridin-3-yl)oxypyrido[3,4-d]pyrimidin-4-ol

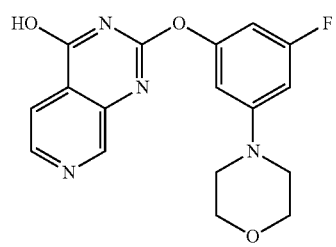 [SMILES: Oc1nc(Oc2cc(F)cc(N3CCOCC3)c2)nc2cnccc12]

2-(3-fluoro-5-morpholin-4-ylphenoxy)pyrido[3,4-d]pyrimidin-4-ol

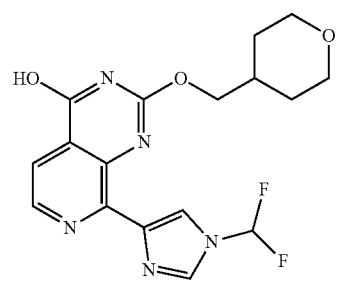 [SMILES: Oc1nc(OCC2CCOCC2)nc2c(-c3cn(C(F)F)cn3)nccc12]

8-[1-(difluoromethyl)imidazol-4-yl]-2-(oxan-4-ylmethoxy)pyrido[3,4-d]pyrimidin-4-ol

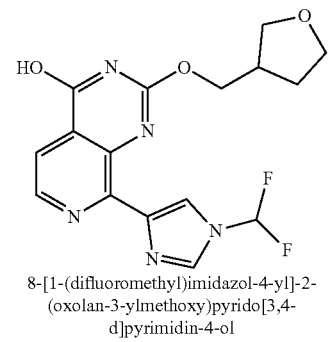

8-[1-(difluoromethyl)imidazol-4-yl]-2-(oxolan-3-ylmethoxy)pyrido[3,4-d]pyrimidin-4-ol

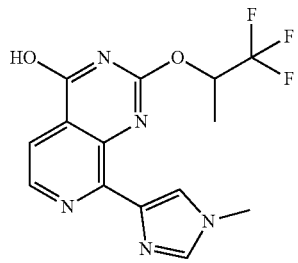 [SMILES: CC(Oc1nc(O)c2ccnc(-c3cn(C)cn3)c2n1)C(F)(F)F]

8-(1-methylimidazol-4-yl)-2-(1,1,1-trifluoropropan-2-yloxy)pyrido[3,4-d]pyrimidin-4-ol TABLE 2-continued 8-[1-(2-hydroxyethyl)imidazol-4-yl]pyrido[3,4-d]pyrimidin-4-ol 8-[1-[2-(dimethylamino)ethyl]imidazol-4-yl]pyrido[3,4-d]pyrimidin-4-ol 8-[1-[2-(benzylamino)ethyl]imidazol-4-yl]pyrido[3,4-d]pyrimidin-4-ol 8-[1-(2-phenylmethoxyethyl)imidazol-4-yl]pyrido[3,4-d]pyrimidin-4-ol 8-(1-cyclopropylimidazol-4-yl)-2-[1-(difluoromethyl)pyrazol-4-yl]oxypyrido[3,4-d]pyrimidin-4-ol 8-(1-cyclopropylimidazol-4-yl)-2-[1-(oxan-4-yl)pyrazol-4-yl]oxypyrido[3,4-d]pyrimidin-4-ol 8-[1-(2-pyrrolidin-1-ylethyl)imidazol-4-yl]-2-(2,2,2-trifluoroethoxy)pyrido[3,4-d]pyrimidin-4-ol 8-(1-cyclopropylimidazol-4-yl)-2-(2,2,2-trifluoroethoxy)pyrido[3,4-d]pyrimidin-4-ol 8-[1-(2-morpholin-4-ylethyl)imidazol-4-yl]-2-(2,2,2-trifluoroethoxy)pyrido[3,4-d]pyrimidin-4-ol 8-[1-[2-(methylamino)ethyl]imidazol-4-yl]-2-(2,2,2-trifluoroethoxy)pyrido[3,4-d]pyrimidin-4-ol TABLE 2-continued

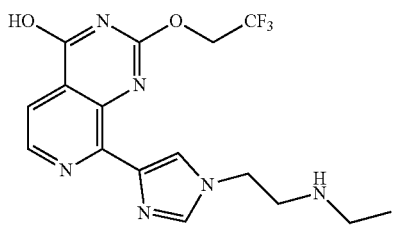 [SMILES: CCNCCn1cnc(-c2nccc3c(O)nc(OCC(F)(F)F)nc23)c1]

8-[1-[2-(ethylamino)ethyl]imidazol-4-yl]-2-
(2,2,2-trifluoroethoxy)pyrido[3,4-
d]pyrimidin-4-ol

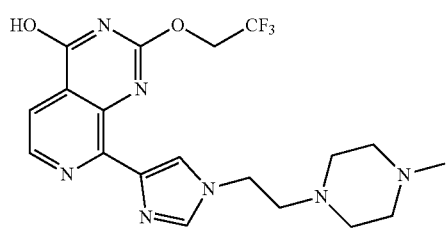 [SMILES: CN1CCN(CCn2cnc(-c3nccc4c(O)nc(OCC(F)(F)F)nc34)c2)CC1]

8-[1-[2-(4-methylpiperazin-1-
yl)ethyl]imidazol-4-yl]-2-(2,2,2-
trifluoroethoxy)pyrido[3,4-d]pyrimidin-4-ol

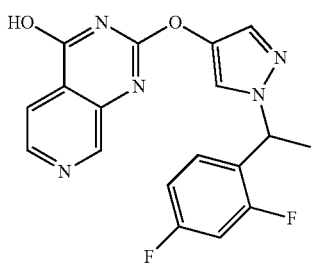 [SMILES: CC(c1ccc(F)cc1F)n1cc(Oc2nc(O)c3ccncc3n2)cn1]

2-[1-[1-(2,4-difluorophenyl)ethyl]pyrazol-4-
yl]oxypyrido[3,4-d]pyrimidin-4-ol

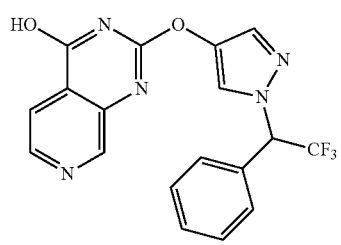 [SMILES: Oc1nc(Oc2cnn(C(c3ccccc3)C(F)(F)F)c2)nc2cnccc12]

2-[1-(2,2,2-trifluoro-1-phenylethyl)pyrazol-
4-yl]oxypyrido[3,4-d]pyrimidin-4-ol

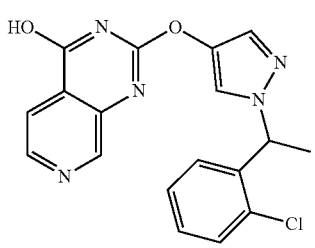 [SMILES: CC(c1ccccc1Cl)n1cc(Oc2nc(O)c3ccncc3n2)cn1]

2-[1-[1-(2-chlorophenyl)ethyl]pyrazol-4-
yl]oxypyrido[3,4-d]pyrimidin-4-ol

TABLE 2-continued

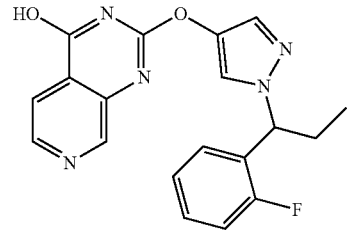 [SMILES: CCC(c1ccccc1F)n1cc(Oc2nc(O)c3ccncc3n2)cn1]

2-[1-[1-(2-fluorophenyl)propyl]pyrazol-4-
yl]oxypyrido[3,4-d]pyrimidin-4-ol

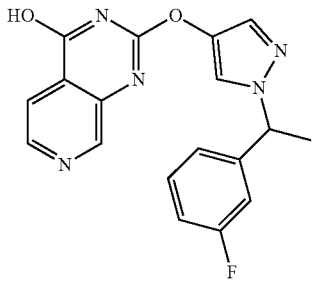 [SMILES: CC(c1cccc(F)c1)n1cc(Oc2nc(O)c3ccncc3n2)cn1]

2-[1-[1-(3-fluorophenyl)ethyl]pyrazol-4-
yl]oxypyrido[3,4-d]pyrimidin-4-ol

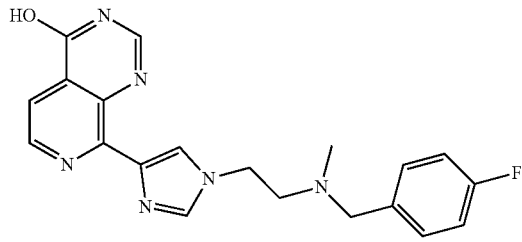 [SMILES: CN(CCn1cnc(-c2nccc3c(O)ncnc23)c1)Cc1ccc(F)cc1]

8-(1-(2-((4-
fluorobenzyl)(methyl)amino)ethyl)-1H-
imidazol-4-yl)pyrido[3,4-d]pyrimidin-4-ol

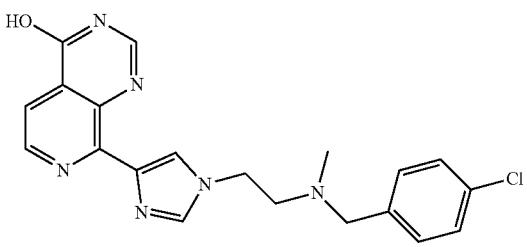 [SMILES: CN(CCn1cnc(-c2nccc3c(O)ncnc23)c1)Cc1ccc(Cl)cc1]

8-(1-(2-((4-
chlorobenzyl)(methyl)amino)ethyl)-1H-
imidazol-4-yl)pyrido[3,4-d]pyrimidin-4-ol

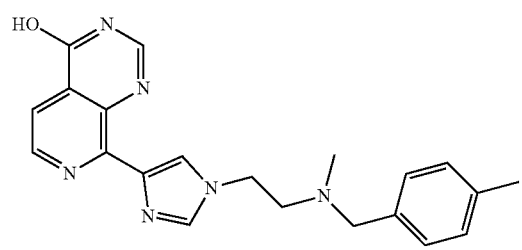 [SMILES: Cc1ccc(CN(C)CCn2cnc(-c3nccc4c(O)ncnc34)c2)cc1]

8-(1-(2-(methyl(4-
methylbenzyl)amino)ethyl)-1H-imidazol-4-
yl)pyrido[3,4-d]pyrimidin-4-ol

Preparation of the Substituted Pyrido[3,4-d]pyrimidin-4-one Derivative Compounds The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted pyrido[3,4-d]pyrimidin-4-one derivative compounds described herein is P. H. Stahl & C. G. Wermuth "Handbook of Pharmaceutical Salts", Verlag Helvetica Chimica Acta, Zurich, 2002.

The substituted pyrido[3,4-d]pyrimidin-4-one derivative compounds are prepared by the general synthetic routes described below in Schemes 1-3.

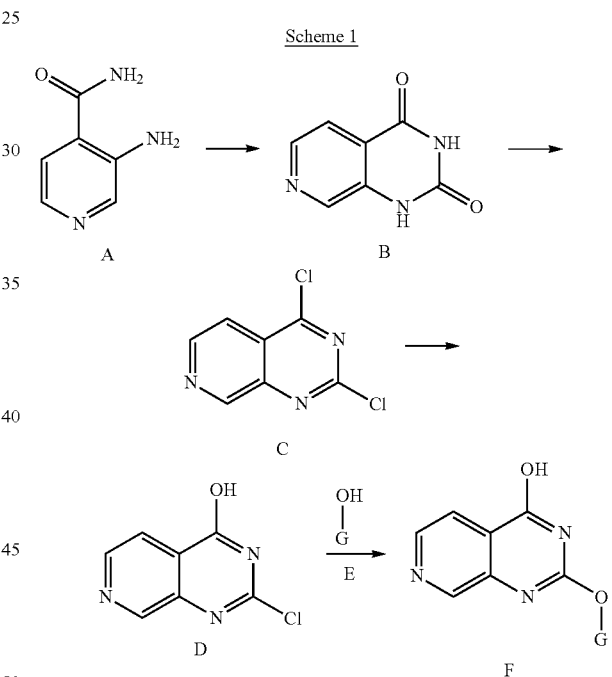

Referring to Scheme 1, compound A is converted to compound B by condensation with urea. The azaquinazolinedione compound B is converted to compound C using an appropriate chlorinating agent, such as POCl₃. Compound C is selectively hydrolyzed to form compound D under a variety of basic conditions, such as hydrolysis in a NaOH solution. Nucleophilic substitution of the chloride in compound D is carried out with an alcohol, such as G-OH, under a variety of basic conditions to form compound F. For example, compound D can be treated with the sodium salt of the alcohol E. Additionally, compound D can be heated with the alcohol or phenol G-OH in the presence of CuI and CsCO₃ in an appropriate solvent to form compound F.

Referring to Scheme 2, compound H is chlorinated to produce compound J. For example, chlorination can occur through the formation of the pyridine N-oxide in the presence of a chlorine source such as HCl. The biaryl compound L is prepared from aryl halide compound J using aryl coupling conditions, such as Stille conditions with the N-alkyl-imidiazole stannane K. Compound L is converted to compound M by condensation with urea. The azaquinazolinedione compound M is converted to dichloro compound N using an appropriate chlorinating agent, such as POCl₃. Compound N is selectively hydrolyzed to form compound P under a variety of basic conditions, such as hydrolysis in a NaOH solution. Nucleophilic substitution of the chloride in compound P is carried out with an alcohol G-OH under a variety of basic conditions to form compound Q. For example, compound P can be treated with the sodium salt of the alcohol E. Additionally, compound P can be heated with the alcohol or phenol G-OH in the presence of CuI and CsCO₃ in an appropriate solvent to form compound Q.

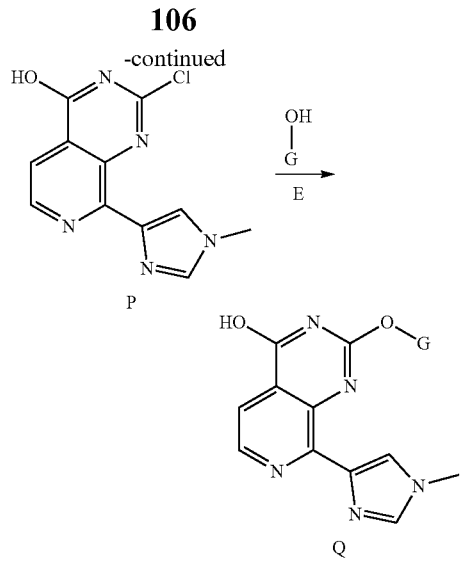

Referring to Scheme 3, compound R is converted to compound S by condensation with triethyl orthoformate. The compound U is prepared from aryl halide compound S using aryl coupling conditions, such as Stille conditions with the N-alkyl-imidiazole stannane T.

In each of the above reaction procedures or schemes, the various substituents may be selected from among the various substituents otherwise taught herein.

Pharmaceutical Compositions

In certain embodiments, a substituted pyrido[3,4-d]pyrimidin-4-one derivative compound as described by Formula (I) or (II) is administered as a pure chemical. In other embodiments, the substituted pyrido[3,4-d]pyrimidin-4-one derivative compound as described by Formula (I) or (II) is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and*

*Practice of Pharmacy* (Gennaro, 21$^{st}$ Ed. Mack Pub. Co., Easton, Pa. (2005)), the disclosure of which is hereby incorporated herein by reference, in its entirety.

Accordingly, provided herein is a pharmaceutical composition comprising at least one substituted pyrido[3,4-d] pyrimidin-4-one derivative compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I) or a pharmaceutically acceptable salt thereof. One embodiment provides a pharmaceutical composition comprising a pharmaceutically acceptable carrier and a compound of Formula (II) or a pharmaceutically acceptable salt thereof.

In certain embodiments, the substituted pyrido[3,4-d] pyrimidin-4-one derivative compound as described by Formula (I) or (II) is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, Pa. (2005)).

The dose of the composition comprising at least one substituted pyrido[3,4-d]pyrimidin-4-one derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses can typically range from about 1.0 mg to about 1000 mg, one to four times, or more, per day.

Histone Demethylase

Chromatin is the complex of DNA and protein that makes up chromosomes. Histones are the major protein component of chromatin, acting as spools around which DNA winds. Changes in chromatin structure are affected by covalent modifications of histone proteins and by non-histone binding proteins. Several classes of enzymes are known which can covalently modify histones at various sites.

Proteins can be post-translationally modified by methylation on amino groups of lysines and guanidino groups of arginines or carboxymethylated on aspartate, glutamate, or on the C-terminus of the protein. Post-translational protein methylation has been implicated in a variety of cellular processes such as RNA processing, receptor mediated signaling, and cellular differentiation. Post-translational protein methylation is widely known to occur on histones, such reactions known to be catalyzed by histone methyltransferases, which transfer methyl groups from S-adenyosyl methionine (SAM) to histones. Histone methylation is known to participate in a diverse range of biological processes including heterochromatin formation, X-chromosome inactivation, and transcriptional regulation (Lachner et al., (2003) J. Cell Sci. 116:2117-2124; Margueron et al., (2005) Curr. Opin. Genet. Dev. 15:163-176).

Unlike acetylation, which generally correlates with transcriptional activation, whether histone methylation leads to transcription activation or repression depends on the particular site of methylation and the degree of methylation (e.g., whether a particular histone lysine residue is mono-, di-, or tri-methylated). However, generally, methylation on H3K9, H3K27 and H4K20 is linked to gene silencing, while methylation on H3K4, H3K36, and H3K79 is generally associated with active gene expression. In addition, tri- and di-methylation of H3K4 generally marks the transcriptional start sites of actively transcribed genes, whereas mono-methylation of H3K4 is associated with enhancer sequences.

A "demethylase" or "protein demethylase," as referred to herein, refers to an enzyme that removes at least one methyl group from an amino acid side chain. Some demethylases act on histones, e.g., act as a histone H3 or H4 demethylase. For example, an H3 demethylase may demethylate one or more of H3K4, H3K9, H3K27, H3K36 and/or H3K79. Alternately, an H4 demethylase may demethylate histone H4K20. Demethylases are known which can demethylate either a mono-, di- and/or a tri-methylated substrate. Further, histone demethylases can act on a methylated core histone substrate, a mononucleosome substrate, a dinucleosome substrate and/or an oligonucleosome substrate, peptide substrate and/or chromatin (e.g., in a cell-based assay).

The first lysine demethylase discovered was lysine specific demethylase 1 (LSD1/KDM1), which demethylates both mono- and di-methylated H3K4 or H3K9, using flavin as a cofactor. A second class of Jumonji C (JmjC) domain containing histone demthylases were predicted, and confirmed when a H3K36 demethylase was found using a formaldehyde release assay, which was named JmjC domain containing histone demethylase 1 (JHDM1/KDM2A).

More JmjC domain-containing proteins were subsequently identified and they can be phylogenetically clustered into seven subfamilies: JHDM1, JHDM2, JHDM3, JMJD2, JARID, PHF2/PHF8, UTX/UTY, and JmjC domain only.

JMJD2 Family

The JMJD2 family of proteins are a family of histone-demethylases known to demethylate tri- and di-methylated H3-K9, and were the first identified histone tri-methyl demethylases. In particular, ectopic expression of JMJD2 family members was found to dramatically decrease levels of tri-and di-methylated H3-K9, while increasing levels of mono-methylated H3-K9, which delocalized Heterochromatin Protein 1 (HP1) and reduced overall levels of heterochromatin in vivo. Members of the JMJD2 subfamily of jumonji proteins include JMJD2C and its homologues JMJD2A, JMJD2B, JMJD2D and JMJD2E. Common structural features found in the JMJD2 subfamily of Jumonji proteins include the JmjN, JmjC, PHD and Tdr sequences.

JMJD2C, also known as GASC1 and KDM4C, is known to demethylate tri-methylated H3K9 and H3K36. Histone demethylation by JMJD2C occurs via a hydroxylation reaction dependent on iron and α-ketoglutarate, wherein oxidative decarboxylation of α-ketoglutarate by JMJD2C produces carbon dioxide, succinate, and ferryl and ferryl subsequently hydroxylates a methyl group of lysine H3K9, releasing formaldehyde. JMJD2C is known to modulate regulation of adipogenesis by the nuclear receptor PPARγ and is known to be involved in regulation of self-renewal in embryonic stem cells.

JARID Family

As used herein, a "JARID protein" includes proteins in the JARID1 subfamily (e.g., JARID1A, JARID1B, JARID1C and JARID1D proteins) and the JARID2 subfamily, as well as homologues thereof. A further description and listing of JARID proteins can be found in Klose et al. (2006) Nature Reviews/Genetics 7:715-727. The JARID1 family contains several conserved domains: JmjN, ARID, JmjC, PHD and a C5HC2 zing finger.

JARID1A, also called KDM5A or RBP2, was initially found as a binding partner of retinoblastoma (Rb) protein. JARID1A was subsequently found to function as a demethylase of tri- and di-methylated H3K4, and has been found to promote cell growth, while inhibiting senescence and differentiation. For instance, abrogation of JARID1A from mouse cells inhibits cell growth, induces senescence and differentiation, and causes loss of pluripotency of embryonic stem cells in vitro. JARID1A has been found to be overexpressed in gastric cancer and the loss of JARID1A has been found to reduce tumorigenesis in a mouse cancer model. Additionally, studies have demonstrated that loss of the retinoblastome binding protein 2 (RBP2) histone demethylase suppresses tumorigenesis in mice lacking Rb1 or Men1 (Lin et al. Proc. Natl. Acad. Sci. USA, Aug. 16, 2011, 108(33), 13379-86; doi: 10.1073/pnas.1110104108) and lead to the conclusion that RBP2-inhibitory drugs would have anti-cancer activity.

JARID1B, also referred to as KDM5B and PLU1, was originally found in experiments to discover genes regulated by the HER2 tyrosine kinase. JARID1B has consistently been found to be expressed in breast cancer cell lines, although restriction of JARID1B has been found in normal adult tissues, with the exception of the testis. In addition, 90% of invasive ductal carcinomas have been found to express JARID1B. In addition, JARID1B has been found to be up-regulated in prostate cancers, while having more limited expression in benign prostate, and has also been found to be up-regulated in bladder cancer and lung cancer (both SCLC and NSCLC). JARID1B has also been found to repress tumor suppressor genes such as BRCA1, CAV1 and 14-3-3σ, and knockdown of JARID1B was found to increase the levels of tri-methylated H3K4 at these genes.

In an additional embodiment is a method for inhibiting a histone-demethylase enzyme comprising contacting a histone demethylase enzyme with a compound of Formula (I) or a pharmaceutically acceptable salt thereof. In an additional embodiment is a method for inhibiting a histone-demethylase enzyme comprising contacting a histone demethylase enzyme with a compound of Formula (II) or a pharmaceutically acceptable salt thereof.

In an additional embodiment is the method for inhibiting a histone-demethylase enzyme, wherein the histone-demethylase enzyme comprises a JmjC domain. In an additional embodiment is the method for inhibiting a histone-demethylase enzyme, wherein the histone-demethylase enzyme is selected from JARID1A, JARID1B, JMJD2C, or JMJD2A.

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation. For example, in particular embodiments, the invention provides a method of treating a disease regulated by histone methylation and/or demethylation in a subject in need thereof by modulating the activity of a demethylase comprising a JmjC domain (e.g., a histone demethylase such as a JHDM protein(s)).

In an additional embodiment is a method for treating cancer in subject comprising administering a composition comprising a compound of Formula (I) or a pharmaceutically acceptable salt thereof. In an additional embodiment is a method for treating cancer in subject comprising administering a composition comprising a compound of Formula (II) or a pharmaceutically acceptable salt thereof.

In a further embodiment is the method for treating cancer in a subject wherein the cancer is selected from prostate cancer, breast cancer, bladder cancer, lung cancer or melanoma.

In an additional embodiment is a method for inhibiting the growth of a tumor comprising administering a composition comprising a compound of Formula (I) or (II), or a pharmaceutically acceptable salt thereof, wherein the tumor is characterized by a loss of retinoblastoma gene (RB1) function.

In an additional embodiment is a method for inhibiting the growth of a tumor comprising administering a composition comprising a compound of Formula (I) or (II), or a pharmaceutically acceptable salt thereof, wherein the tumor is characterized by a loss of multiple endocrine neoplasia type 1 gene (Men1) function.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Preparation 1A:
pyrido[3,4-d]pyridine-2,4(1H,3H)-dione

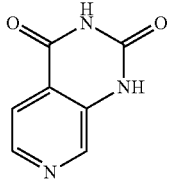

To a solution of 3-aminopyridine-4-carboxamide (5 g, 36.5 mmol) in THF (100 mL) was added triphosgene (11.9 g, 40.1 mmol) and TEA (7.4 g, 73 mmol). The reaction mixture was refluxed for 2 h. The solution was concentrated in vacuo and the residue was triturated in water. The solid was filtered and washed with water and THF. The solid was dried to give 4.1 g (70%) of the title compound. $^1$H NMR (400 MHz, DMSO-d$_6$): δ 11.62 (s, 1H), 11.58 (s, 1H), 8.66 (s, 1H), 8.40 (d, 1H, J=5.2 Hz), 7.80 (d, 1H, J=5.2 Hz).

Preparation 1B:
2,4-dichloropyrido[3,4-d]pyrimidine

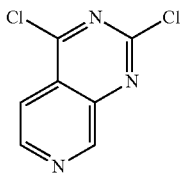 [SMILES: Clc1nc(Cl)c2ccncc2n1]

To a mixture of pyrido[3,4-d]pyridine-2,4(1H,3H)-dione (2.0 g, 12.3 mmol) in toluene (50 mL) was added DIEA (3.15 g, 25 mmol) and POCl$_3$ (9.5 g, 61.4 mmol). The reaction mixture was refluxed overnight. The solution was concentrated in vacuo and the residue was taken in ethyl acetate, washed with aq. NaHCO$_3$ and brine. The organics were dried and concentrated. The residue was purified by silica gel chromatography (25% EA:PE) to give 1.0 g (41%) of the title compound. $^1$H NMR (400 MHz, DMSO-d$_6$): δ 9.50 (s, 1H), 8.90 (d, 1H, J=5.2 Hz), 8.02 (d, 1H, J=5.2 Hz).

Preparation 1C:
2-chloropyrido[3,4-d]pyrimidin-4-ol

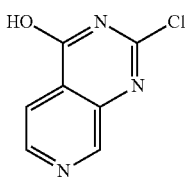

To a solution of 2,4-dichloropyrido[3,4-d]pyrimidine (1 g, 5 mmol) in THF (20 mL) was added a solution of NaOH (0.5 g, 12.5 mmol) in water (20 mL). The reaction mixture was stirred at rt for 2 h. The solution was adjusted to pH=2 using 5N HCl and the resulting precipitate was filtered and washed with water and THF, and dried to give 0.8 g (88%) of the title compound. $^1$H NMR (400 MHz, DMSO-d$_6$): δ 13.61 (s, 1H), 8.99 (s, 1H), 8.69 (d, 1H, J=5.2 Hz), 7.94 (d, 1H, J=5.2 Hz).

Example 1: 2-propan-2-yloxy-3H-pyrido[3,4-d]pyrimidin-4-one

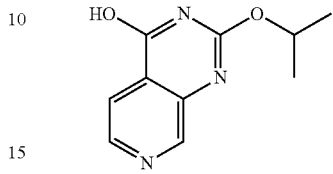

To a flask was added isopropanol (5 ml) and Na (20 mg, 0.87 mmol). The reaction mixture was heated to 60° C. and stirred for 30 minutes until Na had disappeared. 2-Chloropyrido[3,4-d]pyrimidin-4-ol (80 mg, 0.43 mmol) was added to the mixture and stirred at 90° C. for 2 h. The solution was concentrated in vacuo and purified by silica gel chromatography (5% MeOH/DCM) to give 43 mg (48%) of the title compound as white solid. $^1$H NMR (400 MHz, DMSO-d$_6$): δ 1.37 (6H, d, J=6 Hz), 5.38-5.41 (1H, m), 7.83 (1H, d, J=5.2 Hz), 8.48 (1H, d, J=4.8 Hz), 8.83 (1H, s), 12.51 (1H, s). [M+H] Calc'd for C$_{19}$H$_{11}$N$_3$O$_2$, 206; Found, 206.

Example 2: 2-ethoxypyrido[3,4-d]pyrimidin-4-ol

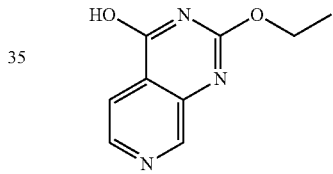

To a solution of 2-chloropyrido[3,4-d]pyrimidin-4-ol (100 mg, 0.55 mmol) in ethanol (20 mL) was added EtONa (150 mg, 2.77 mmol) and the mixture was refluxed overnight. The solution was concentrated in vacuo. The residue was purified by silica gel chromatography (3% MeOH/DCM) to give 50 mg (44%) of the title compound as white solid. $^1$H NMR (400 MHz, DMSO-d$_6$): δ 12.61 (s, 1H), 8.84 (s, 1H), 8.50 (d, 1H, J=5.2 Hz), 7.85 (d, 1H, J=5.2 Hz), 4.47 (q, 2H, J=6.8 Hz), 1.36 (t, 3H, J=6.8 Hz). [M+H] Calc'd for C$_9$H$_9$N$_3$O$_2$, 192; Found, 192.

Example 3: 2-(2-hydroxyethoxy)pyrido[3,4-d]pyrimidin-4-ol

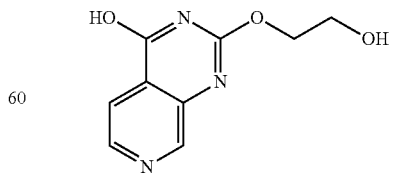

To a flask was added ethane-1,2-diol (5 mL) and Na (50 mg, 2.2 mmol). The reaction mixture was stirred until Na was dissolved. 2-Chloropyrido[3,4-d]pyrimidin-4-ol (80 mg, 0.45 mmol) was added and the reaction mixture was stirred at 80° C. overnight. The solution was concentrated in vacuo. The residue was purified by preparative HPLC to afford 20 mg (22%) of the title compound as white solid. $^1$H NMR (400 MHz, DMSO-d$_6$): δ 12.66 (s, 1H), 8.84 (s, 1H), 8.49 (d, 1H, J=5.2 Hz), 7.85 (d, 1H, J=5.2 Hz), 4.91 (s, 1H), 4.46 (t, 2H, J=3.6 Hz), 3.75 (t, 2H, J=3.6 Hz). [M+H] Calc'd for C$_{10}$H$_{11}$N$_3$O$_2$, 208; Found, 208.

Example 4: 2-phenylmethoxypyrido[3,4-d]pyrimidin-4-ol

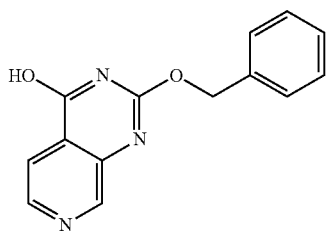

To a solution of benzyl alcohol (360 mg, 3.3 mmol) in DMF (10 mL) was added NaH (170 mg, 4.3 mmol). The reaction mixture was stirred at rt for 30 min. 2-Chloropyrido[3,4-d]pyrimidin-4-ol (150 mg, 0.83 mmol) was added and the mixture was stirred at 80° C. overnight. The solution was concentrated in vacuo and purified by silica gel chromatography (3% MeOH/DCM) to give 85 mg (40%) of the title compound as white solid. $^1$H NMR (400 MHz, DMSO-d$_6$): δ 12.71 (s, 1H), 8.89 (s, 1H), 8.50 (d, 1H, J=5.2 Hz), 7.86 (d, 1H, J=5.2 Hz), 7.53-7.36 (m, 5H), 5.50 (s, 2H). [M+H] Calc'd for C$_{10}$H$_{11}$N$_3$O$_2$, 254; Found, 254.

Example 5: 2-(cyclopropylmethoxy)-3H-pyrido[3,4-d]pyrimidin-4-one

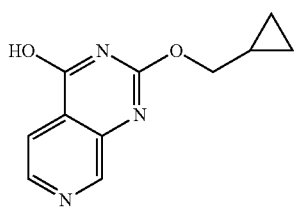 [SMILES: Oc1nc(OCC2CC2)nc2cnccc12]

The title compound was prepared in 41% yield from cyclopropylmethanol and 2-chloropyrido[3,4-d]pyrimidin-4-ol according to the procedure for the preparation of Example 1. $^1$H NMR (400 MHz, DMSO-d$_6$): δ 0.38-0.42 (2H, m), 0.57-0.62 (2H, m), 1.27-1.30 (1H, m), 4.27 (2H, d, J=7.2 Hz), 7.83 (1H, d, J=5.2 Hz), 8.48 (1H, d, J=5.2 Hz), 8.82 (1H, s), 12.64 (1H, s). [M+H] Calc'd for C$_{11}$H$_{11}$N$_3$O$_2$, 218; Found, 218.

Example 6: 2-cyclopentyloxy-3H-pyrido[3,4-d]pyrimidin-4-one

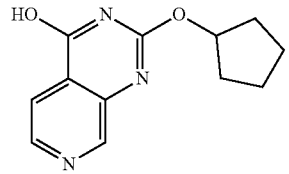 [SMILES: Oc1nc(OC2CCCC2)nc2cnccc12]

The title compound was prepared in 33% yield from cyclopentanol and 2-chloropyrido[3,4-d]pyrimidin-4-ol according to the procedure for the preparation of Example 1. $^1$H NMR (400 MHz, DMSO-d$_6$): δ 1.61-1.64 (2H, m), 1.70-1.74 (2H, m), 1.80-1.82 (2H, m), 1.96-1.99 (2H, m), 5.52-5.53 (1H, m), 7.83 (1H, d, J=5.2 Hz), 8.48 (1H, d, J=5.2 Hz), 8.83 (1H, s), 12.50 (1H, s). [M+H] Calc'd for C$_{12}$H$_{13}$N$_3$O$_2$, 232; Found, 232.

Example 7: 2-propoxy-3H-pyrido[3,4-d]pyrimidin-4-one

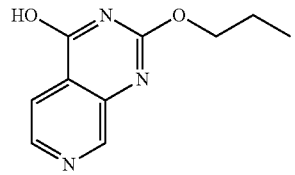

The title compound was prepared in 24% yield from propan-1-ol and 2-chloropyrido[3,4-d]pyrimidin-4-ol according to the procedure for the preparation of Example 1. $^1$H NMR (400 MHz, DMSO-d$_6$): δ 0.98 (3H, t, J=7.2 Hz), 1.73-1.79 (2H, m), 4.38 (2H, t, J=6.8 Hz), 7.84 (1H, d, J=5.2 Hz), 8.49 (1H, d, J=5.2 Hz), 8.83 (1H, s), 12.61 (1H, s). [M+H] Calc'd for C$_{10}$H$_{11}$N$_3$O$_2$, 206; Found, 206.

Example 8: 2-methoxypyrido[3,4-d]pyrimidin-4-ol

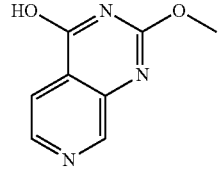

To a solution of chloropyrido[3,4-d]pyrimidin-4-ol (100 mg, 0.55 mmol) in methanol (20 mL) was added MeONa (150 mg, 2.77 mmol) and the reaction mixture was refluxed overnight. The solvent was removed and the residue was purified by silica gel chromatography (3% MeOH:DCM) to give 25 mg (26%) of the title compound. $^1$H NMR (400 MHz, DMSO-d$_6$): 12.66 (s, 1H), 8.82 (s, 1H), 8.52 (d, 1H, J=5.2 Hz), 7.80 (d, 1H, J=5.2 Hz), 4.02 (s, 3H). [M+H] Calc'd for C$_8$H$_7$N$_3$O$_2$, 178; Found, 178.

Example 9: 2-butan-2-yloxy-3H-pyrido[3,4-d]pyrimidin-4-one

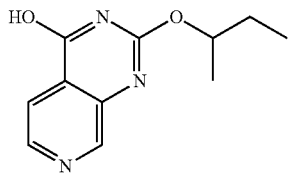 [SMILES: CCC(C)Oc1nc(O)c2ccncc2n1]

The title compound was prepared in 83% yield from butan-2-ol and 2-chloropyrido[3,4-d]pyrimidin-4-ol according to the procedure for the preparation of Example 1. $^1$H NMR (400 MHz, DMSO-$d_6$): δ 0.94 (3H, t, J=7.6 Hz), 1.34 (3H, d, J=6.4 Hz), 1.68-1.72 (2H, m), 5.21-5.24 (1H, m), 7.83 (1H, d, J=5.2 Hz), 8.48 (1H, d, J=5.2 Hz), 8.82 (1H, s), 12.52 (1H, s). [M+H] Calc'd for $C_{11}H_{13}N_3O_2$, 220; Found, 220.

Example 10: 2-(2-phenoxyethoxy)-3H-pyrido[3,4-d]pyrimidin-4-one

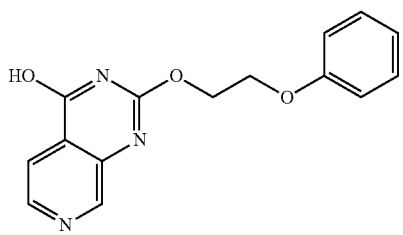 [SMILES: Oc1nc(OCCOc2ccccc2)nc2cnccc12]

Sodium hydride (45 mg, 1.12 mmol) was added to 2-phenoxyethanol (0.5 mL) in DMF (1 mL). The reaction was stirred for 20 min and 2-chloropyrido[3,4-d]pyrimidin-4-ol (25 mg, 0.14 mmol) was added. The mixture was stirred at 120° C. for 16 h. Water (0.2 mL) was added and the solvent was concentrated. The residue was purified by flash chromatography (0-15% MeOH:DCM) to give 19 mg of the desired product as a beige solid (24%). $^1$H NMR (400 MHz, DMSO-$d_6$): δ 4.26-4.44 (m, 2H), 4.77 (br. s., 2H), 6.89-7.04 (m, 3H), 7.31 (t, J=7.58 Hz, 2H), 7.85 (d, J=5.05 Hz, 1H), 8.49-8.53 (m, 1H), 8.85 (s, 1H), 12.74 (br. s., 1H). [M+H] Calc'd for $C_{15}H_{13}N_3O_3$, 284; Found, 284.

Example 11: 2-(cyclobutylmethoxy)-3H-pyrido[3,4-d]pyrimidin-4-one

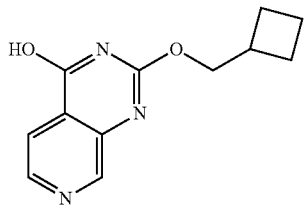 [SMILES: Oc1nc(OCC2CCC2)nc2cnccc12]

The title compound was prepared in 16% yield from cyclobutylmethanol and 2-chloropyrido[3,4-d]pyrimidin-4-ol according to the procedure for the preparation of Example 10. [M+H] Calc'd for $C_{12}H_{13}N_3O_2$, 232; Found, 232.

Example 12: 2-(2,2,2-trifluoroethoxy)pyrido[3,4-d]pyrimidin-4-ol

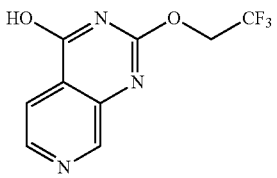 [SMILES: Oc1nc(OCC(F)(F)F)nc2cnccc12]

The title compound was prepared in 48% yield from 2,2,2-trifluoroethanol and 2-chloropyrido[3,4-d]pyrimidin-4-ol according to the procedure for the preparation of Example 1. $^1$H NMR (400 MHz, DMSO-$d_6$): δ 5.13-5.20 (2H, m), 7.88 (1H, d, J=6.4 Hz), 8.56 (1H, d, J=4.8 Hz), 8.88 (1H, s), 13.05 (1H, s). [M+H] Calc'd for $C_9H_6F_3N_3O_2$, 258; Found, 258.

Example 13: 2-(3,3,3-trifluoropropoxy)pyrido[3,4-d]pyrimidin-4-ol

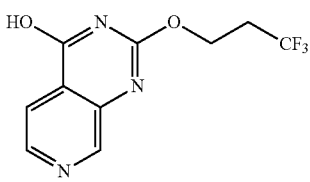

The title compound was prepared in 50% yield from 3,3,3-trifluoropropan-1-ol and 2-chloropyrido[3,4-d]pyrimidin-4-ol according to the procedure for the preparation of Example 1. $^1$H NMR (300 MHz, DMSO-$d_6$): δ 2.81-2.92 (2H, m), 4.55 (2H, t, J=6.0 Hz), 7.85 (1H, d, J=5.1 Hz), 8.52 (1H, d, J=5.1 Hz), 8.86 (1H, s), 12.77 (1H, s). [M+H] Calc'd for $C_{10}H_8F_3N_3O_2$, 260; Found, 260.

Example 14: 2-(2-methylpropoxy)pyrido[3,4-d]pyrimidin-4-ol

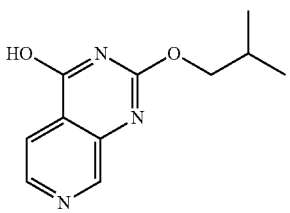 [SMILES: CC(C)COc1nc(O)c2ccncc2n1]

The title compound was prepared in 26% yield from 2-methylpropan-1-ol and 2-chloropyrido[3,4-d]pyrimidin-4-ol according to the procedure for the preparation of Example 1. $^1$H NMR (400 MHz, DMSO-$d_6$): δ 0.99 (6H, d, J=6.8 Hz), 2.04-2.08 (1H, m), 4.20 (2H, d, J=6.8 Hz), 7.83 (1H, d, J=5.2 Hz), 8.48 (1H, d, J=5.2 Hz), 8.83 (1H, s), 12.61 (1H, s). [M+H] Calc'd for $C_{11}H_{13}N_3O_2$, 220; Found, 220.

Example 15: 2-(3-methylbutoxy)pyrido[3,4-d]pyrimidin-4-ol

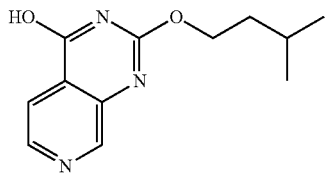

The title compound was prepared in 58% yield from 3-methylbutan-1-ol and 2-chloropyrido[3,4-d]pyrimidin-4-ol according to the procedure for the preparation of Example 1. $^1$H NMR (400 MHz, DMSO-$d_6$): δ 0.94 (6H, d, J=6.8 Hz), 1.62-1.66 (2H, m), 1.75-1.78 (1H, m), 4.46 (2H, t, J=6.8 Hz), 7.83 (1H, d, J=5.2 Hz), 8.48 (1H, d, J=5.2 Hz), 8.83 (1H, s), 12.59 (1H, s). [M+H] Calc'd for $C_{12}H_{15}N_3O_2$, 234; Found, 234.

Example 16: 2-(2-methylbutoxy)pyrido[3,4-d]pyrimidin-4-ol

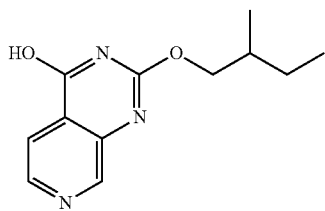

The title compound was prepared in 71% yield from 2-methylbutan-1-ol and 2-chloropyrido[3,4-d]pyrimidin-4-ol according to the procedure for the preparation of Example 1. $^1$H NMR (400 MHz, DMSO-$d_6$): δ 0.92 (3H, t, J=8.0 Hz), 0.97 (3H, d, J=6.8 Hz), 1.20-1.27 (1H, m), 1.47-1.53 (1H, m), 1.82-1.87 (1H, m), 4.20-4.32 (2H, m), 7.83 (1H, d, J=5.2 Hz), 8.48 (1H, d, J=5.2 Hz), 8.83 (1H, s), 12.60 (1H, s). [M+H] Calc'd for $C_{12}H_{15}N_3O_2$, 234; Found, 234.

Example 17: 2-(2-phenylpropoxy)pyrido[3,4-d]pyrimidin-4-ol

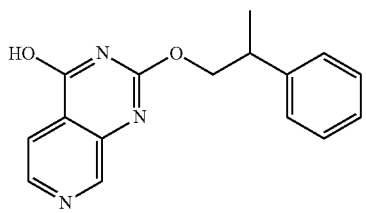 [SMILES: CC(COc1nc(O)c2ccncc2n1)c1ccccc1]

The title compound was prepared in 72% yield from 2-phenylpropan-1-ol and 2-chloropyrido[3,4-d]pyrimidin-4-ol according to the procedure for the preparation of Example 1. $^1$H NMR (400 MHz, DMSO-$d_6$): δ 1.33 (3H, d, J=6.8 Hz), 3.25-3.28 (1H, m), 4.45-4.57 (2H, m), 7.21-7.25 (1H, m), 7.31-7.38 (4H, m), 7.82 (1H, d, J=5.2 Hz), 8.48 (1H, d, J=5.2 Hz), 8.83 (1H, s), 12.62 (1H, s). [M+H] Calc'd for $C_{16}H_{15}N_3O_2$, 282; Found, 282.

Example 18: 2-(2-phenylethoxy)pyrido[3,4-d]pyrimidin-4-ol

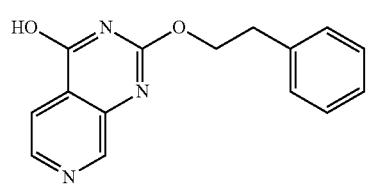 [SMILES: Oc1nc(OCCc2ccccc2)nc2cnccc12]

The title compound was prepared in 27% yield from 2-phenylethanol and 2-chloropyrido[3,4-d]pyrimidin-4-ol according to the procedure for the preparation of Example 1. $^1$H NMR (400 MHz, DMSO-$d_6$): δ 3.08 (2H, t, J=6.8 Hz), 4.63 (2H, t, J=7.2 Hz), 7.23-7.25 (1H, m), 7.30-7.36 (4H, m), 7.83 (1H, d, J=5.2 Hz), 8.49 (1H, d, J=5.2 Hz), 8.84 (1H, s), 12.64 (1H, s). [M+H] Calc'd for $C_{15}H_{13}N_3O_2$, 268; Found, 268.

Example 19: 2-(1-phenylpropan-2-yloxy)pyrido[3,4-d]pyrimidin-4-ol

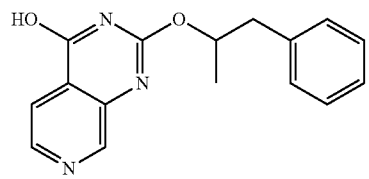 [SMILES: CC(Cc1ccccc1)Oc1nc(O)c2ccncc2n1]

The title compound was prepared in 19% yield from 1-phenylpropan-2-ol and 2-chloropyrido[3,4-d]pyrimidin-4-ol according to the procedure for the preparation of Example 1. $^1$H NMR (400 MHz, DMSO-$d_6$): δ 1.34 (3H, d, J=6 Hz), 2.93-3.08 (2H, m), 5.44-5.49 (1H, m), 7.20-7.22 (1H, m), 7.28-7.34 (4H, m), 7.81 (1H, d, J=5.2 Hz), 8.47 (1H, d, J=5.2 Hz), 8.82 (1H, s), 12.56 (1H, s). [M+H] Calc'd for $C_{16}H_{15}N_3O_2$, 282; Found, 282.

Example 20: 2-(4,4,4-trifluorobutoxy)pyrido[3,4-d]pyrimidin-4-ol

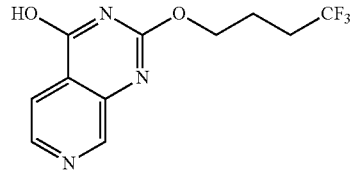 [SMILES: Oc1nc(OCCCC(F)(F)F)nc2cnccc12]

The title compound was prepared in 63% yield from 4,4,4-trifluorobutan-1-ol and 2-chloropyrido[3,4-d]pyrimidin-4-ol according to the procedure for the preparation of Example 1. $^1$H NMR (300 MHz, DMSO-$d_6$): δ 1.95-2.03 (2H, m), 2.40-2.50 (2H, m), 4.48 (2H, t, J=6.3 Hz), 7.85 (1H, d, J=5.1 Hz), 8.50 (1H, d, J=5.1 Hz), 8.84 (1H, s), 12.64 (1H, s). [M+H] Calc'd for $C_{11}H_{10}F_3N_3O_2$, 274; Found, 274.

Example 21: 2-[3-(dimethylamino)propoxy]pyrido[3,4-d]pyrimidin-4-ol

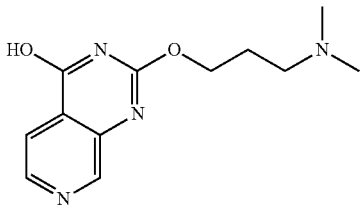 [SMILES: CN(C)CCCOc1nc(O)c2ccncc2n1]

Sodium hydride (45 mg, 1.12 mmol) was added to 3-(dimethylamino)propan-1-ol (0.5 mL) in dioxane (1 mL) at 0° C. The reaction was stirred for 20 min and 2-chloropyrido[3,4-d]pyrimidin-4-ol (50 mg, 0.28 mmol) was added. The mixture was stirred at 120° C. for 16 h. The reaction mixture was cooled to ambient temperature. The reaction was quenched with ice water (0.2 mL). The reaction mixture was concentrated in vacuo and purified by silica gel chromatography (0% to 20% MeOH:DCM) to give 13 mg (19%) of the title compound as white solid. $^1$H NMR (400 MHz, DMSO-$d_6$) δ 1.97-2.09 (m, 2H), 2.46 (s, 6H), 2.73-2.79 (m, 2H), 4.47 (t, J=6.57 Hz, 2H), 7.85 (d, J=5.31 Hz, 1H), 8.50 (d, J=5.31 Hz, 1H), 8.84 (s, 1H).

Example 22: 2-(2-methoxyethoxy)pyrido[3,4-d]pyrimidin-4-ol

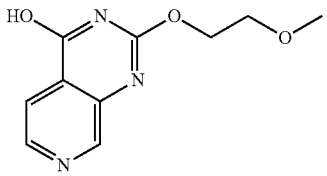

The title compound was prepared in 49% yield from 2-methoxyethanol and 2-chloropyrido[3,4-d]pyrimidin-4-ol according to the procedure for the preparation of Example 21. $^1$H NMR (400 MHz, DMSO-$d_6$): δ 3.31 (s, 3H), 3.63-3.76 (m, 2H), 4.49-4.63 (m, 2H), 7.84 (d, J=5.05 Hz, 1H), 8.50 (d, J=5.31 Hz, 1H), 8.84 (s, 1H), 12.69 (br. s., 1H).

Example 23: 2-[2-(2,2,2-trifluoroethoxy)ethoxy]pyrido[3,4-d]pyrimidin-4-ol

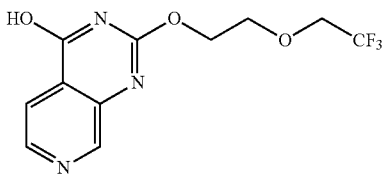 [SMILES: Oc1nc(OCCOCC(F)(F)F)nc2cnccc12]

The title compound was prepared in 54% yield from 2-(2,2,2-trifluoroethoxy)ethanol and 2-chloropyrido[3,4-d]pyrimidin-4-ol according to the procedure for the preparation of Example 21. $^1$H NMR (400 MHz, DMSO-$d_6$): δ 3.94-4.03 (m, 2H), 4.17 (q, J=9.52 Hz, 2H), 4.59 (dt, J=4.11, 2.37 Hz, 2H), 7.85 (d, J=5.31 Hz, 1H), 8.50 (d, J=5.05 Hz, 1H), 8.84 (s, 1H), 12.73 (br. s., 1H).

Example 24: 2-(3-hydroxy-3-methylbutoxy)pyrido[3,4-d]pyrimidin-4-ol

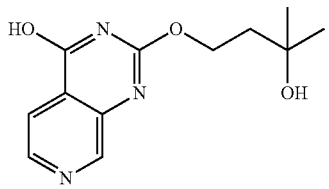

The title compound was prepared in 52% yield from 3-methylbutane-1,3-diol and 2-chloropyrido[3,4-d]pyrimidin-4-ol according to the procedure for the preparation of Example 21. $^1$H NMR (400 MHz, DMSO-$d_6$): δ 1.17 (s, 6H), 1.86 (t, J=7.33 Hz, 2H), 4.53 (t, J=7.33 Hz, 2H), 7.84 (d, J=5.05 Hz, 1H), 8.49 (d, J=5.05 Hz, 1H), 8.85 (s, 1H), 12.60 (s, 1H).

Example 25: 2-(3-hydroxy-2-methylpropoxy)pyrido[3,4-d]pyrimidin-4-ol

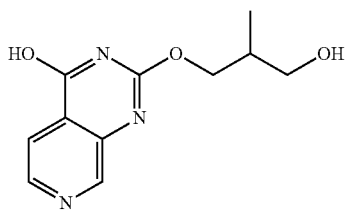 [SMILES: CC(CO)COc1nc(O)c2ccncc2n1]

The title compound was prepared in 36% yield from 2-methylpropane-1,3-diol and 2-chloropyrido[3,4-d]pyrimidin-4-ol according to the procedure for the preparation of Example 21. $^1$H NMR (400 MHz, DMSO-$d_6$): δ 0.96 (d, J=6.82 Hz, 3H), 1.97-2.10 (m, 1H), 4.26 (dd, J=10.36, 6.57 Hz, 1H), 4.31 (t, J=5.31 Hz, 1H), 4.40 (dd, J=10.36, 6.06 Hz, 1H), 4.62 (t, J=5.31 Hz, 1H), 7.84 (d, J=5.05 Hz, 2H), 8.49 (d, J=5.05 Hz, 2H), 8.84 (s, 2H), 12.62 (s, 2H).

Example 26: 2-(oxolan-2-ylmethoxy)pyrido[3,4-d]pyrimidin-4-ol

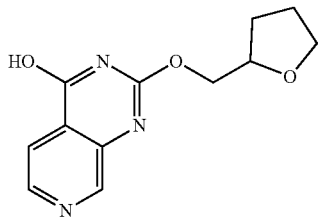 [SMILES: Oc1nc(OCC2CCCO2)nc2cnccc12]

The title compound was prepared in 23% yield from tetrahydrofuran-2-ylmethanol and 2-chloropyrido[3,4-d]pyrimidin-4-ol according to the procedure for the preparation of Example 21. $^1$H NMR (400 MHz, DMSO-$d_6$): δ 1.62-2.05 (m, 4H), 3.69 (s, 1H), 3.80 (d, J=7.83 Hz, 1H), 4.16-4.24 (m, 1H), 4.36 (d, J=6.82 Hz, 1H), 4.43 (d, J=3.54 Hz, 1H), 7.84 (d, J=5.05 Hz, 1H), 8.50 (d, J=5.05 Hz, 1H), 8.83 (s, 1H), 12.70 (s, 1H).

Example 27: 2-(oxolan-3-ylmethoxy)pyrido[3,4-d]pyrimidin-4-ol

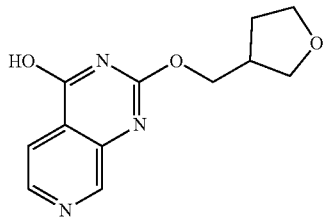 [SMILES: Oc1nc(OCC2CCOC2)nc2cnccc12]

The title compound was prepared in 13% yield from tetrahydrofuran-3-ylmethanol and 2-chloropyrido[3,4-d]pyrimidin-4-ol according to the procedure for the preparation of Example 21. $^1$H NMR (400 MHz, DMSO-$d_6$): δ 1.56-1.77 (m, 1H), 1.91-2.11 (m, 1H), 3.49-3.59 (m, 1H), 3.60-3.71 (m, 2H), 3.74-3.81 (m, 2H), 4.28-4.36 (m, 1H), 4.36-4.47 (m, 1H), 7.79-7.90 (m, 1H), 8.49 (d, J=5.05 Hz, 1H), 8.84 (s, 1H), 12.65 (s, 1H).

Example 28: N-[2-(4-hydroxypyrido[3,4-d]pyrimidin-2-yl)oxyethyl]-N-methylacetamide

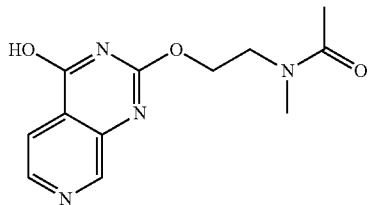

The title compound was prepared in 26% yield from N-(2-hydroxyethyl)-N-methylacetamide and 2-chloropyrido[3,4-d]pyrimidin-4-ol according to the procedure for the preparation of Example 21. $^1$H NMR (400 MHz, DMSO-$d_6$): δ 2.01 (d, J=5.00 Hz, 3H), 2.86 (d, J=10.00 Hz, 3H), 3.63-3.76 (m, 1H), 4.48-4.63 (m, 1H), 7.85 (dd, J=5.18, 2.65 Hz, 1H), 8.51 (dd, J=5.05, 4.04 Hz, 1H), 8.84 (s, 1H), 12.73 (d, J=5.50 Hz, 1H). [M+H] Calc'd for $C_{12}H_{14}N_3O_4$, 263; Found, 263.

Example 29: 2-(2-propan-2-yloxyethoxy)pyrido[3,4-d]pyrimidin-4-ol

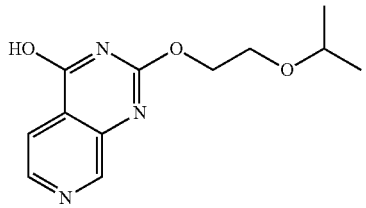 [SMILES: CC(C)OCCOc1nc(O)c2ccncc2n1]

The title compound was prepared in 51% yield from 2-(propan-2-yloxy)ethanol and 2-chloropyrido[3,4-d]pyrimidin-4-ol according to the procedure for the preparation of Example 21. $^1$H NMR (400 MHz, DMSO-$d_6$): δ 1.10 (d, J=6.06 Hz, 6H), 3.57-3.68 (m, 1H), 3.69-3.76 (m, 2H), 4.52 (dd, J=5.31, 3.79 Hz, 2H), 7.84 (d, J=5.05 Hz, 1H), 8.50 (d, J=5.05 Hz, 1H), 8.84 (s, 1H), 12.69 (s, 1H). [M+H] Calc'd for $C_{12}H_{15}N_3O_3$, 250; Found, 250.

Example 30: 2-(2-phenylmethoxyethoxy)pyrido[3,4-d]pyrimidin-4-ol

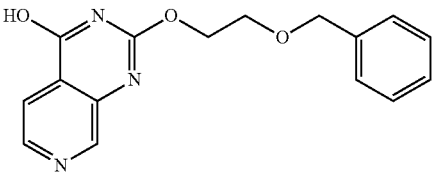 [SMILES: Oc1nc(OCCOCc2ccccc2)nc2cnccc12]

The title compound was prepared in 61% yield from 2-(benzyloxy)ethanol and 2-chloropyrido[3,4-d]pyrimidin-4-ol according to the procedure for the preparation of Example 21. $^1$H NMR (400 MHz, DMSO-$d_6$): δ 3.76-3.85 (m, 2H), 4.56 (s, 2H), 4.58-4.63 (m, 2H), 7.20-7.40 (m, 5H), 7.84 (d, J=5.05 Hz, 1H), 8.50 (d, J=5.05 Hz, 1H), 8.83 (s, 1H), 12.73 (br. s., 1H). [M+H] Calc'd for $C_{16}H_{15}N_3O_3$, 298; Found, 298.

Example 31: N-[2-(4-hydroxypyrido[3,4-d]pyrimidin-2-yl)oxyethyl]benzamide

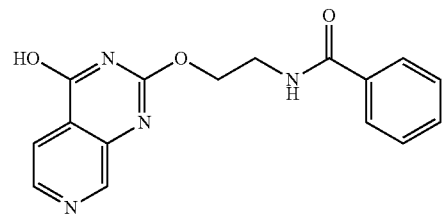

The title compound was prepared in 23% yield from N-(2-hydroxyethyl)benzamide and 2-chloropyrido[3,4-d]pyrimidin-4-ol according to the procedure for the preparation of Example 21. $^1$H NMR (400 MHz, DMSO-$d_6$): δ 3.70 (q, J=5.47 Hz, 2H), 4.60 (t, J=5.56 Hz, 2H), 7.43-7.48 (m, 2H), 7.50-7.55 (m, 1H), 7.81-7.96 (m, 3H), 8.50 (d, J=5.05 Hz, 1H), 8.62-8.70 (m, 1H), 8.82 (s, 1H), 12.67 (s, 1H). [M+H] Calc'd for $C_{16}H_{14}N_4O_3$, 311; Found, 311.

Example 32: 3-[(4-hydroxypyrido[3,4-d]pyrimidin-2-yl)oxymethyl]benzonitrile

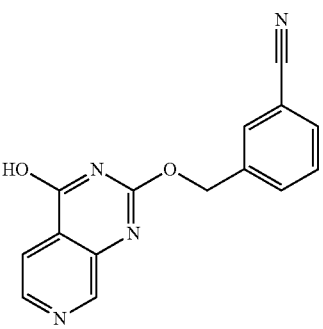 [SMILES: N#Cc1cccc(COc2nc(O)c3ccncc3n2)c1]

The title compound was prepared in 42% yield from 3-hydroxymethyl)benzonitrile and 2-chloropyrido[3,4-d]pyrimidin-4-ol according to the procedure for the preparation of Example 21. $^1$H NMR (400 MHz, DMSO-$d_6$): δ 5.56 (s, 2H), 7.66 (d, J=7.83 Hz, 1H), 7.83-7.92 (m, 3H), 8.02 (s, 1H), 8.52 (d, J=5.05 Hz, 1H), 8.88 (s, 1H), 12.77 (br. s., 1H). [M+H] Calc'd for $C_{15}H_{10}N_4O_2$, 279; Found, 279.

Example 33: 2-[(1-methylpyrazol-3-yl)methoxy]pyrido[3,4-d]pyrimidin-4-ol

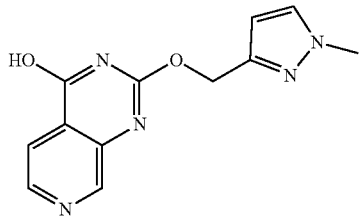 [SMILES: Cn1ccc(COc2nc(O)c3ccncc3n2)n1]

The title compound was prepared in 43% yield from (1-methyl-1H pyrazol-3-yl)methanol and 2-chloropyrido[3,4-d]pyrimidin-4-ol according to the procedure for the preparation of Example 21. $^1$H NMR (400 MHz, DMSO-$d_6$): δ 3.84 (s, 3H), 5.40 (s, 2H), 6.40 (d, J=2.02 Hz, 1H), 7.69 (d, J=2.27 Hz, 1H), 7.85 (d, J=5.05 Hz, 1H), 8.51 (d, J=5.05 Hz, 1H), 8.90 (s, 1H), 12.65 (s, 1H). [M+H] Calc'd for $C_{12}H_{11}N_5O_2$, 258; Found, 258.

Example 34: 2-phenoxypyrido[3,4-d]pyrimidin-4-ol

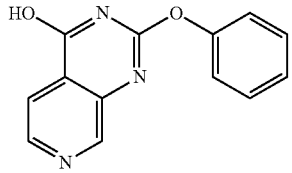

To a solution of 2-chloropyrido[3,4-d]pyrimidin-4-ol (100 mg, 0.55 mmol) in DMF (5 mL) was added phenol (260 mg, 2.7 mmol), CuI (105 mg, 0.55 mmol) and $Cs_2CO_3$ (360 mg, 1.1 mmol). The reaction mixture was refluxed for 3 h and concentrated. The residue was purified by silica gel chromatography (0% to 3% MeOH:DCM) to give 35 mg (26%) of the title compound as a light pink solid. $^1$H NMR (400 MHz, DMSO-$d_6$): δ 13.11 (s, 1H), 8.66 (s, 1H), 8.52 (d, 1H, J=5.2 Hz), 7.89 (d, 1H, J=5.2 Hz), 7.53-7.31 (m, 5H). [M+H] Calc'd for $C_{13}H_9N_3O_2$, 240; Found, 240.

Example 35: N-[4-(4-hydroxypyrido[3,4-d]pyrimidin-2-yl)oxyphenyl]acetamide

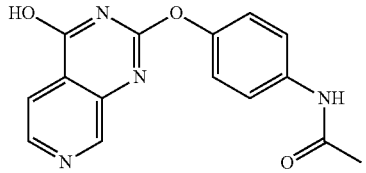 [SMILES: CC(=O)Nc1ccc(Oc2nc(O)c3ccncc3n2)cc1]

The title compound was prepared in 15% yield from N-(4-hydroxyphenyl)acetamide and 2-chloropyrido[3,4-d]pyrimidin-4-ol according to the procedure for the preparation of Example 34. $^1$H NMR (400 MHz, DMSO-$d_6$): δ 2.07 (s, 3H), 7.26 (d, J=8.84 Hz, 2H), 7.65 (d, J=8.84 Hz, 2H), 7.88 (d, J=5.05 Hz, 1H), 8.52 (d, J=5.31 Hz, 1H), 8.69 (s, 1H), 10.06 (s, 1H), 13.09 (br. s., 1H). [M+H] Calc'd for $C_{15}H_{12}N_4O_3$, 297; Found, 297.

Example 36: tert-butyl N-[3-(4-hydroxypyrido[3,4-d]pyrimidin-2-yl)oxyphenyl]carbamate

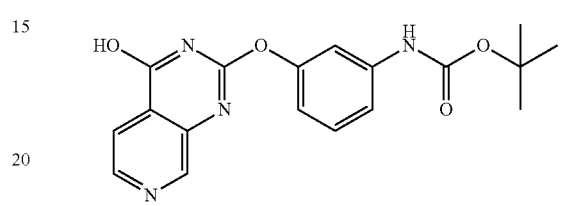

The title compound was prepared in 13% yield from tert-butyl(3-hydroxyphenyl)carbamate and 2-chloropyrido[3,4-d]pyrimidin-4-ol according to the procedure for the preparation of Example 34. $^1$H NMR (400 MHz, DMSO-$d_6$): δ 1.47 (s, 9H), 6.90-6.99 (m, 1H), 7.34 (d, J=5.31 Hz, 2H), 7.48 (s, 1H), 7.88 (d, J=5.05 Hz, 1H), 8.52 (d, J=5.05 Hz, 1H), 8.69 (s, 1H), 9.58 (s, 1H), 13.09 (s, 1H). [M+H] Calc'd for $C_{18}H_{18}N_4O_4$, 355; Found, 355.

Example 37: 2-(3,4-difluorophenoxy)pyrido[3,4-d]pyrimidin-4-ol

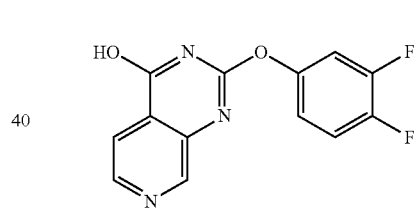

The title compound was prepared in 23% yield from 3,4-difluorophenol and 2-chloropyrido[3,4-d]pyrimidin-4-ol according to the procedure for the preparation of Example 34. $^1$H NMR (400 MHz, DMSO-$d_6$): δ 7.22-7.33 (m, 1H), 7.53-7.62 (m, 1H), 7.62-7.72 (m, 1H), 7.89 (d, J=5.05 Hz, 1H), 8.54 (d, J=5.05 Hz, 1H), 8.72 (s, 1H), 13.22 (br. s., 1H). [M+H] Calc'd for $C_{13}H_7F_2N_3O_2$, 276; Found, 276.

Example 38: 2-(3,4-dimethoxyphenoxy)pyrido[3,4-d]pyrimidin-4-ol

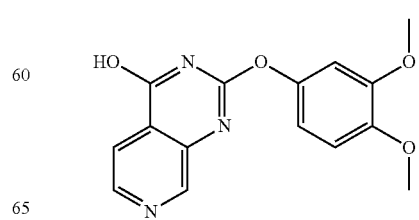

The title compound was prepared in 16% yield from 3,4-dimethoxyphenol and 2-chloropyrido[3,4-d]pyrimidin-4-ol according to the procedure for the preparation of Example 34. $^1$H NMR (400 MHz, DMSO-d$_6$): δ 3.75 (s, 3H), 3.79 (s, 3H), 6.85 (dd, J=8.72, 2.65 Hz, 1H), 7.01 (dd, J=5.81, 3.03 Hz, 2H), 7.88 (d, J=5.05 Hz, 1H), 8.52 (d, J=5.05 Hz, 1H), 8.70 (s, 1H), 13.07 (s, 1H). [M+H] Calc'd for C$_{15}$H$_{13}$N$_3$O$_4$, 300; Found, 300.

Example 39: 2-(3-propan-2-ylphenoxy)pyrido[3,4-d]pyrimidin-4-ol

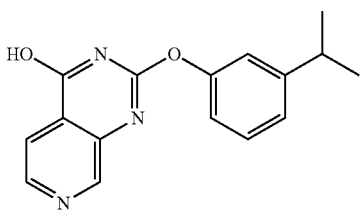

The title compound was prepared in 15% yield from 3-(propan-2-yl)phenol and 2-chloropyrido[3,4-d]pyrimidin-4-ol according to the procedure for the preparation of Example 34. $^1$H NMR (400 MHz, DMSO-d$_6$): δ 1.23 (d, J=6.82 Hz, 6H), 2.95 (dt, J=13.71, 6.66 Hz, 1H), 7.13-7.28 (m, 3H), 7.39 (t, J=8.08 Hz, 1H), 7.90 (br. s., 1H), 8.55 (br. s., 1H), 8.70 (br. s., 1H), 13.10 (s, 1H). [M+H] Calc'd for C$_{16}$H$_{15}$N$_3$O$_2$, 282; Found, 282.

Example 40: 2-(3-fluorophenoxy)pyrido[3,4-d]pyrimidin-4-ol

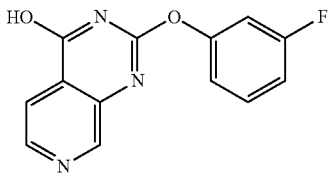

The title compound was prepared in 40% yield from 3-fluorophenol and 2-chloropyrido[3,4-d]pyrimidin-4-ol according to the procedure for the preparation of Example 34. $^1$H NMR (400 MHz, DMSO-d$_6$): δ 7.18-7.24 (2H, m), 7.35-7.38 (1H, m), 7.51-7.57 (1H, m), 7.90 (1H, d, J=5.2 Hz), 8.72 (1H, s), 8.54 (1H, d, J=5.2 Hz), 13.19 (1H, s). [M+H] Calc'd for C$_{13}$H$_8$FN$_3$O$_2$, 258; Found, 258.

Example 41: 2-(3-chlorophenoxy)pyrido[3,4-d]pyrimidin-4-ol

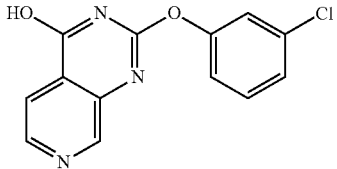 [SMILES: Oc1nc(Oc2cccc(Cl)c2)nc2cnccc12]

The title compound was prepared in 17% yield from 3-chlorophenol and 2-chloropyrido[3,4-d]pyrimidin-4-ol according to the procedure for the preparation of Example 34. $^1$H NMR (400 MHz, DMSO-d$_6$): δ 7.35-7.4 (2H, m), 7.51-7.57 (2H, m), 7.90 (1H, d, J=5.2 Hz), 8.54 (1H, d, J=5.2 Hz), 8.72 (1H, s), 13.19 (1H, s). [M+H] Calc'd for C$_{13}$H$_8$FN$_3$O$_2$, 274; Found, 274.

Example 42: 2-(2,3-difluorophenoxy)pyrido[3,4-d]pyrimidin-4-ol

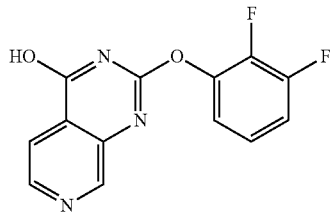 [SMILES: Oc1nc(Oc2cccc(F)c2F)nc2cnccc12]

The title compound was prepared in 56% yield from 2,3-difluorophenol and 2-chloropyrido[3,4-d]pyrimidin-4-ol according to the procedure for the preparation of Example 34. $^1$H NMR (400 MHz, DMSO-d$_6$): δ 7.26-7.57 (m, 3H), 7.92 (br. s., 1H), 8.58 (br. s., 1H), 8.73 (br. s., 1H), 13.45 (br. s., 1H). [M+H] Calc'd for C$_{13}$H$_7$F$_2$N$_3$O$_2$, 276; Found, 276.

Example 43: 2-(3,5-difluoro-4-methoxyphenoxy)pyrido[3,4-d]pyrimidin-4-ol

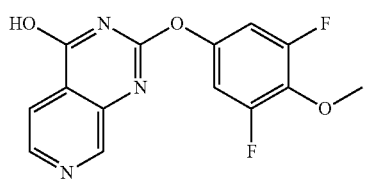 [SMILES: COc1c(F)cc(Oc2nc(O)c3ccncc3n2)cc1F]

The title compound was prepared in 9% yield from 3,5-difluoro-4-methoxyphenol and 2-chloropyrido[3,4-d]pyrimidin-4-ol according to the procedure for the preparation of Example 34. $^1$H NMR (400 MHz, DMSO-d$_6$): δ 3.96 (s, 3H), 7.30-7.36 (m, 1H), 7.36-7.44 (m, 1H), 7.91 (br. s., 1H), 8.57 (br. s., 1H), 8.77 (br. s., 1H), 13.22 (br. s., 1H). [M+H] Calc'd for C$_{14}$H$_9$F$_2$N$_3$O$_3$, 306; Found, 306.

Example 44: 2-(3-methoxyphenoxy)pyrido[3,4-d]pyrimidin-4-ol

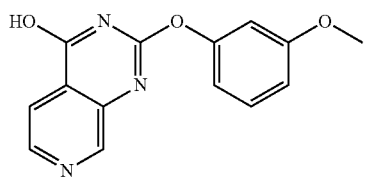

The title compound was prepared in 34% yield from 3-methoxyphenol and 2-chloropyrido[3,4-d]pyrimidin-4-ol according to the procedure for the preparation of Example 34. $^1$H NMR (400 MHz, DMSO-d$_6$): δ 3.78 (3H, s), 6.90-

6.97 (3H, m), 7.37-7.40 (1H, m), 7.90 (1H, d, J=5.2 Hz), 8.52 (1H, d, J=5.2 Hz), 8.70 (1H, s), 13.11 (1H, s). [M+H] Calc'd for $C_{14}H_{11}N_3O_3$, 270; Found, 270.

Example 45: 2-(4-ethoxy-3,5-difluorophenoxy)pyrido[3,4-d]pyrimidin-4-ol

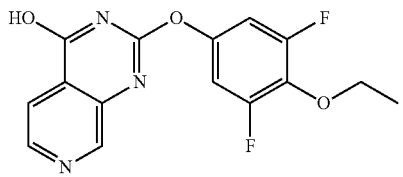 [SMILES: CCOc1c(F)cc(Oc2nc(O)c3ccncc3n2)cc1F]

The title compound was prepared in 8% yield from 4-ethoxy-3,5-difluorophenol and 2-chloropyrido[3,4-d]pyrimidin-4-ol according to the procedure for the preparation of Example 34. $^1$H NMR (400 MHz, DMSO-d$_6$): δ 1.33 (t, J=6.95 Hz, 3H), 4.18 (q, J=6.99 Hz, 2H), 7.33 (s, 1H), 7.35 (s, 1H), 7.89 (d, J=5.05 Hz, 1H), 8.54 (br. s., 1H), 8.75 (br. s., 1H), 13.24 (br. s., 1H). [M+H] Calc'd for $C_{15}H_{11}F_2N_3O_3$, 320; Found, 320.

Example 46: 2-(2-fluorophenoxy)pyrido[3,4-d]pyrimidin-4-ol

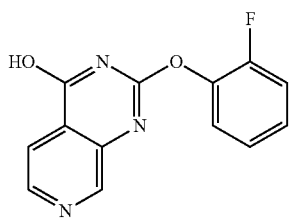

The title compound was prepared in 30% yield from 2-fluorophenol and 2-chloropyrido[3,4-d]pyrimidin-4-ol according to the procedure for the preparation of Example 34. $^1$H NMR (400 MHz, DMSO-d$_6$): δ 7.31-7.55 (4H, m), 7.90 (1H, d, J=4.8 Hz), 8.55 (1H, d, J=4.8 Hz), 8.69 (1H, s), 13.38 (1H, s). [M+H] Calc'd for $C_{13}H_8FN_3O_2$, 258; Found, 258.

Example 47: 2-(4-fluorophenoxy)pyrido[3,4-d]pyrimidin-4-ol

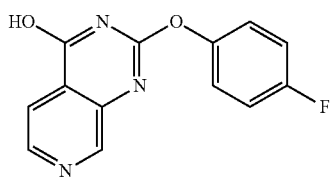

The title compound was prepared in 23% yield from 4-fluorophenol and 2-chloropyrido[3,4-d]pyrimidin-4-ol according to the procedure for the preparation of Example 34. $^1$H NMR (400 MHz, DMSO-d$_6$): δ 7.31-7.35 (2H, m), 7.40-7.43 (2H, m), 7.89 (1H, d, J=5.2 Hz), 8.53 (1H, d, J=5.2 Hz), 8.69 (1H, s), 13.16 (1H, s). [M+H] Calc'd for $C_{13}H_8FN_3O_2$, 258; Found, 258.

Example 48: 2-(4-methoxyphenoxy)pyrido[3,4-d]pyrimidin-4-ol

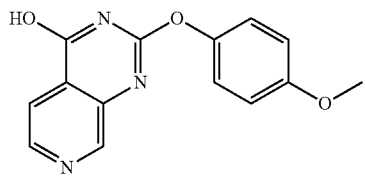

The title compound was prepared in 40% yield from 4-methoxyphenol and 2-chloropyrido[3,4-d]pyrimidin-4-ol according to the procedure for the preparation of Example 34. $^1$H NMR (400 MHz, DMSO-d$_6$): δ 3.79 (3H, s), 7.01 (2H, d, J=8.8 Hz), 7.26 (2H, s, d, J=8.8 Hz), 7.88 (1H, d, J=5.2 Hz), 8.51 (2H, d, J=5.2 Hz), 13.01 (1H, s). [M+H] Calc'd for $C_{14}H_{11}N_3O_3$, 270; Found, 270.

Example 49: 2-(4-chlorophenoxy)pyrido[3,4-d]pyrimidin-4-ol

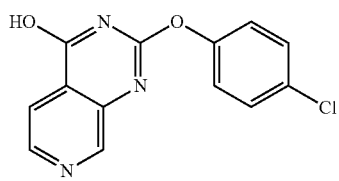 [SMILES: Oc1nc(Oc2ccc(Cl)cc2)nc2cnccc12]

The title compound was prepared in 29% yield from 4-chlorophenol and 2-chloropyrido[3,4-d]pyrimidin-4-ol according to the procedure for the preparation of Example 34. $^1$H NMR (400 MHz, DMSO-d$_6$): δ 7.40-7.43 (2H, m), 7.55-7.57 (2H, m), 7.90 (1H, s), 8.56-8.73 (2H, m), 13.19 (1H, s). [M+H] Calc'd for $C_{13}H_8ClN_3O_2$, 274; Found, 274.

Example 50: 2-[3-(dimethylamino)phenoxy]pyrido[3,4-d]pyrimidin-4-ol

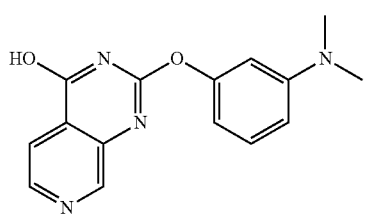 [SMILES: CN(C)c1cccc(Oc2nc(O)c3ccncc3n2)c1]

The title compound was prepared in 16% yield from 3-(dimethylamino)phenol and 2-chloropyrido[3,4-d]pyrimidin-4-ol according to the procedure for the preparation of Example 34. $^1$H NMR (400 MHz, DMSO-d$_6$): δ 2.91 (6H, s) 6.57-6.65 (3H, m), 7.23-7.27 (1H, m), 7.89 (1H, d, J=5.2 Hz), 8.54 (1H, s), 8.72 (1H, s), 13.05 (1H, s). [M+H] Calc'd for $C_{15}H_{14}N_4O_2$, 283; Found, 283.

Example 51: 2-(1-methylindazol-5-yl)oxypyrido[3,4-d]pyrimidin-4-ol

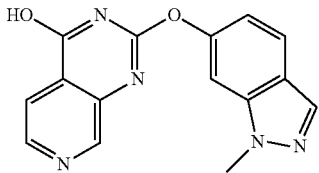

The title compound was prepared in 19% yield from 1-methyl-1H-indazol-6-ol and 2-chloropyrido[3,4-d]pyrimidin-4-ol according to the procedure for the preparation of Example 34. $^1$H NMR (400 MHz, DMSO-$d_6$): δ 4.04 (3H, s), 7.14 (1H, s), 7.69 (1H, s), 7.83-7.91 (2H, m), 8.11 (1H, s), 8.52 (1H, d, J=5.2 Hz), 8.66 (1H, s), 13.22 (1H, s). [M+H] Calc'd for $C_{15}H_{11}N_5O_2$, 294; Found, 294.

Example 52: 2-[3-(trifluoromethyl)phenoxy]pyrido[3,4-d]pyrimidin-4-ol

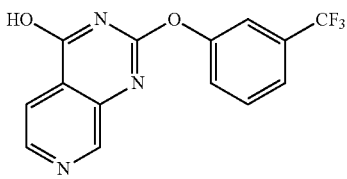

The title compound was prepared in 76% yield from 3-(trifluoromethyl)phenol and 2-chloropyrido[3,4-d]pyrimidin-4-ol according to the procedure for the preparation of Example 34. $^1$H NMR (400 MHz, DMSO-$d_6$): δ 7.67-7.77 (m, 3H), 7.82 (br. s., 1H), 7.92 (br. s., 1H), 8.57 (br. s., 1H), 8.72 (br. s., 1H), 13.25 (br. s., 1H). [M+H] Calc'd for $C_{14}H_8F_3N_3O_2$, 308; Found, 308.

Example 53: 2-(3-fluoro-4-methoxyphenoxy)pyrido[3,4-d]pyrimidin-4-ol

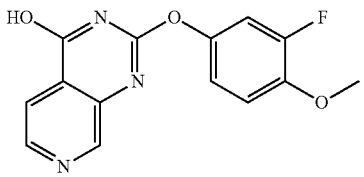 [SMILES: COc1ccc(Oc2nc(O)c3ccncc3n2)cc1F]

The title compound was prepared in 42% yield from 3-fluoro-4-methoxyphenol and 2-chloropyrido[3,4-d]pyrimidin-4-ol according to the procedure for the preparation of Example 34. $^1$H NMR (400 MHz, DMSO-$d_6$): δ 3.88 (s, 3H), 7.13-7.19 (m, 1H), 7.22-7.28 (m, 1H), 7.39 (dd, J=12.13, 2.53 Hz, 1H), 7.90 (br. s., 1H), 8.55 (br. s., 1H), 8.72 (br. s., 1H), 13.13 (br. s., 1H). [M+H] Calc'd for $C_{14}H_{10}F_1N_3O_3$, 288; Found, 288.

Example 54: 2-(1-propylpyrazol-4-yl)oxypyrido[3,4-d]pyrimidin-4-ol

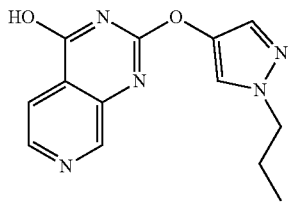 [SMILES: CCCn1cc(Oc2nc(O)c3ccncc3n2)cn1]

The title compound was prepared in 19% yield from 1-propyl-1H-pyrazol-4-ol and 2-chloropyrido[3,4-d]pyrimidin-4-ol according to the procedure for the preparation of Example 34. $^1$H NMR (400 MHz, DMSO-$d_6$): δ 0.86 (3H, t, J=7.2 Hz), 1.83-1.78 (2H, m), 4.08 (2H, t, J=2.8 Hz), 7.61 (1H, s), 7.88 (1H, d, J=5.2 Hz), 8.08 (1H, s), 8.54 (1H, d, J=4.4 Hz), 8.84 (1H, s). 13.09 (1H, s). [M+H] Calc'd for $C_{13}H_{13}N_5O_2$, 272; Found, 272.

Example 55: 2-{[1-(3-methylbutyl)pyrazol-4-yl]oxy}pyrido[3,4-d]pyrimidin-4-ol

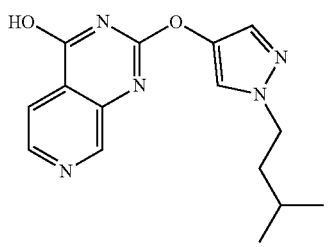 [SMILES: CC(C)CCn1cc(Oc2nc(O)c3ccncc3n2)cn1]

The title compound was prepared in 12% yield from 1-(3-methylbutyl)-1H-pyrazol-4-ol and 2-chloropyrido[3,4-d]pyrimidin-4-ol according to the procedure for the preparation of Example 34. $^1$H NMR (400 MHz, DMSO-$d_6$): δ 0.92 (d, J=6.82 Hz, 6H), 1.51 (dt, J=13.26, 6.76 Hz, 1H), 1.69 (d, J=7.58 Hz, 2H), 4.12 (t, J=7.20 Hz, 2H), 7.59 (s, 1H), 7.88 (d, J=5.31 Hz, 1H), 8.08 (s, 1H), 8.54 (d, J=5.31 Hz, 1H), 8.83 (s, 1H), 13.08 (br. s., 1H). [M+H] Calc'd for $C_{15}H_{17}N_5O_2$, 300; Found, 300.

Example 56: 2-[(1-cyclopentylpyrazol-4-yl)oxy]pyrido[3,4-d]pyrimidin-4-ol

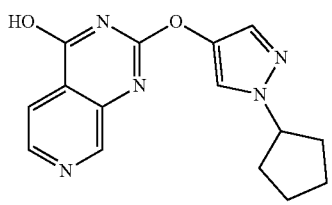 [SMILES: Oc1nc(Oc2cnn(C3CCCC3)c2)nc2cnccc12]

The title compound was prepared in 23% yield from 1-cyclopentyl-1H-pyrazol-4-ol and 2-chloropyrido[3,4-d]pyrimidin-4-ol according to the procedure for the preparation of Example 34. $^1$H NMR (400 MHz, DMSO-$d_6$): δ 1.57-2.16 (m, 8H), 4.64-4.74 (m, 1H), 7.61 (s, 1H), 7.88 (d, J=5.05 Hz, 1H), 8.09 (s, 1H), 8.54 (d, J=5.05 Hz, 1H), 8.84 (s, 1H), 13.08 (br. s., 1H). [M+H] Calc'd for $C_{15}H_{15}N_5O_2$, 300; Found, 300.

Example 57: 2-(3-ethylphenoxy)pyrido[3,4-d]pyrimidin-4-ol

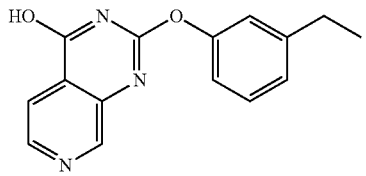

To a solution of 2-chloropyrido[3,4-d]pyrimidin-4-ol (100 mg, 0.55 mmol) and 3-ethylphenol (200 mg, 1.64 mmol) in DMF (1 mL) was added anhydrous potassium carbonate (227 mg, 1.64 mmol). The mixture was stirred for 16 h at 110° C. and cooled to rt The suspension was diluted with water (10 mL) and the pH was then adjusted to 4 with 1N HCl. The suspension was extracted with EtOAc (3×20 mL) and the organics were dried (MgSO$_4$), filtered, concentrated, and chromatographed on silica gel (80:20 EA:Hex) to give 62 mg (42%) of the title as a beige solid. $^1$H NMR (400 MHz, DMSO-d$_6$): δ 1.22 (3H, m), 2.63 (2H, m), 7.07-7.18 (3H, m), 7.38 (1H, m), 7.85 (1H, d, J=12 Hz), 8.51 (1H, d, J=12 Hz), 8.66 (1H, s). [M+H] Calc'd for $C_{15}H_{13}N_3O_2$, 267; Found, 267.

Example 58: 2-(3-propylphenoxy)pyrido[3,4-d]pyrimidin-4-ol

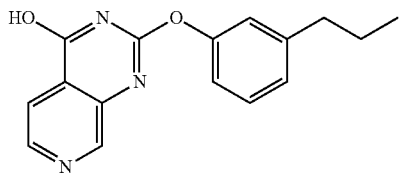 [SMILES: CCCc1cccc(Oc2nc(O)c3ccncc3n2)c1]

To a solution of 2-chloropyrido[3,4-d]pyrimidin-4-ol (100 mg, 0.55 mmol) and 3-propylphenol (226 mg, 1.65 mmol) in DMF (1 mL) was added anhydrous potassium carbonate (227 mg, 1.65 mmol). The mixture was stirred for 24 h at 110° C. and cooled to rt. The suspension was diluted with water (10 mL) and the pH was then adjusted to 4 with 1N HCl. The suspension was extracted with EtOAc (3×20 mL) and the organics were dried (MgSO$_4$), filtered, concentrated, and chromatographed on silica gel (60:40 EA:Hex) to give 38 mg (25%) of the title as a beige solid. $^1$H NMR (400 MHz, DMSO): δ 0.88 (3H, t, J=8.1 Hz), 1.59 (2H, m), 2.57 (2H, q, J=7.2 Hz), 7.05-7.17 (3H, m), 7.36 (1H, m), 7.86 (1H, d, J=12 Hz), 8.42 (1H, d, J=12 Hz), 8.63 (1H, s). [M+H] Calc'd for $C_{16}H_{15}N_3O_2$, 281; Found, 281.

Example 59: 2-[4-(dimethylamino)phenoxy]pyrido[3,4-d]pyrimidin-4-ol

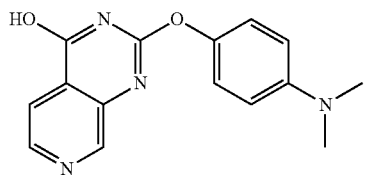

The title compound was prepared in 19% yield from 4-(dimethylamino)phenol and 2-chloropyrido[3,4-d]pyrimidin-4-ol according to the procedure for the preparation of Example 34. $^1$H NMR (400 MHz, DMSO-d$_6$): δ 2.73 (6H, s), 6.77 (2H, d, J=8.4 Hz), 7.13 (2H, d, J=8.8 Hz), 7.87 (1H, d, J=5.2 Hz), 8.51 (1H, d, J=5.2 Hz), 8.68 (1H, s), 13.01 (1H, s). [M+H] Calc'd for $C_{15}H_{14}N_4O_2$, 284; Found, 284.

Preparation 60A: (3-fluoro-5-hydroxyphenyl)(morpholin-4-yl)methanone

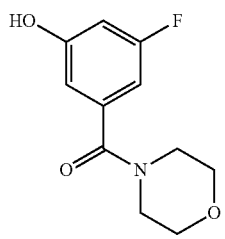 [SMILES: O=C(c1cc(O)cc(F)c1)N1CCOCC1]

To 3-fluoro-5-hydroxy-benzoic acid (300 mg, 1.92 mmol) in DMF (5 ml) were added TEA (400 µL, 2.88 mmol), HATU (801 mg, 2.11 mol) and morpholine (184 µL, 2.11 mmol). The reaction mixture was stirred for 2 h. The reaction mixture was concentrated, taken in ethyl acetate and washed with water. The organics were concentrated and the residue was purified by silica gel chromatography (0% to 10% MeOH:DCM) to give 264 mg (61%) of the title compound. $^1$H NMR (400 MHz, DMSO-d$_6$): δ 3.57 (br. s., 8H), 6.38-6.89 (m, 3H), 10.03-10.39 (m, 1H). [M+H] Calc'd for $C_{11}H_{12}FNO_3$, 226; Found, 226.

Example 60: 3-fluoro-5-(4-hydroxypyrido[3,4-d]pyrimidin-2-yl)oxyphenyl]-morpholin-4-ylmethanone

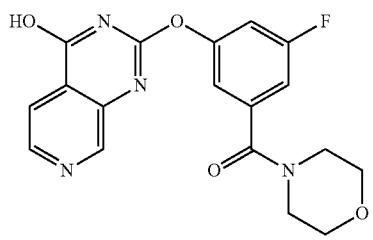 [SMILES: O=C(c1cc(F)cc(Oc2nc(O)c3ccncc3n2)c1)N1CCOCC1]

The title compound was prepared in 16% yield from (3-fluoro-5-hydroxyphenyl)(morpholin-4-yl)methanone and 2-chloropyrido[3,4-d]pyrimidin-4-ol according to the procedure for the preparation of Example 34. ¹H NMR (400 MHz, DMSO-d₆): δ 3.42-3.80 (m, 8H), 7.25-7.31 (m, 1H), 7.34 (s, 1H), 7.48 (dt, J=9.54, 2.31 Hz, 1H), 7.90 (d, J=5.05 Hz, 1H), 8.55 (d, J=5.30 Hz, 1H), 8.73 (s, 1H), 13.25 (br. s., 1H). [M+H] Calc'd for $C_{18}H_{15}F_1N_4O_4$, 371; Found, 371.

Preparation 61A: 1-(2-methoxyethyl)-1H-indazol-6-ol

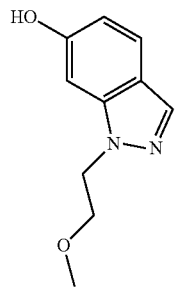

A solution of 1-(2-methoxyethyl)-1H-indazol-6-amine (1.0 g, 5.23 mmol) in H₂SO₄/H₂O (1:1, 15 mL) was cooled to 0° C. and a solution of NaNO₂ (0.36 g, 5.23 mmol) in H₂O (1.5 mL) was added dropwise. This dark solution was stirred for 2 h and water (5 mL) was added and then heated at 110° C. for 2 h. The reaction was cooled to rt, carefully neutralized with a saturated solution of NaHCO₃ and extracted with ethyl acetate. The extracts were washed with brine, dried, and evaporated. The residue was purified by silica gel chromatography (0 to 100% EtOAc:Hexanes) to give 620 mg (62%) the title compound as a white solid. [M+H] Calc'd for $C_{10}H_{12}N_2O_2$, 193; Found, 193.

Example 61: 2-{[1-(2-methoxyethyl)-1H-indazol-6-yl]oxy}pyrido[3,4-d]pyrimidin-4-ol

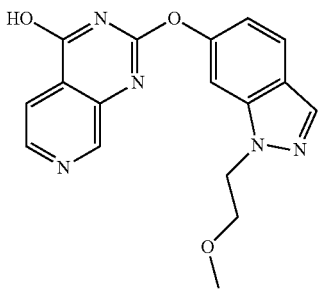 [SMILES: COCCn1ncc2ccc(Oc3nc(O)c4ccncc4n3)cc21]

The title compound was prepared in 31% yield from 1-(2-methoxyethyl)-1H-indazol-6-ol and 2-chloropyrido[3,4-d]pyrimidin-4-ol according to the procedure for the preparation of Example 34. ¹H NMR (400 MHz, DMSO-d₆): δ 3.19 (s, 3H), 3.76 (t, J=5.18 Hz, 2H), 4.55 (t, J=5.18 Hz, 2H), 7.13 (dd, J=8.72, 1.89 Hz, 1H), 7.70 (s, 1H), 7.83 (d, J=8.84 Hz, 1H), 7.90 (d, J=5.31 Hz, 1H), 8.13 (s, 1H), 8.53 (d, J=5.05 Hz, 1H), 8.67 (s, 1H), 13.21 (s, 1H). [M+H] Calc'd for $C_{17}H_{15}N_5O_3$, 338; Found, 338.

Preparation 62A: 1-ethylpyrazole-4-boronic acid

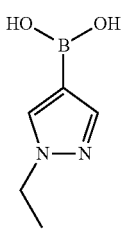

To a solution of 1-ethyl-1H-pyrazole-4-boronic acid, pinacol ester (320 mg, 1.44 mmol) in acetone/H₂O (5 mL, 1:1) was added NaIO₄ (925 mg, 4.32 mmol) and NH₄OAc (277 mg, 3.60 mmol). The reaction mixture was stirred at rt for 16 h and concentrated in vacuo. The crude was purified by gel chromatography (5% MeOH:DCM) to give 127 mg (60%) of the title compound as yellow oil. [M+H] Calc'd for $C_5H_9BN_2O_2$, 141; Found, 141.

Preparation 62B: 1-ethyl-1H-pyrazol-4-ol

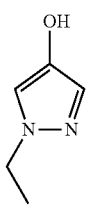

A mixture of 1-ethylpyrazole-4-boronic acid (127 mg, 0.90 mmol), AcOH (0.35 mL), H₂O₂ (0.32 mL), H₂O (0.32 mL) in Et₂O (5 mL) was stirred at rt for 1 h and then refluxed for 16 h. The pH was adjusted to 7 using aqueous NaHCO₃. The solution was concentrated in vacuo and purified by gel chromatography (5% MeOH:DCM) to give 30 mg of the title compound (30%) as colorless oil. [M+H] Calc'd for $C_5H_8N_2O$, 113; Found, 113.

Example 62: 2-[(1-ethyl-1H-pyrazol-4-yl)oxy]pyrido[3,4-d]pyrimidin-4-ol

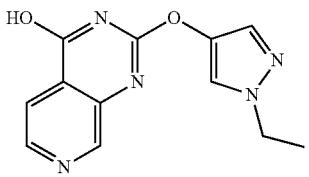 [SMILES: CCn1cc(Oc2nc(O)c3ccncc3n2)cn1]

The title compound was prepared in 3% yield from 1-ethyl-1H-pyrazol-4-ol and 2-chloropyrido[3,4-d]pyrimidin-4-ol according to the procedure for the preparation of Example 34. ¹H NMR (400 MHz, DMSO-d₆): ¹H NMR (400 MHz, DMSO-d₆): δ 1.40 (3H, t, J=7.2 Hz), 4.14 (2H, q, J=7.2 Hz), 7.60 (1H, s), 7.88 (1H, d, J=5.2 Hz), 8.08 (1H, s), 8.54 (1H, d, J=4.4 Hz), 8.85 (1H, s). 13.08 (1H, s). [M+H] Calc'd for $C_{12}H_{11}N_5O_2$, 257; Found, 257.

Preparation 63A: 1-(isopropyl)-1H-pyrazol-4-ol

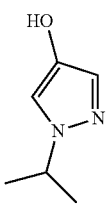

To a solution of 1-isopropyl-1H-pyrazole-4-boronic acid, pinacol ester (2.12 g, 9.0 mmol) in THF (30 mL) was added NaOH (2.5 N, 4 mL) and $H_2O_2$ (30%, 2 mL) at 0° C. The mixture was stirred at rt for 3 h. The solution was acidified with 2N HCl to pH=2, concentrated and purified by silica gel chromatography (5% MeOH:DCM) to give the title compound (816 mg, 71%) as a white solid. $^1$H NMR (300 MHz, $CDCl_3$): δ 1.45 (6H, d, J=6.6 Hz), 4.36-4.40 (1H, m), 7.13 (1H, s), 7.15 (1H, s). [M+H] Calc'd for $C_6H_{10}N_2O$, 127; Found, 127.

Example 63: 2-{[1-(propan-2-yl)-1H-pyrazol-4-yl]oxy}pyrido[3,4-d]pyrimidin-4-ol

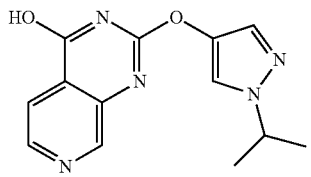 [SMILES: CC(C)n1cc(Oc2nc(O)c3ccncc3n2)cn1]

The title compound was prepared in 37% yield from 1-(isopropyl)-1H-pyrazol-4-ol and 2-chloropyrido[3,4-d]pyrimidin-4-ol according to the procedure for the preparation of Example 34. $^1$H NMR (400 MHz, DMSO-$d_6$): δ 1.44 (6H, d, J=6.4 Hz), 4.98-4.51 (1H, m), 7.61 (1H, s), 7.89 (1H, d, J=5.2 Hz), 8.09 (1H, s), 8.54 (1H, d, J=4.8 Hz), 8.85 (1H, s), 13.09 (1H, s). [M+H] Calc'd for $C_{13}H_{13}N_5O_2$, 272; Found, 272.

Preparation 64A: 1-(2-methoxyethyl)-1H-pyrazole-4-boronic acid, pinacol ester

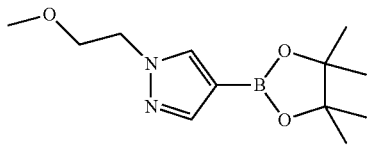

A mixture of 4-(4,4,5,5-tetramethyl-1,3,2-dioxaborolan-2-yl)-1H-pyrazole (1.94 g, 10 mmol), 2-bromoethyl methyl ether (1.68 g, 12 mmol) and $K_2CO_3$ (2.76 g, 20 mmol) in DMF (16 mL) was stirred at 160° C. for 2 h in the microwave. The reaction mixture was concentrated and purified by silica gel chromatography (30% EA:PE) to give 2.2 g (90%) of the title compound as yellow oil. $^1$H NMR (400 MHz, $CDCl_3$): δ 1.32 (12H, s), 3.32 (3H, s), 3.75 (2H, t, J=5.2 Hz), 4.30 (2H, t, J=5.2 Hz), 7.77 (1H, s), 7.79 (1H, s). [M+H] Calc'd for $C_{12}H_{21}BN_2O_3$, 253; Found, 253.

Preparation 64B: 1-(2-methoxyethyl)-1H-pyrazol-4-ol

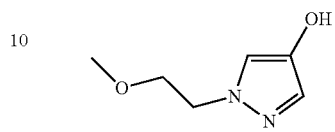

The title compound was prepared in 80% yield from 1-(2-methoxyethyl)-1H-pyrazole-4-boronic acid, pinacol ester, according to the procedure for Preparation 63A. $^1$H NMR (400 MHz, $CDCl_3$): δ 3.30 (3H, s), 3.67 (2H, t, J=5.2 Hz), 4.15 (2H, t, J=5.2 Hz), 7.09 (1H, s), 7.18 (1H, s). [M+H] Calc'd for $C_6H_{10}N_2O_2$, 143; Found, 143.

Example 64: 2-{[1-(2-methoxyethyl)-1H-pyrazol-4-yl]oxy}pyrido[3,4-d]pyrimidin-4-ol

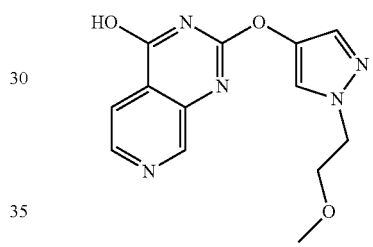

The title compound was prepared in 40% yield from 1-(2-methoxyethyl)-1H-pyrazol-4-ol and 2-chloropyrido[3,4-d]pyrimidin-4-ol according to the procedure for the preparation of Example 34. $^1$H NMR (400 MHz, DMSO-$d_6$): δ 3.26 (3H, s), 3.71 (2H, t, J=5.2 Hz), 4.26 (2H, t, J=5.2 Hz), 7.62 (1H, s), 7.89 (1H, d, J=5.1 Hz), 8.05 (1H, s), 8.54 (1H, d, J=4.8 Hz), 8.83 (1H, s). 13.09 (1H, s). [M+H] Calc'd for $C_{13}H_{13}N_5O_3$, 288; Found, 288.

Preparation 65A: 1-(3-methoxypropyl)-1H-pyrazole-4-boronic acid, pinacol ester

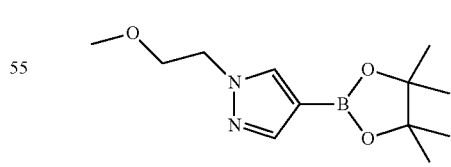

The title compound was prepared in 70% yield from 4-(4,4,5,5-tetramethyl-1,3,2-dioxaborolan-2-yl)-1H-pyrazole and 1-bromo-3-methoxypropane according to the procedure for Preparation 64A. $^1$H NMR (400 MHz, $CDCl_3$): δ 1.32 (12H, s), 2.04-2.11 (2H, m), 3.30-3.32 (5H, m), 4.23 (2H, t, J=6.8 Hz), 7.68 (1H, s), 7.79 (1H, s). [M+H] Calc'd for $C_{13}H_{23}BN_2O_3$, 267; Found, 267.

Preparation 65B: 1-(3-methoxypropyl)-1H-pyrazol-4-ol

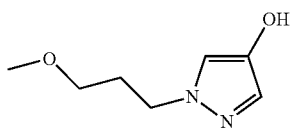

The title compound was prepared in 85% yield from 1-(3-methoxypropyl)-1H-pyrazole-4-boronic acid, pinacol ester, according to the procedure for the Preparation 64B. $^1$H NMR (300 MHz, CDCl$_3$): δ 2.01-2.08 (2H, m), 3.30-3.33 (5H, m), 4.10 (2H, t, J=7.2 Hz), 7.09 (1H, s), 7.18 (1H, s). [M+H] Calc'd for C$_7$H$_{12}$N$_2$O$_2$, 157; Found, 157.

Example 65: 2-{[1-(3-methoxypropyl)-1H-pyrazol-4-yl]oxy}pyrido[3,4-d]pyrimidin-4-ol

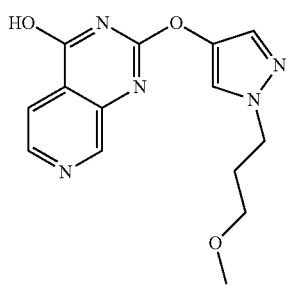 [SMILES: COCCCn1cc(Oc2nc(O)c3ccncc3n2)cn1]

The title compound was prepared in 27% yield from 1-(3-methoxypropyl)-1H-pyrazol-4-ol and 2-chloropyrido[3,4-d]pyrimidin-4-ol according to the procedure for the preparation of Example 34. $^1$H NMR (400 MHz, DMSO-d$_6$): δ 2.00-2.04 (2H, m), 3.26 (3H, s), 3.32 (2H, t, J=6.0 Hz), 4.16 (2H, t, J=6.8 Hz), 7.62 (1H, s), 7.88 (1H, d, J=4.8 Hz), 8.07 (1H, s), 8.54 (1H, d, J=5.2 Hz), 8.83 (1H, s). 13.09 (1H, s). [M+H] Calc'd for C$_{14}$H$_{15}$N$_5$O$_3$, 302; Found, 302.

Preparation 66A: 1-benzyl-1H-pyrazol-4-ol

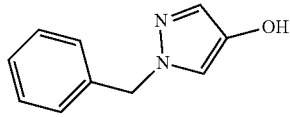 [SMILES: Oc1cnn(Cc2ccccc2)c1]

The title compound was prepared in 63% yield from 1-benzyl-4-(4,4,5,5-tetramethyl-1,3,2-dioxaborolan-2-yl)-1H-pyrazole, according to the procedure for Preparation 64B. $^1$H NMR (400 MHz, DMSO-d$_6$): δ 5.14 (s, 2H), 7.01 (d, J=0.76 Hz, 1H), 7.13-7.22 (m, 2H), 7.25 (d, J=0.80 Hz, 1H), 7.26-7.36 (m, 3H), 8.40 (s, 1H). [M+H] Calc'd for C$_{10}$H$_{10}$N$_2$O, 175; Found, 175.

Example 66: 2-[(1-benzyl-1H-pyrazol-4-yl)oxy]pyrido[3,4-d]pyrimidin-4-ol

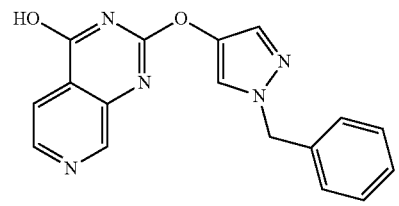 [SMILES: Oc1nc(Oc2cnn(Cc3ccccc3)c2)nc2cnccc12]

The title compound was prepared in 79% yield from 1-benzyl-1H-pyrazol-4-ol and 2-chloropyrido[3,4-d]pyrimidin-4-ol according to the procedure for the preparation of Example 34. $^1$H NMR (400 MHz, DMSO-d$_6$): δ 5.34 (s, 2H), 7.25-7.34 (m, 3H), 7.33-7.41 (m, 2H), 7.65 (s, 1H), 7.88 (d, J=4.29 Hz, 1H), 8.20 (s, 1H), 8.54 (br. s., 1H), 8.82 (br. s., 1H), 13.11 (s, 1H). [M+H] Calc'd for C$_{17}$H$_{13}$N$_5$O$_2$, 320; Found, 320.

Preparation 67A: tetrahydro-2H-pyran-4-yl methanesulfonate

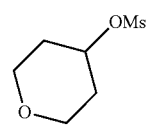 [SMILES: CS(=O)(=O)OC1CCOCC1]

To a solution of tetrahydro-2H-pyran-4-ol (4.5 g, 44 mmol) in DCM (200 mL) was added TEA (5.4 g, 53.5 mmol) and MeSO$_2$Cl (3.73 mL, 50 mmol) at ice-bath temperature. The reaction mixture was stirred at rt for 16 h. The reaction was quenched with water and the organic layer was washed with brine, dried and concentrated to give 7.9 g of the title compound (100%). $^1$H NMR (400 MHz, CDCl$_3$): δ 1.84-1.93 (2H, m), 2.03-2.08 (2H, m), 3.05 (3H, s), 3.52-3.58 (2H, m), 3.92-3.97 (2H, m), 4.87-4.94 (1H, m).

Preparation 67B: 1-(tetrahydro-2H-pyran-4-yl)-1H-pyrazole-4-boronic acid, Pinacol Ester

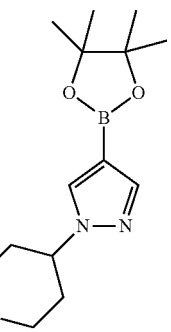

To a solution of 4-(4,4,5,5-tetramethyl-1,3,2-dioxaborolan-2-yl)-1H-pyrazole (1.0 g, 5.2 mmol) in DMF (10 mL) was added NaH (0.3 g, 7.5 mmol) at 0° C. and the mixture was stirred at rt for 30 min. Tetrahydro-2H-pyran-4-yl methanesulfonate (1.1 g, 6.1 mmol) was added and the mixture was stirred at 110° C. overnight. The reaction mixture was cooled to rt and filtered. The filtrate was concentrated and the residue was purified by silica gel chromatography (30% EA:PE) to give 550 mg of the title compound (40%). [M+H] Calc'd for C$_{14}$H$_{23}$BN$_2$O$_3$, 279; Found, 279.

Preparation 67C: 1-(tetrahydro-2H-pyran-4-yl)-1H-pyrazol-4-ol

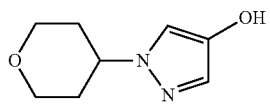

To a solution of 1-(tetrahydro-2H-pyran-4-yl)-1H-pyrazole-4-boronic acid, pinacol ester (550 mg, 2.0 mmol) in THF (20 mL) were added NaOH (2.5 N, 0.6 mL) and H$_2$O$_2$ (0.4 mL). The mixture was stirred at rt for 3 h and adjusted to pH=6 using 1N HCl. The solution was concentrated and purified by silica gel chromatography (5% MeOH:DCM) to give 250 mg (76%) of the title compound. $^1$H NMR (400 MHz, CD$_3$OD): δ 1.96-2.04 (4H, m), 3.63-3.59 (2H, m), 4.05-4.07 (2H, m), 4.23-4.27 (1H, m), 7.11 (1H, s), 7.25 (1H, s).

Example 67: 2-{[1-(tetrahydro-2H-pyran-4-yl)-1H-pyrazol-4-yl]oxy}pyrido[3,4-d]pyrimidin-4-ol

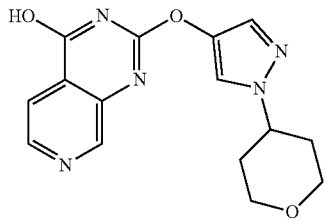 [SMILES: Oc1nc(Oc2cnn(C3CCOCC3)c2)nc2cnccc12]

The title compound was prepared in 17% yield from 1-(tetrahydro-2H-pyran-4-yl)-1H-pyrazol-4-ol and 2-chloropyrido[3,4-d]pyrimidin-4-ol according to the procedure for the preparation of Example 34. $^1$H NMR (400 MHz, DMSO-d$_6$): 1.94-1.99 (4H, m), 3.45-3.50 (2H, m), 3.96-3.99 (2H, m), 4.39-4.42 (1H, m), 7.65 (1H, s), 7.88 (1H, d, J=4.4 Hz), 8.15 (1H, s), 8.55 (1H, d, J=4.4 Hz), 8.86 (1H, s), 13.11 (1H, s). [M+H] Calc'd for C$_{15}$H$_{15}$N$_5$O$_3$, 314; Found, 314.

Preparation 68A: methyl 3-amino-2-chloropyridine-4-carboxylate

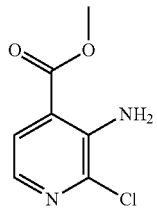

To a solution of methyl 3-aminopyridine-4-carboxylate (30.4 g, 0.2 mol) in concentrated HCl was added H$_2$O$_2$ (24.9 g, 0.22 mol) dropwise at ice-bath temperature, and the mixture was stirred at rt for 1 h. Aq. Na$_2$S$_2$O$_3$ (10 mL) was added, and the precipitate was filtered. The filtrate was adjusted to pH=8 using aq. NaHCO$_3$, and the solution was extracted with EA, dried and concentrated in vacuo. The crude was purified by silica gel chromatography (20:1:1 PE:EA:DCM) to give 18.3 g (50%) of the title compound as an off-white solid. $^1$H NMR (400 MHz, CDCl$_3$): δ 7.69 (d, J=5.2 Hz, 1H), 7.58 (d, J=5.2 Hz, 1H), 6.18 (br. s., 2H), 3.91 (s, 3H). [M+H] Calc'd for C$_7$H$_7$ClN$_2$O$_2$, 187; Found, 187.

Preparation 68B: methyl 3-amino-2-(1-methyl-1H-imidazol-4-yl)pyridine-4-carboxylate

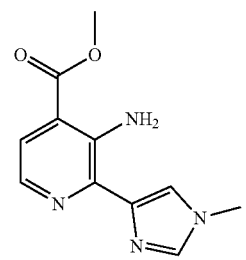 [SMILES: COC(=O)c1ccnc(-c2cn(C)cn2)c1N]

A mixture of methyl 3-amino-2-chloropyridine-4-carboxylate (1.0 g, 5.4 mmol), 1-methyl-4-tributylatannanyl-1H-imidazole (2.0 g, 5.4 mmol) and Pd-118 (400 mg, 0.54 mmol) in DMF (10 mL) was stirred under N$_2$ at 130° C. for 3 h. The solution was concentrated in vacuo and the residue was purified by silica gel chromatography (5% MeOH:DCM) to give 1.3 g (76%) of the title compound. $^1$H NMR (400 MHz, CDCl$_3$): δ 3.78 (3H, s), 3.92 (3H, s), 7.30-7.36 (2H, m), 7.65 (1H, d, J=2.0 Hz), 7.81 (1H, d, J=6.4 Hz), 8.25 (2H, s).

Preparation 68C: 8-(1-methyl-1H-imidazol-4-yl)pyrido[3,4-d]pyrimidine-2,4-diol

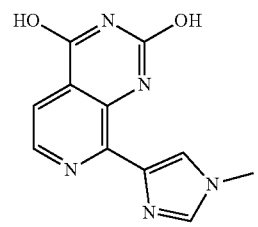 [SMILES: Cn1cnc(-c2nccc3c(O)nc(O)nc23)c1]

A mixture of methyl 3-amino-2-(1-methyl-1H-imidazol-4-yl)pyridine-4-carboxylate (1.0 g, 4.3 mmol), and urea (5.2 g, 86.7 mmol) was stirred at 190° C. for 2 h. The reaction was cooled to rt, and water was added. The mixture was stirred 2 h and the precipitate was filtered and washed with hot water and THF. The solid was dried to give 0.8 g (76%) of the title compound. $^1$H NMR (400 MHz, DMSO-d$_6$): δ 3.80 (3H, s), 7.63 (1H, d, J=5.2 Hz), 7.99 (2H, d, J=10.0 Hz), 8.35 (1H, d, J=5.2 Hz), 11.68 (1H, s), 12.44 (1H, s).

Preparation 68D: 2,4-dichloro-8-(1-methyl-1H-imidazol-4-yl)pyrido[3,4-d]pyrimidine

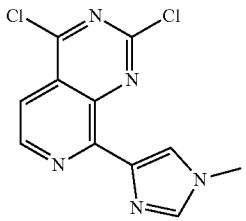 [SMILES: Cn1cnc(-c2nccc3c(Cl)nc(Cl)nc23)c1]

To a flask was added 8-(1-methyl-1H-imidazol-4-yl)pyrido[3,4-d]pyrimidine-2,4-diol (2.0 g, 8.2 mmol), POCl$_3$ (20 mL) and DIEA (2.1 g, 16.4 mmol). The mixture was stirred at 125° C. for 5 h. POCl$_3$ was removed in vacuo and the residue was poured onto ice-water. The solution was adjusted to pH=7 using aq. NaHCO$_3$ and extracted with DCM. The combined organic layers were washed with brine and concentrated to give 1.6 g (70%) of the title compound. $^1$H NMR (400 MHz, CD$_3$OD): δ 4.13 (3H, s), 8.24 (1H, d, J=7.6 Hz), 8.83 (1H, s), 8.99 (1H, d, J=7.2 Hz), 9.19 (1H, s).

Preparation 68E: 2-chloro-8-(1-methyl-1H-imidazol-4-yl)pyrido[3,4-d]pyrimidin-4-ol

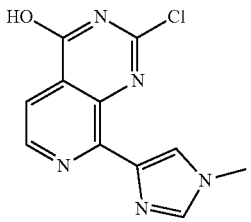 [SMILES: Cn1cnc(-c2nccc3c(O)nc(Cl)nc23)c1]

To a solution 2,4-dichloro-8-(1-methyl-1H-imidazol-4-yl)pyrido[3,4-d]pyrimidine (2.0 g, 7.1 mmol) in THF (50 mL) and water (50 mL) was added NaOH (0.71 g, 17.9 mmol). The mixture was stirred at rt for 2 h. The solution was adjusted to pH=7 using 5N HCl. The solid was filtered, washed with water and THF, and dried to give 1.3 g (70%) of the title compound. $^1$H NMR (400 MHz, DMSO-d$_6$): δ 3.89 (3H, s), 7.79 (1H, d, J=6.8 Hz), 8.39-8.53 (3H, m).

Example 68: 2-methoxy-8-(1-methyl-1H-imidazol-4-yl)pyrido[3,4-d]pyrimidin-4-ol

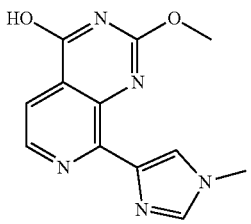 [SMILES: COc1nc(O)c2ccnc(-c3cn(C)cn3)c2n1]

To a sealed tube was added methanol and Na (50 mg, 2.2 mmol). After Na was dissolved, 2-chloro-8-(1-methyl-1H-imidazol-4-yl)pyrido[3,4-d]pyrimidin-4-ol (100 mg, 0.38 mmol) was added. The reaction mixture was stirred at 100° C. overnight. The reaction was concentrated in vacuo and the residue was washed with water and THF to give 55 mg (57%) of the title compound. $^1$H NMR (400 MHz, DMSO-d$_6$): δ 3.89 (3H, s), 4.09 (3H, s), 7.79 (1H, d, J=4.8 Hz), 8.31 (1H, s), 8.53 (2H, d, J=4.8 Hz). [M+H] Calc'd for C$_{12}$H$_{11}$N$_5$O$_2$, 258; Found, 258.

Example 69: 2-ethoxy-8-(1-methyl-1H-imidazol-4-yl)pyrido[3,4-d]pyrimidin-4-ol

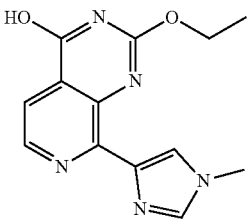 [SMILES: CCOc1nc(O)c2ccnc(-c3cn(C)cn3)c2n1]

The title compound was prepared in 28% yield from ethanol and 2-chloro-8-(1-methyl-1H-imidazol-4-yl)pyrido[3,4-d]pyrimidin-4-ol according to the procedure for the preparation of Example 68. $^1$H NMR (400 MHz, DMSO-d$_6$): δ 1.41 (3H, t, J=7.2 Hz), 3.78 (3H, s), 4.50 (2H, m), 7.66 (1H, d, J=5.2 Hz), 7.84 (1H, s), 8.13 (1H, s), 8.45 (1H, d, J=5.2 Hz). [M+H] Calc'd for C$_{13}$H$_{13}$N$_5$O$_2$, 272; Found, 272.

Example 70: 8-(1-methyl-1H-imidazol-4-yl)-2-(2,2,2-trifluoroethoxy)pyrido[3,4-d]pyrimidin-4-ol

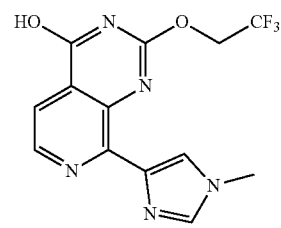 [SMILES: Cn1cnc(-c2nccc3c(O)nc(OCC(F)(F)F)nc23)c1]

The title compound was prepared in 23% yield from 2,2,2-trifluoroethanol and 2-chloro-8-(1-methyl-1H-imidazol-4-yl)pyrido[3,4-d]pyrimidin-4-ol according to the procedure for the preparation of Example 68. $^1$H NMR (400 MHz, DMSO-d$_6$): δ 3.80 (3H, s), 5.16-5.23 (2H, m), 7.71 (1H, d, J=4.8 Hz), 7.90 (1H, s), 8.17 (1H, s), 8.50 (1H, d, J=5.2 Hz). [M+H] Calc'd for C$_{13}$H$_{10}$F$_3$N$_5$O$_2$, 326; Found, 326.

Example 71: 2-[(4-fluorobenzyl)oxy]-8-(1-methyl-1H-imidazol-4-yl)pyrido[3,4-d]pyrimidin-4-ol

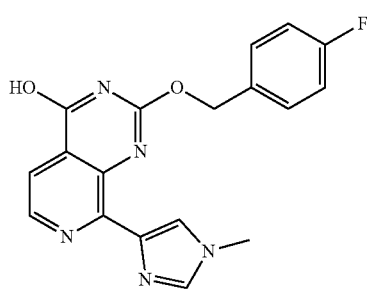 [SMILES: Cn1cnc(-c2nccc3c(O)nc(OCc4ccc(F)cc4)nc23)c1]

Sodium hydride (46 mg, 1.24 mmol) was added at 0° C. to 4-fluorobenzylalcohol (1.0 mL, 9.2 mmol) in dioxane (1 mL). The reaction mixture was stirred for 2 h. 2-chloro-8-(1-methyl-1H-imidazol-4-yl)pyrido[3,4-d]pyrimidin-4-ol (50 mg, 0.19 mmol) was added. The mixture was stirred at 100° C. for 3 h. The reaction mixture was quenched with 0.2 mL of iced water. Solvent was concentrated. The residue was purified by silica gel chromatography (0-20% MeOH:DCM) to give 34 mg (35%) of the title product as a light yellow solid. $^1$H NMR (400 MHz, DMSO-$d_6$): δ 3.76 (br. s., 3H), 5.55 (br. s., 2H), 7.19-7.38 (m, 4H), 7.61 (dd, J=8.59, 5.56 Hz, 1H), 7.69 (d, J=4.80 Hz, 1H), 7.96-8.06 (m, 1H), 8.48 (d, J=5.05 Hz, 1H). [M+H] Calc'd for $C_{18}H_{14}FN_5O_2$, 352; Found, 352.

Example 72: 2-(cyclopropylmethoxy)-8-(1-methyl-imidazol-4-yl)pyrido[3,4-d]pyrimidin-4-ol

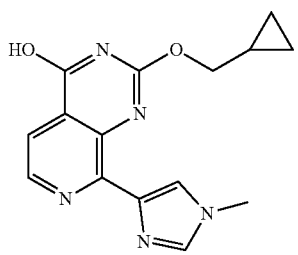 [SMILES: Cn1cnc(-c2nccc3c(O)nc(OCC4CC4)nc23)c1]

To a solution of cyclopropyl-methanol (276 mg, 3.8 mmol) in DMF (10 mL) was added NaH (155 mg, 3.8 mmol) at 0° C. The reaction mixture was stirred at rt for 20 min. 2-chloro-8-(1-methyl-1H-imidazol-4-yl)pyrido[3,4-d]pyrimidin-4-ol was added. The mixture was stirred at 120° C. for 5 h. Solvent was concentrated and the residue was purified by preparative HPLC to give 100 mg (44%) of the title product. $^1$H NMR (400 MHz, DMSO-$d_6$): δ 0.48-0.68 (4H, m), 1.33-1.37 (1H, m), 3.98 (3H, s), 4.41 (2H, d, J=7.2 Hz) 7.95 (1H, d, J=4.8 Hz), 8.41 (1H, s), 8.59 (1H, d, J=4.8 Hz), 9.19 (1H, s). [M+H] Calc'd for $C_{15}H_{15}N_5O_2$, 298; Found, 298.

Example 73: 2-(3-hydroxy-3-methylbutoxy)-8-(1-methylimidazol-4-yl)pyrido[3,4-d]pyrimidin-4-ol

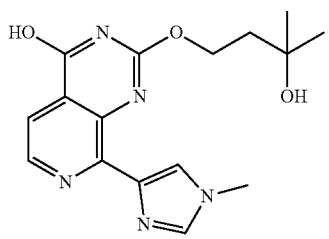 [SMILES: Cn1cnc(-c2nccc3c(O)nc(OCCC(C)(C)O)nc23)c1]

The title compound was prepared in 20% yield from 3-methylbutane-1,3-diol and 2-chloro-8-(1-methyl-1H-imidazol-4-yl)pyrido[3,4-d]pyrimidin-4-ol according to the procedure for the preparation of Example 72. $^1$H NMR (400 MHz, DMSO-$d_6$): $^1$H NMR (400 MHz, DMSO-$d_6$): δ 1.21 (6H, s), 1.92 (2H, t, J=7.2 Hz), 3.81 (3H, s), 4.59 (2H, t, J=5.2 Hz), 7.75 (1H, d, J=5.2 Hz), 8.21 (1H, s), 8.30 (1H, d, J=5.2 Hz), 8.51 (1H, s). [M+H] Calc'd for $C_{16}H_{19}N_5O_3$, 330; Found, 330.

Example 74: 8-(1-methylimidazol-4-yl)-2-(4,4,4-trifluorobutoxy)pyrido[3,4-d]pyrimidin-4-ol

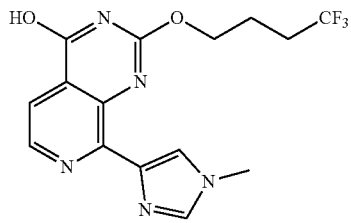 [SMILES: Cn1cnc(-c2nccc3c(O)nc(OCCCC(F)(F)F)nc23)c1]

The title compound was prepared in 10% yield from 4,4,4-trifluorobutan-1-ol and 2-chloro-8-(1-methyl-1H-imidazol-4-yl)pyrido[3,4-d]pyrimidin-4-ol according to the procedure for the preparation of Example 72. $^1$H NMR (400 MHz, CD$_3$OD): δ 2.07-2.10 (2H, m), 2.34-2.38 (2H, m), 3.98 (3H, s), 4.59 (2H, t, J=6.4 Hz), 7.92 (1H, d, J=5.2 Hz), 8.38 (1H, s), 8.52 (1H, d, J=5.2 Hz), 8.94 (1H, s). [M+H] Calc'd for $C_{15}H_{14}F_3N_5O_2$, 354; Found, 354.

Example 75: 2-(2-hydroxyethoxy)-8-(1-methylimidazol-4-yl)pyrido[3,4-d]pyrimidin-4-ol

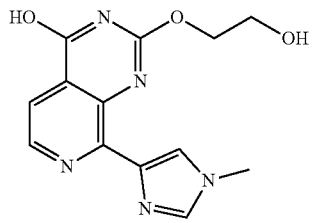 [SMILES: Cn1cnc(-c2nccc3c(O)nc(OCCO)nc23)c1]

The title compound was prepared in 45% yield from ethane-1,2-diol and 2-chloro-8-(1-methyl-1H-imidazol-4-yl)pyrido[3,4-d]pyrimidin-4-ol according to the procedure for the preparation of Example 72. $^1$H NMR (400 MHz, DMSO-$d_6$): δ 3.84 (2H, t, J=4.8 Hz), 4.01 (3H, s), 4.61 (2H, t, J=4.8 Hz) 7.94 (1H, d, J=5.2 Hz), 8.45 (1H, s), 8.59 (1H, d, J=4.8 Hz), 9.27 (1H, s). [M+H] Calc'd for $C_{13}H_{13}N_5O_3$, 288; Found, 288.

Example 76: 2-[2-(dimethylamino)ethoxy]-8-(1-methylimidazol-4-yl)pyrido[3,4-d]pyrimidin-4-ol

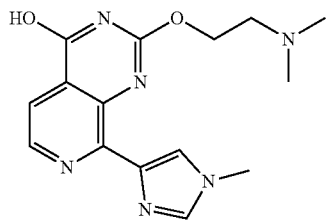 [SMILES: CN(C)CCOc1nc(O)c2ccnc(-c3cn(C)cn3)c2n1]

The title compound was prepared in 30% yield from 2-(dimethylamino)ethanol and 2-chloro-8-(1-methyl-1H-imidazol-4-yl)pyrido[3,4-d]pyrimidin-4-ol according to the procedure for the preparation of Example 72. $^1$H NMR (400 MHz, DMSO-$d_6$): δ 2.92 (6H, s), 3.63 (2H, t, J=4.8 Hz), 3.98 (3H, s), 4.93 (2H, t, J=4.8 Hz), 7.98 (1H, d, J=5.2 Hz), 8.40 (1H, s), 8.67 (1H, d, J=5.2 Hz), 9.17 (1H, s). [M+H] Calc'd for $C_{15}H_{18}N_6O_2$, 315; Found, 315.

Example 77: 2-(2,2-difluoroethoxy)-8-(1-methylimidazol-4-yl)pyrido[3,4-d]pyrimidin-4-ol

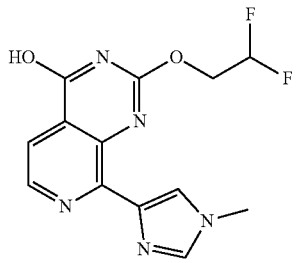 [SMILES: Cn1cnc(-c2nccc3c(O)nc(OCC(F)F)nc23)c1]

The title compound was prepared in 28% yield from 2,2-difluoroethanol and 2-chloro-8-(1-methyl-1H-imidazol-4-yl)pyrido[3,4-d]pyrimidin-4-ol according to the procedure for the preparation of Example 72. $^1$H NMR (400 MHz, DMSO-$d_6$): δ 3.98 (3H, s), 4.87-4.94 (2H, m), 6.52 (1H, m), 7.97 (1H, d, J=5.2 Hz), 8.45 (1H, s), 8.64 (1H, d, J=5.2 Hz), 9.20 (1H, s). [M+H] Calc'd for $C_{15}H_{17}N_5O_3$, 308; Found, 308.

Example 78: 2-(2-cyclopropylethoxy)-8-(1-methylimidazol-4-yl)pyrido[3,4-d]pyrimidin-4-ol

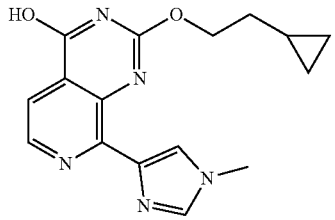 [SMILES: Cn1cnc(-c2nccc3c(O)nc(OCCC4CC4)nc23)c1]

The title compound was prepared in 45% yield from 2-cyclopropylethanol and 2-chloro-8-(1-methyl-1H-imidazol-4-yl)pyrido[3,4-d]pyrimidin-4-ol according to the procedure for the preparation of Example 72. $^1$H NMR (400 MHz, DMSO-$d_6$): δ 0.26-0.20 (2H, m), 0.45-0.49 (2H, m), 0.85-0.92 (1H, m), 1.70-1.75 (2H, m), 3.98 (3H, s), 4.61 (2H, t, J=6.0 Hz), 7.94 (1H, d, J=5.2 Hz), 8.42 (1H, s), 8.59 (1H, d, J=5.2 Hz), 9.20 (1H, s). [M+H] Calc'd for $C_{16}H_{17}N_5O_2$, 312; Found, 312.

Example 79: 2-(1-benzylpyrazol-4-yl)oxy-8-(1-methylimidazol-4-yl)pyrido[3,4-d]pyrimidin-4-ol

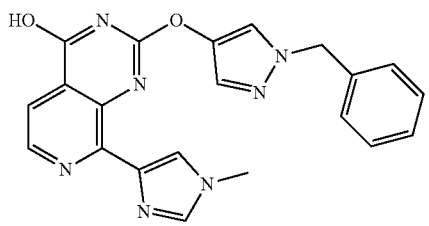 [SMILES: Cn1cnc(-c2nccc3c(O)nc(Oc4cnn(Cc5ccccc5)c4)nc23)c1]

A mixture of DIEA (0.26 mL, 1.5 mmol), 1-benzyl-1H-pyrazol-4-ol (130 mg, 0.76 mmol) and 2-chloro-8-(1-methyl-1H-imidazol-4-yl)pyrido[3,4-d]pyrimidin-4-ol (100 mg, 0.38 mmol) in THF (5 mL) were stirred at 75° C. for 18 h. The reaction mixture was concentrated and dried under high vacuum. The reaction mixture was purified by silica gel chromatography (0-20%, MeOH:DCM) to afford 55 mg (37%) of the desired product as a pale yellow solid. $^1$H NMR (400 MHz, DMSO-$d_6$): δ 3.44 (s, 3H), 5.40 (s, 2H), 7.22-7.39 (m, 6H), 7.67-7.74 (m, 3H), 8.39 (br. s., 1H), 8.49 (d, J=5.05 Hz, 1H), 13.01-13.40 (br. s., 1H). [M+H] Calc'd for $C_{21}H_{17}N_7O_2$, 400; Found, 400.

Example 80: 2-[1-(3-methylbutyl)pyrazol-4-yl]oxy-8-(1-methylimidazol-4-yl)pyrido[3,4-d]pyrimidin-4-ol

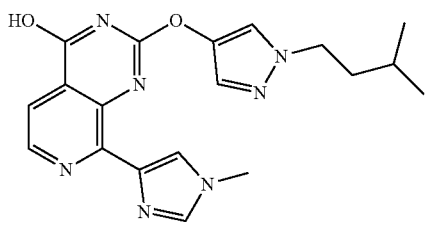 [SMILES: CC(C)CCn1cc(Oc2nc(O)c3ccnc(-c4cn(C)cn4)c3n2)cn1]

The title compound was prepared in 43% yield from 1-(3-methylbutyl)-1H-pyrazol-4-ol and 2-chloro-8-(1-methyl-1H-imidazol-4-yl)pyrido[3,4-d]pyrimidin-4-ol according to the procedure for the preparation of Example 79. $^1$H NMR (400 MHz, DMSO-$d_6$): δ 0.92 (d, J=6.82 Hz, 6H), 1.48-1.61 (m, 1H), 1.72 (q, J=6.91 Hz, 2H), 3.68 (s, 3H), 4.19 (t, J=7.33 Hz, 2H), 7.66 (s, 1H), 7.71 (s, 1H), 7.84 (d, J=5.05 Hz, 1H), 8.48 (br. s., 1H), 8.57 (d, J=5.05 Hz, 1H), 8.72 (br. s., 1H). [M+H] Calc'd for $C_{19}H_{21}N_7O_2$, 380; Found, 380.

Example 81: 2-(3,4-difluorophenoxy)-8-(1-methylimidazol-4-yl)pyrido[3,4-d]pyrimidin-4-ol

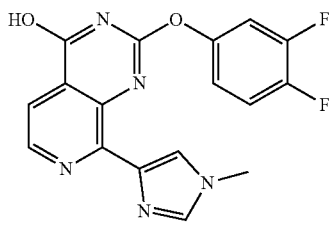 [SMILES: Cn1cnc(-c2nccc3c(O)nc(Oc4ccc(F)c(F)c4)nc23)c1]

The title compound was prepared in 51% yield from 3,4-difluorophenol and 2-chloro-8-(1-methyl-imidazol-4-yl)pyrido[3,4-d]pyrimidin-4-ol according to the procedure for the preparation of Example 79. $^1$H NMR (400 MHz, DMSO-$d_6$): δ 3.42 (s, 3H), 7.35 (d, J=8.59 Hz, 2H), 7.66-7.81 (m, 4H), 8.48 (d, J=5.05 Hz, 1H), 13.45 (br. s., 1H). [M+H] Calc'd for $C_{17}H_{11}F_2N_5O_2$, 356; Found, 356.

Example 82: 2-[4-(2-methoxyethoxy)phenoxy]-8-(1-methylimidazol-4-yl)pyrido[3,4-d]pyrimidin-4-ol

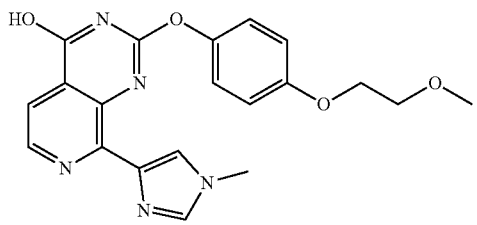 [SMILES: COCCOc1ccc(Oc2nc(O)c3ccnc(-c4cn(C)cn4)c3n2)cc1]

The title compound was prepared in 40% yield from 4-(2-methoxyethoxy)phenol and 2-chloro-8-(1-methyl-1H-imidazol-4-yl)pyrido[3,4-d]pyrimidin-4-ol according to the procedure for the preparation of Example 79. $^1$H NMR (400 MHz, DMSO-d$_6$): δ 3.61 (s, 3H), 3.68-3.75 (m, 2H), 4.13-4.25 (m, 2H), 7.13 (s, 1H), 7.19 (d, J=9.09 Hz, 2H), 7.35 (d, J=9.09 Hz, 2H), 7.92 (d, J=5.05 Hz, 1H), 8.58 (d, J=5.05 Hz, 1H), 8.89 (br. s., 1H), 13.44 (s, 1H). [M+H] Calc'd for C$_{20}$H$_{19}$N$_5$O$_4$, 394; Found, 394.

Example 83: 8-(1-methylimidazol-4-yl)-2-(1-methylindazol-6-yl)oxypyrido[3,4-d]pyrimidin-4-ol

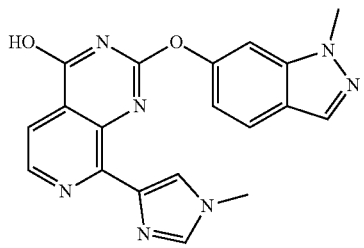 [SMILES: Cn1cnc(-c2nccc3c(O)nc(Oc4ccc5cnn(C)c5c4)nc23)c1]

The title compound was prepared in 25% yield from 1-methyl-1H-indazol-6-ol and 2-chloro-8-(1-methyl-1H-imidazol-4-yl)pyrido[3,4-d]pyrimidin-4-ol according to the procedure for the preparation of Example 79. $^1$H NMR (400 MHz, DMSO-d$_6$): δ 2.97 (br. s., 3H), 4.06 (s, 3H), 6.98 (br. s., 1H), 7.21 (d, J=8.84 Hz, 1H), 7.52 (br. s., 1H), 7.68 (d, J=5.05 Hz, 1H), 7.79 (s, 1H), 7.96 (d, J=8.84 Hz, 1H), 8.18 (s, 1H), 8.47 (d, J=5.05 Hz, 1H), 13.40 (br. s., 1H). [M+H] Calc'd for C$_{19}$H$_{15}$N$_7$O$_2$, 374; Found, 374.

Preparation 84A: 1-ethyl-1H-indazol-6-ol

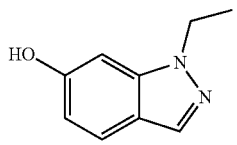

The title compound was prepared in 67% yield from 1-ethylindazol-6-amine according to the procedure for the preparation of 61A. [M+H] Calc'd for C$_9$H$_{10}$N$_2$O, 163; Found, 163.

Example 84: 2-(1-ethylindazol-6-yl)oxy-8-(1-methylimidazol-4-yl)pyrido[3,4-d]pyrimidin-4-ol

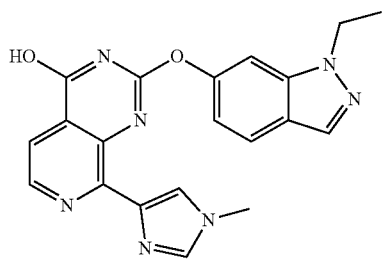 [SMILES: CCn1ncc2ccc(Oc3nc(O)c4ccnc(-c5cn(C)cn5)c4n3)cc21]

The title compound was prepared in 27% yield from 1-ethyl-1H-indazol-6-ol and 2-chloro-8-(1-methyl-1H-imidazol-4-yl)pyrido[3,4-d]pyrimidin-4-ol according to the procedure for the preparation of Example 79. $^1$H NMR (400 MHz, DMSO-d$_6$): δ 1.27-1.41 (m, 3H), 2.91 (br. s., 3H), 4.37-4.52 (m, 2H), 6.90 (br. s., 1H), 7.20 (dd, J=8.72, 1.89 Hz, 1H), 7.51 (br. s., 1H), 7.68 (d, J=5.05 Hz, 1H), 7.83 (s, 1H), 7.96 (d, J=8.59 Hz, 1H), 8.19 (s, 1H), 8.46 (d, J=5.05 Hz, 1H), 13.39 (br. s., 1H). [M+H] Calc'd for C$_{20}$H$_{17}$N$_7$O$_2$, 388; Found, 388.

Preparation 85A: 1,3-dimethyl-1H-indazol-6-ol

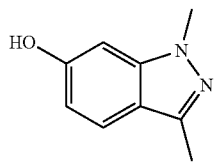

The title compound was prepared in 57% yield from 1,3-dimethylindazol-6-amine according to the procedure for the preparation of 61A. [M+H] Calc'd for C$_9$H$_{10}$N$_2$O, 163; Found, 163.

Example 85: 2-(1,3-dimethylindazol-6-yl)oxy-8-(1-methylimidazol-4-yl)pyrido[3,4-d]pyrimidin-4-ol

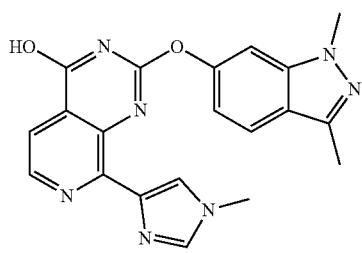 [SMILES: Cc1nn(C)c2cc(Oc3nc(O)c4ccnc(-c5cn(C)cn5)c4n3)ccc12]

The title compound was prepared in 16% yield from 1,3-dimethyl-1H-indazol-6-ol and 2-chloro-8-(1-methyl-1H-imidazol-4-yl)pyrido[3,4-d]pyrimidin-4-ol according to the procedure for the preparation of Example 79. $^1$H NMR (400 MHz, DMSO-d$_6$): δ 2.53 (s, 3H), 3.01 (br. s., 3H), 3.96 (s, 3H), 7.06 (br. s., 1H), 7.12 (dd, J=8.59, 1.77 Hz, 1H), 7.51 (br. s., 1H), 7.65 (d, J=5.31 Hz, 2H), 7.88 (d, J=8.59 Hz, 1H), 8.40 (d, J=5.05 Hz, 1H). [M+H] Calc'd for C$_{20}$H$_{17}$N$_7$O$_2$, 388; Found, 388.

Preparation 86A: 1-(4-fluorobenzyl)-4-(4,4,5,5-tetramethyl-[1,3,2]dioxaborolan-2-yl)-1H-pyrazole

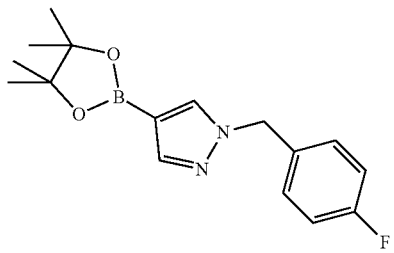 [SMILES: CC1(C)OB(c2cnn(Cc3ccc(F)cc3)c2)OC1(C)C]

A mixture of 4-(4,4,5,5-tetramethyl-1,3,2-dioxaborolan-2-yl)-1H-pyrazole (1.94 g, 10 mmol), 4-fluorobenzyl bromide (2.23 g, 12 mmol) and K$_2$CO$_3$ (2.76 g, 20 mmol) in DMF (20 mL) was stirred at 130° C. for 16 h. The reaction mixture was concentrated and purified by silica gel chromatography (0-80%, EA:Hexanes) to give 1.36 g (45%) of the title compound as yellow oil. $^1$H NMR (400 MHz, DMSO-d$_6$): δ 1.18-1.29 (m, 12H), 5.32 (s, 2H), 7.08-7.25 (m, 2H), 7.27-7.35 (m, 2H), 7.61 (s, 1H), 8.05 (s, 1H). [M+H] Calc'd for C$_{16}$H$_{20}$BFN$_2$O$_2$, 303; Found, 303.

Preparation 86B:
1-(4-fluorobenzyl)-1H-pyrazol-4-ol

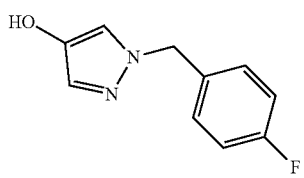 [SMILES: Oc1cnn(Cc2ccc(F)cc2)c1]

The title compound was prepared in 67% yield from 1-(4-fluorobenzyl)-4-(4,4,5,5-tetramethyl-[1,3,2]dioxaborolan-2-yl)-1H-pyrazole according to the procedure for the preparation 66A. $^1$H NMR (400 MHz, DMSO-d$_6$): δ 5.12 (s, 2H), 7.01 (s, 1H), 7.11-7.18 (m, 2H), 7.20-7.25 (m, 2H), 7.25 (s, 1H), 8.41 (s, 1H). [M+H] Calc'd for C$_{10}$H$_9$FN$_2$O, 193; Found, 193.

Example 86: 2-[1-(4-fluorobenzyl)pyrazol-4-yl]oxypyrido[3,4-d]pyrimidin-4-ol

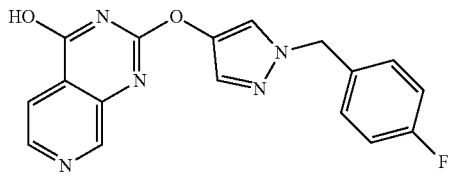 [SMILES: Oc1nc(Oc2cnn(Cc3ccc(F)cc3)c2)nc2cnccc12]

The title compound was prepared in 66% yield from 1-(4-fluorobenzyl)-1H-pyrazol-4-ol and 2-chloropyrido[3,4-d]pyrimidin-4-ol according to the procedure for the preparation of Example 34. $^1$H NMR (400 MHz, DMSO-d$_6$): δ 5.34 (s, 2H), 7.21 (m, 2H), 7.35 (m, 2H), 7.65 (s, 1H), 7.88 (d, J=4.55 Hz, 1H), 8.20 (s, 1H), 8.55 (br. s., 1H), 8.83 (br. s., 1H), 13.09 (s, 1H). [M+H] Calc'd for C$_{17}$H$_{12}$FN$_5$O$_2$, 338; Found, 338.

Preparation 87A: 1-(2-fluorobenzyl)-4-(4,4,5,5-tetramethyl-[1,3,2]dioxaborolan-2-yl)-1H-pyrazole

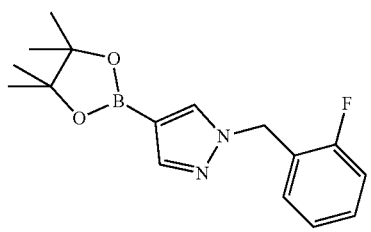 [SMILES: CC1(C)OB(c2cnn(Cc3ccccc3F)c2)OC1(C)C]

The title compound was prepared in 38% yield from 2-fluorobenzyl bromide according to the procedure for the preparation 86A. [M+H] Calc'd for C$_{16}$H$_{20}$BFN$_2$O$_2$, 303; Found, 303.

Preparation 87B:
1-(2-fluorobenzyl)-1H-pyrazol-4-ol

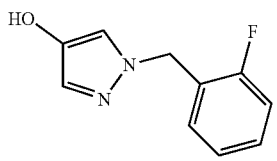 [SMILES: Oc1cnn(Cc2ccccc2F)c1]

The title compound was prepared in 82% yield from 1-(2-fluorobenzyl)-4-(4,4,5,5-tetramethyl-[1,3,2]dioxaborolan-2-yl)-1H-pyrazole according to the procedure for the preparation 66A. [M+H] Calc'd for C$_{10}$H$_9$FN$_2$O, 193; Found, 193.

Example 87: 2-[1-(2-fluorobenzyl)pyrazol-4-yl]oxypyrido[3,4-d]pyrimidin-4-ol

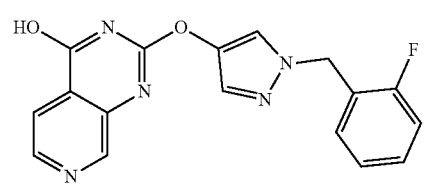 [SMILES: Oc1nc(Oc2cnn(Cc3ccccc3F)c2)nc2cnccc12]

The title compound was prepared in 54% yield from 1-(2-fluorobenzyl)-1H-pyrazol-4-ol and 2-chloropyrido[3,4-d]pyrimidin-4-ol according to the procedure for the preparation of Example 34. $^1$H NMR (400 MHz, DMSO-d$_6$): δ 5.41 (s, 2H), 7.19-7.29 (m, 3H), 7.36-7.44 (m, 1H), 7.66 (s, 1H), 7.88 (d, J=5.05 Hz, 1H), 8.19 (s, 1H), 8.55 (br. s., 1H), 8.82 (br. s., 1H), 13.10 (s, 1H). [M+H] Calc'd for C$_{17}$H$_{12}$FN$_5$O$_2$, 338; Found, 338.

Preparation 88A: tert-butyl 4-(4-hydroxypyrazol-1-yl)piperidine-1-carboxylate

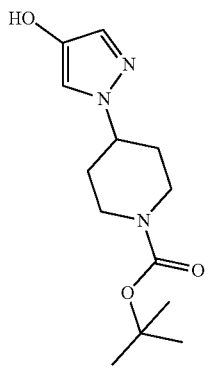 [SMILES: CC(C)(C)OC(=O)N1CCC(n2cc(O)cn2)CC1]

The title compound was prepared in 91% yield from tert-butyl 4-[4-(4,4,5,5-tetramethyl-1,3,2-dioxaborolan-2-yl)pyrazol-1-yl]piperidine-1-carboxylate according to the procedure for the preparation 66A. $^1$H NMR (400 MHz, DMSO-d$_6$): δ 1.41 (s, 9H), 1.62-1.79 (m, 2H), 1.82-1.99 (m, 2H), 2.86 (br. s., 2H), 3.94-4.06 (m, 2H), 4.13 (tt, J=11.46, 3.95 Hz, 1H), 6.98 (s, 1H), 7.23 (s, 1H), 8.32 (s, 1H). [M+H] Calc'd for C$_{13}$H$_{21}$N$_3$O$_3$, 268; Found, 268.

Example 88: tert-butyl 4-[4-(4-hydroxypyrido[3,4-d]pyrimidin-2-yl)oxypyrazol-1-yl]piperidine-1-carboxylate

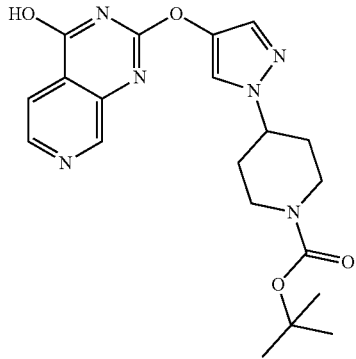 [SMILES: CC(C)(C)OC(=O)N1CCC(n2cc(Oc3nc(O)c4ccncc4n3)cn2)CC1]

The title compound was prepared in 48% yield from tert-butyl 4-(4-hydroxypyrazol-1-yl)piperidine-1-carboxylate and 2-chloropyrido[3,4-d]pyrimidin-4-ol according to the procedure for the preparation of Example 34. $^1$H NMR (400 MHz, DMSO-d$_6$): δ 1.42 (s, 9H), 1.80 (qd, J=12.08, 4.42 Hz, 2H), 1.89-2.13 (m, 2H), 2.92 (br. s., 2H), 4.05 (d, J=11.87 Hz, 2H), 4.25-4.49 (m, 1H), 7.61 (br. s., 1H), 7.91 (br. s., 1H), 8.15 (br. s., 1H), 8.60 (br. s., 1H), 8.92 (br. s., 1H), 12.97-13.28 (m, 1H). [M+H] Calc'd for C$_{20}$H$_{24}$N$_6$O$_4$, 413; Found, 413.

Example 89: 2-(1-piperidin-4-ylpyrazol-4-yl)oxypyrido[3,4-d]pyrimidin-4-ol

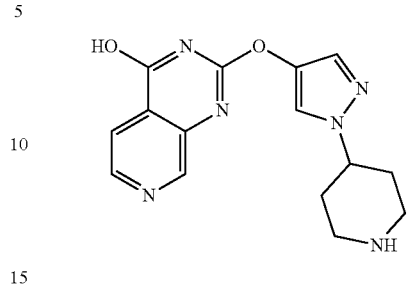

To tert-butyl 4-[4-(4-hydroxypyrido[3,4-d]pyrimidin-2-yl)oxypyrazol-1-yl]piperidine-1-carboxylate (200 mg, 0.24 mmol) in 1,4-dioxane (10 mL) at 0° C. was added a 4 M HCl solution in dioxane (2.4 mL). The solution was stirred at room temperature for 7 h. The volatiles were removed in vacuo and dried under high vacuum to give 220 mg (100%) of the title compound (hydrochloride salt) as a pale yellow solid. $^1$H NMR (400 MHz, DMSO-d$_6$): δ 2.03-2.35 (m, 4H), 2.85-3.10 (m, 2H), 3.24-3.41 (m, 1H), 3.99-4.67 (m, 2H), 7.70 (s, 1H), 7.85-8.19 (m, 2H), 8.48-8.94 (m, 2H), 13.14 (br. s., 1H). [M+H] Calc'd for C$_{15}$H$_{16}$N$_6$O$_2$, 313; Found, 313.

Example 90: 1-[4-[4-(4-hydroxypyrido[3,4-d]pyrimidin-2-yl)oxypyrazol-1-yl]piperidin-1-yl]ethanone

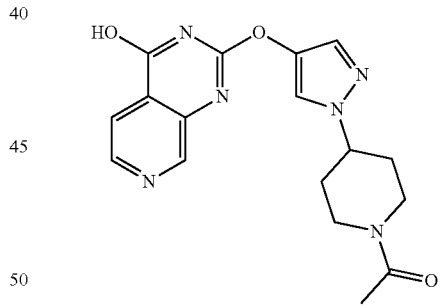

To a solution of 2-(1-piperidin-4-ylpyrazol-4-yl)oxypyrido[3,4-d]pyrimidin-4-ol (25 mg, 0.065 mmol) in THF (1 mL) was added triethylamine (27 μL, 0.2 mmol) and acetyl chloride (5.2 μL, 0.065 mmol) at 0° C. The reaction mixture was stirred at 0° C. for 30 min and at rt for 16 h. The reaction was quenched with water (0.1 mL) and the mixture was concentrated in vacuo. The crude product was purified by silica gel chromatography (0-20%, MeOH:DCM) to afford 12 mg (53%) of the desired product as a white solid. $^1$H NMR (400 MHz, DMSO-d$_6$): δ 1.69-1.96 (m, 2H), 1.98-2.13 (m, 5H), 2.60-2.77 (m, 2H), 3.93 (s, 1H), 4.37-4.53 (m, 2H), 7.64 (s, 1H), 7.88 (d, J=5.05 Hz, 1H), 8.13 (s, 1H), 8.54 (d, J=4.80 Hz, 1H), 8.85 (s, 1H), 13.01-13.23 (m, 1H). [M+H] Calc'd for C$_{17}$H$_{18}$N$_6$O$_3$, 355; Found, 355.

Example 91: 1-[4-[4-(4-hydroxypyrido[3,4-d]pyrimidin-2-yl)oxypyrazol-1-yl]piperidin-1-yl]prop-2-en-1-one

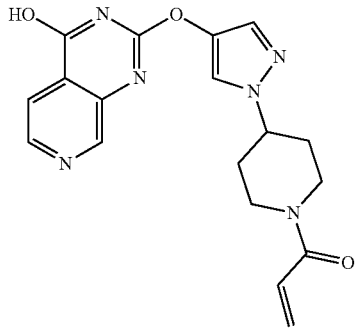 [SMILES: C=CC(=O)N1CCC(n2cc(Oc3nc(O)c4ccncc4n3)cn2)CC1]

The title compound was prepared in 25% yield from acryloyl chloride and of 2-(1-piperidin-4-ylpyrazol-4-yl)oxypyrido[3,4-d]pyrimidin-4-ol according to the procedure for the preparation of Example 90. $^1$H NMR (400 MHz, DMSO-d$_6$): δ 1.83 (br. s., 2H), 2.04-2.16 (m, 2H), 2.60-2.90 (m, 2H), 4.20 (br. s., 1H), 4.40-4.59 (m, 2H), 5.70 (dd, J=10.48, 2.40 Hz, 1H), 6.12 (dd, J=16.80, 2.40 Hz, 1H), 6.86 (dd, J=16.67, 10.61 Hz, 1H), 7.65 (s, 1H), 7.88 (d, J=5.05 Hz, 1H), 8.14 (s, 1H), 8.54 (d, J=5.05 Hz, 1H), 8.85 (s, 1H), 13.09 (s, 1H). [M+H] Calc'd for C$_{18}$H$_{18}$N$_6$O$_3$, 367; Found, 367.

Example 92: cyclopropyl-[4-[4-(4-hydroxypyrido[3,4-d]pyrimidin-2-yl)oxypyrazol-1-yl]piperidin-1-yl]methanone

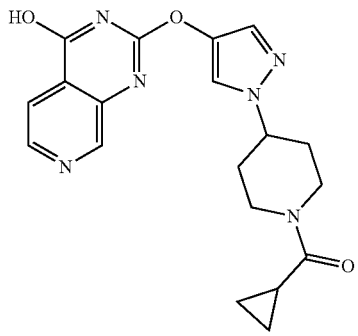 [SMILES: O=C(C1CC1)N1CCC(n2cc(Oc3nc(O)c4ccncc4n3)cn2)CC1]

The title compound was prepared in 25% yield from cyclopropanecarbonyl chloride and of 2-(1-piperidin-4-ylpyrazol-4-yl)oxypyrido[3,4-d]pyrimidin-4-ol according to the procedure for the preparation of Example 90. $^1$H NMR (400 MHz, DMSO-d$_6$): δ 0.72 (d, J=7.83 Hz, 4H), 1.68-1.97 (m, 2H), 1.98-2.18 (m, 3H), 2.60-2.88 (m, 2H), 4.31-4.56 (m, 3H), 7.65 (s, 1H), 7.88 (d, J=5.05 Hz, 1H), 8.15 (s, 1H), 8.54 (d, J=5.05 Hz, 1H), 8.79-8.92 (m, 1H), 13.10 (s, 1H). [M+H] Calc'd for C$_{19}$H$_{20}$N$_6$O$_3$, 381; Found, 381.

Example 93: (4-fluorophenyl)-[4-[4-(4-hydroxypyrido[3,4-d]pyrimidin-2-yl)oxypyrazol-1-yl]piperidin-1-yl]methanone

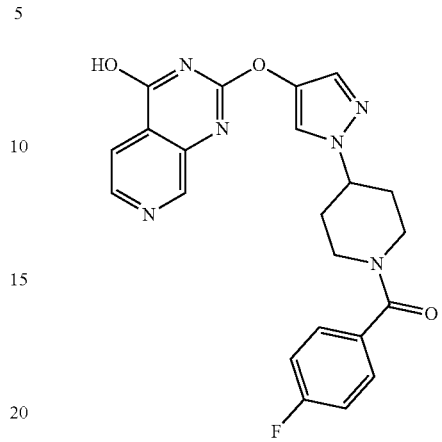

The title compound was prepared in 29% yield from 4-fluorobenzoyl chloride and of 2-(1-piperidin-4-ylpyrazol-4-yl)oxypyrido[3,4-d]pyrimidin-4-ol according to the procedure for the preparation of Example 90. $^1$H NMR (400 MHz, DMSO-d$_6$): δ 1.84-2.23 (m, 4H), 2.59-2.65 (m, 1H), 2.88-3.13 (m, 1H), 4.38-4.53 (m, 2H), 4.54-4.65 (m, 1H), 7.24-7.33 (m, 2H), 7.52 (dd, J=8.59, 5.56 Hz, 2H), 7.65 (s, 1H), 7.88 (d, J=5.05 Hz, 1H), 8.16 (s, 1H), 8.53 (d, J=5.05 Hz, 1H), 8.85 (s, 1H), 13.10 (s, 1H). [M+H] Calc'd for C$_{22}$H$_{19}$FN$_6$O$_3$, 435; Found, 435.

Example 94: 2-[1-(1-cyclopropylsulfonylpiperidin-4-yl)pyrazol-4-yl]oxypyrido[3,4-d]pyrimidin-4-ol

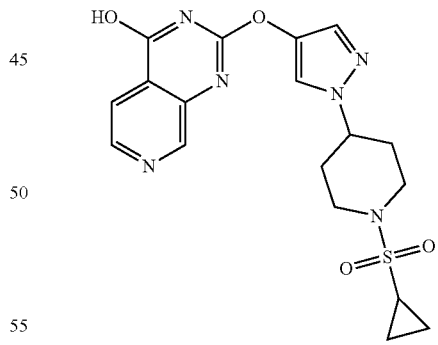

The title compound was prepared in 21% yield from cyclopropanesulfonyl chloride and of 2-(1-piperidin-4-ylpyrazol-4-yl)oxypyrido[3,4-d]pyrimidin-4-ol according to the procedure for the preparation of Example 90. $^1$H NMR (400 MHz, DMSO-d$_6$): δ 0.89-1.06 (m, 4H), 1.94-2.24 (m, 4H), 2.58-2.70 (m, 1H), 2.96-3.14 (m, 1H), 3.65-3.81 (m, 1H), 4.02-4.17 (m, 2H), 4.28-4.43 (m, 1H), 7.63-7.75 (m, 1H), 7.83-7.93 (m, 1H), 8.10-8.21 (m, 1H), 8.54 (d, J=5.05 Hz, 1H), 8.85 (s, 1H), 13.10 (br. s., 1H). [M+H] Calc'd for C$_{18}$H$_{20}$N$_6$O$_4$S, 417; Found, 417.

Example 95: 2-[1-[1-(benzenesulfonyl)piperidin-4-yl]pyrazol-4-yl]oxypyrido[3,4-d]pyrimidin-4-ol

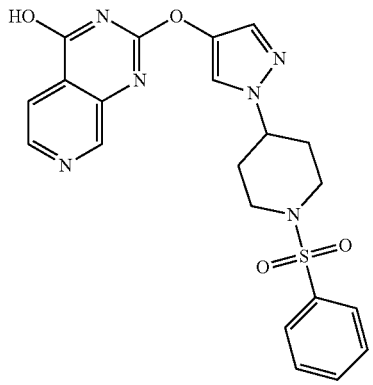 [SMILES: O=S(=O)(c1ccccc1)N1CCC(n2cc(Oc3nc(O)c4ccncc4n3)cn2)CC1]

The title compound was prepared in 18% yield from and benzenesulfonyl chloride and of 2-(1-piperidin-4-ylpyrazol-4-yl)oxypyrido[3,4-d]pyrimidin-4-ol according to the procedure for the preparation of Example 90. $^1$H NMR (400 MHz, DMSO-$d_6$): δ 1.94-2.06 (m, 2H), 2.11 (d, J=9.85 Hz, 2H), 2.59 (br. s., 2H), 3.75 (d, J=11.87 Hz, 2H), 4.21 (t, J=11.24 Hz, 1H), 7.62 (s, 1H), 7.69 (d, J=7.58 Hz, 2H), 7.73-7.83 (m, 3H), 7.87 (d, J=5.05 Hz, 1H), 8.08 (s, 1H), 8.54 (d, J=5.05 Hz, 1H), 8.83 (s, 1H), 13.09 (s, 1H). [M+H] Calc'd for $C_{21}H_{20}N_6O_4S$, 453; Found, 453.

Preparation 96A: tert-butyl 4-(4-hydroxypyridin-2-yl)piperazine-1-carboxylate

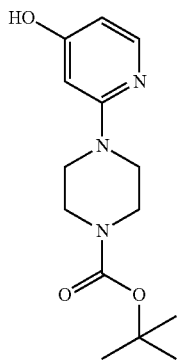 [SMILES: CC(C)(C)OC(=O)N1CCN(c2cc(O)ccn2)CC1]

The title compound was prepared in 65% yield from tert-butyl 4-[4-(4,4,5,5-tetramethyl-1,3,2-dioxaborolan-2-yl)pyridin-2-yl]piperazine-1-carboxylate according to the procedure for the preparation of 67C. $^1$H NMR (400 MHz, DMSO-$d_6$): δ 1.38-1.46 (m, 9H), 3.43-3.67 (m, 8H), 6.11 (s, 1H), 6.16 (d, J=5.31 Hz, 1H), 7.83 (d, J=5.56 Hz, 1H), 10.03-10.24 (m, 1H). [M+H] Calc'd for $C_{14}H_{21}N_3O_3$, 280; Found, 280.

Preparation 96B: tert-butyl 4-[4-(4-hydroxypyrido[3,4-d]pyrimidin-2-yl)oxypyridin-2-yl]piperazine-1-carboxylate

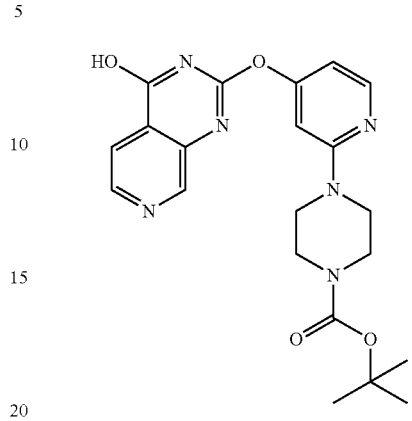

The title compound was prepared in 22% yield from tert-butyl 4-(4-hydroxypyridin-2-yl)piperazine-1-carboxylate and 2-chloropyrido[3,4-d]pyrimidin-4-ol according to the procedure for the preparation of Example 34. $^1$H NMR (400 MHz, DMSO-$d_6$): δ 1.43 (s, 9H), 3.39-3.45 (m, 4H), 3.49-3.57 (m, 4H), 6.71 (dd, J=5.56, 1.77 Hz, 1H), 6.85 (d, J=1.77 Hz, 1H), 7.90 (d, J=5.31 Hz, 1H), 8.18 (d, J=5.56 Hz, 1H), 8.55 (d, J=5.05 Hz, 1H), 8.76 (s, 1H), 13.22 (br. s., 1H). [M+H] Calc'd for $C_{21}H_{24}N_6O_4$, 425; Found, 425.

Example 96: 2-(2-piperazin-1-ylpyridin-4-yl)oxypyrido[3,4-d]pyrimidin-4-ol

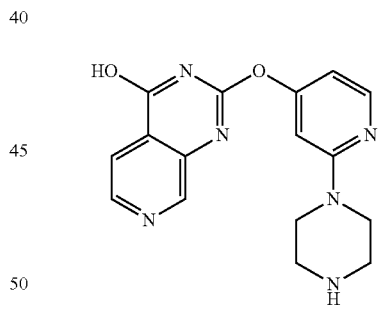

To a solution of tert-butyl 4-[4-(4-hydroxypyrido[3,4-d]pyrimidin-2-yl)oxypyridin-2-yl]piperazine-1-carboxylate (50 mg, 0.12 mmol) in dioxane (5 mL) at 0° C. was added dropwise HCl solution (4N) in dioxane (1 mL). The reaction was stirred at rt for 6 h. Solvent was concentrated and the residue was triturated in diethyl ether. The solid was filtered to give 17 mg (43%) of the desired product (hydrochloride salt) as a yellow solid. $^1$H NMR (400 MHz, DMSO-$d_6$): δ 3.19 (br. s., 4H), 3.80 (br. s., 4H), 6.86 (d, J=5.56 Hz, 1H), 7.04 (s, 1H), 7.91-7.98 (m, 1H), 8.17-8.26 (m, 1H), 8.53-8.61 (m, 1H), 8.79 (s, 1H), 9.22 (br. s., 2H), 13.09-13.66 (m, 1H). [M+H] Calc'd for $C_{16}H_{16}N_6O_2$, 325; Found, 325.

Preparation 97A: 2-morpholin-4-ylpyridin-4-ol

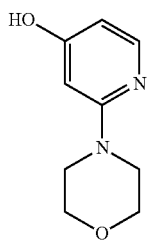 [SMILES: Oc1ccnc(N2CCOCC2)c1]

The title compound was prepared in 88% yield from 4-[4-(4,4,5,5-tetramethyl-1,3,2-dioxaborolan-2-yl)pyridin-2-yl]morpholine according to the procedure for the preparation of 67C. $^1$H NMR (400 MHz, DMSO-$d_6$) δ 3.31-3.43 (m, 4H), 3.61-3.74 (m, 4H), 6.08 (s, 1H), 6.17 (d, J=5.31 Hz, 1H), 7.83 (d, J=5.31 Hz, 1H), 10.16 (br. s., 1H). [M+H] Calc'd for $C_9H_{12}N_2O_2$, 181; Found, 181.

Example 97: 2-(2-morpholin-4-ylpyridin-4-yl)oxy-pyrido[3,4-d]pyrimidin-4-ol

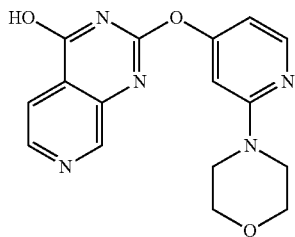 [SMILES: Oc1nc(Oc2ccnc(N3CCOCC3)c2)nc2cnccc12]

The title compound was prepared in 22% yield from 2-morpholin-4-ylpyridin-4-ol and 2-chloropyrido[3,4-d]pyrimidin-4-ol according to the procedure for the preparation of Example 34. $^1$H NMR (400 MHz, DMSO-$d_6$): δ 3.43-3.55 (m, 4H), 3.64-3.75 (m, 4H), 6.68-6.77 (m, 1H), 6.81-6.91 (m, 1H), 7.86-7.96 (m, 1H), 8.19 (d, J=5.81 Hz, 1H), 8.55 (d, J=5.05 Hz, 1H), 8.76 (s, 1H), 13.21 (br. s., 1H). [M+H] Calc'd for $C_{16}H_{15}N_5O_3$, 326; Found, 326.

Example 98: 2-(2-hydroxy-2-methylpropoxy)-8-(1-methylimidazol-4-yl)pyrido[3,4-d]pyrimidin-4-ol

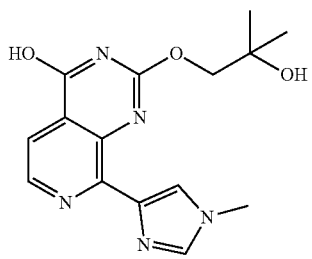 [SMILES: Cn1cnc(-c2nccc3c(O)nc(OCC(C)(C)O)nc23)c1]

The title compound was prepared in 20% yield from 2-methylpropane-1,2-diol and 2-chloro-8-(1-methyl-1H-imidazol-4-yl)pyrido[3,4-d]pyrimidin-4-ol according to the procedure for the preparation of Example 72. $^1$H NMR (400 MHz, DMSO-$d_6$): δ 1.27 (6H, s), 3.98 (3H, s), 4.34 (2H, s), 7.95 (1H, d, J=5.2 Hz), 8.47 (1H, s), 8.60 (1H, d, J=5.2 Hz), 9.20 (1H, s). [M+H] Calc'd for $C_{15}H_{17}N_5O_3$, 316; Found, 316.

Preparation 99A: 1-(1-phenylethyl)-4-(4,4,5,5-tetramethyl-1,3,2-dioxaborolan-2-yl)pyrazole

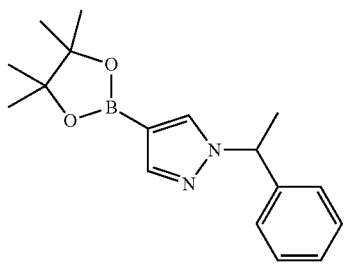 [SMILES: CC(c1ccccc1)n1cc(B2OC(C)(C)C(C)(C)O2)cn1]

The title compound was prepared in 22% yield from 1-bromoethylbenzene according to the procedure for the preparation 86A. [M+H] Calc'd for $C_{17}H_{23}BN_2O_2$, 299; Found, 299.

Preparation 99B: 1-(1-phenylethyl)pyrazol-4-ol

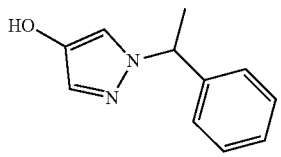

The title compound was prepared in 67% yield from 1-(1-phenylethyl)-4-(4,4,5,5-tetramethyl-1,3,2-dioxaborolan-2-yl)pyrazole according to the procedure for the preparation 66A. [M+H] Calc'd for $C_{11}H_{12}N_2O$, 189; Found, 189.

Example 99: 1-(1-phenylethyl)-4-(4,4,5,5-tetramethyl-1,3,2-dioxaborolan-2-yl)pyrazole

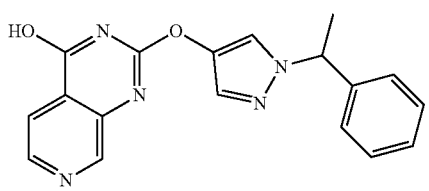 [SMILES: CC(c1ccccc1)n1cc(Oc2nc(O)c3ccncc3n2)cn1]

The title compound was prepared in 23% yield from 1-(1-phenylethyl)pyrazol-4-ol and 2-chloropyrido[3,4-d]pyrimidin-4-ol according to the procedure for the preparation of Example 34. $^1$H NMR (400 MHz, DMSO-$d_6$): δ 1.83 (d, J=7.07 Hz, 3H), 5.57-5.69 (m, 1H), 7.24-7.44 (m, 5H), 7.66 (s, 1H), 7.88 (d, J=5.05 Hz, 1H), 8.20 (s, 1H), 8.54 (d, J=5.05 Hz, 1H), 8.82 (s, 1H), 13.10 (s, 1H). [M+H] Calc'd for $C_{18}H_{15}N_5O_2$, 334; Found, 334.

Example 100: 8-(1-methylimidazol-4-yl)-2-[1-(oxan-4-yl)pyrazol-4-yl]oxypyrido[3,4-d]pyrimidin-4-ol

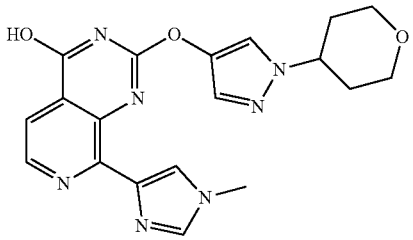 [SMILES: Cn1cnc(-c2nccc3c(O)nc(Oc4cnn(C5CCOCC5)c4)nc23)c1]

The title compound was prepared in 28% yield from 1-(tetrahydro-2H-pyran-4-yl)-1H-pyrazol-4-ol and 2-chloropyrido[3,4-d]pyrimidin-4-ol according to the procedure for the preparation of Example 34. $^1$H NMR (400 MHz, DMSO-d$_6$): δ 1.90-2.12 (m, 4H), 3.49 (td, J=11.24, 3.03 Hz, 2H), 3.66 (s, 3H), 3.99 (d, J=10.61 Hz, 2H), 4.38-4.55 (m, 1H), 7.71 (s, 2H), 7.83 (d, J=5.05 Hz, 1H), 8.22 (s, 1H), 8.39 (br. s., 1H), 8.56 (d, J=5.05 Hz, 1H). [M+H] Calc'd for C$_{19}$H$_{19}$N$_7$O$_3$, 394; Found, 394.

Example 101: 8-(1-methylimidazol-4-yl)-2-phenylmethoxypyrido[3,4-d]pyrimidin-4-ol

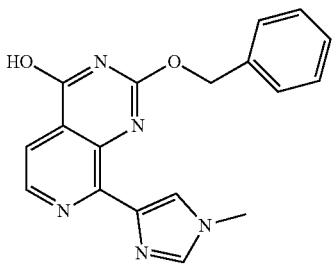 [SMILES: Cn1cnc(-c2nccc3c(O)nc(OCc4ccccc4)nc23)c1]

The title compound was prepared in 35% yield from benzyl alcohol and 2-chloro-8-(1-methyl-1H-imidazol-4-yl)pyrido[3,4-d]pyrimidin-4-ol according to the procedure for the preparation of Example 72. $^1$H NMR (400 MHz, DMSO-d$_6$): δ 3.74 (br. s., 3H), 5.58 (br. s., 2H), 7.35-7.49 (m, 3H), 7.54 (d, J=7.33 Hz, 2H), 7.69 (d, J=5.05 Hz, 2H), 7.98-8.19 (m, 1H), 8.48 (d, J=5.05 Hz, 1H), 12.66-13.47 (m, 1H). [M+H] Calc'd for C$_{18}$H$_{15}$N$_5$O$_2$, 334; Found, 334.

Example 102: 8-(1-methyl-1H-imidazol-4-yl)-2-(oxan-4-ylmethoxy)pyrido[3,4-d]pyrimidin-4-ol

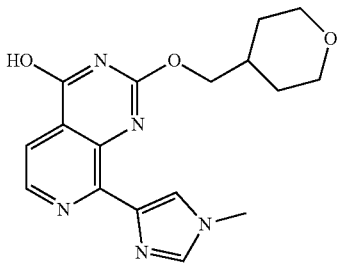 [SMILES: Cn1cnc(-c2nccc3c(O)nc(OCC4CCOCC4)nc23)c1]

The title compound was prepared in 8% yield from tetrahydropyran-4-methanol and 2-chloro-8-(1-methyl-1H-imidazol-4-yl)pyrido[3,4-d]pyrimidin-4-ol according to the procedure for the preparation of Example 72. $^1$H NMR (400 MHz, DMSO-d$_6$): δ ppm 1.40 (br. s., 2H) 1.68 (br. s., 2H) 2.13 (br. s., 1H) 3.33-3.39 (m, 3H) 3.60-4.03 (m, 4H) 4.19-4.46 (m, 2H) 7.52-8.27 (m, 3H) 8.47 (d, J=4.80 Hz, 1H) 12.56-13.40 (m, 1H). [M+H] Calc'd for C$_{17}$H$_{19}$N$_5$O$_3$, 342; Found, 342.

Example 103: 8-(1-methyl-1H-imidazol-4-yl)-2-(oxolan-3-ylmethoxy)pyrido[3,4-d]pyrimidin-4-ol

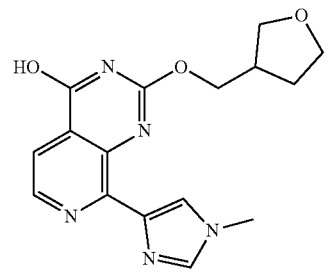 [SMILES: Cn1cnc(-c2nccc3c(O)nc(OCC4CCOC4)nc23)c1]

The title compound was prepared in 27% yield from tetrahydrofuran-3-ylmethanol and 2-chloro-8-(1-methyl-1H-imidazol-4-yl)pyrido[3,4-d]pyrimidin-4-ol according to the procedure for the preparation of Example 72. $^1$H NMR (400 MHz, DMSO-d$_6$): δ ppm 1.55-1.89 (m, 1H) 2.04 (br. s., 1H) 2.77 (br. s., 1H) 3.67 (d, J=8.08 Hz, 2H) 3.70-3.96 (m, 5H) 4.46 (br. s., 2H) 7.57-8.31 (m, 3H) 8.47 (d, J=5.05 Hz, 1H) 12.40-13.45 (m, 1H). [M+H] Calc'd for C$_{16}$H$_{17}$N$_5$O$_3$, 328; Found, 328.

Example 104: 2-[(3-fluorophenyl)methoxy]-8-(1-methyl-1H-imidazol-4-yl)pyrido[3,4-d]pyrimidin-4-ol

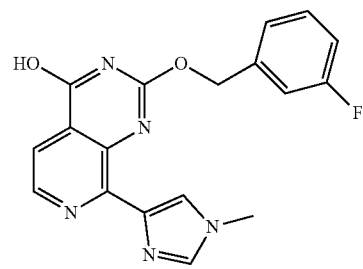 [SMILES: Cn1cnc(-c2nccc3c(O)nc(OCc4cccc(F)c4)nc23)c1]

The title compound was prepared in 40% yield from 3-fluorobenzyl alcohol and 2-chloro-8-(1-methyl-1H-imidazol-4-yl)pyrido[3,4-d]pyrimidin-4-ol according to the procedure for the preparation of Example 72. $^1$H NMR (400 MHz, DMSO-d$_6$): δ ppm 3.82 (s, 3H) 5.53 (s, 2H) 7.11-7.32 (m, 1H) 7.27-7.55 (m, 3H) 7.65-7.81 (m, 1H) 7.96-8.22 (m, 2H) 8.51 (d, J=4.80 Hz, 1H) 12.71-13.58 (m, 1H). [M+H] Calc'd for C$_{18}$H$_{14}$FN$_5$O$_2$, 352; Found, 352.

Example 105: 2-[(2-chlorophenyl)methoxy]-8-(1-methyl-1H-imidazol-4-yl)pyrido[3,4-d]pyrimidin-4-ol

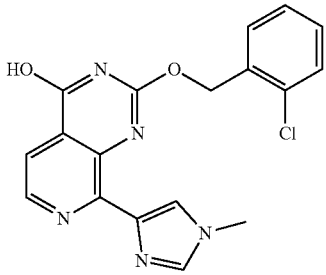 [SMILES: Cn1cnc(-c2nccc3c(O)nc(OCc4ccccc4Cl)nc23)c1]

To a solution of (2-chlorophenyl)methan-1-ol (220 mg, 1.55 mmol) in DMA (10 mL) at 0° C. was added NaH (75 mg, 1.92 mmol), and the mixture was stirred at RT for 30 min. 2-Chloro-8-(1-methyl-1H-imidazol-4-yl)pyrido[3,4-d]pyrimidin-4-ol (200 mg, 0.77 mmol) was then added, and the mixture was stirred at 120° C. overnight. DMA was removed in vacuo and the residue was purified by prep-HPLC to obtain 160 mg (57%) of the title product. $^1$H NMR (400 MHz, DMSO-$d_6$): δ ppm 3.70 (s, 3H), 5.46 (s, 2H), 7.34-7.36 (m, 2H), 7.52-7.57 (m, 3H), 7.66 (s, 1H), 8.16-8.21 (m, 2H). [M+H] Calc'd for $C_{18}H_{14}ClN_5O_2$, 368; Found, 368.

Example 106: 2-[(2,3-dichlorophenyl)methoxy]-8-(1-methyl-1H-imidazol-4-yl)pyrido[3,4-d]pyrimidin-4-ol

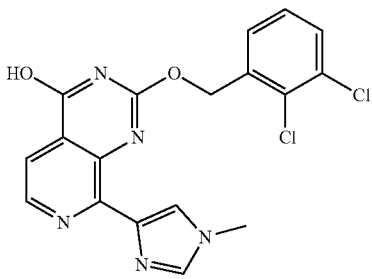 [SMILES: Cn1cnc(-c2nccc3c(O)nc(OCc4cccc(Cl)c4Cl)nc23)c1]

The title compound was prepared in 32.5% yield from (2,3-dichlorophenyl)methan-1-ol and 2-chloro-8-(1-methyl-1H-imidazol-4-yl)pyrido[3,4-d]pyrimidin-4-ol according to the procedure for the preparation of Example 105. $^1$H NMR (400 MHz, DMSO-$d_6$): δ ppm 3.69 (s, 3H), 5.51 (s, 2H), 7.37-7.62 (m, 4H), 7.66 (s, 1H), 8.12 (s, 1H), 8.19 (d, J=4.8 Hz, 1H). [M+H] Calc'd for $C_{18}H_{13}Cl_2N_5O_2$, 402; Found, 402.

Example 107: 8-(1-methyl-1H-imidazol-4-yl)-2-{[2-(trifluoromethyl)phenyl]methoxy}pyrido[3,4-d]pyrimidin-4-ol

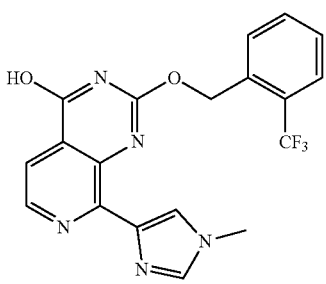 [SMILES: Cn1cnc(-c2nccc3c(O)nc(OCc4ccccc4C(F)(F)F)nc23)c1]

The title compound was prepared in 30% yield from [2-(trifluoromethyl)phenyl]methan-1-ol and 2-chloro-8-(1-methyl-1H-imidazol-4-yl)pyrido[3,4-d]pyrimidin-4-ol according to the procedure for the preparation of Example 105. $^1$H NMR (400 MHz, DMSO-$d_6$): δ ppm 3.72 (s, 3H), 5.72 (s, 2H), 7.66-7.85 (m, 6H), 8.03 (s, 1H), 8.50 (d, J=4.8 Hz, 1H). [M+H] Calc'd for $C_{19}H_{14}F_3N_5O_2$, 402; Found, 402.

Example 108: 8-(1-methyl-1H-imidazol-4-yl)-2-[(1R)-2,2,2-trifluoro-1-phenylethoxy]pyrido[3,4-d]pyrimidin-4-ol

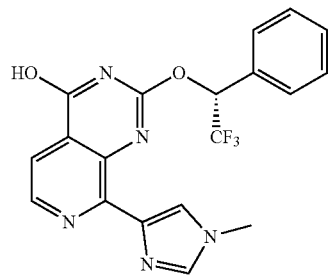 [SMILES: Cn1cnc(-c2nccc3c(O)nc(O[C@H](c4ccccc4)C(F)(F)F)nc23)c1]

The title compound was prepared in 26% yield from (1R)-2,2,2-trifluoro-1-phenylethan-1-ol and 2-chloro-8-(1-methyl-1H-imidazol-4-yl)pyrido[3,4-d]pyrimidin-4-ol according to the procedure for the preparation of Example 105. $^1$H NMR (400 MHz, DMSO-$d_6$): δ ppm 3.81 (s, 3H), 6.75-6.77 (m, 1H), 7.40-7.70 (m, 7H), 8.13 (s, 1H), 8.23 (d, J=4.8 Hz, 1H). [M+H] Calc'd for $C_{19}H_{14}F_3N_5O_2$, 402; Found, 402.

Example 109: 8-(1-methyl-1H-imidazol-4-yl)-2-[(1S)-2,2,2-trifluoro-1-phenylethoxy]pyrido[3,4-d]pyrimidin-4-ol

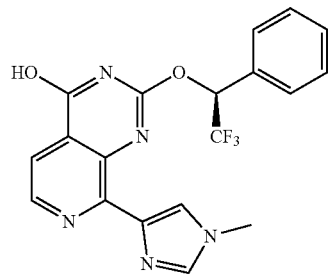 [SMILES: Cn1cnc(-c2nccc3c(O)nc(O[C@@H](c4ccccc4)C(F)(F)F)nc23)c1]

The title compound was prepared in 20% yield from (1S)-2,2,2-trifluoro-1-phenylethan-1-ol and 2-chloro-8-(1-methyl-1H-imidazol-4-yl)pyrido[3,4-d]pyrimidin-4-ol according to the procedure for the preparation of Example 105. $^1$H NMR (400 MHz, DMSO-$d_6$): δ ppm 3.81 (s, 3H), 6.75-6.77 (m, 1H), 7.40-7.70 (m, 7H), 8.13 (s, 1H), 8.23 (d, J=4.8 Hz, 1H). [M+H] Calc'd for $C_{19}H_{14}F_3N_5O_2$, 402; Found, 402.

Example 110: 8-(1-methyl-1H-imidazol-4-yl)-2-[(1,1,1-trifluorobutan-2-yl)oxy]pyrido[3,4-d]pyrimidin-4-ol

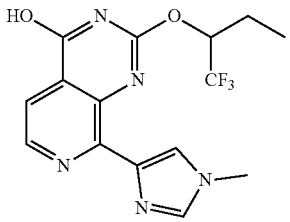 [SMILES: CCC(Oc1nc(O)c2ccnc(-c3cn(C)cn3)c2n1)C(F)(F)F]

The title compound was prepared in 14% yield from 1,1,1-trifluoro-2-butanol and 2-chloro-8-(1-methyl-1H-imidazol-4-yl)pyrido[3,4-d]pyrimidin-4-ol according to the procedure for the preparation of Example 72. $^1$H NMR (400 MHz, DMSO-d$_6$): δ ppm 0.82-1.24 (m, 3H) 1.63-2.11 (m, 2H) 3.60-3.95 (m, 3H) 5.76-6.07 (m, 1H) 7.50-8.21 (m, 3H) 8.52 (d, J=5.05 Hz, 1H). [M+H] Calc'd for C$_{15}$H$_{14}$F$_3$N$_5$O$_2$, 354; Found, 354.

Example 111: 8-(1-methyl-1H-imidazol-4-yl)-2-{[4-(trifluoromethyl)phenyl]methoxy}pyrido[3,4-d]pyrimidin-4-ol

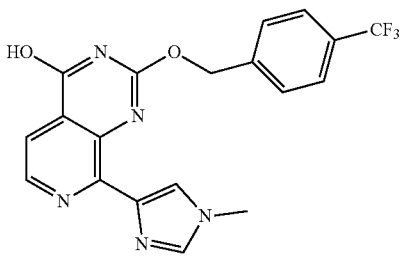 [SMILES: Cn1cnc(-c2nccc3c(O)nc(OCc4ccc(C(F)(F)F)cc4)nc23)c1]

The title compound was prepared in 37% yield from 4-hydroxymethylbenzotrifluoride and 2-chloro-8-(1-methyl-1H-imidazol-4-yl)pyrido[3,4-d]pyrimidin-4-ol according to the procedure for the preparation of Example 72. $^1$H NMR (400 MHz, DMSO-d$_6$): δ ppm 3.81 (s, 3H) 5.72 (s, 2H) 7.69 (d, J=5.05 Hz, 1H) 7.73-7.84 (m, 2H) 7.88 (d, J=8.34 Hz, 1H) 7.95 (s, 1H) 8.05 (s, 1H) 8.14 (d, J=8.34 Hz, 1H) 8.49 (d, J=4.80 Hz, 1H) 12.67-13.71 (m, 1H). [M+H] Calc'd for C$_{19}$H$_{14}$F$_3$N$_5$O$_2$, 402; Found, 402.

Example 112: 2-[(4-chlorophenyl)methoxy]-8-(1-methyl-1H-imidazol-4-yl)pyrido[3,4-d]pyrimidin-4-ol

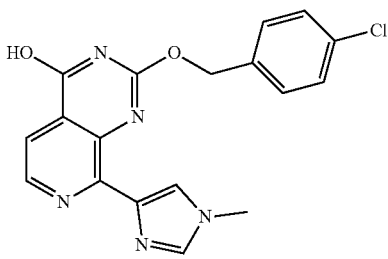 [SMILES: Cn1cnc(-c2nccc3c(O)nc(OCc4ccc(Cl)cc4)nc23)c1]

The title compound was prepared in 50% yield from 4-chlorobenzyl alcohol and 2-chloro-8-(1-methyl-1H-imidazol-4-yl)pyrido[3,4-d]pyrimidin-4-ol according to the procedure for the preparation of Example 72. $^1$H NMR (400 MHz, DMSO-d$_6$): δ ppm 3.80 (s, 3H) 5.74 (s, 2H) 7.69 (d, J=5.05 Hz, 1H) 7.73-7.84 (m, 2H) 7.88 (d, J=8.34 Hz, 1H) 7.93 (s, 1H) 8.04 (s, 1H) 8.12 (d, J=8.34 Hz, 1H) 8.48 (d, J=4.80 Hz, 1H) 12.61-13.70 (m, 1H). [M+H] Calc'd for C$_{18}$H$_{14}$ClN$_5$O$_2$, 368; Found, 368.

Example 113: 2-(3,4-dichlorophenoxy)-8-(1-methyl-1H-imidazol-4-yl)pyrido[3,4-d]pyrimidin-4-ol

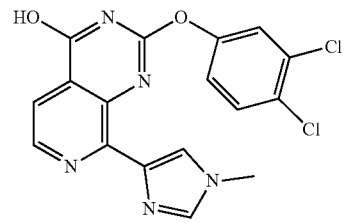 [SMILES: Cn1cnc(-c2nccc3c(O)nc(Oc4ccc(Cl)c(Cl)c4)nc23)c1]

To a solution of 2-chloro-8-(1-methyl-1H-imidazol-4-yl)pyrido[3,4-d]pyrimidin-4-ol (100 mg, 0.38 mmol) in DMF (10 mL) was added 3,4-dichlorophenol (190 mg, 1.15 mmol) and DIEA (150 mg, 1.15 mmol). The mixture was stirred at 90° C. overnight. DMF was concentrated in vacuo and the residue was purified by HPLC to give 35 mg (23.6%) of the title product. $^1$H NMR (400 MHz, DMSO-d$_6$): δ ppm 3.70 (s, 3H), 7.15 (s, 1H), 7.55-7.58 (m, 1H), 7.95-7.98 (m, 3H), 8.61 (d, J=6.4 Hz, 1H), 9.14 (s, 1H). [M+H] Calc'd for C$_{17}$H$_{11}$C$_{12}$N$_5$O$_2$, 388; Found, 388.

Example 114: 2-(3,4-dichlorophenoxy)pyrido[3,4-d]pyrimidin-4-ol

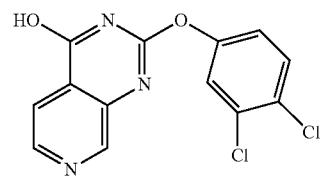 [SMILES: Oc1nc(Oc2ccc(Cl)c(Cl)c2)nc2cnccc12]

The title compound was prepared in 15% yield from 2-chloro-pyrido[3,4-d]pyrimidin-4-ol and 3,4-dichloro-phenol according to the procedure for the preparation of Example 113. $^1$H NMR (400 MHz, DMSO): δ 7.42-7.45 (m, 1H), 7.76-7.82 (m, 2H), 7.89 (d, J=5.6 Hz, 1H), 8.54 (d, J=5.6 Hz, 1H), 8.73 (s, 1H), 13.24 (s, 1H). [M+H] Calc'd for C$_{13}$H$_7$Cl$_2$N$_3$O$_2$, 308; Found, 308.

Preparation 115 A: 1-(1-phenylpropyl)-4-(4,4,5,5-tetramethyl-1,3,2-dioxaborolan-2-yl)pyrazole

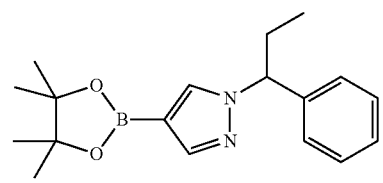 [SMILES: CCC(c1ccccc1)n1cc(B2OC(C)(C)C(C)(C)O2)cn1]

To a mixture of 4-(4,4,5,5-tetramethyl-1,3,2-dioxaborolan-2-yl)-1H-pyrazole (0.97 g, 5 mmol), 1-Phenyl-1-propanol (1.36 g, 10 mmol) and triphenylphosphine (2.63 g, 10 mmol) in THF (50 mL) was slowly added a solution of di-tertbutyl azodicarboxylate (2.3 g, 10 mmol) in THF (5 mL). The reaction solution was stirred for 30 min at reflux and concentrated. The residue was purified by silica gel chromatography (0-30%, EA:Hexanes) to give 1.36 g (45%) of the title compound as yellow oil. [M+H] Calc'd for $C_{18}H_{25}BN_2O_2$, 313; Found, 313.

Preparation 115 B: 1-(1-phenylpropyl)pyrazol-4-ol

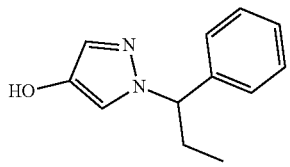

1-(1-phenylpropyl)-4-(4,4,5,5-tetramethyl-1,3,2-dioxaborolan-2-yl)pyrazole (1.9 g, 6.9 mmol) was dissolved in THF (20 mL) and cooled to 0° C. NaOH 2.5 M (6 mL, 15.8 mmol) and $H_2O_2$ 30 percent solution in water (1.6 mL, 15.8 mmol) were added and the reaction mixture was stirred at room temperature for 45 min. Then the pH was adjusted to 2 by the addition of aqueous 2N HCl and the mixture was extracted with dichloromethane. The organic layer was dried over $Na_2SO_4$, filtered, and concentrated under reduced pressure to give the title compound 1-benzyl-1H-pyrazol-4-ol as an off-white solid (0.56 g, 40%). [M+H] Calc'd for $C_{12}H_{14}N_2O$, 203; Found, 203.

Example 115: 2-{[1-(1-phenylpropyl)-1H-pyrazol-4-yl]oxy}pyrido[3,4-d]pyrimidin-4-ol

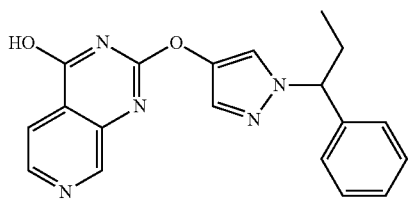 [SMILES: CCC(c1ccccc1)n1cc(Oc2nc(O)c3ccncc3n2)cn1]

A mixture of cesium carbonate (1.82 g, 5.6 mmol), 1-(1-phenylpropyl)pyrazol-4-ol (0.56 g, 2.8 mmol), CuI (25 mg, 0.14 mmol) and 2-chloro-7-azaquinazolone (254 mg, 1.4 mmol) in DMF (10 mL) were stirred at 140° C. for 6 hours. The reaction mixture was concentrated and dried under high vacuum. The reaction mixture was purified by silica chromatography (0-15%, MeOH:DCM) to afford 140 mg (29%) of the desired product as a beige solid. $^1$H NMR (400 MHz, DMSO-$d_6$): δ ppm 0.85 (t, J=7.20 Hz, 3H) 1.98-2.44 (m, 2H) 5.30 (dd, J=9.35, 6.32 Hz, 1H) 7.22-7.43 (m, 5H) 7.58-7.73 (m, 1H) 7.78-7.94 (m, 1H) 8.24 (s, 1H) 8.44-8.91 (m, 2H) 13.09 (s, 1H). [M+H] Calc'd for $C_{19}H_{17}N_5O_2$, 348; Found, 348.

Preparation 116 A: 1-[cyclopropyl(phenyl)methyl]-4-(4,4,5,5-tetramethyl-1,3,2-dioxaborolan-2-yl)pyrazole

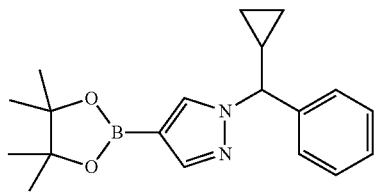 [SMILES: CC1(C)OB(c2cnn(C(c3ccccc3)C3CC3)c2)OC1(C)C]

To a mixture of 4-(4,4,5,5-tetramethyl-1,3,2-dioxaborolan-2-yl)-1H-pyrazole (0.97 g, 5 mmol), 1-α-cyclopropyl-benzyl alcohol (1.04 g, 7 mmol) and triphenylphosphine (1.45 g, 5.5 mmol) in THF (10 mL) was slowly added a solution of di-tertbutyl azodicarboxylate (1.15 g, 5 mmol) in THF (5 mL). The reaction solution was stirred for 30 min and concentrated. The residue was purified by silica gel chromatography (0-30%, EA:Hexanes) to give 1.12 g (70%) of the title compound as yellow oil. [M+H] Calc'd for $C_{19}H_{25}BN_2O_2$, 325; Found, 325.

Preparation 116 B: 1-[cyclopropyl(phenyl)methyl]pyrazol-4-ol

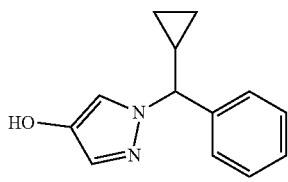 [SMILES: Oc1cnn(C(c2ccccc2)C2CC2)c1]

1-[cyclopropyl(phenyl)methyl]-4-(4,4,5,5-tetramethyl-1,3,2-dioxaborolan-2-yl)pyrazole (1.12 g, 3.6 mmol) was dissolved in THF (10 mL) and cooled to 0° C. NaOH 2.5 M (2.9 mL, 7.2 mmol) and $H_2O_2$ 30 percent solution in water (0.8 mL, 7.2 mmol) were added and the reaction mixture was stirred at room temperature for 45 min. Then the pH was adjusted to 2 by the addition of aqueous 2N HCl and the mixture was extracted with dichloromethane. The organic layer was dried over $Na_2SO_4$, filtered, and concentrated under reduced pressure to give the title compound 1-benzyl-1H-pyrazol-4-ol as an off-white solid (0.48 g, 62%). [M+H] Calc'd for $C_{13}H_{14}N_2O$, 215; Found, 215.

Example 116: 2-({1-[cyclopropyl(phenyl)methyl]-1H-pyrazol-4-yl}oxy)pyrido[3,4-d]pyrimidin-4-ol

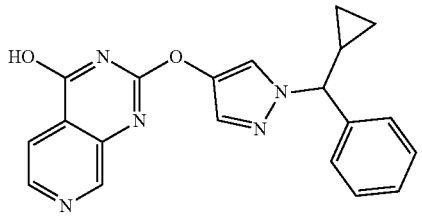 [SMILES: Oc1nc(Oc2cnn(C(c3ccccc3)C3CC3)c2)nc2cnccc12]

A mixture of cesium carbonate (1.43 g, 4.4 mmol), 1-[cyclopropyl(phenyl)methyl]pyrazol-4-ol (0.48 g, 2.2 mmol), CuI (20 mg, 0.11 mmol) and 2-chloro-7-azaquinazolone (200 mg, 1.1 mmol) in DMF (10 mL) were stirred at 130° C. for 6 hours. The reaction mixture was concentrated and dried under high vacuum. The reaction mixture was purified by silica chromatography (0-15%, MeOH:DCM) to afford 224 mg (57%) of the desired product as a beige solid. $^1$H NMR (400 MHz, DMSO-$d_6$): δ ppm 0.35-0.96 (m, 4H) 1.68-1.98 (m, 1H) 4.69 (d, J=10.11 Hz, 1H) 7.15-7.50 (m, 5H) 7.66 (s, 1H) 7.78-8.06 (m, 1H) 8.19-8.37 (m, 1H) 8.54 (d, J=4.29 Hz, 1H) 8.83 (br. s., 1H) 13.11 (br. s., 1H). [M+H] Calc'd for $C_{20}H_{17}N_5O_2$, 360; Found, 360.

Example 117: 2-({1-[(1R)-1-phenylethyl]-1H-pyrazol-4-yl}oxy)pyrido[3,4-d]pyrimidin-4-ol

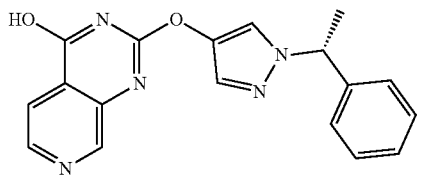 [SMILES: C[C@H](c1ccccc1)n1cc(Oc2nc(O)c3ccncc3n2)cn1]

To a solution of 2-chloropyridino[3,4-d]pyrimidin-4-ol (150 mg, 0.83 mmol) in DMF (10 mL) was added 1-((1R)-1-phenylethyl)pyrazol-4-ol (470 mg, 2.5 mmol), CuI (160 mg, 0.83 mmol) and Cs$_2$CO$_3$ (540 mg, 1.66 mmol), and the mixture was stirred at 125° C. overnight. DMF was removed and the residue was purified by FC (2:1, MeOH:DCM) to give 30 mg (11%) of the title compound. $^1$H NMR (400 MHz, DMSO-$d_6$): δ ppm 1.84 (d, J=7.2 Hz, 3H), 5.62 (m, 1H), 7.28-7.38 (m, 5H), 7.68 (s, 1H), 7.88 (d, J=4.8 Hz, 1H), 8.22 (s, 1H), 8.55 (s, 1H), 8.83 (s, 1H), 13.12 (s, 1H). [M+H] Calc'd for $C_{18}H_{15}N_5O_2$, 334; Found, 334.

Example 118: 2-({1-[(1S)-1-phenylethyl]-1H-pyrazol-4-yl}oxy pyrido) [3,4-d]pyrimidin-4-ol

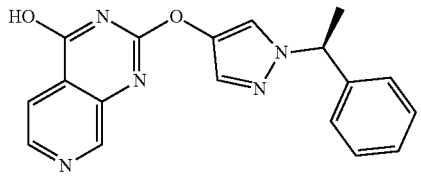 [SMILES: C[C@@H](c1ccccc1)n1cc(Oc2nc(O)c3ccncc3n2)cn1]

The title compound was prepared in 22% yield from 2-chloropyridino[3,4-d]pyrimidin-4-ol and 1-((1S)-1-phenylethyl)pyrazol-4-ol according to the procedure for the preparation of Example 117. $^1$H NMR (400 MHz, DMSO-$d_6$): δ ppm 1.84 (d, J=7.2 Hz, 3H), 5.62 (m, 1H), 7.28-7.38 (m, 5H), 7.68 (s, 1H), 7.88 (d, J=4.8 Hz, 1H), 8.22 (s, 1H), 8.55 (s, 1H), 8.83 (s, 1H), 13.12 (s, 1H). [M+H] Calc'd for $C_{18}H_{15}N_5O_2$, 334; Found, 334.

Example 119: 2-({1-[(1R)-1-(2-fluorophenyl)ethyl]-1H-pyrazol-4-yl}oxy)pyrido[3,4-d]pyrimidin-4-ol

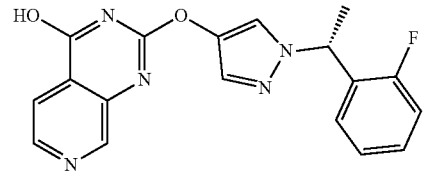 [SMILES: C[C@H](c1ccccc1F)n1cc(Oc2nc(O)c3ccncc3n2)cn1]

The title compound was prepared in 10% yield from 1-[(1R)-(2-fluoro-phenyl)-ethyl]-1H-pyrazol-4-ol and 2-chloro-pyrido[3,4-d]pyrimidin-4-ol according to the procedure for the preparation of Example 117. $^1$H NMR (300 MHz, DMSO): δ 1.83 (d, J=6.9 Hz, 3H), δ 5.88 (q, J=7.2 Hz, 1H), 7.20-7.36 (m, 4H), 7.69 (s, 1H), 7.88 (d, J=4.8 Hz, 1H), 8.25 (s, 1H), 8.54 (d, J=5.1 Hz, 1H,), 8.82 (s, 1H), 13.13 (s, 1H). [M+H] Calc'd for $C_{18}H_{14}FN_5O_2$, 352; Found, 352.

Example 120: 2-({1-[(1s)-1-(2-fluorophenyl)ethyl]-1H-pyrazol-4-yl}oxy)pyrido[3,4-d]pyrimidin-4-ol

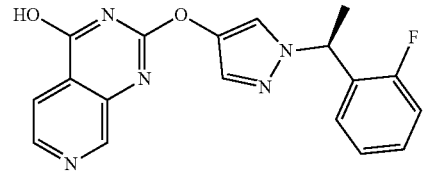 [SMILES: C[C@@H](c1ccccc1F)n1cc(Oc2nc(O)c3ccncc3n2)cn1]

The title compound was prepared in 10% yield from 1-[(1S)-(2-fluoro-phenyl)-ethyl]-1H-pyrazol-4-ol and 2-chloro-pyrido[3,4-d]pyrimidin-4-ol according to the procedure for the preparation of Example 117. $^1$H NMR (300 MHz, DMSO): δ 1.83 (d, J=6.9 Hz, 3H), δ 5.88 (q, J=7.2 Hz, 1H), 7.20-7.36 (m, 4H), 7.69 (s, 1H), 7.88 (d, J=4.8 Hz, 1H), 8.25 (s, 1H), 8.54 (d, J=5.1 Hz, 1H), 8.82 (s, 1H), 13.13 (s, 1H). [M+H] Calc'd for $C_{18}H_{14}FN_5O_2$, 352; Found, 352.

Preparation 121 A: 1-[(2-chlorophenyl)methyl]-4-(4,4,5,5-tetramethyl-1,3,2-dioxaborolan-2-yl)pyrazole

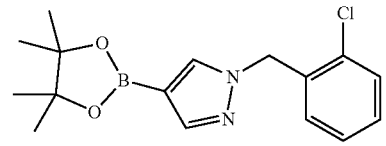 [SMILES: CC1(C)OB(c2cnn(Cc3ccccc3Cl)c2)OC1(C)C]

To a mixture of 4-(4,4,5,5-tetramethyl-1,3,2-dioxaborolan-2-yl)-1H-pyrazole (2 g, 10 mmol), 2-chlorobenzyl alcohol (2.9 g, 20 mmol) and triphenylphosphine (5.3 g, 20 mmol) in THF (50 mL) was slowly added a solution of di-tertbutyl azodicarboxylate (4.6 g, 20 mmol) in THF (10 mL). The reaction solution was stirred for 30 min at reflux and concentrated. The residue was purified by silica gel chromatography (0-30%, EA:Hexanes) to give 1.9 g (59%) of the title compound as yellow oil. [M+H] Calc'd for $C_{16}H_{20}BClN_2O_2$, 319; Found, 319.

Preparation 121 B: 1-[(2-chlorophenyl)methyl]pyrazol-4-ol

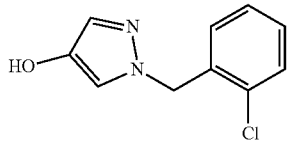 [SMILES: Oc1cnn(Cc2ccccc2Cl)c1]

1-[(2-chlorophenyl)methyl]-4-(4,4,5,5-tetramethyl-1,3,2-dioxaborolan-2-yl)pyrazole (1.9 g, 6.9 mmol) was dissolved in THF (20 mL) and cooled to 0° C. NaOH 2.5 M (6 mL, 15.8 mmol) and $H_2O_2$ 30 percent solution in water (1.6 mL, 15.8 mmol) were added and the reaction mixture was stirred at room temperature for 45 min. Then the pH was adjusted to 2 by the addition of aqueous 2N HCl and the mixture was extracted with dichloromethane. The organic layer was dried over $Na_2SO_4$, filtered, and concentrated under reduced pressure to give the title compound 1-benzyl-1H-pyrazol-4-ol as an off-white solid (0.48 g, 34%). [M+H] Calc'd for $C_{10}H_9ClN_2O$, 209; Found, 209.

Example 121: 2-({1-[(2-chlorophenyl)methyl]-1H-pyrazol-4-yl}oxy)pyrido[3,4-d]pyrimidin-4-ol

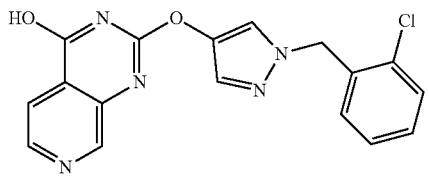 [SMILES: Oc1nc(Oc2cnn(Cc3ccccc3Cl)c2)nc2cnccc12]

A mixture of cesium carbonate (1.10 g, 3.4 mmol), 1-[(2-chlorophenyl)methyl]pyrazol-4-ol (0.48 g, 1.7 mmol), CuI (18 mg, 0.01 mmol) and 2-chloro-7-azaquinazolone (154 mg, 0.85 mmol) in DMF (10 mL) were stirred at 140° C. for 6 hours. The reaction mixture was concentrated and dried under high vacuum. The reaction mixture was purified by silica chromatography (0-15%, MeOH:DCM) to afford 280 mg (92%) of the desired product as a beige solid. $^1$H NMR (400 MHz, DMSO-$d_6$): δ ppm 5.39 (s, 2H) 7.01-7.19 (m, 1H) 7.29-7.42 (m, 2H) 7.45-7.57 (m, 1H) 7.63-7.75 (m, 1H) 7.78-7.99 (m, 1H) 8.22 (s, 1H) 8.55 (br. s., 1H) 8.76 (br. s, 1H) 13.11 (br. s., 1H). [M+H] Calc'd for $C_{17}H_{12}ClN_5O_2$, 354; Found, 354.

Preparation 122 A: 1-[(3-chlorophenyl)methyl]-4-(4,4,5,5-tetramethyl-1,3,2-dioxaborolan-2-yl)pyrazole

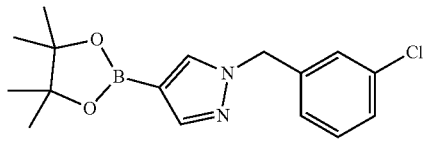 [SMILES: CC1(C)OB(c2cnn(Cc3cccc(Cl)c3)c2)OC1(C)C]

To a mixture of 4-(4,4,5,5-tetramethyl-1,3,2-dioxaborolan-2-yl)-1H-pyrazole (2 g, 10 mmol), 3-chlorobenzyl alcohol (2.9 g, 20 mmol) and triphenylphosphine (5.3 g, 20 mmol) in THF (50 mL) was slowly added a solution of di-tertbutyl azodicarboxylate (4.6 g, 20 mmol) in THF (10 mL). The reaction solution was stirred for 30 min at reflux and concentrated. The residue was purified by silica gel chromatography (0-30%, EA:Hexanes) to give 2.9 g (91%) of the title compound as yellow oil. [M+H] Calc'd for $C_{16}H_{20}BClN_2O_2$, 319; Found, 319.

Preparation 122 B: 1-[(3-chlorophenyl)methyl]pyrazol-4-ol

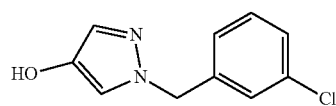 [SMILES: Oc1cnn(Cc2cccc(Cl)c2)c1]

1-[(3-chlorophenyl)methyl]-4-(4,4,5,5-tetramethyl-1,3,2-dioxaborolan-2-yl)pyrazole (2.9 g, 9.1 mmol) was dissolved in THF (20 mL) and cooled to 0° C. NaOH 2.5 M (7.9 mL, 18.3 mmol) and $H_2O_2$ 30 percent solution in water (2.1 mL, 18.3 mmol) were added and the reaction mixture was stirred at room temperature for 45 min. Then the pH was adjusted to 2 by the addition of aqueous 2N HCl and the mixture was extracted with dichloromethane. The organic layer was dried over $Na_2SO_4$, filtered, and concentrated under reduced pressure to give 0.56 g (40%). of the title compound as an off-white solid. [M+H] Calc'd for $C_{10}H_9ClN_2O$, 209; Found, 209.

Example 122: 2-({1-[(3-chlorophenyl)methyl]-1H-pyrazol-4-yl}oxy)pyrido[3,4-d]pyrimidin-4-ol

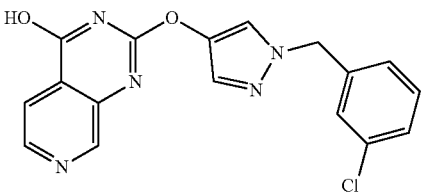 [SMILES: Oc1nc(Oc2cnn(Cc3cccc(Cl)c3)c2)nc2cnccc12]

A mixture of cesium carbonate (1.82 g, 5.6 mmol), 1-[(3-chlorophenyl)methyl]pyrazol-4-ol (0.56 g, 2.8 mmol), CuI (25 mg, 0.14 mmol) and 2-chloro-7-azaquinazolone (254 mg, 1.4 mmol) in DMF (10 mL) were stirred at 140° C. for 6 h. The reaction mixture was concentrated and dried under high vacuum. The reaction mixture was concentrated and dried under high vacuum. The reaction mixture was purified by silica chromatography (0-15%, MeOH:DCM) to afford 140 mg (29%) of the desired product as a beige solid. $^1$H NMR (400 MHz, DMSO-$d_6$): δ ppm 5.36 (s, 2H) 7.20-7.47 (m, 4H) 7.67 (s, 1H) 7.88 (br. s., 1H) 8.23 (s, 1H) 8.53 (br. s., 1H) 8.84 (s, 1H) 13.11 (br. s., 1H). [M+H] Calc'd for $C_{17}H_{12}ClN_5O_2$, 354; Found, 354.

Example 123: 2-{[1-(1-benzylpiperidin-4-yl)-1H-pyrazol-4-yl]oxy}pyrido[3,4-d]pyrimidin-4-ol

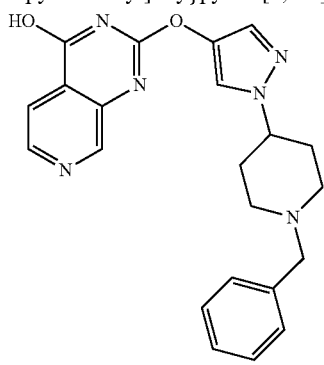

To a solution of 2-(1-piperidin-4-ylpyrazol-4-yl)oxypyrido[3,4-d]pyrimidin-4-ol (25 mg, 0.065 mmol) in DMF (1 mL) and benzaldehyde (35 μL, 0.33 mmol) at 0° C. was added STAB (21 mg, 0.1 mmol). The reaction mixture was stirred at 0° C. for 30 min and at RT for 16 h. The reaction was quenched with water (0.1 ml) and the mixture was concentrated in vacuo. The crude product was purified by silica gel chromatography (0-20%, MeOH:DCM) to afford 6 mg (21%) of the desired product as a white solid. $^1$H NMR (400 MHz, DMSO-$d_6$): δ ppm 1.74-2.22 (m, 6H) 2.82-3.03 (m, 2H) 3.44-3.61 (m, 2H) 4.00-4.32 (m, 1H) 7.14-7.45 (m, 5H) 7.62 (s, 1H) 7.87 (d, J=5.31 Hz, 1H) 8.10 (s, 1H) 8.47-8.58 (m, 1H) 8.84 (s, 1H) 12.94 (br. s, 1H). [M+H] Calc'd for $C_{22}H_{22}N_6O_2$, 403; Found, 403.

Preparation 124: 1-(2-morpholin-4-ylethyl)pyrazol-4-ol

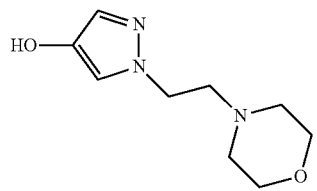 [SMILES: Oc1cnn(CCN2CCOCC2)c1]

The title compound was prepared in 45% yield from 4-[2-[4-(4,4,5,5-tetramethyl-1,3,2-dioxaborolan-2-yl)pyrazol-1-yl]ethyl]morpholine according to the procedure for the preparation 115 B. [M+H] Calc'd for $C_9H_{15}N_3O_2$, 198; Found, 198.

Example 124: 2-({1-[2-(morpholin-4-yl)ethyl]-1H-pyrazol-4-yl}oxy)pyrido[3,4-d]pyrimidin-4-ol

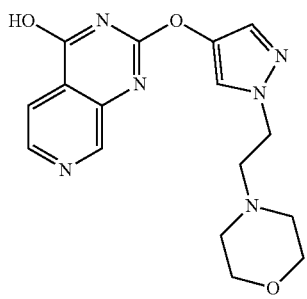 [SMILES: Oc1nc(Oc2cnn(CCN3CCOCC3)c2)nc2cnccc12]

The title compound was prepared in 39% yield from 1-(2-morpholin-4-ylethyl)pyrazol-4-ol and 2-chloro-7-azaquinazolone according to the procedure for the preparation of compound 115. $^1$H NMR (400 MHz, DMSO-$d_6$): δ ppm 2.47 (d, J=4.04 Hz, 4H) 2.67-3.01 (m, 2H) 3.49-3.70 (m, 4H) 4.10-4.34 (m, 2H) 7.61 (s, 1H) 7.89 (d, J=5.05 Hz, 1H) 8.10 (s, 1H) 8.54 (d, J=5.05 Hz, 1H) 8.82 (s, 1H) 12.99 (br. s, 1H). [M+H] Calc'd for $C_{16}H_{18}N_6O_3$, 343; Found, 343.

Example 125: 2-({1-[(3R)-pyrrolidin-3-yl]-1H-pyrazol-4-yl}oxy)pyrido[3,4-d]pyrimidin-4-ol

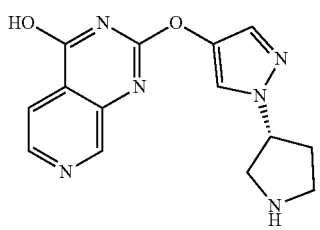 [SMILES: Oc1nc(Oc2cnn([C@@H]3CCNC3)c2)nc2cnccc12]

To a mixture tert-butyl (3R)-3-[4-(4-hydroxypyridino[3,4-d]pyrimidin-2-yloxy)pyrazolyl]pyrrolidinecarboxylate (125 mg, 0.31 mmol) in DCM was added $CF_3COOH$ (5 mL) at RT. The mixture was stirred for 1 h and concentrated to give (84 mg, 91%) of the title compound. $^1$H NMR 400 MHz, MeOD-$d_4$): δ 2.32-2.50 (m, 2H), 3.20-3.75 (m, 4H), 5.13-5.18 (m, 1H), 7.61 (s, 1H), 7.91 (d, J=5.2 Hz, 1H), 8.03 (s, 1H), 8.43 (d, J=5.2 Hz, 1H), 8.73 (s, 1H). [M+H] Calc'd for $C_{14}H_{14}N_6O_2$, 299; Found, 299.

Example 126: 2-({1-[(3R)-1-(ethanesulfonyl)pyrrolidin-3-yl]-1H-pyrazol-4-yl}oxy)pyrido[3,4-d]pyrimidin-4-ol

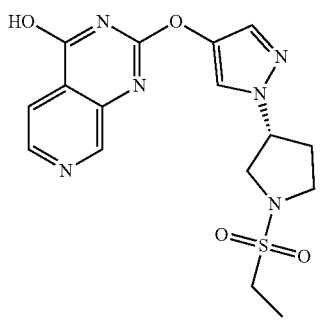 [SMILES: CCS(=O)(=O)N1CC[C@@H](n2cc(Oc3nc(O)c4ccncc4n3)cn2)C1]

To a solution of 2-[1-(3R)pyrrolidin-3-yl)pyrazol-4-yloxy]pyridino[3,4-d]pyrimidin-4-ol (100 mg, 0.34 mmol) in THF (20 mL) was added chloroethylsulfone (86 mg, 0.67 mmol) and DIEA (216 mg, 1.68 mmol). The mixture was stirred at RT for 2 h and the solvent was concentrated in vacuo. The residue was purified by HPLC to obtain 50 mg (38%) of the title compound. $^1$H NMR (400 MHz, DMSO-$d_6$): δ 1.21 (t, J=7.6 Hz, 3H), 2.41-2.50 (m, 2H), 3.06-3.17 (m, 2H), 3.46-3.81 (m, 4H), 5.02-5.07 (m, 1H), 7.12 (s, 1H), 7.89 (d, J=4.8 Hz, 1H), 8.25 (s, 1H), 8.54 (d, J=4.8 Hz, 1H), 8.84 (s, 1H), 13.13 (s, 1H). [M+H] Calc'd for $C_{16}H_{18}N_6O_4S_3$, 391; Found, 391.

Example 127: 2-({1-[(3R)-1-(cyclopropanesulfonyl)pyrrolidin-3-yl]-1H-pyrazol-4-yl}oxy)pyrido[3,4-d]pyrimidin-4-ol

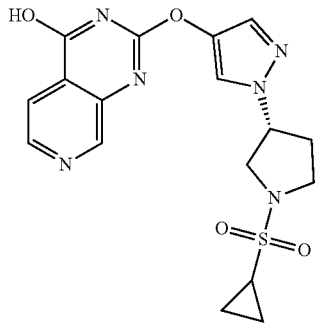 [SMILES: O=S(=O)(C1CC1)N1CC[C@@H](n2cc(Oc3nc(O)c4ccncc4n3)cn2)C1]

The title compound was prepared in 45% yield from 2-[1-((3R)pyrrolidin-3-yl)pyrazol-4-yloxy]pyridino[3,4-d]pyrimidin-4-ol and chlorocyclopropylsulfone according to the procedure for the preparation of Example 126. $^1$H NMR (400 MHz, DMSO-$d_6$): δ ppm 0.94-0.097 (m, 4H), 2.43-2.67 (m, 3H), 3.48-3.83 (m, 4H), 5.06 (t, J=5.6 Hz, 1H), 7.71 (s, 1H), 7.89 (d, 1H), 8.26 (s, 1H), 8.55 (d, J=4.8 Hz 1H), 8.83 (s, 1H), 13.12 (s, 1H). [M+H] Calc'd for $C_{17}H_{18}N_6O_4S$, 403; Found, 403.

Example 128: 2-({1-[(3R)-1-(benzenesulfonyl)pyrrolidin-3-yl]-1H-pyrazol-4-yl}oxy)pyrido[3,4-d]pyrimidin-4-ol

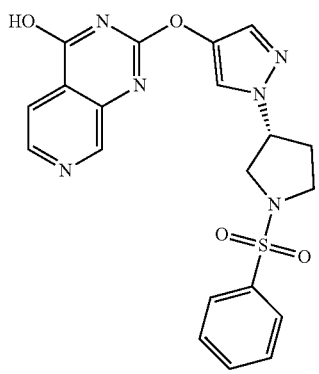 [SMILES: O=S(=O)(c1ccccc1)N1CC[C@@H](n2cc(Oc3nc(O)c4ccncc4n3)cn2)C1]

The title compound was prepared in 45% yield from 2-[1-((3R)pyrrolidin-3-yl)pyrazol-4-yloxy]pyridino[3,4-d]pyrimidin-4-ol and chlorophenylsulfone according to the procedure for the preparation of Example 126. $^1$H NMR (400 MHz, DMSO-$d_6$): δ ppm 2.25-2.30 (m, 2H), 3.34-3.69 (m, 4H), 4.91 (t, J=4.8 Hz, 1H), 7.56-7.89 (m, 7H), 8.06 (s, 1H), 8.56 (s, 1H), 8.85 (s, 1H), 13.12 (s, 1H). [M+H] Calc'd for $C_{20}H_{18}N_6O_4S$, 439, Found, 439.

Example 129: 1-[(3R)-3-[4-({4-hydroxypyrido[3,4-d]pyrimidin-2-yl}oxy)-1H-pyrazol-1-yl]pyrrolidin-1-yl]ethan-1-one

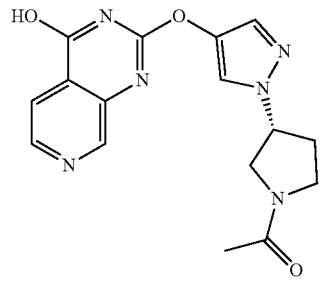 [SMILES: CC(=O)N1CC[C@@H](n2cc(Oc3nc(O)c4ccncc4n3)cn2)C1]

The title compound was prepared in 35% yield from 2-[1-((3R)pyrrolidin-3-yl)pyrazol-4-yloxy]pyridino[3,4-d]pyrimidin-4-ol and acetyl chloride according to the procedure for the preparation of Example 126. $^1$H NMR (400 MHz, DMSO-$d_6$): δ ppm 1.97 (s, 3H), 2.30-2.45 (m, 2H), 3.44-3.98 (m, 4H), 4.97-5.06 (m, 1H), 7.69 (d, J=4.4 Hz, 1H), 7.89 (d, J=4.8 Hz, 1H), 8.18 (d, J=12.0 Hz, 1H), 8.55 (d, J=5.2 Hz, 1H), 8.85 (s, 1H), 13.12 (s, 1H). [M+H] Calc'd for $C_{16}H_{16}N_6O_3$, 341, Found, 341.

Example 130: 3-[(3R)-3-[4-({4-hydroxypyrido[3,4-d]pyrimidin-2-yl}oxy)-1H-pyrazol-1-yl]pyrrolidin-1-yl]-3-oxopropanenitrile

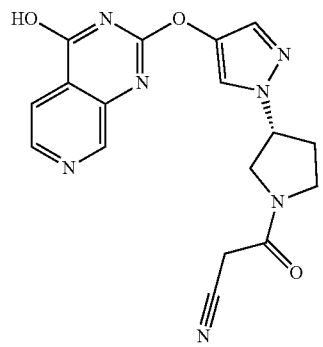 [SMILES: N#CCC(=O)N1CC[C@@H](n2cc(Oc3nc(O)c4ccncc4n3)cn2)C1]

To a mixture of compound 2-[1-((3R)pyrrolidin-3-yl)pyrazol-4-yloxy]pyridino[3,4-d]pyrimidin-4-ol (150 mg, 0.50 mmol) and Et$_3$N (254 mg, 2.52 mmol) in MeOH was added cyano-acetic acid 2,5-dioxo-pyrrolidin-1-yl ester (110 mg, 0.60 mmol) at RT and stirred for 2 h. The reaction mixture was concentrated and the residue was purified by flash chromatography (20:1, DCM:MeOH) to give 74 mg (41%) of the title compound. $^1$H NMR (400 MHz, DMSO-$d_6$): δ ppm 2.30-2.49 (m, 2H), 3.50-4.0 0 (m, 6H), 4.98-5.09 (m, 1H), 7.69 (d, J=5.2 Hz, 1H), 7.87 (d, J=6.8 Hz, 1H), 8.16 (d, J=8.0 Hz, 1H), 8.51 (d, J=6.8 Hz, 1H), 13.12 (s, 1H). [M+H] Calc'd for $C_{17}H_{15}N_7O_3$, 366, Found, 366.

Example 131: 2-({1-[(3R)-1-cyclopropanecarbonylpyrrolidin-3-yl]-1H-pyrazol-4-yl}oxy)pyrido[3,4-d]pyrimidin-4-ol

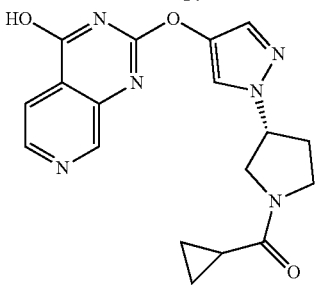

The title compound was prepared in 35% yield from 2-[1-((3R)pyrrolidin-3-yl)pyrazol-4-yloxy]pyridino[3,4-d]pyrimidin-4-ol and cyclopropanecarbonyl chloride according to the procedure for the preparation of Example 126. $^1$H NMR (400 MHz, DMSO-d$_6$): δ ppm 0.72-0.74 (m, 4H), 1.77-1.82 (m, 1H), 2.34-2.48 (m, 2H), 3.46-4.16 (m, 4H), 4.98-5.11 (m, 1H), 7.69 (d, J=5.6 Hz, 1H), 7.89 (d, J=4.4 Hz, 1H), 8.21 (d, J=14.4 Hz, 1H), 8.55 (d, J=4.8 Hz, 1H), 8.85 (s, 1H), 13.12 (s, 1H). [M+H] Calc'd for C$_{18}$H$_{18}$N$_6$O$_3$, 367, Found, 367.

Example 132: 2-({1-[(3R)-1-benzoylpyrrolidin-3-yl]-1H-pyrazol-4-yl}oxy)pyrido[3,4-d]pyrimidin-4-ol

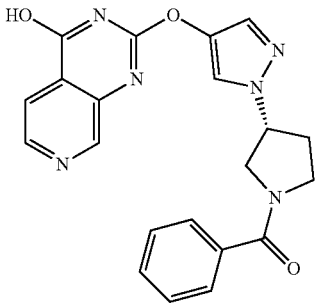 [SMILES: O=C(c1ccccc1)N1CC[C@@H](n2cc(Oc3nc(O)c4ccncc4n3)cn2)C1]

The title compound was prepared in 45% yield from 2-[1-((3R)pyrrolidin-3-yl)pyrazol-4-yloxy]pyridino[3,4-d]pyrimidin-4-ol and benzoyl chloride according to the procedure for the preparation of Example 126. $^1$H NMR (400 MHz, DMSO-d$_6$): δ ppm 2.34-2.48 (m, 2H), 3.57-3.97 (m, 4H), 4.96-5.11 (m, 1H), 7.44-7.89 (m, 7H), 8.20 (s, 1H), 8.55 (s, 1H), 8.83 (s, 1H), 13.12 (s, 1H). [M+H] Calc'd for C$_{21}$H$_{18}$N$_6$O$_3$, 403, Found, 403.

Example 133: 2-({1-[(3R)-1-benzylpyrrolidin-3-yl]-1H-pyrazol-4-yl}oxy)pyrido[3,4-d]pyrimidin-4-ol

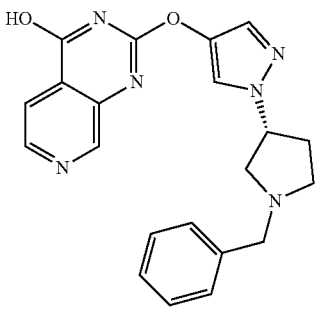 [SMILES: Oc1nc(Oc2cnn([C@@H]3CCN(Cc4ccccc4)C3)c2)nc2cnccc12]

The title compound was prepared in 18% yield from 2-[1-((3R)pyrrolidin-3-yl)pyrazol-4-yloxy]pyridino[3,4-d]pyrimidin-4-ol and (bromomethyl)benzene according to the procedure for the preparation of Example 126. $^1$H NMR (400 MHz, DMSO-d$_6$): δ ppm 2.12-2.58 (m, 3H), 2.79-2.95 (m, 3H), 3.66 (s, 2H), 4.88-4.92 (m, 1H), 7.25-7.36 (m, 5H), 7.61 (s, 1H), 7.88 (d, J=6.8 Hz, 1H), 8.13 (s, 1H), 8.53 (d, J=6.8 Hz, 1H), 8.82 (s, 1H), 13.12 (s, 1H). [M+H] Calc'd for C$_{21}$H$_{20}$N$_6$O$_2$, 489, Found, 489.

Example 134: 2-({1-[(3R)-1-(4-fluorophenyl)pyrrolidin-3-yl]-1H-pyrazol-4-yl}oxy)pyrido[3,4-d]pyrimidin-4-ol

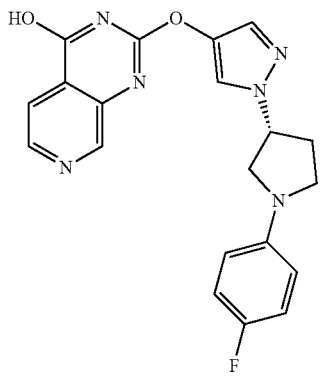 [SMILES: Oc1nc(Oc2cnn([C@@H]3CCN(c4ccc(F)cc4)C3)c2)nc2cnccc12]

A mixture of 2-[1-((3R)pyrrolidin-3-yl)pyrazol-4-yl]pyridino[3,4-d]pyrimidin-4-ol (150 mg, 0.50 mmol), 1-fluoro-4-iodo-benzene (0.76 mmol), t-BuONa (242 mg, 2.5 mmol), BINAP (31 mg, 0.05 mmol) and Pd$_2$(dba)$_3$ (23 mg, 0.025 mmol) in DMF was stirred for 2 h under N$_2$ at 130° C. in the microwave. The reaction mixture was concentrated. The residue was purified by HPLC to give 4 mg (2%) of the title compound. $^1$H NMR (400 MHz, DMSO-d$_6$): δ 2.47-2.50 (2H, m), 3.33-3.74 (4H, m), 5.12-5.15 (1H, m), 6.58-6.60 (2H, m), 7.03 (2H, t. J=8.4 Hz), 7.67 (1H, s), 7.88 (1H, d, J=4.8 Hz), 8.17 (1H, s), 8.54 (1H, d, J=4.4 Hz). 8.81 (1H, s), 13.10 (1H, s). [M+H] Calc'd for C$_{20}$H$_{17}$FN$_6$O$_2$, 393; Found, 393.

Example 135: 2-({1-[(3S)-pyrrolidin-3-yl]-1H-pyrazol-4-yl}oxy)pyrido[3,4-d]pyrimidin-4-ol

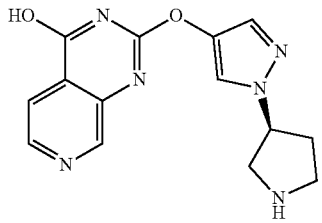 [SMILES: Oc1nc(Oc2cnn([C@H]3CCNC3)c2)nc2cnccc12]

The title compound was prepared in 90% yield from tert-butyl (3S)-3-[4-(4hydroxypyridino[3,4-d]pyrimidin-2-yloxy)pyrazolyl]pyrrolidinecarboxylate according to the procedure for the preparation of Example 125. $^1$H NMR 400 MHz, MeOD-d$_4$): δ 2.32-2.50 (m, 2H,), 3.20-3.75 (m, 4H), 5.13-5.18 (m, 1H), 7.61 (s, 1H), 7.91 (d, J=5.2 Hz, 1H), 8.03

(s, 1H), 8.43 (d, J=5.2 Hz, 1H), 8.73 (s, 1H). [M+H] Calc'd for C₁₄H₁₄N₆O₂, 299; Found, 299.

Example 136: 2-{(1-[(3S)-1-(ethanesulfonyl)pyrrolidin-3-yl]-1H-pyrazol-4-yl}oxy)pyrido[3,4-d]pyrimidin-4-ol

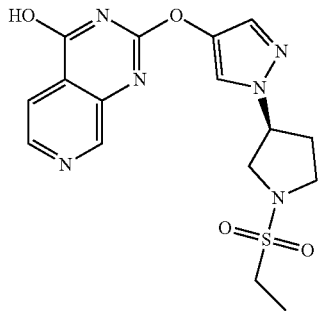 [SMILES: CCS(=O)(=O)N1CC[C@H](n2cc(Oc3nc(O)c4ccncc4n3)cn2)C1]

The title compound was prepared in 20% yield from 2-[1-((3S)pyrrolidin-3-yl)pyrazol-4-yloxy]pyridino[3,4-d]pyrimidin-4-ol and chloroethylsulfone according to the procedure for the preparation of Example 126. ¹H NMR (400 MHz, DMSO-d₆): δ 1.21 (t, J=7.6 Hz, 3H), 2.41-2.50 (m, 2H), 3.06-3.17 (m, 2H), 3.46-3.81 (m, 4H), 5.02-5.07 (m, 1H), 7.12 (s, 1H), 7.89 (d, J=4.8 Hz, 1H), 8.25 (s, 1H), 8.54 (d, J=4.8 Hz, 1H), 8.84 (s, 1H), 13.13 (s, 1H). [M+H] Calc'd for C₁₆H₁₈N₆O₄S, 391; Found, 391.

Example 137: 2-({1-[(3S)-1-(cyclopropanesulfonyl)pyrrolidin-3-yl]-1H-pyrazol-4-yl}oxy)pyrido[3,4-d]pyrimidin-4-ol

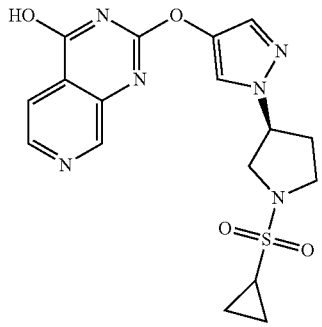 [SMILES: O=S(=O)(C1CC1)N1CC[C@H](n2cc(Oc3nc(O)c4ccncc4n3)cn2)C1]

The title compound was prepared in 50% yield from 2-[1-((3S)pyrrolidin-3-yl)pyrazol-4-yloxy]pyridino[3,4-d]pyrimidin-4-ol and chlorocyclopropylsulfone according to the procedure for the preparation of Example 126. ¹H NMR (400 MHz, DMSO-d₆): δ ppm 0.94-0.97 (m, 4H), 2.43-2.67 (m, 3H), 3.48-3.83 (m, 4H), 5.06 (t, J=5.6 Hz, 1H), 7.71 (s, 1H), 7.89 (d, J=4.8 Hz 1H), 8.26 (s, 1H), 8.55 (d, J=4.8 Hz 1H), 8.83 (s, 1H), 13.12 (s, 1H). [M+H] Calc'd for C₁₇H₁₈N₆O₄S, 403; Found, 403.

Example 138: 2-({1-[(3S)-1-(benzenesulfonyl)pyrrolidin-3-yl]-1H-pyrazol-4-yl}oxy)pyrido[3,4-d]pyrimidin-4-ol

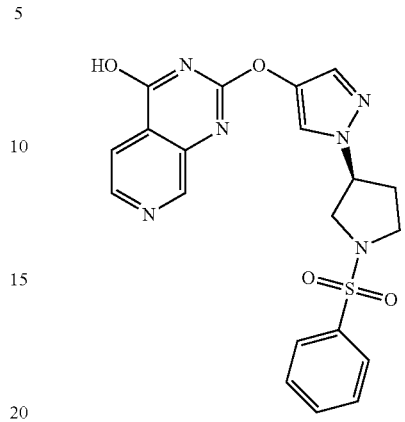

The title compound was prepared in 74% yield from 2-[1-((3S)pyrrolidin-3-yl)pyrazol-4-yloxy]pyridino[3,4-d]pyrimidin-4-ol and chlorophenylsulfone according to the procedure for the preparation of Example 126. ¹H NMR (400 MHz, DMSO-d₆): δ ppm 2.25-2.30 (m, 2H), 3.34-3.69 (m, 4H), 4.91 (t, J=4.8 Hz, 1H), 7.56-7.89 (m, 7H), 8.06 (s, 1H), 8.56 (s, 1H), 8.85 (s, 1H), 13.12 (s, 1H). [M+H] Calc'd for C₂₀H₁₈N₆O₄S, 439, Found, 439.

Example 139: 1-[(3S)-3-[4-({4-hydroxypyrido[3,4-d]pyrimidin-2-yl}oxy)-1H-pyrazol-1-yl]pyrrolidin-1-yl]ethan-1-one

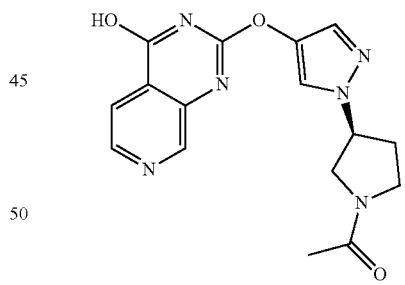

The title compound was prepared in 60% yield from 2-[1-((3S)pyrrolidin-3-yl)pyrazol-4-yloxy]pyridino[3,4-d]pyrimidin-4-ol and acetyl chloride according to the procedure for the preparation of Example 126. ¹H NMR (400 MHz, DMSO-d₆): δ ppm 1.97 (s, 3H), 2.30-2.45 (m, 2H), 3.44-3.98 (m, 4H), 4.97-5.06 (m, 1H), 7.69 (d, J=4.4 Hz, 1H), 7.89 (d, J=4.8 Hz, 1H), 8.18 (d, J=12.0 Hz, 1H), 8.55 (d, J=5.2 Hz, 1H), 8.85 (s, 1H), 13.12 (s, 1H). [M+H] Calc'd for C₁₆H₁₆N₆O₃, 341, Found, 341.

Example 140: 3-[(3S)-3-[4-({4-hydroxypyrido[3,4-d]pyrimidin-2-yl}oxy)-1H-pyrazol-1-yl]pyrrolidin-1-yl]-3-oxopropanenitrile

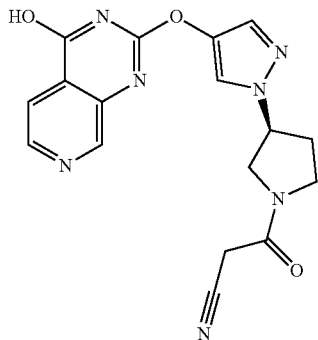 [SMILES: N#CCC(=O)N1CC[C@H](n2cc(Oc3nc(O)c4ccncc4n3)cn2)C1]

The title compound was prepared in 22% yield from 2-[1-((3S)pyrrolidin-3-yl)pyrazol-4-yloxy]pyridino[3,4-d]pyrimidin-4-ol and cyano-acetic acid 2,5-dioxo-pyrrolidin-1-yl ester according to the procedure for the preparation of Example 130. $^1$H NMR (400 MHz, DMSO-$d_6$): δ ppm 2.30-2.49 (m, 2H), 3.50-4.00 (m, 6H), 4.98-5.09 (m, 1H), 7.69 (d, J=5.2 Hz, 1H), 7.87 (d, J=6.8 Hz, 1H), 8.16 (d, J=8.0 Hz, 1H), 8.51 (d, J=6.8 Hz, 1H), 8.85 (s, 1H), 13.12 (s, 1H). [M+H] Calc'd for $C_{17}H_{15}N_7O_3$, 366, Found, 366.

Example 141: 2-({1-[(3S)-1-cyclopropanecarbonylpyrrolidin-3-yl]-1H-pyrazol-4-yl}oxy)pyrido[3,4-d]pyrimidin-4-ol

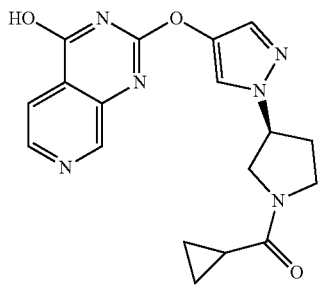 [SMILES: O=C(C1CC1)N1CC[C@H](n2cc(Oc3nc(O)c4ccncc4n3)cn2)C1]

The title compound was prepared in 30% yield from 2-[1-((3S)pyrrolidin-3-yl)pyrazol-4-yloxy]pyridino[3,4-d]pyrimidin-4-ol and cyclopropanecarbonyl chloride according to the procedure for the preparation of Example 126. $^1$H NMR (400 MHz, DMSO-$d_6$): δ ppm 0.72-0.74 (m, 4H), 1.77-1.82 (m, 1H), 2.34-2.48 (m, 2H), 3.46-4.16 (m, 4H), 4.98-5.11 (m, 1H), 7.69 (d, J=5.6 Hz, 1H), 7.89 (d, J=4.4 Hz, 1H), 8.21 (d, J=14.4 Hz, 1H), 8.55 (d, J=4.8 Hz, 1H), 8.85 (s, 1H), 13.12 (s, 1H). [M+H] Calc'd for $C_{18}H_{18}N_6O_3$, 367, Found, 367.

Example 142: 2-({1-[(3S)-1-benzoylpyrrolidin-3-yl]-1H-pyrazol-4-yl}oxy)pyrido[3,4-d]pyrimidin-4-ol

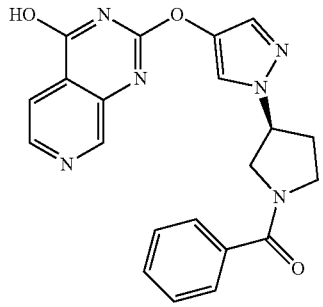 [SMILES: O=C(c1ccccc1)N1CC[C@H](n2cc(Oc3nc(O)c4ccncc4n3)cn2)C1]

The title compound was prepared in 40% yield from 2-[1-((3S)pyrrolidin-3-yl)pyrazol-4-yloxy]pyridino[3,4-d]pyrimidin-4-ol and benzoyl chloride according to the procedure for the preparation of Example 126. $^1$H NMR (400 MHz, DMSO-$d_6$): δ ppm 2.34-2.48 (m, 2H), 3.57-3.97 (m, 4H), 4.96-5.11 (m, 1H), 7.44-7.89 (m, 7H), 8.20 (s, 1H), 8.55 (s, 1H), 8.83 (s, 1H), 13.12 (s, 1H). [M+H] Calc'd for $C_{21}H_{18}N_6O_3$, 403, Found, 403.

Preparation 143 A: tert-butyl 4-({(3S)-3-[4-(4-hydroxypyridino[3,4-d]pyrimidin-2-yl)pyrazolyl]pyrrolidinyl}carbonyl)piperidinecarboxylate

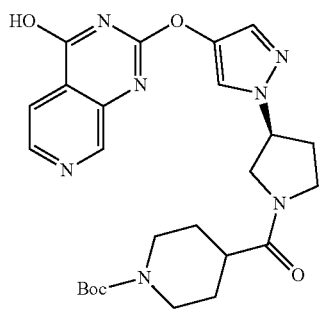 [SMILES: CC(C)(C)OC(=O)N1CCC(C(=O)N2CC[C@H](n3cc(Oc4nc(O)c5ccncc5n4)cn3)C2)CC1]

A mixture of 2-[1-((3S)pyrrolidin-3-yl)pyrazol-4-yl]pyridino[3,4-d]pyrimidin-4-ol (150 mg, 0.50 mmol), piperidine-1,4-dicarboxylic acid mono-tert-butyl ester (138 mg, 0.60 mmol), DIEA (1 ml) and HATU (267 mg, 0.70 mmol) in DCM was stirred overnight at RT and then concentrated. The residue was purified by HPLC to give 126 mg (50%) of the title compound. [M+H] Calc'd for $C_{25}H_{31}N_7O_5$, 510; Found, 510.

Example 143: 2-({1-[(3S)-1-(piperidine-4-carbonyl)pyrrolidin-3-yl]-1H-pyrazol-4-yl}oxy)pyrido[3,4-d]pyrimidin-4-ol

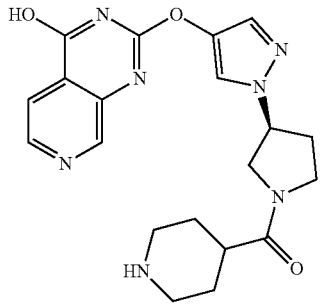 [SMILES: O=C(C1CCNCC1)N1CC[C@H](n2cc(Oc3nc(O)c4ccncc4n3)cn2)C1]

To a mixture of tert-butyl 4-({(3S)-3-[4-(4-hydroxypyridino[3,4-d]pyrimidin-2-yl)pyrazolyl]pyrrolidinyl}carbonyl)piperidinecarboxylate (126 mg, 0.25 mmol) in DCM was added $CF_3COOH$ (2 mL), and the mixture was stirred at RT for 1 h and then concentrated. The residue was purified by HPLC to give 20 mg (30%) of the title compound. $^1$H NMR (400 MHz, DMSO): δ 1.88-2.02 (m, 4H), 2.48-2.55 (m, 2H), 3.04-3.10 (m, 3H), 3.33-3.96 (m, 5H), 4.09 (d, J=5.2 Hz, 1H), 4.90-5.06 (m, 1H), 7.57 (s, 1H), 7.94-7.99 (m, 2H), 8.33 (d, J=5.2 Hz, 1H). 8.78 (s, 1H). [M+H] Calc'd for $C_{20}H_{23}N_7O_3$, 410; Found, 410.

Preparation 144 A: 1-{(3S)-3-[4-(4-hydroxypyridino[3,4-d]pyrimidin-2-yl)pyrazolyl]pyrrolidinyl}-2-chloroethan-1-one)

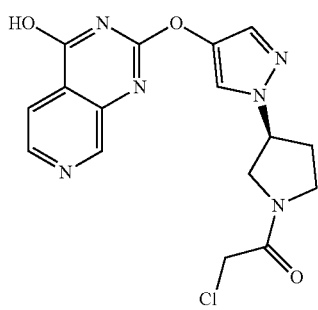 [SMILES: O=C(CCl)N1CC[C@H](n2cc(Oc3nc(O)c4ccncc4n3)cn2)C1]

To a solution of 2-[1-((3S)pyrrolidin-3-yl)pyrazol-4-yl]pyridino[3,4-d]pyrimidin-4-ol (150 mg, 0.50 mmol) and DIEA (1 mL) in THF was added chloro-acetyl chloride (68 mg, 0.60 mmol) at 0° C. The reaction mixture was stirred for 2 h at RT, filtered and concentrated. The residue was purified by FC (20:1, DCM:MeOH) to give 188 mg (91%) of the title compound.

Example 144: 1-[(3S)-3-[4-({4-hydroxypyrido[3,4-d]pyrimidin-2-yl}oxy)-1H-pyrazol-1-yl]pyrrolidin-1-yl]-2-(methylamino)ethan-1-one

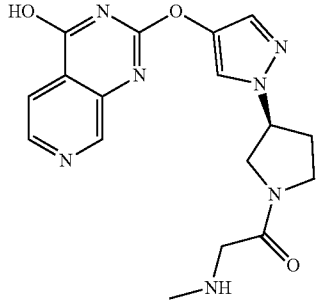 [SMILES: CNCC(=O)N1CC[C@H](n2cc(Oc3nc(O)c4ccncc4n3)cn2)C1]

1-{(3S)-3-[4-(4-hydroxypyridino[3,4-d]pyrimidin-2-yl)pyrazolyl]pyrrolidinyl}-2-chloroethan-1-one) (188 mg, 0.05 mmol) and a solution of methylamine in EtOH (10 mL) was stirred overnight at RT. The mixture was concentrated and the residue was purified by HPLC to give 9 mg (4.5%) of the title compound. $^1$H NMR (400 MHz, $CD_3OD$): δ 2.47-2.58 (m, 2H), 2.71 (d, J=2.8 Hz, 3H), 3.68-4.02 (m, 6H), 5.02-5.10 (m, 1H), 7.58 (s, 1H), 7.95-7.99 (m, 2H,), 8.36 (d, J=5.2 Hz, 1H). 8.79 (s, 1H). [M+H] Calc'd for $C_{17}H_{19}N_7O_3$, 370; Found, 370.

Example 145: 2-({1-[(3S)-1-phenylpyrrolidin-3-yl]-1H-pyrazol-4-yl}oxy)pyrido[3,4-d]pyrimidin-4-ol

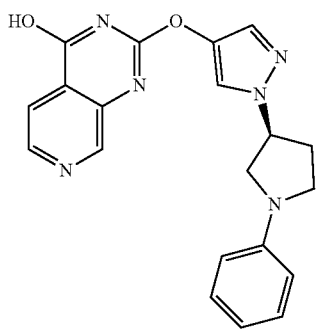 [SMILES: Oc1nc(Oc2cnn([C@H]3CCN(c4ccccc4)C3)c2)nc2cnccc12]

A mixture of 2-[1-((3S)pyrrolidin-3-yl)pyrazol-4-yl]pyridino[3,4-d]pyrimidin-4-ol (150 mg, 0.50 mmol), bromobenzene (95 mg, 0.60 mmol), t-BuONa (216 mg, 2.25 mmol), BINAP (31 mg, 0.05 mmol) and $Pd_2(dba)_3$ (50 mg, 0.05 mmol) in toluene was refluxed for 24 h under $N_2$ and then concentrated in vacuo. The residue was purified by HPLC to give 9 mg (5%) of the title compound. $^1$H NMR (400 MHz, DMSO): δ 2.48-2.53 (m, 2H), 3.32-3.78 (m, 4H), 5.12-5.15 (m, 1H), 6.59-6.65 (m, 3H), 7.19 (t, J=7.6 Hz, 2H), 7.69 (s, 1H), 7.87 (d, J=5.2 Hz, 1H), 8.17 (s, 1H), 8.53 (d, J=5.2 Hz, 1H). 8.80 (s, 1H,), 13.10 (s, 1H,). [M+H] Calc'd for $C_{20}H_{18}N_6O_2$, 375; Found, 375.

Example 146: 2-({1-[(3S)-1-(4-fluorophenyl)pyrrolidin-3-yl]-1H-pyrazol-4-yl}oxy)pyrido[3,4-d]pyrimidin-4-ol

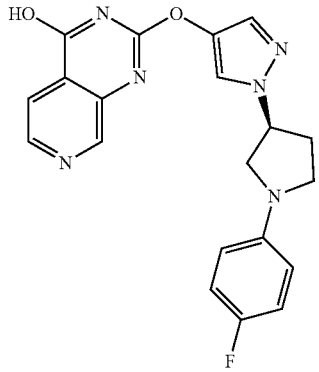 [SMILES: Oc1nc(Oc2cnn([C@H]3CCN(c4ccc(F)cc4)C3)c2)nc2cnccc12]

The title compound was prepared in 7% yield from 2-[1-((3S)pyrrolidin-3-yl)pyrazol-4-yl]pyridino[3,4-d]pyrimidin-4-ol and 1-fluoro-4-iodo-benzene according to the procedure for the preparation of Example 145. ¹H NMR (400 MHz, DMSO): δ 2.47-2.50 (m, 2H), 3.33-3.73 (m, 4H), 5.12-5.15 (m, 1H), 6.58-6.60 (m, 2H), 7.03 (t, J=8.4 Hz, 2H), 7.67 (s, 1H,), 7.88 (d, J=4.8 Hz, 1H), 8.17 (s, 1H), 8.54 (d, J=4.4 Hz, 1H), 8.81 (s, 1H), 13.10 (s, 1H). [M+H] Calc'd for $C_{20}H_{17}FN_6O_2$, 393; Found, 393.

Example 147: 2-({1-[(3S)-1-(2-fluorophenyl)pyrrolidin-3-yl]-1H-pyrazol-4-yl}oxy)pyrido[3,4-d]pyrimidin-4-ol

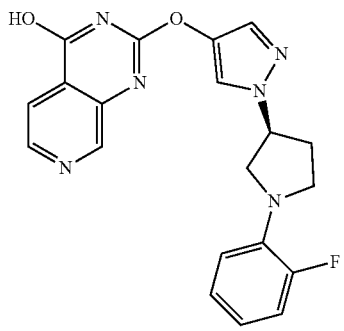 [SMILES: Oc1nc(Oc2cnn([C@H]3CCN(c4ccccc4F)C3)c2)nc2cnccc12]

The title compound was prepared in 12% yield from 2-[1-((3S)pyrrolidin-3-yl)pyrazol-4-yl]pyridino[3,4-d]pyrimidin-4-ol and 1-fluoro-2-iodo-benzene according to the procedure for the preparation of Example 145. ¹H NMR (400 MHz, DMSO): δ 2.41-2.50 (m, 2H), 3.46-3.84 (m, 4H,), 5.08-5.10 (m, 1H), 6.71-6.83 (m, 2H), 7.01-7.11 (m, 2H), 7.67 (s, 1H), 7.88 (d, J=6.0 Hz, 1H), 8.19 (s, 1H), 8.54 (d, J=4.8 Hz, 1H), 8.81 (s, 1H,), 13.10 (s, 1H). [M+H] Calc'd for $C_{20}H_{17}FN_6O_2$, 393; Found, 393.

Example 148: 2-({1-[(3S)-1-(4-chlorophenyl)pyrrolidin-3-yl]-1H-pyrazol-4-yl}oxy)pyrido[3,4-d]pyrimidin-4-ol

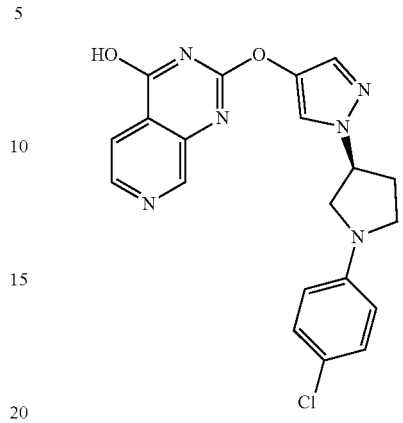

The title compound was prepared in 6.7% yield from 2-[1-((3S)pyrrolidin-3-yl)pyrazol-4-yl]pyridino[3,4-d]pyrimidin-4-ol and 1-chloro-4-iodo-benzene according to the procedure for the preparation of Example 145. ¹H NMR (400 MHz, DMSO): δ 2.48-2.50 (m, 2H), 3.38-3.77 (m, 4H), 5.13-5.15 (m, 1H), 6.51 (d, J=8.0 Hz, 2H), 7.20 (d, J=8.0 Hz, 2H), 7.67 (s, 1H), 7.88 (d, J=5.2 Hz, 1H), 8.17 (s, 1H), 8.54 (d, J=5.2 Hz, 1H), 8.81 (s, 1H), 13.10 (s, 1H). [M+H] Calc'd for $C_{20}H_{17}ClN_6O_2$, 409; Found, 409.

Example 149: 2-({1-[(3R)-piperidin-3-yl]-1H-pyrazol-4-yl}oxy)pyrido[3,4-d]pyrimidin-4-ol

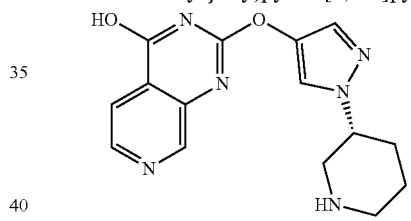

The title compound was prepared in 82% yield from tert-butyl (3R)-3-[4-(4-hydroxypyridino[3,4-d]pyrimidin-2-yloxy)pyrazolyl]piperidinecarboxylate according to the procedure for the preparation of Example 125. ¹H NMR (300 MHz, MeOD-d₄): δ 1.87-2.28 (m, 4H,), 3.25-3.37 (m, 2H), 3.65-3.74 (m, 2H), 4.68-4.71 (m, 1H), 7.74 (s, 1H), 8.03 (d, J=5.2 Hz, 1H), 8.16 (s, 1H), 8.54 (d, J=5.1 Hz, 1H), 8.45 (s, 1H). [M+H] Calc'd for $C_{15}H_{16}N_6O_2$, 313; Found, 313.

Example 150: 2-({1-[(3R)-1-(ethanesulfonyl)piperidin-3-yl]-1H-pyrazol-4-yl}oxy)pyrido[3,4-d]pyrimidin-4-ol

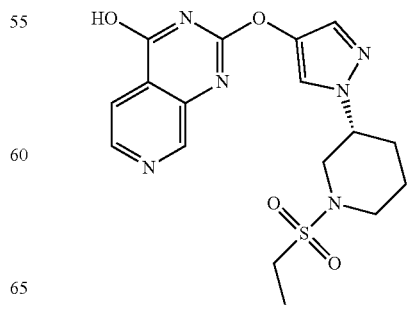

The title compound was prepared in 42% yield from 2-[1-((3R)-3-piperidyl)pyrazol-4-yloxy]pyridino[3,4-d]pyrimidin-4-ol and chloroethylsulfone according to the procedure for the preparation of Example 126. $^1$H NMR (300 MHz, DMSO): δ 1.21 (t, J=7.6 Hz, 3H), 1.85-2.12 (m, 4H), 2.92-3.32 (m, 4H), 3.52-3.56 (m, 1H), 3.80-3.86 (m, 1H), 4.32-4.37 (m, 1H), 7.69 (s, 1H), 7.89 (d, J=5.1 Hz, 1H), 8.25 (s, 1H), 8.54 (d, J=5.1 Hz, 1H), 8.56 (s, 1H), 13.09 (s, 1H). [M+H] Calc'd for $C_{17}H_{20}N_6O_4S$, 405; Found, 405.

Example 151: 2-({1-[(3S)-1-(cyclopropanesulfonyl)piperidin-3-yl]-1H-pyrazol-4-yl}oxy)pyrido[3,4-d]pyrimidin-4-ol

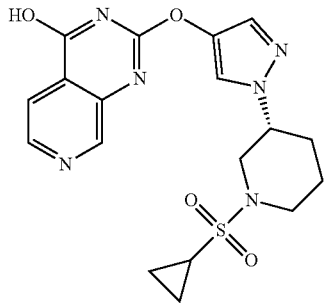 [SMILES: O=S(=O)(C1CC1)N1CCC[C@@H](n2cc(Oc3nc(O)c4ccncc4n3)cn2)C1]

The title compound was prepared in 38% yield from 2-[1-((3R)-3-piperidyl)pyrazol-4-yloxy]pyridino[3,4-d]pyrimidin-4-ol and chlorocyclopropylsulfone according to the procedure for the preparation of Example 126. $^1$H NMR (300 MHz, DMSO-d$_6$): δ ppm 0.94-.1.01 (m, 4H), 1.68-2.13 (m, 4H), 2.66-2.69 (m, 1H), 2.95-3.01 (m, 1H), 3.22-3.28 (m, 1H), 3.53-3.56 (m, 1H), 3.80-3.84 (m, 1H), 4.37-4.41 (m, 1H), 7.70 (s, 1H), 7.89 (d, J=5.1 Hz, 1H), 8.23 (s, 1H), 8.54 (d, J=5.1 Hz, 1H), 8.86 (s, 1H), 13.09 (s, 1H). [M+H] Calc'd for $C_{18}H_{20}N_6O_4S$, 417; Found, 417.

Example 152: 2-({1-[(3R)-1-(benzenesulfonyl)piperidin-3-yl]-1H-pyrazol-4-yl}oxy)pyrido[3,4-d]pyrimidin-4-ol

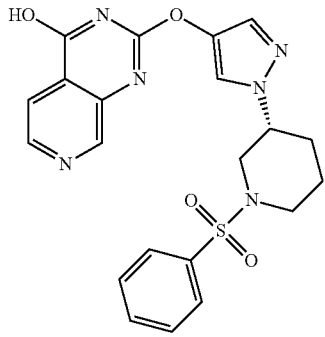 [SMILES: O=S(=O)(c1ccccc1)N1CCC[C@@H](n2cc(Oc3nc(O)c4ccncc4n3)cn2)C1]

The title compound was prepared in 45% yield from 2-[1-((3R)-3-piperidyl)pyrazol-4-yloxy]pyridino[3,4-d]pyrimidin-4-ol and chlorophenylsulfone according to the procedure for the preparation of Example 126. $^1$H NMR (400 MHz, DMSO-d$_6$): δ ppm 1.65-2.05 (m, 4H), 2.47-2.50 (m, 1H), 2.74 (t, J=10.4 Hz, 1H), 3.50 (d, J=11.2 Hz, 1H), 3.76 (d, J=11.2 Hz, 1H), 4.40-4.44 (m, 1H), 7.76-7.80 (m, 6H), 7.88 (d, J=4.8 Hz, 1H), 8.21 (s, 1H), 8.55 (d, J=4.8 Hz, 1H), 8.87 (s, 1H), 13.10 (s, 1H) [M+H] Calc'd for $C_{21}H_{20}N_6O_4S$, 453, Found, 453.

Example 153: 1-[(3R)-3-[4-({4-hydroxypyrido[3,4-d]pyrimidin-2-yl}oxy)-1H-pyrazol-1-yl]piperidin-1-yl]ethan-1-one

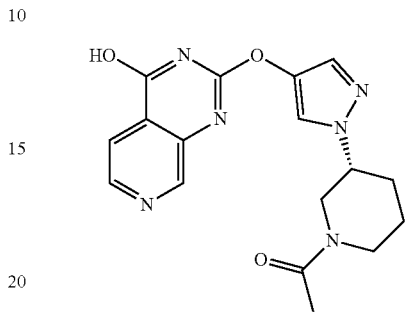

The title compound was prepared in 55% yield from 2-[1-((3R)-3-piperidyl)pyrazol-4-yloxy]pyridino[3,4-d]pyrimidin-4-ol and acetyl chloride according to the procedure for the preparation of Example 126. $^1$H NMR (400 MHz, DMSO-d$_6$): δ ppm 1.23-2.14 (m, 7H), 3.07-4.16 (m, 5H), 7.68 (d, J=3.2 Hz, 1H), 7.88 (d, J=4.8 Hz, 1H), 8.17 (d, J=11.6 Hz, 1H), 8.54 (d, J=4.8 Hz, 1H), 8.86 (d, J=8.4 Hz, 1H), 13.10 (s, 1H). [M+H] Calc'd for $C_{17}H_{18}N_6O_3$, 355, Found, 355.

Example 154: 3-[(3R)-3-[4-({4-hydroxypyrido[3,4-d]pyrimidin-2-yl}oxy)-1H-pyrazol-1-yl]piperidin-1-yl]-3-oxopropanenitrile

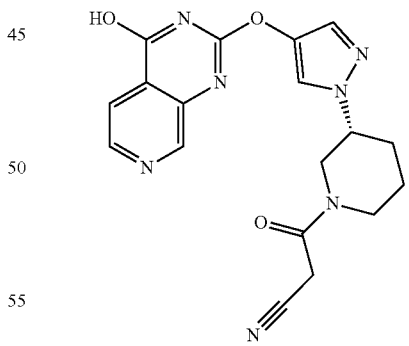

The title compound was prepared in 15% yield from 2-[1-((3R)-3-piperidyl)pyrazol-4-yloxy]pyridino[3,4-d]pyrimidin-4-ol and cyano-acetic acid 2,5-dioxo-pyrrolidin-1-yl ester according to the procedure for the preparation of Example 130. $^1$H NMR (300 MHz, DMSO-d$_6$): δ ppm 1.40-2.15 (m, 4H), 3.12-4.53 (m, 7H), 7.69 (s, 1H), 7.88 (d, J=5.1 Hz, 1H), 8.15 (s, 1H), 8.54 (d, J=5.1 Hz, 1H), 8.85 (d, J=5.4 Hz, 1H), 13.10 (s, 1H). [M+H] Calc'd for $C_{18}H_{17}N_7O_3$, 380, Found, 380.

Preparation 155 A: 2-{(3S)-3-[4-(4-hydroxypyridino[3,4-d]pyrimidin-2-yloxy)pyrazolyl]pyrrolidinyl}-2-oxoethyl acetate

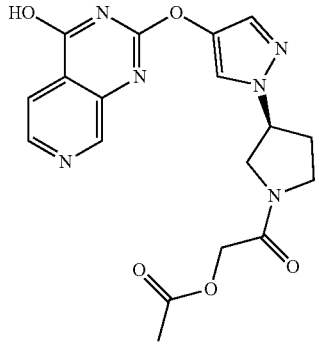 [SMILES: CC(=O)OCC(=O)N1CC[C@H](n2cc(Oc3nc(O)c4ccncc4n3)cn2)C1]

The title compound was prepared in prepared in 85% yield from 2-[1-((3S)pyrrolidin-3-yl)pyrazol-4-yloxy]pyridino[3,4-d]pyrimidin-4-ol and acetic acid chlorocarbonylmethyl ester according to the procedure for the preparation of Example 126. [M+H] Calc'd for $C_{18}H_{18}N_6O_5$, 399; Found, 399.

Example 155: 2-hydroxy-1-[(3S)-3-[4-({4-hydroxypyrido[3,4-d]pyrimidin-2-yl}oxy)-1H-pyrazol-1-yl]pyrrolidin-1-yl]ethan-1-one

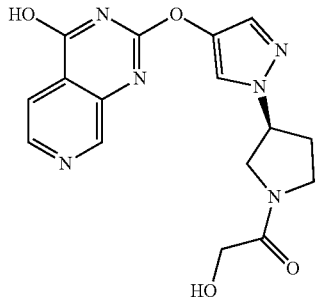 [SMILES: O=C(CO)N1CC[C@H](n2cc(Oc3nc(O)c4ccncc4n3)cn2)C1]

A mixture of 2-{(3S)-3-[4-(4-hydroxypyridino[3,4-d]pyrimidin-2-yloxy)pyrazolyl]pyrrolidinyl}-2-oxoethyl acetate (100 mg, 0.25 mmol) and $K_2CO_3$ (42 mg, 0.30 mmol) in MeOH (5 mL) was stirred for 3 h at RT. The reaction mixture was concentrated, and the residue was purified by flash chromatography (20:1, DCM:MeOH) to afford 69 mg (78%) of the title compound. $^1$H NMR (400 MHz, DMSO-$d_6$): δ ppm 2.31-2.42 (m, 2H), 3.52-4.05 (m, 6H), 4.62-4.64 (m, 1H), 4.99-5.05 (m, 1H), 7.68 (s, 1H), 7.88 (d, J=4.2 Hz, 1H), 8.17 (d, J=7.2 Hz, 1H), 8.54 (d, J=4.2 Hz, 1H), 8.84 (s, 1H), 13.10 (s, 1H). [M+H] Calc'd for $C_{16}H_{16}N_6O_4$, 357; Found, 357.

Example 156: 2-({1-[(3R)-1-cyclopropanecarbonylpiperidin-3-yl]-1H-pyrazol-4-yl}oxy)pyrido[3,4-d]pyrimidin-4-ol

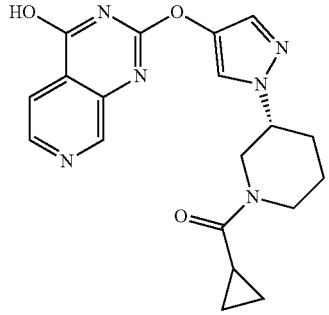 [SMILES: O=C(C1CC1)N1CCC[C@@H](n2cc(Oc3nc(O)c4ccncc4n3)cn2)C1]

The title compound was prepared in 42% yield from 2-[1-((3R)-3-piperidyl)pyrazol-4-yloxy]pyridino[3,4-d]pyrimidin-4-ol and cyclopropanecarbonyl chloride according to the procedure for the preparation of Example 126. $^1$H NMR (300 MHz, DMSO-$d_6$): δ ppm 0.72-0.75 (m, 4H), 1.59-2.16 (m, 5H), 2.75-3.50 (m, 2H), 4.12-4.19 (m, 3H), 7.68 (s, 1H), 7.88 (d, J=4.8 Hz, 1H), 8.16-8.19 (m, 1H), 8.54 (d, J=5.4 Hz, 1H), 8.86 (s, 1H), 13.10 (s, 1H). [M+H] Calc'd for $C_{19}H_{20}N_6O_3$, 381, Found, 381.

Example 157: 2-({1-[(3R)-1-benzoylpiperidin-3-yl]-1H-pyrazol-4-yl}oxy)pyrido[3,4-d]pyrimidin-4-ol

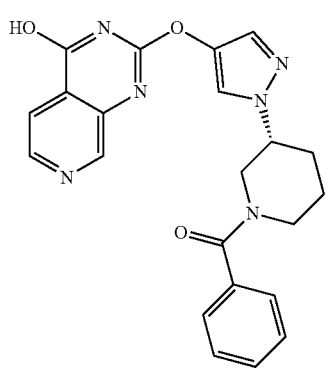 [SMILES: O=C(c1ccccc1)N1CCC[C@@H](n2cc(Oc3nc(O)c4ccncc4n3)cn2)C1]

The title compound was prepared in 47% yield from 2-[1-((3R)-3-piperidyl)pyrazol-4-yloxy]pyridino[3,4-d]pyrimidin-4-ol and benzoyl chloride according to the procedure for the preparation of Example 126. $^1$H NMR (400 MHz, DMSO-$d_6$): δ ppm 1.50-2.19 (m, 4H), 2.98-4.57 (m, 5H), 7.39-7.46 (m, 5H), 7.70-7.72 (m, 1H), 7.88 (d, J=4.2 Hz, 1H), 8.05-8.27 (m, 1H), 8.54 (d, J=4.2 Hz, 1H), 8.85 (s, 1H), 13.10 (s, 1H). [M+H] Calc'd for $C_{22}H_{20}N_6O_3$, 417, Found, 417.

Example 158: 2-({1-[(3R)-1-benzylpiperidin-3-yl]-1H-pyrazol-4-yl}oxy)pyrido[3,4-d]pyrimidin-4-ol

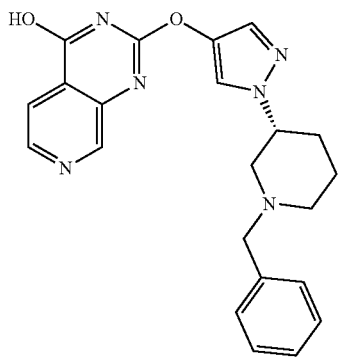 [SMILES: Oc1nc(Oc2cnn([C@@H]3CCCN(Cc4ccccc4)C3)c2)nc2cnccc12]

The title compound was prepared in 42% yield from 2-[1-((3R)-3-piperidyl)pyrazol-4-yloxy]pyridino[3,4-d]pyrimidin-4-ol and (bromomethyl)benzene according to the procedure for the preparation of Example 126. $^1$H NMR (300 MHz, DMSO-$d_6$): δ ppm 1.73-2.08 (m, 5H), 2.37 (t, J=10.2 Hz, 1H), 2.73-2.77 (m, 1H), 3.00-3.04 (m, 1H), 3.30-3.62 (m, 2H), 4.28-4.31 (m, 1H), 7.24-7.32 (m, 5H), 7.61 (s, 1H), 7.87 (d, J=5.4 Hz, 1H), 8.15 (s, 1H), 8.53 (d, J=5.1 Hz, 1H), 8.82 (s, 1H), 13.10 (s, 1H). [M+H] Calc'd for $C_{22}H_{22}N_6O_2$, 403, Found, 403.

Example 159: 2-({1-[(3R)-1-(4-fluorophenyl)piperidin-3-yl]-1H-pyrazol-4-yl}oxy)pyrido[3,4-d]pyrimidin-4-ol

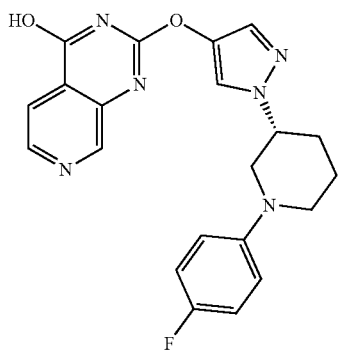 [SMILES: Oc1nc(Oc2cnn([C@@H]3CCCN(c4ccc(F)cc4)C3)c2)nc2cnccc12]

The title compound was prepared in 2% yield from 2-[1-((3R)-3-piperidyl)pyrazol-4-yl]pyridino[3,4-d]pyrimidin-4-ol and 1-fluoro-4-iodo-benzene according to the procedure for the preparation of Example 145. $^1$H NMR (300 MHz, DMSO-$d_6$): δ 1.76-2.15 (m, 4H), 2.78-2.79 (m, 1H), 3.04-3.11 (m, 1H), 3.51-3.55 (m, 1H), 3.77-3.82 (m, 1H), 4.41-4.42 (m, 1H), 7.01-7.06 (m, 4H), 7.68 (s, 1H), 7.88 (d, J=5.1 Hz, 1H), 8.22 (s, 1H), 8.54 (d, J=5.1 Hz, 1H), 8.84 (s, 1H), 13.10 (s, 1H). [M+H] Calc'd for $C_{21}H_{19}FN_6O_2$, 407; Found, 407.

Example 160: 2-({1-[(3S)-piperidin-3-yl]-1H-pyrazol-4-yl}oxy)pyrido[3,4-d]pyrimidin-4-ol

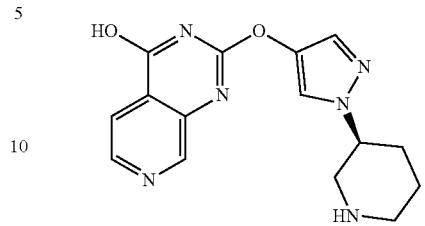

The title compound was prepared in 91% yield from tert-butyl (3S)-3-[4-(4-hydroxypyridino[3,4-d]pyrimidin-2-yloxy)pyrazolyl]piperidinecarboxylate according to the procedure for the preparation of Example 125. $^1$H NMR (300 MHz, MeOD-$d_4$): δ 1.87-2.28 (m, 4H,), 3.25-3.37 (m, 2H), 3.65-3.74 (m, 2H), 4.68-4.71 (m, 1H), 7.74 (s, 1H), 8.03 (d, J=5.2 Hz, 1H), 8.16 (s, 1H), 8.54 (d, J=5.1 Hz, 1H), 8.45 (s, 1H). [M+H] Calc'd for $C_{15}H_{16}N_6O_2$, 313; Found, 313.

Example 161: 2-({1-[(3S)-1-(ethanesulfonyl)piperidin-3-yl]-1H-pyrazol-4-yl}oxy)pyrido[3,4-d]pyrimidin-4-ol

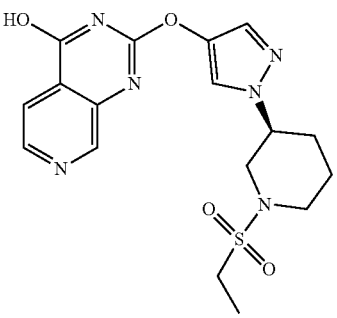 [SMILES: CCS(=O)(=O)N1CCC[C@H](n2cc(Oc3nc(O)c4ccncc4n3)cn2)C1]

The title compound was prepared in 33% yield from 2-[1-((3S)-3-piperidyl)pyrazol-4-yloxy]pyridino[3,4-d]pyrimidin-4-ol a according to the procedure for the preparation of Example 126. $^1$H NMR (300 MHz, DMSO-$d_6$): δ 1.21 (t, J=7.6 Hz, 3H), 1.85-2.12 (m, 4H), 2.92-3.32 (m, 4H), 3.52-3.56 (m, 1H), 3.80-3.857 (m, 1H), 4.32-4.37 (m, 1H), 7.69 (s, 1H), 7.89 (d, J=5.1 Hz, 1H), 8.25 (s, 1H), 8.54 (d, J=5.1 Hz, 1H), 8.56 (s, 1H), 13.09 (s, 1H). [M+H] Calc'd for $C_{17}H_{20}N_6O_4S$, 405; Found, 405.

Example 162: 2-({1-[(3S)-1-(cyclopropanesulfonyl)piperidin-3-yl]-1H-pyrazol-4-yl}oxy)pyrido[3,4-d]pyrimidin-4-ol

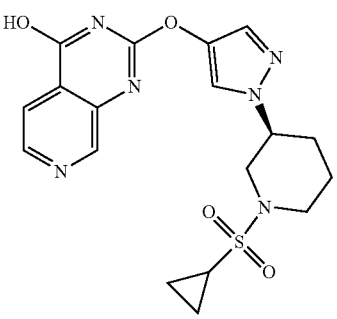 [SMILES: O=S(=O)(C1CC1)N1CCC[C@H](n2cc(Oc3nc(O)c4ccncc4n3)cn2)C1]

The title compound was prepared in 50% yield from 2-[1-(3S)-3-piperidyl)pyrazol-4-yloxy]pyridino[3,4-d]pyrimidin-4-ol according to the procedure for the preparation of Example 126. ¹H NMR (300 MHz, DMSO-d₆): δ ppm 0.94-.1.01 (m, 4H), 1.68-2.13 (m, 4H), 2.66-2.69 (m, 1H), 2.95-3.01 (m, 1H), 3.22-3.28 (m, 1H), 3.53-3.56 (m, 1H), 3.80-3.84 (m, 1H), 4.37-4.41 (m, 1H), 7.70 (s, 1H), 7.89 (d, J=5.1 Hz, 1H), 8.23 (s, 1H), 8.54 (d, J=5.1 Hz, 1H), 8.86 (s, 1H), 13.09 (s, 1H). [M+H] Calc'd for $C_{18}H_{20}N_6O_4S$, 417; Found, 417.

Example 163: 2-({1-[(3S)-1-(benzenesulfonyl)piperidin-3-yl]-1H-pyrazol-4-yl}oxy)pyrido[3,4-d]pyrimidin-4-ol

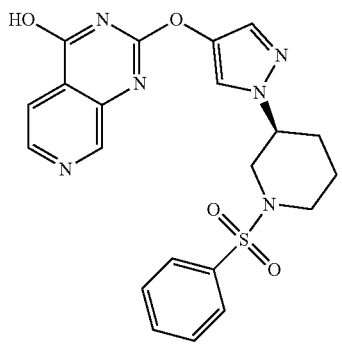 [SMILES: O=S(=O)(c1ccccc1)N1CCC[C@H](n2cc(Oc3nc(O)c4ccncc4n3)cn2)C1]

The title compound was prepared in 40% yield from 2-[1-((3S)-3-piperidyl)pyrazol-4-yloxy]pyridino[3,4-d]pyrimidin-4-ol according to the procedure for the preparation of Example 126. ¹H NMR (400 MHz, DMSO-d₆): δ ppm 1.65-2.05 (m, 4H), 2.47-2.50 (m, 1H), 2.74 (t, J=10.4 Hz, 1H), 3.50 (d, J=11.2 Hz, 1H), 3.76 (d, J=11.2 Hz, 1H), 4.40-4.44 (m, 1H), 7.76-7.80 (m, 6H), 7.88 (d, J=4.8 Hz, 1H), 8.21 (s, 1H), 8.55 (d, J=4.8 Hz, 1H), 8.87 (s, 1H), 13.10 (s, 1H). [M+H] Calc'd for $C_{21}H_{20}N_6O_4S$, 453, Found, 453.

Example 164: 1-[(3S)-3-[4-({4-hydroxypyrido[3,4-d]pyrimidin-2-yl}oxy)-1H-pyrazol-1-yl]piperidin-1-yl]ethan-1-one

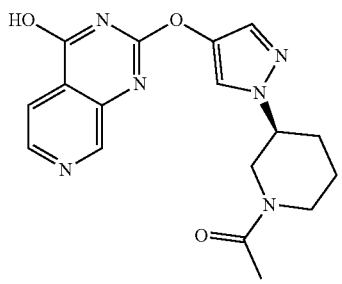 [SMILES: CC(=O)N1CCC[C@H](n2cc(Oc3nc(O)c4ccncc4n3)cn2)C1]

The title compound was prepared in 60% yield from 2-[1-((3S)-3-piperidyl)pyrazol-4-yloxy]pyridino[3,4-d]pyrimidin-4-ol and acetyl chloride according to the procedure for the preparation of Example 126. ¹H NMR (400 MHz, DMSO-d₆): δ ppm 1.23-2.14 (m, 7H), 3.07-4.16 (m, 5H), 7.68 (d, J=3.2 Hz, 1H), 7.88 (d, J=4.8 Hz, 1H), 8.17 (d, J=11.6 Hz, 1H), 8.54 (d, J=4.8 Hz, 1H), 8.86 (d, J=8.4 Hz, 1H), 13.10 (s, 1H). [M+H] Calc'd for $C_{17}H_{18}N_6O_3$, 355, Found, 355.

Example 165: 2-({1-[(3S)-1-cyclopropanecarbonylpiperidin-3-yl]-1H-pyrazol-4-yl}oxy)pyrido[3,4-d]pyrimidin-4-ol

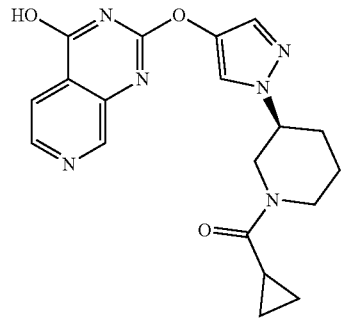 [SMILES: O=C(C1CC1)N1CCC[C@H](n2cc(Oc3nc(O)c4ccncc4n3)cn2)C1]

The title compound was prepared in 35% yield from 2-[1-((3S)-3-piperidyl)pyrazol-4-yloxy]pyridino[3,4-d]pyrimidin-4-ol and cyclopropanecarbonyl chloride according to the procedure for the preparation of Example 126. ¹H NMR (300 MHz, DMSO-d₆): δ ppm 0.72-0.75 (m, 4H), 1.59-2.16 (m, 5H), 2.75-3.50 (m, 2H), 4.12-4.19 (m, 3H), 7.68 (s, 1H), 7.88 (d, J=4.8 Hz, 1H), 8.16-8.19 (m, 1H), 8.54 (d, J=5.4 Hz, 1H), 8.86 (s, 1H), 13.10 (s, 1H). [M+H] Calc'd for $C_{19}H_{20}N_6O_3$, 381, Found, 381.

Example 166: 3-[(3S)-3-[4-({4-hydroxypyrido[3,4-d]pyrimidin-2-yl}oxy)-1H-pyrazol-1-yl]piperidin-1-yl]-3-oxopropanenitrile

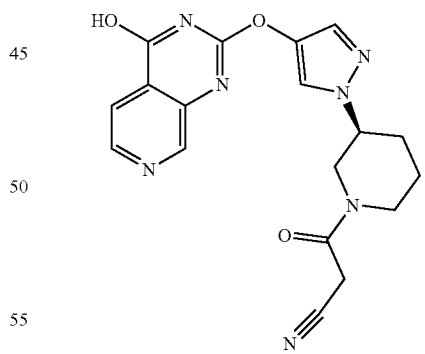

The title compound was prepared in 21% yield from 2-[1-((3S)-3-piperidyl)pyrazol-4-yloxy]pyridino[3,4-d]pyrimidin-4-ol and cyano-acetic acid 2,5-dioxo-pyrrolidin-1-yl ester according to the procedure for the preparation of Example 130. ¹H NMR (300 MHz, DMSO-d₆): δ ppm 1.40-2.15 (m, 4H), 3.12-4.53 (m, 7H), 7.69 (s, 1H), 7.88 (d, J=5.1 Hz, 1H), 8.15 (s, 1H), 8.54 (d, J=5.1 Hz, 1H), 8.85 (d, J=5.4 Hz, 1H), 13.10 (s, 1H). [M+H] Calc'd for $C_{18}H_{17}N_7O_3$, 380, Found, 380.

Example 167: 2-({1-[(3S)-1-benzoylpiperidin-3-yl]-1H-pyrazol-4-yl}oxy)pyrido[3,4-d]pyrimidin-4-ol

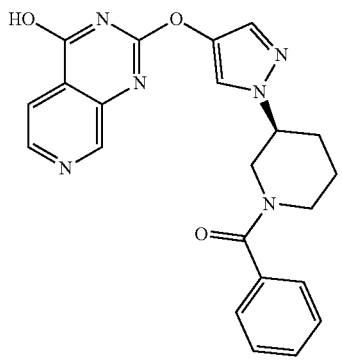 [SMILES: O=C(c1ccccc1)N1CCC[C@H](n2cc(Oc3nc(O)c4ccncc4n3)cn2)C1]

The title compound was prepared in 40% yield from 2-[1-((3S)-3-piperidyl)pyrazol-4-yloxy]pyridino[3,4-d]pyrimidin-4-ol and benzoyl chloride according to the procedure for the preparation of Example 126. $^1$H NMR (400 MHz, DMSO-$d_6$): δ ppm 1.50-2.19 (m, 4H), 2.98-4.57 (m, 5H), 7.39-7.46 (m, 5H), 7.70-7.72 (m, 1H), 7.88 (d, J=4.2 Hz, 1H), 8.05-8.27 (m, 1H), 8.54 (d, J=4.2 Hz, 1H), 8.85 (s, 1H), 13.10 (s, 1H). [M+H] Calc'd for $C_{22}H_{20}N_6O_3$, 417; Found, 417.

Example 168: 2-({1-[(3S)-1-benzylpiperidin-3-yl]-1H-pyrazol-4-yl}oxy)pyrido[3,4-d]pyrimidin-4-ol

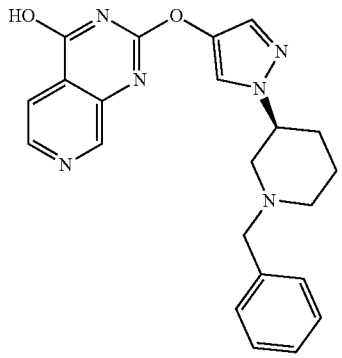 [SMILES: Oc1nc(Oc2cnn([C@H]3CCCN(Cc4ccccc4)C3)c2)nc2cnccc12]

The title compound was prepared in 30% yield from 2-[1-((3S)-3-piperidyl)pyrazol-4-yloxy]pyridino[3,4-d]pyrimidin-4-ol and (bromomethyl)benzene according to the procedure for the preparation of Example 126. $^1$H NMR (300 MHz, DMSO-$d_6$): δ ppm 1.73-2.08 (m, 5H), 2.37 (t, J=10.2 Hz, 1H), 2.73-2.77 (m, 1H), 3.00-3.04 (m, 1H), 3.30-3.62 (m, 2H), 4.28-4.31 (m, 1H), 7.24-7.32 (m, 5H), 7.61 (s, 1H), 7.87 (d, J=5.4 Hz, 1H), 8.15 (s, 1H), 8.53 (d, J=5.1 Hz, 1H), 8.82 (s, 1H), 13.10 (s, 1H). [M+H] Calc'd for $C_{22}H_{22}N_6O_2$, 403, Found, 403.

Example 169: 2-({1-[(3R)-1-(4-fluorophenyl)piperidin-3-yl]-1H-pyrazol-4-yl}oxy)pyrido[3,4-d]pyrimidin-4-ol

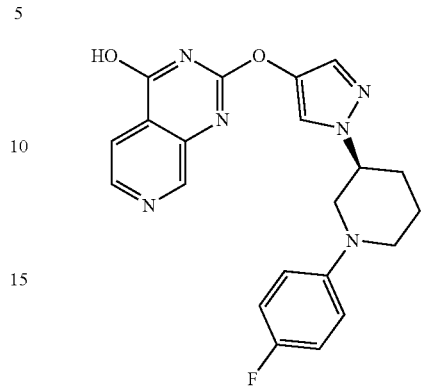

The title compound was prepared in 16% yield from 2-[1-((3S)-3-piperidyl)pyrazol-4-yl]pyridino[3,4-d]pyrimidin-4-ol and 1-fluoro-4-iodo-benzene according to the procedure for the preparation of Example 145. $^1$H NMR (300 MHz, DMSO): δ 1.76-2.15 (m, 4H), 2.78-2.79 (m, 1H), 3.04-3.11 (m, 1H), 3.51-3.55 (m, 1H), 3.77-3.82 (m, 1H), 4.41-4.42 (m, 1H), 7.01-7.06 (m, 4H), 7.68 (s, 1H), 7.88 (d, J=5.1 Hz, 1H), 8.22 (s, 1H), 8.54 (d, J=5.1 Hz, 1H), 8.84 (s, 1H), 13.10 (s, 1H). [M+H] Calc'd for $C_{21}H_{19}FN_6O_2$, 407; Found, 407.

Example 170: 2-{[1-(trifluoromethyl)phenyl]methoxy}pyrido[3,4-d]pyrimidin-4-ol

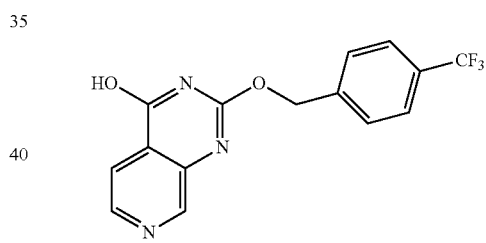

The title compound was prepared in 51% yield from 4-hydroxymethylbenzotrifluoride and 2-chloropyrido[3,4-d]pyrimidin-4-ol according to the procedure for the preparation of Example 21. $^1$H NMR (400 MHz, DMSO-$d_6$): δ ppm 5.61 (s, 2H) 7.71-7.83 (m, 4H) 7.87 (d, J=5.05 Hz, 1H) 8.52 (d, J=5.05 Hz, 1H) 8.92 (s, 1H) 12.91 (s, 1H). [M+H] Calc'd for $C_{15}H_{10}F_3N_3O_2$, 322; Found, 322.

Example 171: 2-[(2-chlorophenyl)methoxy]pyrido[3,4-d]pyrimidin-4-ol

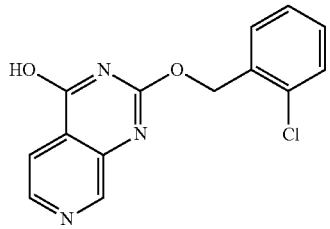

The title compound was prepared in 65% yield from 2-chlorobenzyl alcohol and 2-chloropyrido[3,4-d]pyrimidin-4-ol according to the procedure for the preparation of Example 21. $^1$H NMR (400 MHz, DMSO-d$_6$): δ ppm 5.53 (s, 2H) 7.25-7.50 (m, 2H) 7.50-7.63 (m, 1H) 7.63-7.78 (m, 1H) 7.86 (d, J=5.05 Hz, 1H) 8.52 (d, J=5.05 Hz, 1H) 8.90 (s, 1H) 12.79 (s, 1H). [M+H] Calc'd for C$_{14}$H$_{10}$ClN$_3$O$_2$, 288; Found, 288.

Example 172: 2-[(2,6-dichlorophenyl)methoxy]pyrido[3,4-d]pyrimidin-4-ol

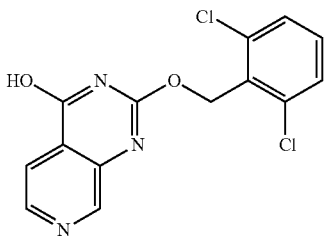

To a solution of (2,6-dichloro-phenyl)-methanol (4.97 mmol) in DMA was added NaH (200 mg, 4.97 mmol) at RT, and the mixture was stirred for 1 h at RT. 2-Chloro-pyrido[3,4-d]pyrimidin-4-ol (150 mg, 0.83 mmol) was added. The mixture was stirred overnight at RT and concentrated. The residue was purified by FC (DCM/MeOH=20/1) to give 140 mg (53%) of the title compound. $^1$H NMR (400 MHz, DMSO): δ 5.68 (s, 2H), 7.49-7.53 (m, 1H), 7.59-7.61 (m, 2H), 7.86 (d, J=4.8 Hz, 1H), 8.53 (d, J=4.8 Hz, 1H), 8.92 (s, 1H), 12.71 (s, 1H). [M+H] Calc'd for C$_{14}$H$_9$Cl$_2$N$_3$O$_2$, 322; Found, 322.

Example 173: 2-[(2,3-dichlorophenyl)methoxy]pyrido[3,4-d]pyrimidin-4-ol

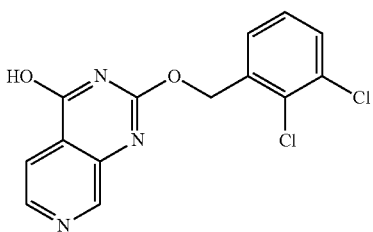 [SMILES: Oc1nc(OCc2cccc(Cl)c2Cl)nc2cnccc12]

The title compound was prepared in 19% yield from 2-chloro-pyrido[3,4-d]pyrimidin-4-ol and (2,3-dichlorophenyl)-methanol according to the procedure for the preparation of Example 172. $^1$H NMR (300 MHz, DMSO): δ 5.60 (s, 2H), 7.46 (t, J=7.8 Hz, 1H), 7.88 (t, J=7.8 Hz, 2H), 7.86 (d, J=5.1 Hz, 1H), 8.53 (d, J=5.4 Hz, 1H), 8.89 (s, 1H), 12.82 (s, 1H). [M+H] Calc'd for C$_{14}$H$_9$Cl$_2$N$_3$O$_2$, 322; Found, 322.

Example 174: 2-[2-(4-chlorophenyl)ethoxy]pyrido[3,4-d]pyrimidin-4-ol

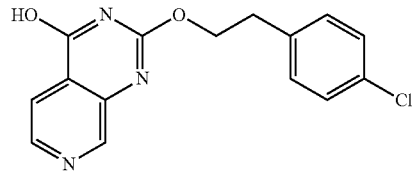 [SMILES: Oc1nc(OCCc2ccc(Cl)cc2)nc2cnccc12]

A mixture of 2-(4-Chloro-phenyl)-ethanol (2 mL) and Na (95 mg, 5 eq, 4.14 mmol) was stirred and heated at 60° C. for 0.5 h until Na disappeared. 2-Chloro-pyrido[3,4-d]pyrimidin-4-ol (150 mg, 0.83 mmol) was added to the mixture and the mixture was stirred overnight at 90° C. The reaction mixture was concentrated and the residue was purified by gel chromatography (20:1, DCM:MeOH) to afford 195 mg (59%) of the title compound as a white solid. $^1$H NMR (400 MHz, DMSO-d$_6$): δ 3.07 (t, J=6.8 Hz, 2H), 4.62 (t, J=6.8 Hz, 2H), 7.38 (s, 4H), 7.83 (d, J=6.8 Hz, 1H), 8.49 (d, J=5.2 Hz, 1H). 8.84 (s, 1H), 12.64 (s, 1H). [M+H] Calc'd for C$_{15}$H$_{12}$ClN$_3$O$_2$, 302; Found, 302.

Example 175: 2-[2-(3,4-dichlorophenyl)ethoxy]pyrido[3,4-d]pyrimidin-4-ol

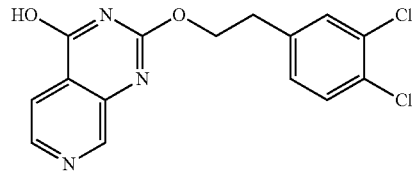 [SMILES: Oc1nc(OCCc2ccc(Cl)c(Cl)c2)nc2cnccc12]

The title compound was prepared in 16% yield from 2-chloro-pyrido[3,4-d]pyrimidin-4-ol and 2-(3,4-dichlorophenyl)-ethanol according to the procedure for the preparation of Example 174. $^1$H NMR (300 MHz, DMSO): δ 3.08 (t, J=6.3 Hz, 2H), 4.63 (t, J=6.3 Hz, 2H), 7.35-7.37 (m, 1H), 7.56-7.58 (m, 1H), 7.66 (s, 1H), 7.83 (d, J=5.1 Hz, 1H), 8.48 (d, J=4.8 Hz, 1H), 8.83 (s, 1H), 12.65 (s, 1H). [M+H] Calc'd for C$_{15}$H$_{11}$Cl$_2$N$_3$O$_2$, 336; Found, 336.

Example 176: 2-(2,2,2-trifluoro-1-phenylethoxy)pyrido[3,4-d]pyrimidin-4-ol

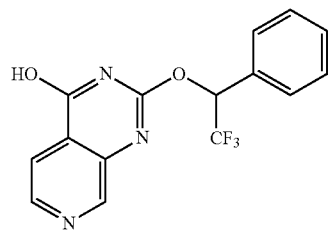

The title compound was prepared in 53% yield from 2,2,2-trifluoro-1-phenylethanol and 2-chloropyrido[3,4-d]pyrimidin-4-ol according to the procedure for the preparation of Example 21. $^1$H NMR (400 MHz, DMSO-d$_6$): δ ppm 6.72-7.02 (m, 1H) 7.36-7.58 (m, 3H) 7.58-7.74 (m, 2H) 7.85 (d, J=5.05 Hz, 1H) 8.53 (d, J=5.05 Hz, 1H) 8.79 (s, 1H) 13.19 (br. s., 1H). [M+H] Calc'd for $C_{15}H_{10}F_3N_3O_2$, 322; Found, 322.

Example 177: 2-{[2-(trifluoromethyl)phenyl]methoxy}pyrido[3,4-d]pyrimidin-4-ol

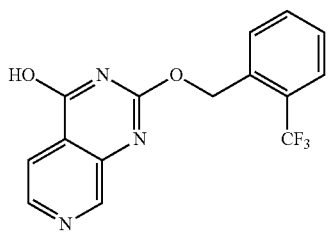

The title compound was prepared in 41% yield from 2-chloro-pyrido[3,4-d]pyrimidin-4-ol and (2-trifluoromethyl-phenyl)-methanol according to the procedure for the preparation of Example 172. $^1$H NMR (400 MHz, DMSO): δ 5.66 (s, 2H), 7.63 (t, J=7.8 Hz, 1H), 7.77 (t, J=7.6 Hz, 1H), 7.82-7.87 (m, 3H), 8.53 (d, J=5.2 Hz, 1H), 8.88 (s, 1H), 12.81 (s, 1H). [M+H] Calc'd for $C_{15}H_{10}F_3N_3O_2$, 322; Found, 322.

Example 178: 2-[(2-fluorophenyl)methoxy]pyrido[3,4-d]pyrimidin-4-ol

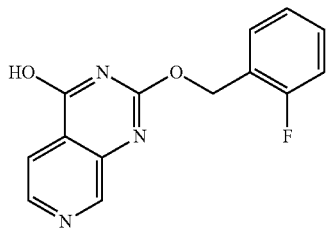

The title compound was prepared in 66% yield from 2-fluorobenzyl alcohol and 2-chloropyrido[3,4-d]pyrimidin-4-ol according to the procedure for the preparation of Example 21. $^1$H NMR (400 MHz, DMSO-d$_6$): δ ppm 5.52 (s, 2H) 7.21 (td, J=8.59, 2.53 Hz, 1H) 7.34-7.41 (m, 2H) 7.47 (td, J=7.96, 6.06 Hz, 1H) 7.87 (d, J=5.05 Hz, 1H) 8.53 (d, J=4.80 Hz, 1H) 8.89 (br. s., 1H) 12.75 (s, 1H). [M+H] Calc'd for $C_{14}H_{10}FN_3O_2$, 272; Found, 272.

Example 179: 2-[(3-fluorophenyl)methoxy]pyrido[3,4-d]pyrimidin-4-ol

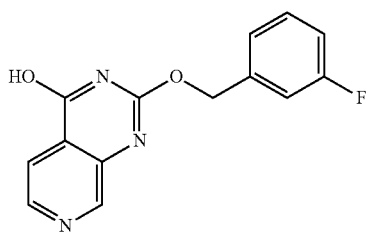

The title compound was prepared in 15% yield from 3-fluorobenzyl alcohol and 2-chloropyrido[3,4-d]pyrimidin-4-ol according to the procedure for the preparation of Example 21. $^1$H NMR (400 MHz, DMSO-d$_6$): δ ppm 5.48 (s, 2H) 7.17-7.27 (m, 1H) 7.38 (t, J=7.45 Hz, 2H) 7.47 (td, J=8.02, 5.94 Hz, 1H) 7.86 (d, J=5.05 Hz, 1H) 8.52 (d, J=5.31 Hz, 1H) 8.88 (s, 1H) 12.56-12.84 (m, 1H). [M+H] Calc'd for $C_{14}H_{10}FN_3O_2$, 272; Found, 272.

Example 180: 2-[(4-fluorophenyl)methoxy]pyrido[3,4-d]pyrimidin-4-ol

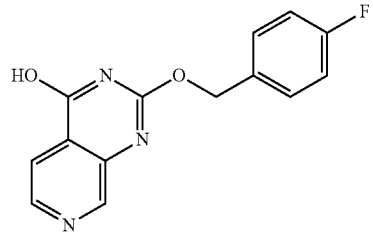 [SMILES: Oc1nc(OCc2ccc(F)cc2)nc2cnccc12]

The title compound was prepared in 52% yield from 4-fluorobenzyl alcohol and 2-chloropyrido[3,4-d]pyrimidin-4-ol according to the procedure for the preparation of Example 21. $^1$H NMR (400 MHz, DMSO-d$_6$): δ ppm 5.48 (s, 2H) 7.25 (t, J=8.97 Hz, 2H) 7.59 (dd, J=8.46, 5.68 Hz, 2H) 7.86 (d, J=5.31 Hz, 1H) 8.52 (d, J=5.05 Hz, 1H) 8.89 (s, 1H) 12.50-12.88 (m, 1H). [M+H] Calc'd for $C_{14}H_{10}FN_3O_2$, 272; Found, 272.

Example 181: 2-[(2,3-difluorophenyl)methoxy]pyrido[3,4-d]pyrimidin-4-ol

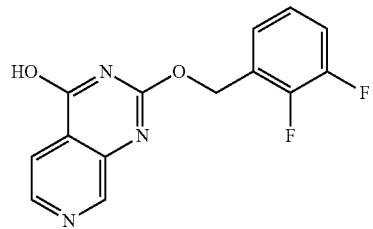

The title compound was prepared in 21% yield from 2,3-difluorobenzyl alcohol and 2-chloropyrido[3,4-d]pyrimidin-4-ol according to the procedure for the preparation of Example 21. $^1$H NMR (400 MHz, DMSO-d$_6$): δ ppm 5.59 (s, 2H) 7.25-7.38 (m, 1H) 7.41-7.56 (m, 2H) 7.86 (d, J=5.31 Hz, 1H) 8.53 (d, J=5.05 Hz, 1H) 8.89 (s, 1H) 12.77 (s, 1H). [M+H] Calc'd for $C_{14}H_9F_2N_3O_2$, 290; Found, 290.

Example 182: 2-[(2,5-difluorophenyl)methoxy]pyrido[3,4-d]pyrimidin-4-ol

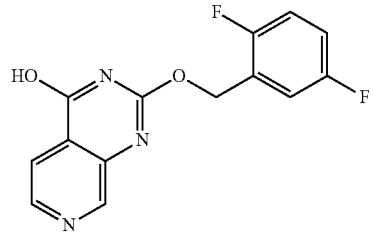 [SMILES: Oc1nc(OCc2cc(F)ccc2F)nc2cnccc12]

The title compound was prepared in 51% yield from 2,5-difluorobenzyl alcohol and 2-chloropyrido[3,4-d]pyrimidin-4-ol according to the procedure for the preparation of Example 21. ¹H NMR (400 MHz, DMSO-$d_6$) δ ppm 5.53 (s, 2H) 7.24-7.45 (m, 2H) 7.52 (ddd, J=8.78, 5.62, 3.28 Hz, 1H) 7.86 (d, J=5.05 Hz, 1H) 8.53 (d, J=5.05 Hz, 1H) 8.89 (s, 1H) 12.76 (br. s., 1H). [M+H] Calc'd for $C_{14}H_9F_2N_3O_2$, 290; Found, 290.

Example 183: 2-[(2,6-difluorophenyl)methoxy]pyrido[3,4-d]pyrimidin-4-ol

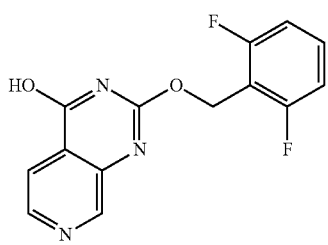

The title compound was prepared in 22% yield from 2,6-difluorobenzyl alcohol and 2-chloropyrido[3,4-d]pyrimidin-4-ol according to the procedure for the preparation of Example 21. ¹H NMR (400 MHz, DMSO-$d_6$) δ ppm 5.43-5.68 (m, 2H) 7.14-7.34 (m, 2H) 7.48-7.70 (m, 1H) 7.85 (d, J=5.05 Hz, 1H) 8.52 (d, J=5.05 Hz, 1H) 8.88 (s, 1H) 12.69 (br. s., 1H). [M+H] Calc'd for $C_{14}H_9F_2N_3O_2$, 290; Found, 290.

Example 184: 2-(naphthalen-1-ylmethoxy)pyrido[3,4-d]pyrimidin-4-ol

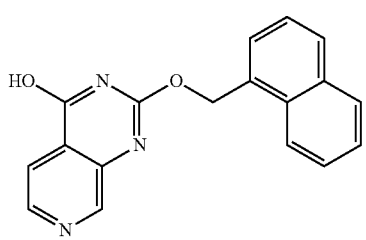 [SMILES: Oc1nc(OCc2cccc3ccccc23)nc2cnccc12]

To a solution of naphthylmethan-1-ol (262 mg, 1.65 mmol) in dioxane (10 mL) was added NaH (67 mg, 1.65 mmol) at 0° C., and the mixture was stirred at RT for 30 min. 2-Chloropyridino[3,4-d]pyrimidin-4-ol (100 mg, 0.55 mmol) was added, and the mixture was refluxed overnight. The solvent was removed and the residue was purified by FC (20:1, DCM:MeOH) to obtain 114 mg (69%) of the title compound. ¹H NMR (400 MHz, DMSO-$d_6$): δ ppm 5.96 (s, 2H), 7.52-8.15 (m, 8H), 8.52 (d, J=6.8 Hz, 1H), 8.94 (s, 1H), 12.67 (s, 1H). [M+H] Calc'd for $C_{18}H_{13}N_3O_2$, 304; Found, 304.

Example 185: 2-[(2-phenylphenyl)methoxy]pyrido[3,4-d]pyrimidin-4-ol

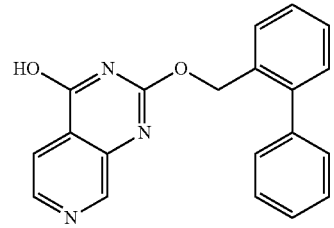 [SMILES: Oc1nc(OCc2ccccc2-c2ccccc2)nc2cnccc12]

The title compound was prepared in 37% yield from (2-phenylphenyl)methan-1-ol and 2-chloropyridino[3,4-d]pyrimidin-4-ol according to the procedure for the preparation of Example 187. ¹H NMR (400 MHz, DMSO-$d_6$): δ ppm 5.37 (s, 2H), 7.33-7.84 (m, 10H), 8.48 (d, J=6.8 Hz, 1H), 8.75 (s, 1H), 12.67 (s, 1H). [M+H] Calc'd for $C_{20}H_{15}N_3O_2$, 330; Found, 330.

Example 186: 2-[(3-phenylphenyl)methoxy]pyrido[3,4-d]pyrimidin-4-ol

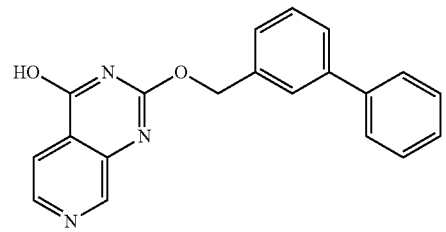 [SMILES: Oc1nc(OCc2cccc(-c3ccccc3)c2)nc2cnccc12]

The title compound was prepared in 37% yield from (3-phenylphenyl)methan-1-ol and 2-chloropyridino[3,4-d]pyrimidin-4-ol according to the procedure for the preparation of Example 187. ¹H NMR (400 MHz, DMSO-$d_6$): δ ppm 5.57 (s, 2H), 7.38-7.87 (m, 10H), 8.52 (d, J=6.8 Hz, 1H), 8.90 (s, 1H), 12.67 (s, 1H). [M+H] Calc'd for $C_{20}H_{15}N_3O_2$, 330; Found, 330.

Example 187: 2-(naphthalen-2-ylmethoxy)pyrido[3,4-d]pyrimidin-4-ol

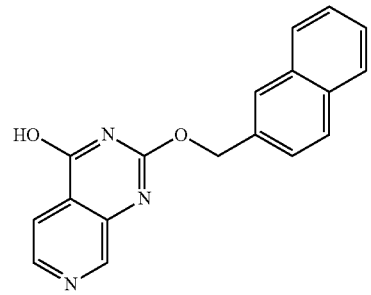 [SMILES: Oc1nc(OCc2ccc3ccccc3c2)nc2cnccc12]

The title compound was prepared in 20% yield from 2-naphthylmethan-1-ol and 2-chloropyridino[3,4-d]pyrimidin-4-ol according to the procedure for the preparation of Example 187. ¹H NMR (400 MHz, DMSO-d₆): δ ppm 5.67 (s, 2H), 7.53-8.06 (m, 8H), 8.52 (d, J=6.8 Hz, 1H), 8.91 (s, 1H), 12.76 (s, 1H). [M+H] Calc'd for $C_{18}H_{13}N_3O_2$, 304; Found, 304.

Example 188: 2-(1,2,3,4-tetrahydronaphthalen-1-ylmethoxy)pyrido[3,4-d]pyrimidin-4-ol

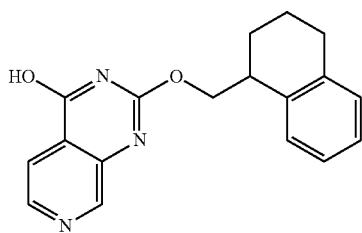 [SMILES: Oc1nc(OCC2CCCc3ccccc32)nc2cnccc12]

The title compound was prepared in 6% yield from 1,2,3,4-tetrahydronaphthylmethan-1-ol and 2-chloropyridino[3,4-d]pyrimidin-4-ol according to the procedure for the preparation of Example 187. ¹H NMR (400 MHz, DMSO-d₆): δ ppm 1.69-1.93 (m, 4H), 2.76 (t, J=5.6 Hz, 2H), 3.30 (d, J=6.8 Hz, 1H), 4.44-4.66 (m, 2H), 7.09-7.18 (m, 3H), 7.38 (d, J=6.4 Hz, 1H), 7.84 (d, J=6.8 Hz, 1H), 8.49 (d, J=6.4 Hz, 1H), 8.85 (s, 1H), 12.69 (s, 1H). [M+H] Calc'd for $C_{18}H_{17}N_3O_2$, 308; Found, 308.

Example 189: 2-(2,3-dihydro-1H-inden-2-yloxy)pyrido[3,4-d]pyrimidin-4-ol

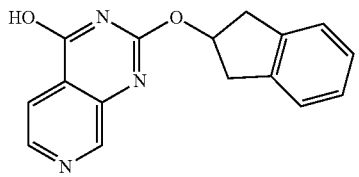 [SMILES: Oc1nc(OC2Cc3ccccc3C2)nc2cnccc12]

The title compound was prepared in 10% yield from indan-2-ol and 2-chloropyridino[3,4-d]pyrimidin-4-ol according to the procedure for the preparation of Example 184. ¹H NMR (300 MHz, DMSO-d₆): δ ppm 3.11-3.18 (m, 2H), 3.40-3.48 (m, 2H), 5.90-5.91 (m, 1H), 7.18-7.20 (m, 2H), 7.28-7.31 (m, 2H), 7.82-7.84 (m, 1H), 8.50 (d, J=5.1 Hz, 1H), 8.88 (s, 1H), 12.50 (s, 1H). [M+H] Calc'd for $C_{16}H_{13}N_3O_2$, 280; Found, 280.

Example 190: 2-(2,3-dihydro-1H-inden-1-ylmethoxy)pyrido[3,4-d]pyrimidin-4-ol

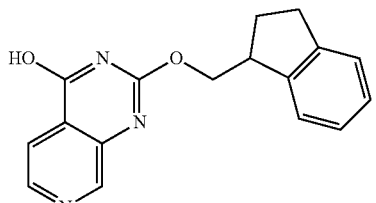

The title compound was prepared in 6% yield from indanylmethan-1-ol and 2-chloropyridino[3,4-d]pyrimidin-4-ol according to the procedure for the preparation of Example 187. ¹H NMR (400 MHz, DMSO-d₆): δ ppm 1.88-1.96 (m, 1H), 2.21-2.32 (m, 1H), 2.48-3.06 (m, 2H), 3.59-3.66 (m, 1H), 4.55 (d, J=9.2 Hz, 2H), 7.14-7.45 (m, 4H), 7.84 (d, J=6.4 Hz, 1H), 8.49 (d, J=6.8 Hz, 1H), 8.85 (s, 1H), 12.69 (s, 1H). [M+H] Calc'd for $C_{17}H_{15}N_3O_2$, 294; Found, 294.

Example 191: 2-(1,2,3,4-tetrahydronaphthalen-2-ylmethoxy)pyrido[3,4-d]pyrimidin-4-ol

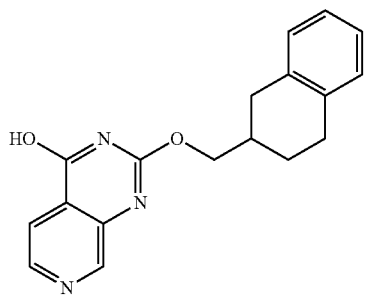 [SMILES: Oc1nc(OCC2CCc3ccccc3C2)nc2cnccc12]

The title compound was prepared in 8% yield from (1,2,3,4-Tetrahydro-naphthalen-2-yl)-methanol and 2-chloropyridino[3,4-d]pyrimidin-4-ol according to the procedure for the preparation of Example 184. ¹H NMR (300 MHz, DMSO-d₆): δ ppm 1.51-1.55 (m, 1H), 2.00-2.02 (m, 1H), 2.26-2.28 (m, 1H), 2.55-2.60 (m, 1H), 2.79-2.95 (m, 3H), 4.41 (d, J=6.9 Hz, 2H), 7.09 (s, 4H), 7.84 (d, J=5.1 Hz, 1H), 8.49 (d, J=5.1 Hz, 1H), 8.84 (s, 1H), 12.66 (s, 1H). [M+H] Calc'd for $C_{18}H_{17}N_3O_2$, 308; Found, 308.

Example 192: 2-(2,3-dihydro-1H-inden-1-yloxy)pyrido[3,4-d]pyrimidin-4-ol

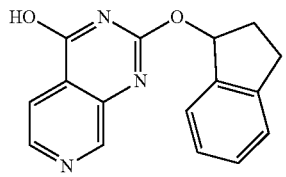 [SMILES: Oc1nc(OC2CCc3ccccc32)nc2cnccc12]

The title compound was prepared in 1% yield from indan-1-ol and 2-chloropyridino[3,4-d]pyrimidin-4-ol according to the procedure for the preparation of Example 197. ¹H NMR (300 MHz, TFA-d): δ ppm 2.35-2.38 (m, 1H), 2.80-2.85 (m, 1H), 3.17-3.31 (m, 2H), 6.97-7.00 (m, 2H), 7.16 (t, J=7.5 Hz, 1H), 7.33-7.43 (m, 2H), 8.32-8.37 (m, 1H), 8.63 (d, J=6.0 Hz, 1H), 8.74 (d, J=6.0 Hz, 1H). [M+H] Calc'd for $C_{16}H_{13}N_3O_2$, 280; Found, 280.

Example 193: 2-(1-benzofuran-3-ylmethoxy)pyrido[3,4-d]pyrimidin-4-ol

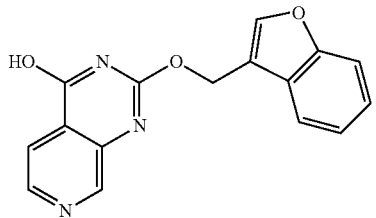 [SMILES: Oc1nc(OCc2coc3ccccc23)nc2cnccc12]

The title compound was prepared in 7% yield from benzofuran-3-yl-methanol and 2-chloropyridino[3,4-d]pyrimidin-4-ol according to the procedure for the preparation of Example 184. $^1$H NMR (300 MHz, DMSO-d$_6$): δ ppm 5.68 (s, 2H), 7.31-7.38 (m, 2H), 7.61-7.64 (m, 1H), 7.81-7.87 (m, 2H), 8.23 (s, 1H), 8.52 (d, J=5.4 Hz, 1H), 8.95 (s, 1H), 12.69 (s, 1H). [M+H] Calc'd for $C_{16}H_{11}N_3O_3$, 294; Found, 294.

Example 194: 2-(2,3-dihydro-1-benzofuran-3-yl-methoxy)pyrido[3,4-d]pyrimidin-4-ol

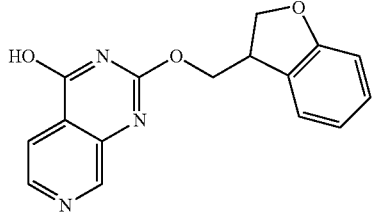 [SMILES: Oc1nc(OCC2COc3ccccc32)nc2cnccc12]

The title compound was prepared in 4% yield from (2,3-dihydro-benzofuran-3-yl)-methanol and 2-chloropyridino[3,4-d]pyrimidin-4-ol according to the procedure for the preparation of Example 184. $^1$H NMR (300 MHz, DMSO-d$_6$): δ ppm 3.85-3.88 (m, 1H), 4.09-4.12 (m, 2H), 4.43-4.49 (m, 2H), 6.79-6.86 (m, 2H), 7.12-7.22 (m, 2H), 7.81 (d, J=4.8 Hz, 1H), 8.43 (d, J=5.4 Hz, 1H), 8.61 (s, 1H), 11.77 (s, 1H). [M+H] Calc'd for $C_{16}H_{13}N_3O_3$, 296; Found, 296.

Example 195: 2-(3,4-dihydro-2H-1-benzopyran-4-ylmethoxy)pyrido[3,4-d]pyrimidin-4-ol

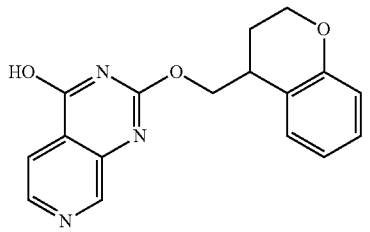 [SMILES: Oc1nc(OCC2CCOc3ccccc32)nc2cnccc12]

The title compound was prepared in 11% yield from chroman-4-yl-methanol and 2-chloropyridino[3,4-d]pyrimidin-4-ol according to the procedure for the preparation of Example 184. $^1$H NMR (300 MHz, DMSO-d$_6$): δ ppm 2.02-2.07 (m, 2H), 3.35 (s, 1H), 4.19-4.23 (m, 2H), 4.54-4.72 (m, 2H), 6.77-6.91 (m, 2H), 7.11-7.13 (m, 1H), 7.38 (d, J=7.5 Hz, 1H), 7.84 (d, J=5.1 Hz, 1H), 8.50 (d, J=5.1 Hz, 1H), 8.86 (s, 1H), 12.73 (s, 1H). [M+H] Calc'd for $C_{17}H_{15}N_3O_3$, 310; Found, 310.

Example 196: 2-(1,2,3,4-tetrahydronaphthalen-1-yloxy)pyrido[3,4-d]pyrimidin-4-ol

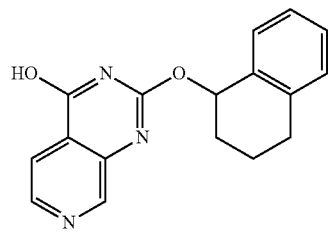

The title compound was prepared in 11% yield from 1,2,3,4-tetrahydronaphthol and 2-chloropyridino[3,4-d]pyrimidin-4-ol according to the procedure for the preparation of Example 184. $^1$H NMR (400 MHz, DMSO-d$_6$): δ ppm 1.79-2.22 (m, 4H), 2.72-2.89 (m, 2H), 6.39 (t, J=5.6 Hz, 1H), 7.17-7.43 (m, 4H), 7.85 (d, J=6.8 Hz, 1H), 8.50 (d, J=6.8 Hz, 1H), 8.90 (s, 1H), 12.54 (s, 1H). [M+H] Calc'd for $C_{17}H_{15}N_3O_2$, 294; Found, 294.

Example 197: 2-(3,4-dihydro-2H-1-benzopyran-4-yloxy)pyrido[3,4-d]pyrimidin-4-ol

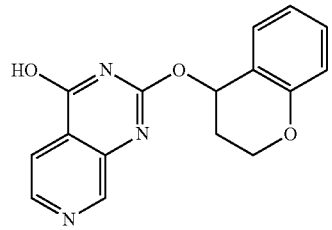

To a solution of 2-chloropyridino[3,4-d]pyrimidin-4-ol (200 mg, 1.10 mmol) and 18-crown-6 (22 mg, 0.082 mmol) in DMSO (5 mL) was added a solution of chroman-4-ol (249 mg, 1.66 mmol) and t-BuOK (186 mg, 1.66 mmol) in DMSO (5 mL) at RT and the mixture was stirred at 130° C. under N$_2$ overnight. The solvent was removed and the residue was purified by FC (20:1, DCM:MeOH) to give 21 mg (6%) of the title compound. $^1$H NMR (300 MHz, DMSO-d$_6$): δ ppm 2.31-2.35 (m, 2H), 4.15-4.19 (m, 1H), 4.33-4.34 (m, 1H), 6.32 (s, 1H), 6.86-6.95 (m, 2H), 7.25-7.28 (m, 1H), 7.46 (d, J=7.8 Hz, 1H), 7.86 (d, J=5.4 Hz, 1H), 8.51-8.53 (m, 1H), 8.92 (s, 1H), 12.59 (s, 1H). [M+H] Calc'd for $C_{16}H_{13}N_3O_3$, 296; Found, 296.

Preparation 198A: 8-chloro-3H-pyrido[3,4-d]pyrimidin-4-one

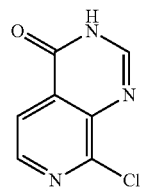

A mixture of 3-amino-2-chloropyridine-4-carboxamide (500 mg, 2.9 mmol) in 5 mL of triethyl orthoformate was stirred at reflux for 18 h. The reaction mixture was concentrated and triturated with hexanes. Solid filtered and dried to give the title compound as a tan solid (510 mg, 97%). $^1$H NMR (400 MHz, DMSO-d$_6$): δ 7.96 (1H, d, J=5.1 Hz), 8.30 (1H, s), 8.44 (1H, d, J=5.2 Hz), 12.85 (1H, br s). [M+H] Calc'd for C$_7$H$_4$ClN$_3$O, 182; Found, 182.

Example 198: 8-(1-methylimidazol-4-yl)-3H-pyrido[3,4-d]pyrimidin-4-one

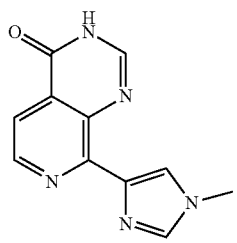 [SMILES: Cn1cnc(-c2nccc3c(=O)[nH]cnc23)c1]

A mixture of 8-chloro-3H-pyrido[3,4-d]pyrimidin-4-one (50 mg, 0.27 mmol), tributyl-(1-methylimidazol-4-yl)stannane (224 mg, 0.027 mmol) and [1,1'-bis(di-tert-butylphosphino)ferrocene]dichloropalladium (18 mg, 0.027 mmol) in DMF (1 mL) was stirred in a sealed vial at 150° C. for 2 h. The reaction mixture was filtered and purified by preparative HPLC. The relevant fractions were concentrated to a yellow oil. The oil was taken in ethanol and HCl (1N) in ethanol was added. The resulting precipitate was filtered and dried to give 12 mg (20%) of the title compound as a white solid (hydrochloride salt). $^1$H NMR (400 MHz, DMSO-d$_6$): δ 3.98 (s, 3H), 8.06 (d, J=5.05 Hz, 1H), 8.36 (s, 1H), 8.68 (s, 1H), 8.76 (d, J=5.05 Hz, 1H), 9.28 (s, 1H), 12.99 (br. s., 1H). [M+H] Calc'd for C$_{11}$H$_9$N$_5$O, 228; Found, 228.

II. Biological Evaluation

Example 1: In Vitro Enzyme Inhibition Assay

This assay determines the ability of a test compound to inhibit Jarid1A, Jarid1B, and JMJD2C demethylase activity. Baculovirus expressed Jarid1A (GenBank Accession #NM_001042603, AA1-1090) was purchased from BPS Bioscience (Cat#50110). Baculovirus expressed Jarid1B (GenBank Accession #NM_006618, AA 2-751) was purchased from BPS Bioscience (Cat #50121) or custom made by MolecularThrouhput. Baculovirus expressed JMJD2C (GenBank Accession #BC143571, AA 2-372) was purchased from BPS Bioscience (Cat#50105).

Jarid1A Assay

The enzymatic assay of Jarid1A activity is based upon Time Resolved-Fluorescence Resonance Energy Transfer (TR-FRET) detection. The ability of test compounds to inhibit the activity of Jarid1A was determined in 384-well plate format under the following reaction conditions: 1 nM Jarid1A, 300 nM H3K4me3-biotin labeled peptide (Anaspec cat #64357), 2 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, and 2 μM ammonium iron(II) sulfate. Reaction product was determined quantitatively by TR-FRET after the addition of detection reagent Phycolink Streptavidin-allophycocyanin (Prozyme) and Europium-anti-mono-or di-methylated histone H3 lysine 4 (H3K4me1-2) antibody (PerkinElmer) in the presence of 5 mM EDTA in LANCE detection buffer (PerkinElmer) at a final concentration of 25 nM and 1 nM, respectively.

The assay reaction was initiated by the following: 2 μl of the mixture of 900 nM H3K4me3-biotin labeled peptide and 6 μM alpha-ketoglutaric acid with 2 μl of 11-point serial diluted inhibitor in 3% DMSO was added to each well of plate, followed by the addition of 2 μl of 3 nM Jarid1A to initiate the reaction. The reaction mixture was incubated at room temperature for 30 minutes, and terminated by the addition of 6 μl of 5 mM EDTA in LANCE detection buffer containing 50 nM Phycolink Streptavidin-allophycocyanin and 2 nM Europium-anti-H3K4me1-2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant (IC$_{50}$).

Jarid1B Assay

The ability of test compounds to inhibit the activity of Jarid1B was determined in 384-well plate format under the following reaction conditions: 0.8 nM Jarid1B, 300 nM H3K4me3-biotin labeled peptide (Anaspec cat #64357), 2 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, and 2 μM ammonium iron(II) sulfate. Reaction product was determined quantitatively by TR-FRET after the addition of detection reagent Phycolink Streptavidin-allophycocyanin (Prozyme) and Europium-anti-mono-or di-methylated histone H3 lysine 4 (H3K4me1-2) antibody (PerkinElmer) in the presence of 5 mM EDTA in LANCE detection buffer (PerkinElmer) at a final concentration of 25 nM and 1 nM, respectively.

The assay reaction was initiated by the following: 2 μl of the mixture of 900 nM H3K4me3-biotin labeled peptide and 6 μM alpha-ketoglutaric acid with 2 μl of 11-point serial diluted inhibitor in 3% DMSO was added to each well of the plate, followed by the addition of 2 μl of 2.4 nM Jarid1B to initiate the reaction. The reaction mixture was incubated at room temperature for 30 minutes, and terminated by the addition of 6 μl of 5 mM EDTA in LANCE detection buffer containing 50 nM Phycolink Streptavidin-allophycocyanin and 2 nM Europium-anti-H3K4me1-2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant (IC$_{50}$).

JMJD2C Assay

The ability of test compounds to inhibit the activity of JMJD2C was determined in 384-well plate format under the following reaction conditions: 0.3 nM JMJD2C, 300 nM H3K9me3-biotin labeled peptide (Anaspec cat #64360), 2 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, and 2 μM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 μl of the mixture of 900 nM H3K9me3-biotin labeled peptide and 6 μM alpha-ketoglutaric acid with 2 μl of 11-point serial diluted inhibitor in 3% DMSO were added to each well of the plate, followed by the addition of 2 µl of 0.9 nM JMJD2C to initiate the reaction. The reaction mixture was incubated at room temperature for 30 minutes, and terminated by the addition of 6 µl of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hour incubation at room temperature. A ratio was calculated (665/615) for each well and fitted to determine inhibition constant ($IC_{50}$).

The ability of the compounds disclosed herein to inhibit demethylase activity was quantified and the respective $IC_{50}$ value was determined. Table 3 provides the $IC_{50}$ values of various compounds disclosed herein.

TABLE 3

| Chemical Synthesis Example | Name | JARID1A $IC_{50}$ (µM) | JARID1B $IC_{50}$ (µM) | JMJD2C $IC_{50}$ (µM) |
|---|---|---|---|---|
| 1 | 2-propan-2-yloxy-3H-pyrido[3,4-d]pyrimidin-4-one | B | B | B |
| 2 | 2-ethoxypyrido[3,4-d]pyrimidin-4-ol | A | A | B |
| 3 | 2-(2-hydroxyethoxy)pyrido[3,4-d]pyrimidin-4-ol | A | B | B |
| 4 | 2-phenylmethoxypyrido[3,4-d]pyrimidin-4-ol | B | B | B |
| 5 | 2-(cyclopropylmethoxy)-3H-pyrido[3,4-d]pyrimidin-4-one | A | B | B |
| 6 | 2-cyclopentyloxy-3H-pyrido[3,4-d]pyrimidin-4-one | B | B | B |
| 7 | 2-propoxy-3H-pyrido[3,4-d]pyrimidin-4-one | A | B | B |
| 8 | 2-methoxypyrido[3,4-d]pyrimidin-4-ol | A | B | B |
| 9 | 2-butan-2-yloxy-3H-pyrido[3,4-d]pyrimidin-4-one | C | C | A |
| 10 | 2-(2-phenoxyethoxy)-3H-pyrido[3,4-d]pyrimidin-4-one | A | B | B |
| 11 | 2-(cyclobutylmethoxy)-3H-pyrido[3,4-d]pyrimidin-4-one | B | B | B |
| 12 | 2-(2,2,2-trifluoroethoxy)pyrido[3,4-d]pyrimidin-4-ol | A | B | B |
| 13 | 2-(3,3,3-trifluoropropoxy)pyrido[3,4-d]pyrimidin-4-ol | A | B | B |
| 14 | 2-(2-methylpropoxy)pyrido[3,4-d]pyrimidin-4-ol | B | B | B |
| 15 | 2-(3-methylbutoxy)pyrido[3,4-d]pyrimidin-4-ol | A | A | B |
| 16 | 2-(2-methylbutoxy)pyrido[3,4-d]pyrimidin-4-ol | B | B | B |
| 17 | 2-(2-phenylpropoxy)pyrido[3,4-d]pyrimidin-4-ol | B | B | B |
| 18 | 2-(2-phenylethoxy)pyrido[3,4-d]pyrimidin-4-ol | A | A | B |
| 19 | 2-(1-phenylpropan-2-yloxy)pyrido[3,4-d]pyrimidin-4-ol | C | C | C |
| 20 | 2-(4,4,4-trifluorobutoxy)pyrido[3,4-d]pyrimidin-4-ol | A | A | B |
| 21 | 2-[3-(dimethylamino)propoxy]pyrido[3,4-d]pyrimidin-4-ol | B | C | B |
| 22 | 2-(2-methoxyethoxy)pyrido[3,4-d]pyrimidin-4-ol | B | B | B |
| 23 | 2-[2-(2,2,2-trifluoroethoxy)ethoxy]pyrido[3,4-d]pyrimidin-4-ol | B | B | B |
| 24 | 2-(3-hydroxy-3-methylbutoxy)pyrido[3,4-d]pyrimidin-4-ol | A | A | B |
| 25 | 2-(3-hydroxy-2-methylpropoxy)pyrido[3,4-d]pyrimidin-4-ol | B | B | B |
| 26 | 2-(oxolan-2-ylmethoxy)pyrido[3,4-d]pyrimidin-4-ol | B | C | B |
| 27 | 2-(oxolan-3-ylmethoxy)pyrido[3,4-d]pyrimidin-4-ol | B | B | B |
| 28 | N-[2-(4-hydroxypyrido[3,4-d]pyrimidin-2-yl)oxyethyl]-N-methylacetamide | B | B | B |
| 29 | 2-(2-propan-2-yloxyethoxy)pyrido[3,4-d]pyrimidin-4-ol | B | B | B |
| 30 | 2-(2-phenylmethoxyethoxy)pyrido[3,4-d]pyrimidin-4-ol | B | B | B |
| 31 | N-[2-(4-hydroxypyrido[3,4-d]pyrimidin-2-yl)oxyethyl]benzamide | A | A | B |
| 32 | 3-[(4-hydroxypyrido[3,4-d]pyrimidin-2-yl)oxymethyl]benzonitrile | B | B | B |
| 33 | 2-[(1-methylpyrazol-3-yl)methoxy]pyrido[3,4-d]pyrimidin-4-ol | C | C | A |
| 34 | 2-phenoxypyrido[3,4-d]pyrimidin-4-ol | A | A | B |
| 35 | N-[4-(4-hydroxypyrido[3,4-d]pyrimidin-2-yl)oxyphenyl]acetamide | A | A | B |
| 36 | tert-butyl N-[3-(4-hydroxypyrido[3,4-d]pyrimidin-2-yl)oxyphenyl]carbamate | A | A | B |
| 37 | 2-(3,4-difluorophenoxy)pyrido[3,4-d]pyrimidin-4-ol | A | A | A |
| 38 | 2-(3,4-dimethoxyphenoxy)pyrido[3,4-d]pyrimidin-4-ol | A | A | B |
| 39 | 2-(3-propan-2-ylphenoxy)pyrido[3,4-d]pyrimidin-4-ol | A | A | B |
| 40 | 2-(3-fluorophenoxy)pyrido[3,4-d]pyrimidin-4-ol | A | A | A |
| 41 | 2-(3-chlorophenoxy)pyrido[3,4-d]pyrimidin-4-ol | A | A | B |
| 42 | 2-(2,3-difluorophenoxy)pyrido[3,4-d]pyrimidin-4-ol | A | B | B |
| 43 | 2-(3,5-difluoro-4-methoxyphenoxy)pyrido[3,4-d]pyrimidin-4-ol | A | A | B |
| 44 | 2-(3-methoxyphenoxy)pyrido[3,4-d]pyrimidin-4-ol | A | A | B |
| 45 | 2-(4-ethoxy-3,5-difluorophenoxy)pyrido[3,4-d]pyrimidin-4-ol | A | A | B |

TABLE 3-continued

| Chemical Synthesis Example | Name | JARID1A IC$_{50}$ (μM) | JARID1B IC$_{50}$ (μM) | JMJD2C IC$_{50}$ (μM) |
|---|---|---|---|---|
| 46 | 2-(2-fluorophenoxy)pyrido[3,4-d]pyrimidin-4-ol | A | B | B |
| 47 | 2-(4-fluorophenoxy)pyrido[3,4-d]pyrimidin-4-ol | A | A | B |
| 48 | 2-(4-methoxyphenoxy)pyrido[3,4-d]pyrimidin-4-ol | A | A | A |
| 49 | 2-(4-chlorophenoxy)pyrido[3,4-d]pyrimidin-4-ol | A | A | A |
| 50 | 2-[3-(dimethylamino)phenoxy]-pyrido[3,4-d]pyrimidin-4-ol | A | A | B |
| 51 | 2-(1-methylindazol-5-yl)oxypyrido[3,4-d]pyrimidin-4-ol | A | A | A |
| 52 | 2-[3-(trifluoromethyl)phenoxy]-pyrido[3,4-d]pyrimidin-4-ol | A | A | B |
| 53 | 2-(3-fluoro-4-methoxyphenoxy)pyrido[3,4-d]pyrimidin-4-ol | A | A | B |
| 54 | 2-(1-propylpyrazol-4-yl)oxypyrido[3,4-d]pyrimidin-4-ol | A | A | B |
| 55 | 2-[1-(3-methylbutyl)pyrazol-4-yl]oxypyrido[3,4-d]pyrimidin-4-ol | A | A | A |
| 56 | 2-(1-cyclopentylpyrazol-4-yl)oxypyrido[3,4-d]pyrimidin-4-ol | A | A | A |
| 57 | 2-(3-ethylphenoxy)pyrido[3,4-d]pyrimidin-4-ol | A | A | A |
| 58 | 2-(3-propylphenoxy)pyrido[3,4-d]pyrimidin-4-ol | A | A | B |
| 59 | 2-[4-(dimethylamino)phenoxy]pyrido[3,4-d]pyrimidin-4-ol | A | A | B |
| 60 | 3-fluoro-5-(4-hydroxypyrido[3,4-d]pyrimidin-2-yl)oxyphenyl]-morpholin-4-ylmethanone | A | A | B |
| 61 | 2-{[1-(2-methoxyethyl)-1H-indazol-6-yl]oxy}pyrido[3,4-d]pyrimidin-4-ol | A | A | B |
| 62 | 2-[(1-ethyl-1H-pyrazol-4-yl)oxy]pyrido[3,4-d]pyrimidin-4-ol | A | A | A |
| 63 | 2-{[1-(propan-2-yl)-1H-pyrazol-4-yl]oxy}pyrido[3,4-d]pyrimidin-4-ol | A | A | B |
| 64 | 2-{[1-(2-methoxyethyl)-1H-pyrazol-4-yl]oxy}pyrido[3,4-d]pyrimidin-4-ol | A | A | B |
| 65 | 2-{[1-(3-methoxypropyl)-1H-pyrazol-4-yl]oxy}pyrido[3,4-d]pyrimidin-4-ol | A | A | B |
| 66 | 2-[(1-benzyl-1H-pyrazol-4-yl)oxy]pyrido[3,4-d]pyrimidin-4-ol | A | A | A |
| 67 | 2-{[1-(tetrahydro-2H-pyran-4-yl)-1H-pyrazol-4-yl]oxy}pyrido[3,4-d]pyrimidin-4-ol | A | A | B |
| 68 | 2-methoxy-8-(1-methyl-1H-imidazol-4-yl)pyrido[3,4-d]pyrimidin-4-ol | A | A | B |
| 69 | 2-ethoxy-8-(1-methyl-1H-imidazol-4-yl)pyrido[3,4-d]pyrimidin-4-ol | A | A | B |
| 70 | 8-(1-methyl-1H-imidazol-4-yl)-2-(2,2,2-trifluoroethoxy)pyrido[3,4-d]pyrimidin-4-ol | A | A | B |
| 71 | 2-[(4-fluorobenzyl)oxy]-8-(1-methyl-1H-imidazol-4-yl)pyrido[3,4-d]pyrimidin-4-ol | A | A | B |
| 72 | 2-(cyclopropylmethoxy)-8-(1-methylimidazol-4-yl)pyrido[3,4-d]pyrimidin-4-ol | A | A | B |
| 72 | 2-(3-hydroxy-3-methylbutoxy)-8-(1-methylimidazol-4-yl)pyrido[3,4-d]pyrimidin-4-ol | A | A | B |
| 74 | 8-(1-methylimidazol-4-yl)-2-(4,4,4-trifluorobutoxy)pyrido[3,4-d]pyrimidin-4-ol | A | A | B |
| 75 | 2-(2-hydroxyethoxy)-8-(1-methylimidazol-4-yl)pyrido[3,4-d]pyrimidin-4-ol | A | A | B |
| 76 | 2-[2-(dimethylamino)ethoxy]-8-(1-methylimidazol-4-yl)pyrido[3,4-d]pyrimidin-4-ol | B | B | B |
| 77 | 2-(2,2-difluoroethoxy)-8-(1-methylimidazol-4-yl)pyrido[3,4-d]pyrimidin-4-ol | A | A | B |
| 78 | 2-(2-cyclopropylethoxy)-8-(1-methylimidazol-4-yl)pyrido[3,4-d]pyrimidin-4-ol | A | A | B |
| 79 | 2-(1-benzylpyrazol-4-yl)oxy-8-(1-methylimidazol-4-yl)pyrido[3,4-d]pyrimidin-4-ol | A | A | B |
| 80 | 2-[1-(3-methylbutyl)pyrazol-4-yl]oxy-8-(1-methylimidazol-4-yl)pyrido[3,4-d]pyrimidin-4-ol | A | A | B |
| 81 | 2-(3,4-difluorophenoxy)-8-(1-methylimidazol-4-yl)pyrido[3,4-d]pyrimidin-4-ol | A | A | B |
| 82 | 2-[4-(2-methoxyethoxy)phenoxy]-8-(1-methylimidazol-4-yl)pyrido[3,4-d]pyrimidin-4-ol | A | A | B |
| 83 | 8-(1-methylimidazol-4-yl)-2-(1-methylindazol-6-yl)oxypyrido[3,4-d]pyrimidin-4-ol | A | A | B |
| 84 | 2-(1-ethylindazol-6-yl)oxy-8-(1-methylimidazol-4-yl)pyrido[3,4-d]pyrimidin-4-ol | A | A | B |
| 85 | 2-(1,3-dimethylindazol-6-yl)oxy-8-(1-methylimidazol-4-yl)pyrido[3,4-d]pyrimidin-4-ol | A | A | B |
| 86 | 2-[1-[(4-fluorophenyl)methyl]pyrazol-4-yl]oxypyrido[3,4-d]pyrimidin-4-ol | A | A | A |
| 87 | 2-[1-[(2-fluorophenyl)methyl]pyrazol-4-yl]oxypyrido[3,4-d]pyrimidin-4-ol | A | A | A |
| 88 | tert-butyl 4-[4-(4-hydroxypyrido[3,4-d]pyrimidin-2-yl)oxypyrazol-1-yl]piperidine-1-carboxylate | A | A | B |
| 89 | 2-(1-piperidin-4-ylpyrazol-4-yl)oxypyrido[3,4-d]pyrimidin-4-ol | A | A | A |

TABLE 3-continued

| Chemical Synthesis Example | Name | JARID1A IC$_{50}$ (μM) | JARID1B IC$_{50}$ (μM) | JMJD2C IC$_{50}$ (μM) |
|---|---|---|---|---|
| 90 | 1-[4-[4-(4-hydroxypyrido[3,4-d]pyrimidin-2-yl)oxypyrazol-1-yl]piperidin-1-yl]ethanone | A | A | A |
| 91 | 1-[4-[4-(4-hydroxypyrido[3,4-d]pyrimidin-2-yl)oxypyrazol-1-yl]piperidin-1-yl]prop-2-en-1-one | A | A | B |
| 92 | cyclopropyl-[4-[4-(4-hydroxypyrido[3,4-d]pyrimidin-2-yl)oxypyrazol-1-yl]piperidin-1-yl]methanone | A | A | A |
| 93 | (4-fluorophenyl)-[4-[4-(4-hydroxypyrido[3,4-d]pyrimidin-2-yl)oxypyrazol-1-yl]piperidin-1-yl]methanone | A | A | A |
| 94 | 2-[1-(1-cyclopropylsulfonylpiperidin-4-yl)pyrazol-4-yl]oxypyrido[3,4-d]pyrimidin-4-ol | A | A | A |
| 95 | 2-[1-[1-(benzenesulfonyl)piperidin-4-yl]pyrazol-4-yl]oxypyrido[3,4-d]pyrimidin-4-ol | A | A | A |
| 96 | 2-(2-piperazin-1-ylpyridin-4-yl)oxypyrido[3,4-d]pyrimidin-4-ol | A | A | B |
| 97 | 2-(2-morpholin-4-ylpyridin-4-yl)oxypyrido[3,4-d]pyrimidin-4-ol | A | A | B |
| 98 | 2-(2-hydroxy-2-methylpropoxy)-8-(1-methylimidazol-4-yl)pyrido[3,4-d]pyrimidin-4-ol | B | B | C |
| 99 | 1-(1-phenylethyl)-4-(4,4,5,5-tetramethyl-1,3,2-dioxaborolan-2-yl)pyrazole | A | A | B |
| 100 | 8-(1-methylimidazol-4-yl)-2-[1-(oxan-4-yl)pyrazol-4-yl]oxypyrido[3,4-d]pyrimidin-4-ol | A | A | B |
| 101 | 8-(1-methylimidazol-4-yl)-2-phenylmethoxypyrido[3,4-d]pyrimidin-4-ol | A | A | B |
| 102 | 8-(1-methyl-1H-imidazol-4-yl)-2-(oxan-4-ylmethoxy)pyrido[3,4-d]pyrimidin-4-ol | B | B | A |
| 103 | 8-(1-methyl-1H-imidazol-4-yl)-2-(oxolan-3-ylmethoxy)pyrido[3,4-d]pyrimidin-4-ol | B | A | A |
| 104 | 2-[(3-fluorophenyl)methoxy]-8-(1-methyl-1H-imidazol-4-yl)pyrido[3,4-d]pyrimidin-4-ol | B | A | A |
| 105 | 2-[(2-chlorophenyl)methoxy]-8-(1-methyl-1H-imidazol-4-yl)pyrido[3,4-d]pyrimidin-4-ol | C | A | A |
| 106 | 2-[(2,3-dichlorophenyl)methoxy]-8-(1-methyl-1H-imidazol-4-yl)pyrido[3,4-d]pyrimidin-4-ol | C | A | B |
| 107 | 8-(1-methyl-1H-imidazol-4-yl)-2-{[2-(trifluoromethyl)phenyl]methoxy}pyrido[3,4-d]pyrimidin-4-ol | B | A | B |
| 108 | 8-(1-methyl-1H-imidazol-4-yl)-2-[(1R)-2,2,2-trifluoro-1-phenylethoxy]pyrido[3,4-d]pyrimidin-4-ol | C | C | B |
| 109 | 8-(1-methyl-1H-imidazol-4-yl)-2-[(1S)-2,2,2-trifluoro-1-phenylethoxy]pyrido[3,4-d]pyrimidin-4-ol | C | C | B |
| 110 | 8-(1-methyl-1H-imidazol-4-yl)-2-[(1,1,1-trifluorobutan-2-yl)oxy]pyrido[3,4-d]pyrimidin-4-ol | B | B | C |
| 111 | 8-(1-methyl-1H-imidazol-4-yl)-2-{[4-(trifluoromethyl)phenyl]methoxy}pyrido[3,4-d]pyrimidin-4-ol | A | B | B |
| 112 | 2-[(4-chlorophenyl)methoxy]-8-(1-methyl-1H-imidazol-4-yl)pyrido[3,4-d]pyrimidin-4-ol | B | A | B |
| 113 | 2-(3,4-dichlorophenoxy)-8-(1-methyl-1H-imidazol-4-yl)pyrido[3,4-d]pyrimidin-4-ol | A | A | A |
| 114 | 2-(3,4-dichlorophenoxy)pyrido[3,4-d]pyrimidin-4-ol | B | A | A |
| 115 | 2-{[1-(1-phenylpropyl)-1H-pyrazol-4-yl]oxy}pyrido[3,4-d]pyrimidin-4-ol | A | A | A |
| 116 | 2-({1-[cyclopropyl(phenyl)methyl]-1H-pyrazol-4-yl}oxy)pyrido[3,4-d]pyrimidin-4-ol | A | A | A |
| 117 | 2-({1-[(1R)-1-phenylethyl]-1H-pyrazol-4-yl}oxy)pyrido[3,4-d]pyrimidin-4-ol | A | A | A |
| 118 | 2-({1-[(1S)-1-phenylethyl]-1H-pyrazol-4-yl}oxy pyrido)[3,4-d]pyrimidin-4-ol | A | A | A |
| 119 | 2-({1-[(1R)-1-(2-fluorophenyl)ethyl]-1H-pyrazol-4-yl}oxy)pyrido[3,4-d]pyrimidin-4-ol | A | A | A |
| 120 | 2-({1-[(1s)-1-(2-fluorophenyl)ethyl]-1H-pyrazol-4-yl}oxy)pyrido[3,4-d]pyrimidin-4-ol | A | A | A |
| 121 | 2-({1-[(2-chlorophenyl)methyl]-1H-pyrazol-4-yl}oxy)pyrido[3,4-d]pyrimidin-4-ol | A | A | A |
| 122 | 2-({1-[(3-chlorophenyl)methyl]-1H-pyrazol-4-yl}oxy)pyrido[3,4-d]pyrimidin-4-ol | A | A | A |
| 123 | 2-{[1-(1-benzylpiperidin-4-yl)-1H-pyrazol-4-yl]oxy}pyrido[3,4-d]pyrimidin-4-ol | A | A | A |
| 124 | 2-({1-[2-(morpholin-4-yl)ethyl]-1H-pyrazol-4-yl}oxy)pyrido[3,4-d]pyrimidin-4-ol | A | A | A |
| 125 | 2-({1-[(3R)-pyrrolidin-3-yl]-1H-pyrazol-4-yl}oxy)pyrido[3,4-d]pyrimidin-4-ol | A | A | A |
| 126 | 2-({1-[(3R)-1-(ethanesulfonyl)pyrrolidin-3-yl]-1H-pyrazol-4-yl}oxy)pyrido[3,4-d]pyrimidin-4-ol | A | A | A |
| 127 | 2-({1-[(3R)-1-(cyclopropanesulfonyl)pyrrolidin-3-yl]-1H-pyrazol-4-yl}oxy)pyrido[3,4-d]pyrimidin-4-ol | A | A | A |

TABLE 3-continued

| Chemical Synthesis Example | Name | JARID1A IC$_{50}$ (μM) | JARID1B IC$_{50}$ (μM) | JMJD2C IC$_{50}$ (μM) |
|---|---|---|---|---|
| 128 | 2-({1-[(3R)-1-(benzenesulfonyl)pyrrolidin-3-yl]-1H-pyrazol-4-yl}oxy)pyrido[3,4-d]pyrimidin-4-ol | A | A | A |
| 129 | 1-[(3R)-3-[4-({4-hydroxypyrido[3,4-d]pyrimidin-2-yl}oxy)-1H-pyrazol-1-yl]pyrrolidin-1-yl]ethan-1-one | A | A | A |
| 130 | 3-[(3R)-3-[4-({4-hydroxypyrido[3,4-d]pyrimidin-2-yl}oxy)-1H-pyrazol-1-yl]pyrrolidin-1-yl]-3-oxopropanenitrile | A | A | A |
| 131 | 2-({1-[(3R)-1-cyclopropanecarbonylpyrrolidin-3-yl]1H-pyrazol-4-yl}oxy)pyrido[3,4-d]pyrimidin-4-ol | A | A | A |
| 132 | 2-({1-[(3R)-1-benzoylpyrrolidin-3-yl]-1H-pyrazol-4-yl}oxy)pyrido[3,4-d]pyrimidin-4-ol | A | A | A |
| 133 | 2-({1-[(3R)-1-benzylpyrrolidin-3-yl]-1H-pyrazol-4-yl}oxy)pyrido[3,4-d]pyrimidin-4-ol | A | A | A |
| 134 | 2-({1-[(3R)-1-(4-fluorophenyl)pyrrolidin-3-yl]-1H-pyrazol-4-yl}oxy)pyrido[3,4-d]pyrimidin-4-ol | A | A | A |
| 135 | 2-({1-[(3S)-pyrrolidin-3-yl]-1H-pyrazol-4-yl}oxy)pyrido[3,4-d]pyrimidin-4-ol | B | A | A |
| 136 | 2-({1-[(3S)-1-(ethanesulfonyl)pyrrolidin-3-yl]-1H-pyrazol-4-yl}oxy)pyrido[3,4-d]pyrimidin-4-ol | A | A | A |
| 137 | 2-({1-](3S)-1-(cyclopropanesulfonyl)pyrrolidin-3-yl]-1H-pyrazol-4-yl}oxy)pyrido[3,4-d]pyrimidin-4-ol | A | A | A |
| 138 | 2-({1-](3S)-1-(benzenesulfonyl)pyrrolidin-3-yl]-1H-pyrazol-4-yl}oxy)pyrido[3,4-d]pyrimidin-4-ol | A | A | A |
| 139 | 1-[(3S)-3-[4-({4-hydroxypyrido[3,4-d]pyrimidin-2-yl}oxy)-1H-pyrazol-1-yl]pyrrolidin-1-yl]ethan-1-one | A | A | A |
| 140 | 3-[(3S)-3-[4-({4-hydroxypyrido[3,4-d]pyrimidin-2-yl}oxy)-1H-pyrazol-1-yl]pyrrolidin-1-yl]-3-oxopropanenitrile | A | A | A |
| 141 | 2-({1-[(3S)-1-cyclopropanecarbonylpyrrolidin-3-yl]-1H-pyrazol-4-yl}oxy)pyrido[3,4-d]pyrimidin-4-ol | A | A | A |
| 142 | 2-({1-[(3S)-1-benzoylpyrrolidin-3-yl]-1H-pyrazol-4-yl}oxy)pyrido[3,4-d]pyrimidin-4-ol | A | A | A |
| 143 | 2-({1-[(3S)-1-(piperidine-4-carbonyl)pyrrolidin-3-yl]-1H-pyrazol-4-yl}oxy)pyrido[3,4-d]pyrimidin-4-ol | A | A | A |
| 144 | 1-[(3S)-3-[4-({4-hydroxypyrido[3,4-d]pyrimidin-2-yl}oxy)-1H-pyrazol-1-yl]pyrrolidin-1-yl]-2-(methylamino)ethan-1-one | A | A | A |
| 145 | 2-({1-[(3S)-1-phenylpyrrolidin-3-yl]-1H-pyrazol-4-yl}oxy)pyrido[3,4-d]pyrimidin-4-ol | A | A | A |
| 146 | 2-({1-[(3S)-1-(4-fluorophenyl)pyrrolidin-3-yl]-1H-pyrazol-4-yl}oxy)pyrido[3,4-d]pyrimidin-4-ol | A | A | A |
| 147 | 2-({1-[(3S)-1-(2-fluorophenyl)pyrrolidin-3-yl]-1H-pyrazol-4-yl}oxy)pyrido[3,4-d]pyrimidin-4-ol | A | A | A |
| 148 | 2-({1-[(3S)-1-(4-chlorophenyl)pyrrolidin-3-yl]-1H-pyrazol-4-yl}oxy)pyrido[3,4-d]pyrimidin-4-ol | A | A | A |
| 149 | 2-({1-[(3R)-piperidin-3-yl]-1H-pyrazol-4-yl}oxy)pyrido[3,4-d]pyrimidin-4-ol | A | A | A |
| 150 | 2-({1-[(3R)-1-(ethanesulfonyl)piperidin-3-yl]-1H-pyrazol-4-yl}oxy)pyrido[3,4-d]pyrimidin-4-ol | A | A | A |
| 151 | 2-({1-[(3S)-1-(cyclopropanesulfonyl)piperidin-3-yl]-1H-pyrazol-4-yl}oxy)pyrido[3,4-d]pyrimidin-4-ol | A | A | A |
| 152 | 2-({1-[(3R)-1-(benzenesulfonyl)piperidin-3-yl]-1H-pyrazol-4-yl}oxy)pyrido[3,4-d]pyrimidin-4-ol | A | A | A |
| 153 | 1-[(3R)-3-[4-({4-hydroxypyrido[3,4-d]pyrimidin-2-yl}oxy)-1H-pyrazol-1-yl]piperidin-1-yl]ethan-1-one | A | A | A |
| 154 | 3-[(3R)-3-[4-({4-hydroxypyrido[3,4-d]pyrimidin-2-yl}oxy)-1H-pyrazol-1-yl]piperidin-1-yl]-3-oxopropanenitrile | A | A | A |
| 155 | 2-hydroxy-1-[(3S)-3-[4-({4-hydroxypyrido[3,4-d]pyrimidin-2-yl}oxy)-1H-pyrazol-1-yl]pyrrolidin-1-yl]ethan-1-one | A | A | A |
| 156 | 2-({1-[(3R)-1-cyclopropanecarbonylpiperidin-3-yl]-1H-pyrazol-4-yl}oxy)pyrido[3,4-d]pyrimidin-4-ol | A | A | A |
| 157 | 2-({1-[(3R)-1-benzoylpiperidin-3-yl]-1H-pyrazol-4-yl}oxy)pyrido[3,4-d]pyrimidin-4-ol | A | A | A |
| 158 | 2-({1-[(3R)-1-benzylpiperidin-3-yl}-1H-pyrazol-4-yl}oxy)pyrido[3,4-d]pyrimidin-4-ol | A | A | A |
| 159 | 2-({1-[(3R)-1-(4-fluorophenyl)piperidin-3-yl]-1H-pyrazol-4-yl}oxy)pyrido[3,4-d]pyrimidin-4-ol | A | A | A |

TABLE 3-continued

| Chemical Synthesis Example | Name | JARID1A IC$_{50}$ (μM) | JARID1B IC$_{50}$ (μM) | JMJD2C IC$_{50}$ (μM) |
|---|---|---|---|---|
| 160 | 2-({1-[(3S)-piperidin-3-yl]-1H-pyrazol-4-yl}oxy)pyrido[3,4-d]pyrimidin-4-ol | A | A | A |
| 161 | 2-({1-[(3S)-1-(ethanesulfonyl)piperidin-3-yl]-1H-pyrazol-4-yl}oxy)pyrido[3,4-d]pyrimidin-4-ol | A | A | A |
| 162 | 2-({1-[(3S)-1-(cyclopropanesulfonyl)piperidin-3-yl]-1H-pyrazol-4-yl}oxy)pyrido[3,4-d]pyrimidin-4-ol | A | A | A |
| 163 | 2-({1-[(3S)-1-(benzenesulfonyl)piperidin-3-yl]-1H-pyrazol-4-yl}oxy)pyrido[3,4-d]pyrimidin-4-ol | A | A | A |
| 164 | 1-[(3S)-3-[4-({4-hydroxypyrido[3,4-d]pyrimidin-2-yl}oxy)-1H-pyrazol-1-yl]piperidin-1-yl]ethan-1-one | A | A | A |
| 165 | 2-({1-[(3S)-1-cyclopropanecarbonylpiperidin-3-yl]-1H-pyrazol-4-yl}oxy)pyrido[3,4-d]pyrimidin-4-ol | A | A | A |
| 166 | 3-[(3S)-3-[4-({4-hydroxypyrido[3,4-d]pyrimidin-2-yl}oxy)-1H-pyrazol-1-yl]piperidin-1-yl]-3-oxopropanenitrile | A | A | A |
| 167 | 2-({1-[(3S)-1-benzoylpiperidin-3-yl]-1H-pyrazol-4-yl}oxy)pyrido[3,4-d]pyrimidin-4-ol | A | A | A |
| 168 | 2-({1-[(3S)-1-benzylpiperidin-3-yl]-1H-pyrazol-4-yl}oxy)pyrido[3,4-d]pyrimidin-4-ol | A | A | A |
| 169 | 2-({1-[(3R)-1-(4-fluorophenyl)piperidin-3-yl]-1H-pyrazol-4-yl}oxy)pyrido[3,4-d]pyrimidin-4-ol | A | A | A |
| 170 | 2-{[4-(trifluoromethyl)phenyl]methoxy}pyrido[3,4-d]pyrimidin-4-ol | C | C | C |
| 171 | 2-[(2-chlorophenyl)methoxy]pyrido[3,4-d]pyrimidin-4-ol | C | B | A |
| 172 | 2-[(2,6-dichlorophenyl)methoxy]pyrido[3,4-d]pyrimidin-4-ol | C | C | C |
| 173 | 2-[(2,3-dichlorophenyl)methoxy]pyrido[3,4-d]pyrimidin-4-ol | C | C | A |
| 174 | 2-[2-(4-chlorophenyl)ethoxy]pyrido[3,4-d]pyrimidin-4-ol | A | A | B |
| 175 | 2-[2-(3,4-dichlorophenyl)ethoxy]pyrido[3,4-d]pyrimidin-4-ol | C | C | A |
| 176 | 2-(2,2,2-trifluoro-1-phenylethoxy)pyrido[3,4-d]pyrimidin-4-ol | C | B | A |
| 177 | 2-{[2-(trifluoromethyl)phenyl]methoxy}pyrido[3,4-d]pyrimidin-4-ol | C | C | A |
| 178 | 2-[(2-fluorophenyl)methoxy]pyrido[3,4-d]pyrimidin-4-ol | C | C | A |
| 179 | 2-[(3-fluorophenyl)methoxy]pyrido[3,4-d]pyrimidin-4-ol | C | C | A |
| 180 | 2-[(4-fluorophenyl)methoxy]pyrido[3,4-d]pyrimidin-4-ol | C | C | A |
| 181 | 2-[(2,3-difluorophenyl)methoxy]pyrido[3,4-d]pyrimidin-4-ol | C | C | A |
| 182 | 2-[(2,5-difluorophenyl)methoxy]pyrido[3,4-d]pyrimidin-4-ol | C | C | A |
| 183 | 2-[(2,6-difluorophenyl)methoxy]pyrido[3,4-d]pyrimidin-4-ol | C | C | B |
| 184 | 2-(naphthalen-1-ylmethoxy)pyrido[3,4-d]pyrimidin-4-ol | C | C | B |
| 185 | 2-[(2-phenylphenyl)methoxy]pyrido[3,4-d]pyrimidin-4-ol | C | C | B |
| 186 | 2-[(3-phenylphenyl)methoxy]pyrido[3,4-d]pyrimidin-4-ol | C | C | B |
| 187 | 2-(naphthalen-2-ylmethoxy)pyrido[3,4-d]pyrimidin-4-ol | C | C | C |
| 188 | 2-(1,2,3,4-tetrahydronaphthalen-1-ylmethoxy)pyrido[3,4-d]pyrimidin-4-ol | B | B | A |
| 189 | 2-(2,3-dihydro-1H-inden-2-yloxy)pyrido[3,4-d]pyrimidin-4-ol | B | B | A |
| 190 | 2-(2,3-dihydro-1H-inden-1-ylmethoxy)pyrido[3,4-d]pyrimidin-4-ol | B | B | A |
| 191 | 2-(1,2,3,4-tetrahydronaphthalen-2-ylmethoxy)pyrido[3,4-d]pyrimidin-4-ol | B | B | A |
| 192 | 2-(2,3-dihydro-1H-inden-1-yloxy)pyrido[3,4-d]pyrimidin-4-ol | C | C | C |
| 193 | 2-(1-benzofuran-3-ylmethoxy)pyrido[3,4-d]pyrimidin-4-ol | B | B | A |
| 194 | 2-(2,3-dihydro-1-benzofuran-3-ylmethoxy)pyrido[3,4-d]pyrimidin-4-ol | C | C | C |
| 195 | 2-(3,4-dihydro-2H-1-benzopyran-4-ylmethoxy)pyrido[3,4-d]pyrimidin-4-ol | B | B | A |
| 196 | 2-(1,2,3,4-tetrahydronaphthalen-1-yloxy)pyrido[3,4-d]pyrimidin-4-ol | C | C | C |
| 197 | 2-(3,4-dihydro-2H-1-benzopyran-4-yloxy)pyrido[3,4-d]pyrimidin-4-ol | B | B | A |
| 198 | 8-(1-methylimidazol-4-yl)-3H-pyrido[3,4-d]pyrimidin-4-one | B | B | B |

Note:
Biochemical assay IC$_{50}$ data are designated within the following ranges:
A: ≤0.10 μM
B: >0.10 μM to ≤1.0 μM
C: >1.0 μM to ≤10 μM
D: >10 μM

Example 2: In Vitro Cell-Based Assay

An assay to measure the degree of cellular inhibition of KDM5A and 5B was developed. This quantitative immuno-blotting assay measures the amount tri-methylated histone H3 at amino acid Lysine number 4, a specific substrate and product of the direct enzymatic activity of the histone demethylases KDM5A and KDM5B from extracts of the ZR-75-1 breast cancer cell line.

Assay Principle

This assay is a fluorometric immunoassay for the quantification of tri-methyl H3K4 extracted from cells treated with test compound and is used as a measure of the cellular inhibition of KDM5A/B.

Assay Method

ZR-75-1 (PTEN null, ER+) breast cancer cells numbering 50,000 (ATCC) were seeded into each well of a 96-well tissue culture treated plate and then exposed to an 11 point dilution of test compound with final concentration ranges of test compound ranging from 1250 μM to 10 nM. Cells were left in the presence of test compound for 72 hours. Extracts were prepared containing all of the cellular histone material using detergent based lysis and sonication methods. These lysates were subsequently normalized for total protein content using a colorimetric bicinchonic acid assay (MicroBCA Pierce/Thermo Scientific). Normalized cell extracts were then subjected to typical immuno-blotting procedures using NuPage reagents (Life Technologies). Electrophoretically separated histones were then transferred and immobilized using polyvinylidene difluoride membrane (Immobilon-FL Millipore). The amount of tri-methylated lysine 4 of histone H3 was detected using an antibody specific to the tri-methylated state (Cell Signaling Technologies) and quantified on an infrared imager using a densitometry software package (Odyssey CLx, Image Studio, Li-Cor). This background subtracted densitometry value was reported as a ration of the GAPDH amount for that sample and then calculated as a percent of the DMSO treated sample. The software package XL-fit (IDBS) was then used to calculate a relative $IC_{50}$ value for the dilution series of a given test compound according to the equation:

$$\text{fit} = (D + ((V\max * (x\hat{\,}n))/((x\hat{\,}n) + (Km\hat{\,}n))))$$

Table 4 provides the cellular $IC_{50}$ values of various compounds disclosed herein.

TABLE 4

| Chemical Synthesis Example | Cellular $IC_{50}$ (μM) |
|---|---|
| 2 | D |
| 4 | C |
| 5 | D |
| 7 | D |
| 10 | D |
| 11 | D |
| 12 | D |
| 13 | D |
| 15 | D |
| 18 | C |
| 20 | D |
| 24 | D |
| 34 | D |
| 35 | C |
| 37 | D |
| 40 | D |
| 41 | D |
| 44 | D |
| 45 | D |
| 47 | D |
| 48 | D |
| 49 | D |
| 50 | D |
| 52 | C |
| 53 | C |
| 54 | C |
| 55 | C |
| 56 | C |
| 57 | D |
| 66 | C |
| 69 | D |
| 70 | C |
| 71 | C |
| 72 | C |
| 74 | B |
| 75 | D |
| 86 | C |
| 87 | B |
| 88 | C |
| 89 | C |
| 113 | B |
| 115 | C |
| 117 | C |
| 118 | B |
| 119 | B |
| 120 | C |
| 121 | C |
| 122 | C |
| 124 | B |
| 125 | D |
| 126 | D |
| 127 | C |
| 128 | C |
| 129 | D |
| 130 | D |
| 131 | C |
| 132 | C |
| 133 | C |
| 134 | B |
| 135 | D |
| 136 | B |
| 137 | B |
| 138 | C |
| 139 | D |
| 140 | D |
| 141 | D |
| 142 | D |
| 145 | C |
| 146 | C |
| 147 | C |
| 148 | C |
| 150 | B |
| 151 | B |
| 153 | C |
| 154 | D |
| 155 | C |
| 156 | D |
| 157 | C |
| 158 | B |
| 159 | C |
| 161 | B |
| 162 | B |
| 163 | B |
| 164 | C |
| 165 | C |
| 166 | D |
| 167 | C |
| 168 | C |

Note:
Cellular assay $IC_{50}$ data are designated within the following ranges:
A: ≤0.10 μM
B: >0.10 μM to ≤1.0 μM
C: >1.0 μM to ≤10 μM
D: >10 μM Example 3: In Vivo Xenograph Study Time release pellets containing 0.72 mg 17-β Estradiol are subcutaneously implanted into nu/nu mice. MCF-7 cells are grown in RPMI containing 10% FBS at 5% $CO_2$, 37° C. Cells are spun down and re-suspended in 50% RPMI (serum free) and 50% Matrigel at $1 \times 10^7$ cells/mL. MCF-7 cells are subcutaneously injected (100 μL/animal) on the right flank 2-3 days post pellet implantation and tumor volume (length× $width^2/2$) is monitored bi-weekly. When tumors reach an average volume of ~200 $mm^3$ animals are randomized and treatment is started. Animals are treated with vehicle or compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

III. Preparation of Pharmaceutical Dosage Forms

Example 1: Oral Tablet

A tablet is prepared by mixing 48% by weight of a compound of Formula (I) or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:
1. A method for treating breast cancer in subject in need thereof comprising administering to the subject a therapeutically effective dose of a compound of Formula (I):

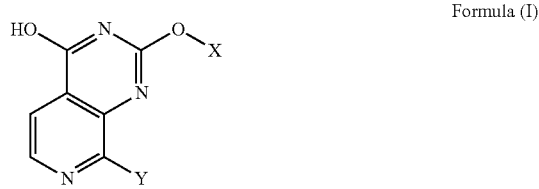

Formula (I)

wherein the compound of Formula (I) includes pharmaceutically acceptable salts thereof, wherein,
X is -L-$R^1$, wherein
L is a bond and
$R^1$ is heteroaryl selected from indazolyl, pyrazolyl, or pyridinyl; and
Y is hydrogen.

2. The method of claim 1, wherein the heteroaryl group is substituted with at least one halogen substituent.

3. The method of claim 1, wherein the heteroaryl group is substituted with at least one alkyl substituent.

4. The method of claim 1, wherein the heteroaryl group is substituted with at least one group selected from hydroxy, alkoxy, aryloxy, amino, alkylamino, arylamino, or diakylamino.

5. The method of claim 1, wherein the heteroaryl group is substituted with at least one group selected from —NHCOR³, —NHCO₂R³, —NHCONHR³, —N(R⁴)COR³, —N(R⁴)CO₂R³, —N(R⁴)CONHR³, —N(R⁴)CON(R⁴)R³, —NHSO₂R³, or —NR⁴SO₂R³, wherein each R³ is independently selected from alkyl, aryl, heteroaryl, carbocyclyl, or heterocyclyl, and each R⁴ is an alkyl.

6. The method of claim 1, wherein the heteroaryl group is substituted with at least one group selected from —CONH₂, —CONHR³, —CON(R³)₂, —COR³, —SO₂NH₂, —SO₂NHR³, —O₂N(R³)₂, or —SO₂R³, wherein each R³ is independently selected from alkyl, aryl, heteroaryl, carbocyclyl, or heterocyclyl.

7. The method of claim 1, wherein the heteroaryl group is substituted with a group selected from aryl, heteroaryl, carbocyclyl, or heterocyclyl.

8. The method of claim 1, wherein the heteroaryl is a pyrazolyl having the structure

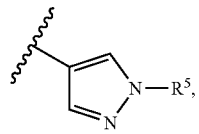

wherein $R^5$ is a group selected from alkyl, carbocyclyl, heterocyclyl, carbocyclylalkyl, heterocyclylalkyl, aralkyl, or heteroarylalkyl.

9. The method of claim 8, wherein the $R^5$ group is a C1-C6 alkyl, optionally substituted with at least one group selected from hydroxy, C1-C4 alkoxy, amino, C1-C4 alkylamino, C1-C4 diakylamino, piperdinyl, pyrrolidnyl, or morpholinyl.

10. The method of claim 8, wherein the $R^5$ group is a heterocyclyl selected from 4-tetrahydropyranyl, 1-morpholinyl, or 4-piperdinyl having the structure

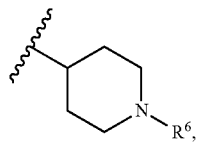

wherein $R^6$ is a —COR⁷, —CO₂R⁷, —CONHR⁷, or —SO₂R⁷, wherein each $R^7$ is independently selected from alkyl, aryl, heteroaryl, carbocyclyl, or heterocyclyl.

11. The method of claim 1, wherein said compound of Formula (I) is selected from the group consisting of:
2-ethoxypyrido[3,4-d]pyrimidin-4-ol;
2-(2-hydroxyethoxy)pyrido[3,4-d]pyrimidin-4-ol;
2-phenylmethoxypyrido[3,4-d]pyrimidin-4-ol;
2-(cyclopropylmethoxy)-3H-pyrido[3,4-d]pyrimidin-4-one;
2-cyclopentyloxy-3H-pyrido[3,4-d]pyrimidin-4-one;
2-propoxy-3H-pyrido[3,4-d]pyrimidin-4-one;
2-methoxypyrido[3,4-d]pyrimidin-4-ol;
2-butan-2-yloxy-3H-pyrido[3,4-d]pyrimidin-4-one;
2-(2-phenoxyethoxy)-3H-pyrido[3,4-d]pyrimidin-4-one;
2-(cyclobutylmethoxy)-3H-pyrido[3,4-d]pyrimidin-4-one;
2-(2,2,2-trifluoroethoxy)pyrido[3,4-d]pyrimidin-4-ol;
2-(3,3,3-trifluoropropoxy)pyrido[3,4-d]pyrimidin-4-ol;
2-(2-methylpropoxy)pyrido[3,4-d]pyrimidin-4-ol;
2-(3-methylbutoxy)pyrido[3,4-d]pyrimidin-4-ol;
2-(2-methylbutoxy)pyrido[3,4-d]pyrimidin-4-ol;
2-(2-phenylpropoxy)pyrido[3,4-d]pyrimidin-4-ol;
2-(2-phenylethoxy)pyrido[3,4-d]pyrimidin-4-ol;
2-(1-phenylpropan-2-yloxy)pyrido[3,4-d]pyrimidin-4-ol;
2-(4,4,4-trifluorobutoxy)pyrido[3,4-d]pyrimidin-4-ol;

2-[3-(dimethylamino)propoxy]pyrido[3,4-d]pyrimidin-4-ol;
2-(2-methoxyethoxy)pyrido[3,4-d]pyrimidin-4-ol;
2-[2-(2,2,2-trifluoroethoxy)ethoxy]pyrido[3,4-d]pyrimidin-4-ol;
2-(3-hydroxy-3-methylbutoxy)pyrido[3,4-d]pyrimidin-4-ol;
2-(3-hydroxy-2-methylpropoxy)pyrido[3,4-d]pyrimidin-4-ol;
2-(oxolan-2-ylmethoxy)pyrido[3,4-d]pyrimidin-4-ol;
2-(oxolan-3-ylmethoxy)pyrido[3,4-d]pyrimidin-4-ol;
N-[2-(4-hydroxypyrido[3,4-d]pyrimidin-2-yl)oxyethyl]-N-methylacetamide;
2-(2-propan-2-yloxyethoxy)pyrido[3,4-d]pyrimidin-4-ol;
2-(2-phenylmethoxyethoxy)pyrido[3,4-d]pyrimidin-4-ol;
N-[2-(4-hydroxypyrido[3,4-d]pyrimidin-2-yl)oxyethyl]benzamide;
3-[(4-hydroxypyrido[3,4-d]pyrimidin-2-yl)oxymethyl]benzonitrile;
2-[(1-methylpyrazol-3-yl)methoxy]pyrido[3,4-d]pyrimidin-4-ol;
2-phenoxypyrido[3,4-d]pyrimidin-4-ol;
N-[4-(4-hydroxypyrido[3,4-d]pyrimidin-2-yl)oxyphenyl]acetamide;
tert-butyl N-[3-(4-hydroxypyrido[3,4-d]pyrimidin-2-yl)oxyphenyl]carbamate;
2-(3,4-difluorophenoxy)pyrido[3,4-d]pyrimidin-4-ol;
2-(3,4-dimethoxyphenoxy)pyrido[3,4-d]pyrimidin-4-ol;
2-(3-propan-2-ylphenoxy)pyrido[3,4-d]pyrimidin-4-ol;
2-(3-fluorophenoxy)pyrido[3,4-d]pyrimidin-4-ol;
2-(3-chlorophenoxy)pyrido[3,4-d]pyrimidin-4-ol;
2-(2,3-difluorophenoxy)pyrido[3,4-d]pyrimidin-4-ol;
2-(3,5-difluoro-4-methoxyphenoxy)pyrido[3,4-d]pyrimidin-4-ol;
2-(3-methoxyphenoxy)pyrido[3,4-d]pyrimidin-4-ol;
2-(4-ethoxy-3,5-difluorophenoxy)pyrido[3,4-d]pyrimidin-4-ol;
2-(2-fluorophenoxy)pyrido[3,4-d]pyrimidin-4-ol;
2-(4-fluorophenoxy)pyrido[3,4-d]pyrimidin-4-ol;
2-(4-methoxyphenoxy)pyrido[3,4-d]pyrimidin-4-ol;
2-(4-chlorophenoxy)pyrido[3,4-d]pyrimidin-4-ol;
2-[3-(dimethylamino)phenoxy]pyrido[3,4-d]pyrimidin-4-ol;
2-(1-methylindazol-5-yl)oxypyrido[3,4-d]pyrimidin-4-ol;
2-[3-(trifluoromethyl)phenoxy]pyrido[3,4-d]pyrimidin-4-ol;
2-(3-fluoro-4-methoxyphenoxy)pyrido[3,4-d]pyrimidin-4-ol;
2-(1-propylpyrazol-4-yl)oxypyrido[3,4-d]pyrimidin-4-ol;
2-{[1-(3-methylbutyl)pyrazol-4-yl]oxy}pyrido[3,4-d]pyrimidin-4-ol;
2-[(1-cyclopentylpyrazol-4-yl)oxy]pyrido[3,4-d]pyrimidin-4-ol;
2-(3-ethylphenoxy)pyrido[3,4-d]pyrimidin-4-ol;
2-(3-propylphenoxy)pyrido[3,4-d]pyrimidin-4-ol;
2-[4-(dimethylamino)phenoxy]pyrido[3,4-d]pyrimidin-4-ol;
3-fluoro-5-(4-hydroxypyrido[3,4-d]pyrimidin-2-yl)oxyphenyl]-morpholin-4-ylmethanone;
2-{[1-(2-methoxyethyl)-1H-indazol-6-yl]oxy}pyrido[3,4-d]pyrimidin-4-ol;
2-[(1-ethyl-1H-pyrazol-4-yl)oxy]pyrido[3,4-d]pyrimidin-4-ol;
2-{[1-(propan-2-yl)-1H-pyrazol-4-yl]oxy}pyrido[3,4-d]pyrimidin-4-ol;
2-{[1-(2-methoxyethyl)-1H-pyrazol-4-yl]oxy}pyrido[3,4-d]pyrimidin-4-ol;
2-{[1-(3-methoxypropyl)-1H-pyrazol-4-yl]oxy}pyrido[3,4-d]pyrimidin-4-ol;
2-[(1-benzyl-1H-pyrazol-4-yl)oxy]pyrido[3,4-d]pyrimidin-4-ol;
2-{[1-(tetrahydro-2H-pyran-4-yl)-1H-pyrazol-4-yl]oxy}pyrido[3,4-d]pyrimidin-4-ol;
2-methoxy-8-(1-methyl-1H-imidazol-4-yl)pyrido[3,4-d]pyrimidin-4-ol;
2-ethoxy-8-(1-methyl-1H-imidazol-4-yl)pyrido[3,4-d]pyrimidin-4-ol;
8-(1-methyl-1H-imidazol-4-yl)-2-(2,2,2-trifluoroethoxy)pyrido[3,4-d]pyrimidin-4-ol;
2-[(4-fluorobenzyl)oxy]-8-(1-methyl-1H-imidazol-4-yl)pyrido[3,4-d]pyrimidin-4-ol;
2-(cyclopropylmethoxy)-8-(1-methylimidazol-4-yl)pyrido[3,4-d]pyrimidin-4-ol;
2-(3-hydroxy-3-methylbutoxy)-8-(1-methylimidazol-4-yl)pyrido[3,4-d]pyrimidin-4-ol;
8-(1-methylimidazol-4-yl)-2-(4,4,4-trifluorobutoxy)pyrido[3,4-d]pyrimidin-4-ol;
2-(2-hydroxyethoxy)-8-(1-methylimidazol-4-yl)pyrido[3,4-d]pyrimidin-4-ol;
2-[2-(dimethylamino)ethoxy]-8-(1-methylimidazol-4-yl)pyrido[3,4-d]pyrimidin-4-ol;
2-(2,2-difluoroethoxy)-8-(1-methylimidazol-4-yl)pyrido[3,4-d]pyrimidin-4-ol;
2-(2-cyclopropylethoxy)-8-(1-methylimidazol-4-yl)pyrido[3,4-d]pyrimidin-4-ol;
2-(1-benzylpyrazol-4-yl)oxy-8-(1-methylimidazol-4-yl)pyrido[3,4-d]pyrimidin-4-ol;
2-[1-(3-methylbutyl)pyrazol-4-yl]oxy-8-(1-methylimidazol-4-yl)pyrido[3,4-d]pyrimidin-4-ol;
2-(3,4-difluorophenoxy)-8-(1-methylimidazol-4-yl)pyrido[3,4-d]pyrimidin-4-ol;
2-[4-(2-methoxyethoxy)phenoxy]-8-(1-methylimidazol-4-yl)pyrido[3,4-d]pyrimidin-4-ol;
8-(1-methylimidazol-4-yl)-2-(1-methylindazol-6-yl)oxypyrido[3,4-d]pyrimidin-4-ol;
2-(1-ethylindazol-6-yl)oxy-8-(1-methylimidazol-4-yl)pyrido[3,4-d]pyrimidin-4-ol;
2-(1,3-dimethylindazol-6-yl)oxy-8-(1-methylimidazol-4-yl)pyrido[3,4-d]pyrimidin-4-ol;
2-[1-[(4-fluorophenyl)methyl]pyrazol-4-yl]oxypyrido[3,4-d]pyrimidin-4-ol;
2-[1-[(2-fluorophenyl)methyl]pyrazol-4-yl]oxypyrido[3,4-d]pyrimidin-4-ol;
tert-butyl 4-[4-(4-hydroxypyrido[3,4-d]pyrimidin-2-yl)oxypyrazol-1-yl]piperidine-1-carboxylate;
2-(1-piperidin-4-ylpyrazol-4-yl)oxypyrido[3,4-d]pyrimidin-4-ol;
1-[4-[4-(4-hydroxypyrido[3,4-d]pyrimidin-2-yl)oxypyrazol-1-yl]piperidin-1-yl]ethanone;
1-[4-[4-(4-hydroxypyrido[3,4-d]pyrimidin-2-yl)oxypyrazol-1-yl]piperidin-1-yl]prop-2-en-1-one;
cyclopropyl-[4-[4-(4-hydroxypyrido[3,4-d]pyrimidin-2-yl)oxypyrazol-1-yl]piperidin-1-yl]methanone;
(4-fluorophenyl)-[4-[4-(4-hydroxypyrido[3,4-d]pyrimidin-2-yl)oxypyrazol-1-yl]piperidin-1-yl]methanone;
2-[1-(1-cyclopropylsulfonylpiperidin-4-yl)pyrazol-4-yl]oxypyrido[3,4-d]pyrimidin-4-ol;
2-[1-[1-(benzenesulfonyl)piperidin-4-yl]pyrazol-4-yl]oxypyrido[3,4-d]pyrimidin-4-ol;
2-(2-piperazin-1-ylpyridin-4-yl)oxypyrido[3,4-d]pyrimidin-4-ol;

2-(2-morpholin-4-ylpyridin-4-yl)oxypyrido[3,4-d]pyrimidin-4-ol;
2-(2-hydroxy-2-methylpropoxy)-8-(1-methylimidazol-4-yl)pyrido[3,4-d]pyrimidin-4-ol;
1-(1-phenylethyl)-4-(4,4,5,5-tetramethyl-1,3,2-dioxaborolan-2-yl)pyrazole;
8-(1-methylimidazol-4-yl)-2-[1-(oxan-4-yl)pyrazol-4-yl]oxypyrido[3,4-d]pyrimidin-4-ol;
8-(1-methylimidazol-4-yl)-2-phenylmethoxypyrido[3,4-d]pyrimidin-4-ol;
8-(1-methyl-1H-imidazol-4-yl)-2-(oxan-4-ylmethoxy)pyrido[3,4-d]pyrimidin-4-ol;
8-(1-methyl-1H-imidazol-4-yl)-2-(oxolan-3-ylmethoxy)pyrido[3,4-d]pyrimidin-4-ol;
2-[(3-fluorophenyl)methoxy]-8-(1-methyl-1H-imidazol-4-yl)pyrido[3,4-d]pyrimidin-4-ol;
2-[(2-chlorophenyl)methoxy]-8-(1-methyl-1H-imidazol-4-yl)pyrido[3,4-d]pyrimidin-4-ol;
2-[(2,3-dichlorophenyl)methoxy]-8-(1-methyl-1H-imidazol-4-yl)pyrido[3,4-d]pyrimidin-4-ol;
8-(1-methyl-1H-imidazol-4-yl)-2-{[2-(trifluoromethyl)phenyl]methoxy}pyrido[3,4-d]pyrimidin-4-ol;
8-(1-methyl-1H-imidazol-4-yl)-2-[(1R)-2,2,2-trifluoro-1-phenylethoxy]pyrido[3,4-d]pyrimidin-4-ol;
8-(1-methyl-1H-imidazol-4-yl)-2-[(1S)-2,2,2-trifluoro-1-phenylethoxy]pyrido[3,4-d]pyrimidin-4-ol;
8-(1-methyl-1H-imidazol-4-yl)-2-[(1,1,1-trifluorobutan-2-yl)oxy]pyrido[3,4-d]pyrimidin-4-ol;
8-(1-methyl-1H-imidazol-4-yl)-2-{[4-(trifluoromethyl)phenyl]methoxy}pyrido[3,4-d]pyrimidin-4-ol;
2-[(4-chlorophenyl)methoxy]-8-(1-methyl-1H-imidazol-4-yl)pyrido[3,4-d]pyrimidin-4-ol;
2-(3,4-dichlorophenoxy)-8-(1-methyl-1H-imidazol-4-yl)pyrido[3,4-d]pyrimidin-4-ol;
2-(3,4-dichlorophenoxy)pyrido[3,4-d]pyrimidin-4-ol;
2-{[1-(1-phenylpropyl)-1H-pyrazol-4-yl]oxy}pyrido[3,4-d]pyrimidin-4-ol;
2-({1-[cyclopropyl(phenyl)methyl]-1H-pyrazol-4-yl}oxy)pyrido[3,4-d]pyrimidin-4-ol;
2-({1-[(1R)-1-phenylethyl]-1H-pyrazol-4-yl}oxy)pyrido[3,4-d]pyrimidin-4-ol;
2-({1-[(1S)-1-phenylethyl]-1H-pyrazol-4-yl}oxy pyrido)[3,4-d]pyrimidin-4-ol;
2-({1-[(1R)-1-(2-fluorophenyl)ethyl]-1H-pyrazol-4-yl}oxy)pyrido[3,4-d]pyrimidin-4-ol;
2-({1-[(is)-1-(2-fluorophenyl)ethyl]-1H-pyrazol-4-yl}oxy)pyrido[3,4-d]pyrimidin-4-ol;
2-({1-[(2-chlorophenyl)methyl]-1H-pyrazol-4-yl}oxy)pyrido[3,4-d]pyrimidin-4-ol;
2-({1-[(3-chlorophenyl)methyl]-1H-pyrazol-4-yl}oxy)pyrido[3,4-d]pyrimidin-4-ol;
2-{[1-(1-benzylpiperidin-4-yl)-1H-pyrazol-4-yl]oxy}pyrido[3,4-d]pyrimidin-4-ol;
2-({1-[2-(morpholin-4-yl)ethyl]-1H-pyrazol-4-yl}oxy)pyrido[3,4-d]pyrimidin-4-ol;
2-({1-[(3R)-pyrrolidin-3-yl]-1H-pyrazol-4-yl}oxy)pyrido[3,4-d]pyrimidin-4-ol;
2-({1-[(3R)-1-(ethanesulfonyl)pyrrolidin-3-yl]-1H-pyrazol-4-yl}oxy)pyrido[3,4-d]pyrimidin-4-ol;
2-({1-[(3R)-1-(cyclopropanesulfonyl)pyrrolidin-3-yl]-1H-pyrazol-4-yl}oxy)pyrido[3,4-d]pyrimidin-4-ol;
2-({1-[(3R)-1-(benzenesulfonyl)pyrrolidin-3-yl]-1H-pyrazol-4-yl}oxy)pyrido[3,4-d]pyrimidin-4-ol;
1-[(3R)-3-[4-({4-hydroxypyrido[3,4-d]pyrimidin-2-yl}oxy)-1H-pyrazol-1-yl]pyrrolidin-1-yl]ethan-1-one;
3-[(3R)-3-[4-({4-hydroxypyrido[3,4-d]pyrimidin-2-yl}oxy)-1H-pyrazol-1-yl]pyrrolidin-1-yl]-3-oxopropanenitrile;
2-({1-[(3R)-1-cyclopropanecarbonylpyrrolidin-3-yl]-1H-pyrazol-4-yl}oxy)pyrido[3,4-d]pyrimidin-4-ol;
2-({1-[(3R)-1-benzoylpyrrolidin-3-yl]-1H-pyrazol-4-yl}oxy)pyrido[3,4-d]pyrimidin-4-ol;
2-({1-[(3R)-1-benzylpyrrolidin-3-yl]-1H-pyrazol-4-yl}oxy)pyrido[3,4-d]pyrimidin-4-ol;
2-({1-[(3R)-1-(4-fluorophenyl)pyrrolidin-3-yl]-1H-pyrazol-4-yl}oxy)pyrido[3,4-d]pyrimidin-4-ol;
2-({1-[(3S)-pyrrolidin-3-yl]-1H-pyrazol-4-yl}oxy)pyrido[3,4-d]pyrimidin-4-ol;
2-({1-[(3S)-1-(ethanesulfonyl)pyrrolidin-3-yl]-1H-pyrazol-4-yl}oxy)pyrido[3,4-d]pyrimidin-4-ol;
2-({1-[(3S)-1-(cyclopropanesulfonyl)pyrrolidin-3-yl]-1H-pyrazol-4-yl}oxy)pyrido[3,4-d]pyrimidin-4-ol;
2-({1-[(3S)-1-(benzenesulfonyl)pyrrolidin-3-yl]-1H-pyrazol-4-yl}oxy)pyrido[3,4-d]pyrimidin-4-ol;
1-[(3S)-3-[4-({4-hydroxypyrido[3,4-d]pyrimidin-2-yl}oxy)-1H-pyrazol-1-yl]pyrrolidin-1-yl]ethan-1-one;
3-[(3S)-3-[4-({4-hydroxypyrido[3,4-d]pyrimidin-2-yl}oxy)-1H-pyrazol-1-yl]pyrrolidin-1-yl]-3-oxopropanenitrile;
2-({1-[(3S)-1-cyclopropanecarbonylpyrrolidin-3-yl]-1H-pyrazol-4-yl}oxy)pyrido[3,4-d]pyrimidin-4-ol;
2-({1-[(3S)-1-benzoylpyrrolidin-3-yl]-1H-pyrazol-4-yl}oxy)pyrido[3,4-d]pyrimidin-4-ol;
2-({1-[(3S)-1-(piperidine-4-carbonyl)pyrrolidin-3-yl]-1H-pyrazol-4-yl}oxy)pyrido[3,4-d]pyrimidin-4-ol;
1-[(3S)-3-[4-({4-hydroxypyrido[3,4-d]pyrimidin-2-yl}oxy)-1H-pyrazol-1-yl]pyrrolidin-1-yl]-2-(methylamino)ethan-1-one;
2-({1-[(3S)-1-phenylpyrrolidin-3-yl]-1H-pyrazol-4-yl}oxy)pyrido[3,4-d]pyrimidin-4-ol;
2-({1-[(3S)-1-(4-fluorophenyl)pyrrolidin-3-yl]-1H-pyrazol-4-yl}oxy)pyrido[3,4-d]pyrimidin-4-ol;
2-({1-[(3S)-1-(2-fluorophenyl)pyrrolidin-3-yl]-1H-pyrazol-4-yl}oxy)pyrido[3,4-d]pyrimidin-4-ol;
2-({1-[(3S)-1-(4-chlorophenyl)pyrrolidin-3-yl]-1H-pyrazol-4-yl}oxy)pyrido[3,4-d]pyrimidin-4-ol;
2-({1-[(3R)-piperidin-3-yl]-1H-pyrazol-4-yl}oxy)pyrido[3,4-d]pyrimidin-4-ol;
2-({1-[(3R)-1-(ethanesulfonyl)piperidin-3-yl]-1H-pyrazol-4-yl}oxy)pyrido[3,4-d]pyrimidin-4-ol;
2-({1-[(3S)-1-(cyclopropanesulfonyl)piperidin-3-yl]-1H-pyrazol-4-yl}oxy)pyrido[3,4-d]pyrimidin-4-ol;
2-({1-[(3R)-1-(benzenesulfonyl)piperidin-3-yl]-1H-pyrazol-4-yl}oxy)pyrido[3,4-d]pyrimidin-4-ol;
1-[(3R)-3-[4-({4-hydroxypyrido[3,4-d]pyrimidin-2-yl}oxy)-1H-pyrazol-1-yl]piperidin-1-yl]ethan-1-one;
3-[(3R)-3-[4-({4-hydroxypyrido[3,4-d]pyrimidin-2-yl}oxy)-1H-pyrazol-1-yl]piperidin-1-yl]-3-oxopropanenitrile;
2-hydroxy-1-[(3 S)-3-[4-({4-hydroxypyrido[3,4-d]pyrimidin-2-yl}oxy)-1H-pyrazol-1-yl]pyrrolidin-1-yl]ethan-1-one;
2-({1-[(3R)-1-cyclopropanecarbonylpiperidin-3-yl]-1H-pyrazol-4-yl}oxy)pyrido[3,4-d]pyrimidin-4-ol;
2-({1-[(3R)-1-benzoylpiperidin-3-yl]-1H-pyrazol-4-yl}oxy)pyrido[3,4-d]pyrimidin-4-ol;
2-({1-[(3R)-1-benzylpiperidin-3-yl]-1H-pyrazol-4-yl}oxy)pyrido[3,4-d]pyrimidin-4-ol;
2-({1-[(3R)-1-(4-fluorophenyl)piperidin-3-yl]-1H-pyrazol-4-yl}oxy)pyrido[3,4-d]pyrimidin-4-ol;
2-({1-[(3S)-piperidin-3-yl]-1H-pyrazol-4-yl}oxy)pyrido[3,4-d]pyrimidin-4-ol;

2-({1-[(3S)-1-(ethanesulfonyl)piperidin-3-yl]-1H-pyrazol-4-yl}oxy)pyrido[3,4-d]pyrimidin-4-ol;
2-({1-[(3S)-1-(cyclopropanesulfonyl)piperidin-3-yl]-1H-pyrazol-4-yl}oxy)pyrido[3,4-d]pyrimidin-4-ol;
2-({1-[(3S)-1-(benzenesulfonyl)piperidin-3-yl]-1H-pyrazol-4-yl}oxy)pyrido[3,4-d]pyrimidin-4-ol;
1-[(3S)-3-[4-({4-hydroxypyrido[3,4-d]pyrimidin-2-yl}oxy)-1H-pyrazol-1-yl]piperidin-1-yl]ethan-1-one;
2-({1-[(3S)-1-cyclopropanecarbonylpiperidin-3-yl]-1H-pyrazol-4-yl}oxy)pyrido[3,4-d]pyrimidin-4-ol;
3-[(3S)-3-[4-({4-hydroxypyrido[3,4-d]pyrimidin-2-yl}oxy)-1H-pyrazol-1-yl]piperidin-1-yl]-3-oxopropanenitrile;
2-({1-[(3S)-1-benzoylpiperidin-3-yl]-1H-pyrazol-4-yl}oxy)pyrido[3,4-d]pyrimidin-4-ol;
2-({1-[(3S)-1-benzylpiperidin-3-yl]-1H-pyrazol-4-yl}oxy)pyrido[3,4-d]pyrimidin-4-ol;
2-({1-[(3R)-1-(4-fluorophenyl)piperidin-3-yl]-1H-pyrazol-4-yl}oxy)pyrido[3,4-d]pyrimidin-4-ol;
2-{[4-(trifluoromethyl)phenyl]methoxy}pyrido[3,4-d]pyrimidin-4-ol;
2-[(2-chlorophenyl)methoxy]pyrido[3,4-d]pyrimidin-4-ol;
2-[(2,6-dichlorophenyl)methoxy]pyrido[3,4-d]pyrimidin-4-ol;
2-[(2,3-dichlorophenyl)methoxy]pyrido[3,4-d]pyrimidin-4-ol;
2-[2-(4-chlorophenyl)ethoxy]pyrido[3,4-d]pyrimidin-4-ol;
2-[2-(3,4-dichlorophenyl)ethoxy]pyrido[3,4-d]pyrimidin-4-ol;
2-(2,2,2-trifluoro-1-phenylethoxy)pyrido[3,4-d]pyrimidin-4-ol;
2-{[2-(trifluoromethyl)phenyl]methoxy}pyrido[3,4-d]pyrimidin-4-ol;
2-[(2-fluorophenyl)methoxy]pyrido[3,4-d]pyrimidin-4-ol;
2-[(3-fluorophenyl)methoxy]pyrido[3,4-d]pyrimidin-4-ol;
2-[(4-fluorophenyl)methoxy]pyrido[3,4-d]pyrimidin-4-ol;
2-[(2,3-difluorophenyl)methoxy]pyrido[3,4-d]pyrimidin-4-ol;
2-[(2,5-difluorophenyl)methoxy]pyrido[3,4-d]pyrimidin-4-ol;
2-[(2,6-difluorophenyl)methoxy]pyrido[3,4-d]pyrimidin-4-ol;
2-(naphthalen-1-ylmethoxy)pyrido[3,4-d]pyrimidin-4-ol;
2-[(2-phenylphenyl)methoxy]pyrido[3,4-d]pyrimidin-4-ol;
2-[(3-phenylphenyl)methoxy]pyrido[3,4-d]pyrimidin-4-ol;
2-(naphthalen-2-ylmethoxy)pyrido[3,4-d]pyrimidin-4-ol;
2-(1,2,3,4-tetrahydronaphthalen-1-ylmethoxy)pyrido[3,4-d]pyrimidin-4-ol;
2-(2,3-dihydro-1H-inden-2-yloxy)pyrido[3,4-d]pyrimidin-4-ol;
2-(2,3-dihydro-1H-inden-1-ylmethoxy)pyrido[3,4-d]pyrimidin-4-ol;
2-(1,2,3,4-tetrahydronaphthalen-2-ylmethoxy)pyrido[3,4-d]pyrimidin-4-ol;
2-(2,3-dihydro-1H-inden-1-yloxy)pyrido[3,4-d]pyrimidin-4-ol;
2-(1-benzofuran-3-ylmethoxy)pyrido[3,4-d]pyrimidin-4-ol;
2-(2,3-dihydro-1-benzofuran-3-ylmethoxy)pyrido[3,4-d]pyrimidin-4-ol;
2-(3,4-dihydro-2H-1-benzopyran-4-ylmethoxy)pyrido[3,4-d]pyrimidin-4-ol;
2-(1,2,3,4-tetrahydronaphthalen-1-yloxy)pyrido[3,4-d]pyrimidin-4-ol;
2-(3,4-dihydro-2H-1-benzopyran-4-yloxy)pyrido[3,4-d]pyrimidin-4-ol; and
8-(1-methylimidazol-4-yl)-3H-pyrido[3,4-d]pyrimidin-4-one.

\* \* \* \* \*